(12) United States Patent
Anthony et al.

(10) Patent No.: US 10,280,438 B2
(45) Date of Patent: May 7, 2019

(54) METHOD FOR THE PRODUCTION OF YEAST

(71) Applicant: BUTAMAX ADVANCED BIOFUELS LLC, Wilmington, DE (US)

(72) Inventors: Larry Cameron Anthony, Aston, PA (US); Caroline Peres, Palo Alto, CA (US); Robert Balcarcel, Palo Alto, CA (US)

(73) Assignee: Butamax Advanced Biofuels LLC, Wilmington, DE (US)

( * ) Notice: Subject to any disclaimer, the term of this patent is extended or adjusted under 35 U.S.C. 154(b) by 0 days.

(21) Appl. No.: 15/502,913

(22) PCT Filed: Aug. 11, 2015

(86) PCT No.: PCT/US2015/044558
§ 371 (c)(1),
(2) Date: Feb. 9, 2017

(87) PCT Pub. No.: WO2016/025425
PCT Pub. Date: Feb. 18, 2016

(65) Prior Publication Data
US 2017/0233771 A1  Aug. 17, 2017

Related U.S. Application Data

(60) Provisional application No. 62/035,945, filed on Aug. 11, 2014.

(51) Int. Cl.
*C12P 7/16* (2006.01)
*C12N 9/24* (2006.01)
*C12N 9/88* (2006.01)
*C12N 9/22* (2006.01)
*C12N 9/04* (2006.01)
*C12N 1/16* (2006.01)

(52) U.S. Cl.
CPC .......... *C12P 7/16* (2013.01); *C12N 1/16* (2013.01); *C12N 9/0006* (2013.01); *C12N 9/22* (2013.01); *C12N 9/2402* (2013.01); *C12N 9/88* (2013.01); *C12Y 101/01006* (2013.01); *C12Y 302/01028* (2013.01); *C12Y 402/03123* (2015.07); *Y02E 50/10* (2013.01)

(58) Field of Classification Search
None
See application file for complete search history.

(56) References Cited

U.S. PATENT DOCUMENTS

| 7,052,724 | B2 | 5/2006 | Oshita et al. |
|---|---|---|---|
| 7,541,173 | B2 | 6/2009 | Bramucci et al. |
| 7,659,104 | B2 | 2/2010 | Bramucci et al. |
| 7,781,646 | B2 | 8/2010 | De La Fuente et al. |
| 7,851,188 | B2 | 12/2010 | Donaldson et al. |
| 7,910,342 | B2 | 3/2011 | Liao et al. |
| 7,993,889 | B1 | 8/2011 | Donaldson et al. |
| 8,017,364 | B2 | 9/2011 | Bramucci et al. |
| 8,129,162 | B2 | 3/2012 | Li et al. |
| 8,178,328 | B2 | 5/2012 | Donaldson et al. |
| 8,188,250 | B2 | 5/2012 | Bramucci et al. |
| 8,206,970 | B2 | 6/2012 | Eliot et al. |
| 8,222,017 | B2 | 7/2012 | Li et al. |
| 8,241,878 | B2 | 8/2012 | Anthony et al. |
| 8,273,558 | B2 | 9/2012 | Donaldson et al. |
| 8,283,144 | B2 | 10/2012 | Donaldson et al. |
| 8,372,612 | B2 | 2/2013 | Larossa et al. |
| 8,389,252 | B2 | 3/2013 | Larossa |
| 8,455,224 | B2 | 6/2013 | Paul |
| 8,455,225 | B2 | 6/2013 | Bramucci et al. |
| 8,465,964 | B2 | 6/2013 | Anthony et al. |
| 8,518,678 | B2 | 8/2013 | Flint et al. |
| 8,557,562 | B2 | 10/2013 | Bramucci et al. |
| 8,614,085 | B2 | 12/2013 | Van Dyk et al. |
| 8,637,281 | B2 | 1/2014 | Paul et al. |
| 8,637,289 | B2 | 1/2014 | Anthony et al. |
| 8,652,823 | B2 | 2/2014 | Flint et al. |
| 8,889,385 | B2 | 2/2014 | Donaldson et al. |
| 8,669,094 | B2 | 3/2014 | Anthony et al. |
| 8,691,540 | B2 | 4/2014 | Bramucci et al. |
| 8,735,114 | B2 | 5/2014 | Donaldson et al. |
| 8,765,433 | B2 | 7/2014 | Gude et al. |
| 8,785,166 | B2 | 7/2014 | Anthony et al. |
| 8,795,992 | B2 | 8/2014 | Bramucci et al. |
| 8,828,694 | B2 | 9/2014 | Anthony et al. |
| 8,828,704 | B2 | 9/2014 | Donaldson et al. |
| 8,871,488 | B2 | 10/2014 | Dauner et al. |
| 8,895,307 | B2 | 11/2014 | Li et al. |
| 8,906,666 | B2 | 12/2014 | Alsaker |
| 8,911,981 | B2 | 12/2014 | Li et al. |

(Continued)

FOREIGN PATENT DOCUMENTS

| WO | WO 2013/173412 | 11/2013 |
|---|---|---|
| WO | WO2013173412 | * 11/2013 |
| WO | WO 2014/151645 | 9/2014 |

OTHER PUBLICATIONS

Krivoruchko et al. J Ind Microbiol Biotechnol. Sep. 2013;40(9):1051-6. Epub Jun. 13, 2013.*
Tao et al. PLoS One. 2012;7(2):e31235.*
An et al. Biotechnol Lett. Jul. 2011;33(7):1367-74.*
Sasano et al. J Biosci Bioeng. Apr. 2012;113(4):451-5.*
Schneider et al. Microb Cell Fact. Jan. 30, 2009;8:12.*
Jorgensen et al. Appl Microbiol Biotechnol. Jul. 2002;59(2-3):310-7.*
Steensma et al. Yeast. Jan. 2008;25(1):9-19.*
Kizer et al. Appl Environ Microbiol. May 2008;74(10):3229-41.*
Prather et al. Curr Opin Biotechnol. Oct. 2008;19(5):468-74.*
Mahmud et al. J Biosci Bioeng. Mar. 2010;109(3):262-6.*

(Continued)

*Primary Examiner* — Christian L Fronda

(57) ABSTRACT

The invention relates to the fields of industrial microbiology and alcohol production including production of yeast products with features suitable for transport, storage, and utilization in fermentation.

16 Claims, 4 Drawing Sheets

Specification includes a Sequence Listing.

(56) References Cited

U.S. PATENT DOCUMENTS

| | | |
|---|---|---|
| 8,940,511 B2 | 1/2015 | Larossa |
| 8,945,859 B2 | 2/2015 | Donaldson et al. |
| 8,945,899 B2 | 2/2015 | Li et al. |
| 8,951,774 B2 | 2/2015 | Donaldson et al. |
| 8,951,937 B2 | 2/2015 | Flint et al. |
| 8,956,850 B2 | 2/2015 | Anthony et al. |
| 8,962,298 B2 | 2/2015 | Donaldson et al. |
| 8,969,065 B2 | 3/2015 | Anthony et al. |
| 8,980,612 B2 | 3/2015 | Donaldson et al. |
| 9,068,190 B2 | 6/2015 | Donaldson et al. |
| 9,080,179 B2 | 7/2015 | Paul |
| 9,163,266 B2 | 10/2015 | Anthony |
| 9,169,467 B2 | 10/2015 | Govindarajan et al. |
| 9,169,499 B2 | 10/2015 | Paul et al. |
| 9,181,566 B2 | 11/2015 | Dauner et al. |
| 9,206,447 B2 | 12/2015 | Anthony et al. |
| 9,238,801 B2 | 1/2016 | Li et al. |
| 9,238,828 B2 | 1/2016 | McElvain et al. |
| 9,260,708 B2 | 2/2016 | Anthony et al. |
| 9,267,157 B2 | 2/2016 | Anthony et al. |
| 9,273,330 B2 | 3/2016 | Bramucci et al. |
| 9,284,612 B2 | 3/2016 | Liao et al. |
| 9,297,016 B2 | 3/2016 | Flint et al. |
| 9,297,028 B2 | 3/2016 | Donaldson et al. |
| 9,297,029 B2 | 3/2016 | Donaldson et al. |
| 9,303,225 B2 | 4/2016 | Donaldson et al. |
| 9,365,872 B2 | 6/2016 | Donaldson et al. |
| 9,388,392 B2 | 7/2016 | Govindarajan et al. |
| 9,404,117 B2 | 8/2016 | Anthony |
| 9,422,581 B2 | 8/2016 | Anthony et al. |
| 9,422,582 B2 | 8/2016 | Anthony et al. |
| 9,512,435 B2 | 12/2016 | Flint et al. |
| 9,580,705 B2 | 2/2017 | Kelly et al. |
| 9,650,624 B2 | 5/2017 | Maggio-Hall et al. |
| 9,663,759 B2 | 5/2017 | Bhalla et al. |
| 9,689,004 B2 | 6/2017 | Maggio-Hall |
| 9,765,365 B2 | 9/2017 | Anthony et al. |
| 9,771,602 B2 | 9/2017 | Anthony et al. |
| 9,790,521 B2 | 10/2017 | Anthony et al. |
| 2003/0211585 A1 | 11/2003 | Gaddy et al. |
| 2009/0017161 A1 | 1/2009 | Nakao et al. |
| 2009/0117227 A1 | 5/2009 | Nakao et al. |
| 2009/0162911 A1 | 6/2009 | Larossa et al. |
| 2009/0226991 A1 | 9/2009 | Feldman et al. |
| 2009/0305369 A1 | 12/2009 | Donaldson et al. |
| 2010/0081154 A1 | 4/2010 | Flint et al. |
| 2010/0081182 A1 | 4/2010 | Paul et al. |
| 2010/0093020 A1 | 4/2010 | Bramucci et al. |
| 2010/0120105 A1 | 5/2010 | Anthony et al. |
| 2011/0195505 A1 | 8/2011 | Euler et al. |
| 2011/0244536 A1 | 10/2011 | Nagarajan et al. |
| 2012/0058541 A1 | 3/2012 | Alsaker et al. |
| 2012/0135017 A1 | 5/2012 | Harel et al. |
| 2012/0149080 A1 | 6/2012 | Bramucci et al. |
| 2012/0196341 A1 | 8/2012 | Donaldson et al. |
| 2012/0258873 A1 | 10/2012 | Gibson et al. |
| 2013/0035515 A1 | 2/2013 | Dobson et al. |
| 2013/0252296 A1 | 9/2013 | Maggio-Hall et al. |
| 2014/0004526 A1 | 1/2014 | Dauner et al. |
| 2014/0038268 A1 | 2/2014 | Flint et al. |
| 2014/0051137 A1 | 2/2014 | Flint et al. |
| 2014/0093930 A1 | 4/2014 | Li et al. |
| 2014/0141479 A1 | 5/2014 | Anthony et al. |
| 2014/0170732 A1 | 6/2014 | Bramucci et al. |
| 2014/0186911 A1 | 7/2014 | Anthony et al. |
| 2014/0273129 A1 | 9/2014 | Bhalla et al. |
| 2014/0349349 A1 | 11/2014 | Dauner et al. |
| 2014/0377824 A1 | 12/2014 | Satagopan et al. |
| 2015/0037855 A1 | 2/2015 | Bhadra et al. |
| 2015/0111269 A1 | 4/2015 | Li et al. |
| 2015/0125920 A1 | 5/2015 | Anthony et al. |
| 2015/0218595 A1 | 8/2015 | Bhadra et al. |
| 2015/0240267 A1 | 8/2015 | Anthony et al. |
| 2016/0024534 A1 | 1/2016 | Anthony et al. |
| 2016/0138050 A1 | 5/2016 | Bramucci et al. |
| 2016/0222370 A1 | 8/2016 | Anthony et al. |
| 2016/0319307 A1 | 11/2016 | Nagarajan et al. |
| 2016/0326551 A1 | 11/2016 | Van Dyk et al. |
| 2016/0326552 A1 | 11/2016 | Dauner et al. |
| 2017/0101653 A1 | 4/2017 | Flint et al. |
| 2017/0218405 A1 | 8/2017 | Maggio-Hall et al. |
| 2017/0226497 A1 | 8/2017 | Kelly et al. |
| 2017/0275652 A1 | 9/2017 | Anthony et al. |
| 2017/0283765 A1 | 10/2017 | Bhalla et al. |

OTHER PUBLICATIONS

Schuler, Moira Monika, Real-time monitoring and control of the specific growth rate in yeast fed-batch cultures based on Process Analytical Technology monitoring tools such as biocalorimetry and spectroscopy, Dissertation, Dublin City University, Sep. 19, 2012.

Lallemand Ethanol Technology, Yeasts yield results, Biofuels Ethanol Fermentation , Jan. 2011, pp. 65-66.

Gómez-Pastor, et al., Recent Advances in Yeast Biomass Production, Biomass—Detection, Production and Usage, Dr. Darko Matovic (Ed.), ISBN: 978-953-307-492-4, InTech, Chapter 11, pp. 201-222, 2011.

Mahmud, et al., Effect of trehalose accumulation on response to saline stress in *Saccharomyces cerevisiae*, Yeast 26:17-30, 2009.

O'Brien, Susannah Sara, Bacterial Contamination of Commercial Yeast, Dissertation, University of the Witwatersrand, 2004.

Quain, Active Dry Yeast—On the Rise, Brewers' Guardian, 135(9): 31, 32, 34, and 35 (Oct. 2006).

Wang, et al., Relationship of trehalose accumulation with ethanol fermentation in industrial *Saccharomyces cerevisiae* yeast strains, Bioresource Technol. 152:371-376, 2014.

Zhao, et al., Impact of zinc supplementation on the improvement of ethanol tolerance and yield of self-flocculating yeast in continuous ethanol fermentation, J. Biotechnol. 139:55-60, 2009.

International Preliminary Report on Patentability for corresponding PCT/US2015/044558, dated Feb. 14, 2017.

International Search Report or corresponding PCT/US2015/044558, dated Nov. 3, 2015.

Jorgensen, et al., Fed-batch cultivation of baker's yeast followed by nitrogen or carbon starvation: effects on fermentative capacity and content of trehalose and glycogen, Appl. Microbiol. Biotechnol. 59:310-317, 2002.

Kana, et al., Novel feeding strategies for *Saccharomyces cerevisiae* DS2155, using glucose limited exponential fedbatch cultures with variable specific growth rates (μ), African J. Biotechnol. 6:1122-1127, 2007.

Guldfeldt, et al., The Effect of Yeast Trehalose Content at Pitching on Fermentation Performance During Brewing Fermentations, J. Inst. Brew. 104:27-39, 1998.

Schneider, et al., Metabolite profiling studies in *Saccharomyces cerevisiae*: an assisting tool to prioritize host targets for antiviral drug screening, Microbial Cell Factories 8:12, 2009.

An, et al., Enhanced thermotolerance for ethanol fermentation of *Saccharomyces cerevisiae* strain by overexpression of the gene coding for trehalose-6-phosphate synthase, Biotechnol. Lett. 33:1367-1374, 2011.

Mahmud, et al., Differential importance of trehalose accumulation in *Saccharomyces cerevisiae* in response to various environmental stresses, J. Biosci. Bioeng. 109:262-266, 2010.

Sasano, et al., Overexpression of the yeast transcription activator Msn2 confers furfural resistance and increases the initial fermentation rate in ethanol production, J. Biosci. Bioeng. 113:451-455, 2012.

Branduardi, et al., A novel pathway to produce butanol and isobutanol in *Saccharomyces cerevisiae*, Biotechnol. Biofuels 6:68, 2013.

\* cited by examiner

METHOD FOR THE PRODUCTION OF YEAST

This application is related to and claims the benefit of priority of U.S. Provisional Application Ser. No. 62/035,945 filed on Aug. 11, 2014, the entirety of which is herein incorporated herein by reference.

The Sequence Listing associated with this application is filed in electronic form via EFS-Web and hereby incorporated by reference into the specification in its entirety.

FIELD OF THE INVENTION

The invention relates to the fields of industrial microbiology and alcohol production. Embodiments of the invention relate to the production of yeast products with features suitable for transport, storage, and utilization in fermentation.

BACKGROUND

Alcohols have a variety of industrial and scientific applications such as fuels, reagents, and solvents. For example, butanol is an important industrial chemical with a variety of applications including use as a fuel additive, as a feedstock chemical in the plastics industry, and as a food-grade extractant in the food and flavor industry. Accordingly, there is a high demand for alcohols such as butanol as well as for efficient and environmentally-friendly production methods including, for example, fermentation processes and the use of biomass as feedstock for these processes.

Production of alcohols by fermentation is one such environmentally friendly production method. As such, effective production of a stable, transportable yeast product for large-scale, commercial fermentations is desirable. Accordingly, there is a need for production methods and genetic modifications which provide attributes advantageous for commercial use.

SUMMARY OF THE INVENTION

The present invention is directed to a method of generating a butanologen yeast product comprising a) culturing a population of butanologen yeast in the presence of a carbon substrate whereby the feed rate of carbon substrate is ramped such that concentration of carbon substrate maintains the growth rate of the population at less than $\mu_{crit}$ and whereby the population reaches a cell density; b) ceasing the ramping of the feed rate whereby the concentration of carbon substrate decreases over a first period of time; and c) subjecting the population of butanologen yeast to a feed rate which is ramped down to less than half of the maximum feed rate of (a). In some embodiments, the carbon substrate is glucose, ethanol, acetate, or a mixture thereof. In some embodiments, the carbon substrate is glucose. In some embodiments, the carbon substrate is ethanol. In some embodiments, the carbon substrate is a dual carbon source. In some embodiments, the dual carbon source is glucose and ethanol, glucose and acetate, or ethanol and acetate. In some embodiments, both glucose and ethanol concentrations are decreased in (b) as compared to (a). In some embodiments, nitrogen concentration is decreased in (b) as compared to (a). In some embodiments, the butanologen yeast comprises one or more alterations in the trehalose biosynthesis pathway. In some embodiments, the butanologen yeast comprises one or more of the following: TPS1 overexpression, TPS2 overexpression, MSN2 overexpression, LSM1 deletion, or NTH1 deletion. In some embodiments, the method further comprises concentrating the population of butanologen yeast to at least about 16% (w/v). In some embodiments, the method further comprises concentrating the population of butanologen yeast to at least about 30% (w/v). In some embodiments, the concentrating is carried out in a centrifuge. In some embodiments, steps (b) and (c) increase the trehalose concentration of the population of butanologen yeast by at least 100%. In some embodiments, steps (b) and (c) increase the trehalose concentration of the population of butanologen yeast by at least 500%. In some embodiments, the trehalose content of the population of butanologen yeast is at least about 5%. In some embodiments, the population of butanologen yeast is further concentrated to at least about 90% (w/v). In some embodiments, the population of butanologen yeast is further concentrated to at least about 90% (w/v) by drying.

The present invention is also directed to a recombinant yeast cell comprising an engineered butanol biosynthetic pathway and an engineered trehalose pathway. In some embodiments, the engineered trehalose pathway comprises one or more of the following: TPS1 overexpression, TPS2 overexpression, MSN2 overexpression, LSM1 deletion, or NTH1 deletion.

DESCRIPTION

Figure 1:
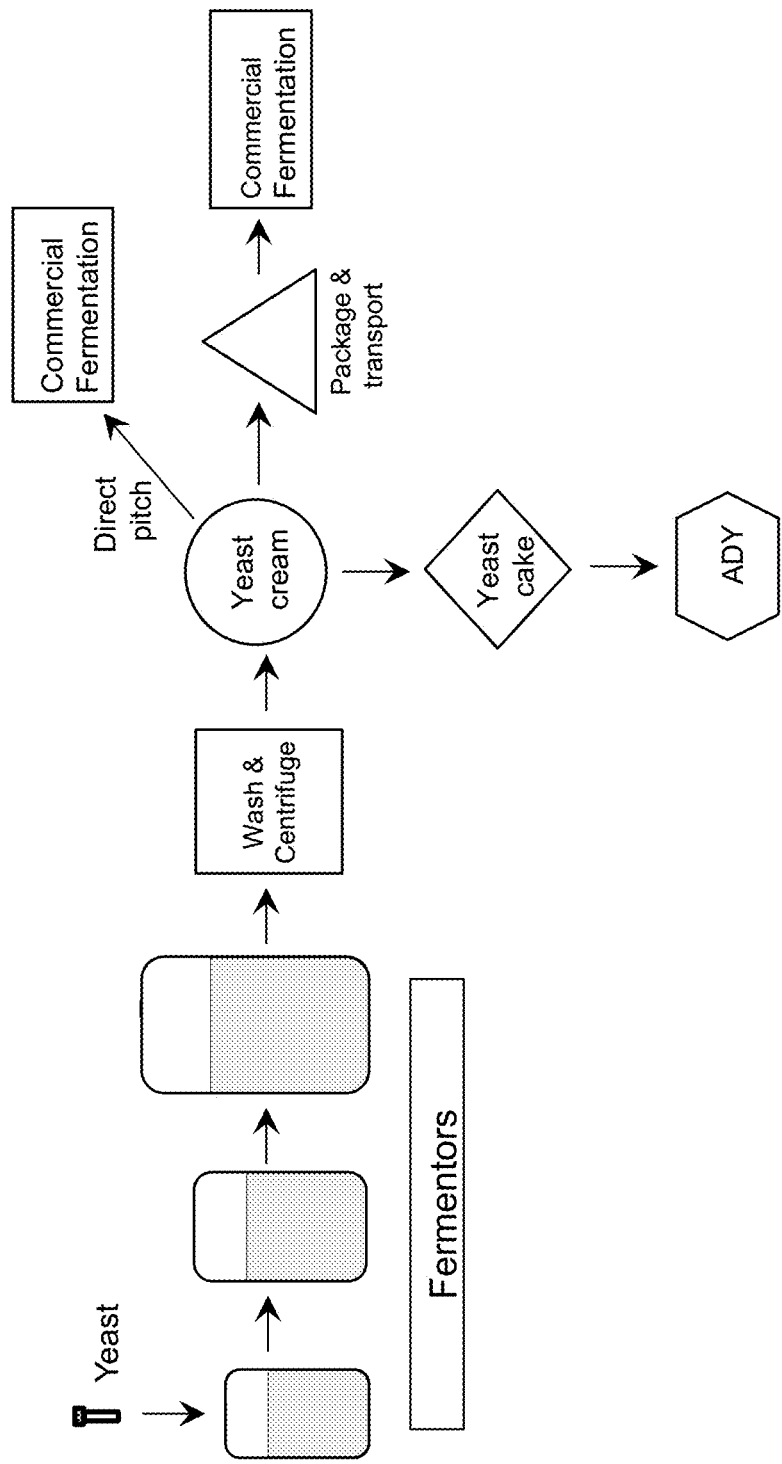
FIG. 1 illustrates a yeast production process.

The invention is directed to methods for generating a yeast product with stability and viability attributes suitable for use in large-scale commercial fermentations. Traditionally, commercial-scale production of yeast may occur on-site at a fermentation facility or through commercial manufacturers. On-site production may utilize a series of seed and propagation fermentors and may involve propagation strategies such as carbon-limited growth which may be controlled through the addition of low but constant amounts of carbon sources (e.g., utilizable sugar, molasses) or appropriate amounts of air ($O_2$). In some embodiments, the seed fermentors may be configured as a production skid. In some embodiments, batch, fed-batch, or continuous fermentations may be utilized for on-site production. In some embodiments, on-site production may comprise one or more fermentations. In some embodiments, on-site production may comprise one or more batch or fed-batch fermentations. In some embodiments, on-site production may comprise two, three, four, five, or more batch or fed-batch fermentations. In some embodiments, the fermentations may be operated in series or in parallel.

Commercial manufacturers can provide yeast product in a number of formats, such as (i) stabilized liquid yeast or yeast cream which is harvested after the spent fermentation medium has been separated by centrifugation and may be further concentrated through the introduction of a salting step; (ii) fresh cake yeast using yeast cream as the starting material and typically harvested after a plate and frame filter press or vacuum filtration dewatering step; or (iii) active dry yeast ("ADY") which uses cake that is further dried, typically using a rotating drum, fluidized bed, or air lift dryer. Active dry yeast generally is optimal for stability and does not require refrigeration; however, it does require rehydration. Fresh cake is optimal for activity, does not require rehydration, and has a shorter lag phase in the fermentor. Yeast cream has higher activity as compared to ADY and yeast cake, is more stable than yeast cake, and is best suited for direct pitch.

Generally, the production of a yeast product begins with a seed preparation. For example, a vial of yeast (e.g., frozen) serves as the inoculum for a culture tank where seed is grown under sterile conditions before transfer to larger pure culture tanks. From the pure culture tanks, the yeast is transferred to a series of semi-seed fermentors. Growth is usually conducted under fed-batch conditions using medium which may include molasses, phosphoric acid, ammonia, and minerals. Following semi-seed fermentation, the yeast is washed with cold water and stored at about 1° C. (about 34° F.) prior to inoculation in commercial fermentors.

For commercial fermentation, seed yeast is added to commercial fermentors and fermentation conditions such as pH, temperature, aeration, foam as well as nutrients may be monitored and adjusted to maintain growth. Generally, the temperature is maintained at about 30° C. and the pH at about 4.5 to 5.5. Nutrients may be added throughout the fermentation, and the rate of nutrient addition may also increase throughout the fermentation. At the completion of fermentation, the fermentation medium is washed with water and centrifuged to yield a yeast cream. The yeast cream may be used directly or further processed by, for example, filter press to yield a yeast cake. The yeast cake may also be further processed by drying (e.g., air lift dryer) to produce active dry yeast. In some embodiments, the solids content of yeast cream may be at least about 15 wt % to at least about 20 wt %. In some embodiments, the water content of the yeast cake may be at least about 50% to at least about 70%.

FIG. 1 illustrates an example of yeast production. In this example, yeast production is conducted in a multi-stage batch fermentation (e.g., fermentation train). During the exponential phase of a batch fermentation, when the specific growth rate may exceed a critical value ($\mu_{crit}$), yeast may produce ethanol under aerobic conditions, known as the Crabtree effect, resulting in a decrease in biomass production. To maximize biomass production and minimize ethanol production, yeast may be grown at a rate close to the critical growth rate ($\mu_{crit}$). In some embodiments, the growth rate of yeast is maintained at less than critical growth rate ($\mu_{crit}$). In some embodiments, the batch fermentation may be aerobic. In some embodiments, the multi-stage fermentation may include a wind down process.

As shown in FIG. 1, yeast is added to a small capacity fermentor or flask and grown to a specific biomass yield (e.g., dry cell weight, dcw). The yeast is then transferred to successively larger fermentors designed to deliver a target biomass yield. During fermentation, various parameters such as fermentor volume, feed rates, dry cell weight, agitation, oxygen uptake rate (OUR), dissolved oxygen, carbon dioxide, respiratory quotient (RQ), fluid viscosity, headspace pressure, off-gas, and air flow may be monitored. For example, by monitoring feed rate, an optimal feed rate profile may be generated and thereby minimize such effects as substrate inhibition, catabolite repression, and glucose effects. In some embodiments, the feed rate may be the amount of a carbon substrate provided over an interval or a unit of time (e.g., grams per minute (g/min), grams per hour (g/h), liter/hour (L/h)).

Certain parameters such as dry cell weight or respiratory quotient (RQ) may be used to assess biomass yield. When the target biomass yield is achieved, the fermentation medium is processed to recover yeast cream. Recovery of yeast cream may include washing (e.g., sterile water) and centrifugation. In some embodiments, the concentration of the yeast may be at least about 15% (w/v) to at least about 30% (w/v). In some embodiments, the concentration of the yeast may be at least about 15% (w/v), at least about 16% (w/v), at least about 17% (w/v), at least about 18% (w/v), at least about 19% (w/v), at least about 20% (w/v), at least about 21% (w/v), at least about 22% (w/v), at least about 23% (w/v), at least about 24% (w/v), at least about 25% (w/v), at least about 26% (w/v), at least about 27% (w/v), at least about 28% (w/v), at least about 29% (w/v), or at least about 30% (w/v). In some embodiments, the concentration of the yeast may be at least about 16% (w/v). In some embodiments, the concentration of the yeast may be at least about 20% (w/v). In some embodiments, the concentration of the yeast may be at least about 25% (w/v). In some embodiments, the concentration of the yeast may be at least about 30% (w/v). As described herein, yeast cream may be pitched directly to commercial fermentors, yeast cream may be packaged and transported to a commercial facility, or the yeast cream may be further processed to generate a yeast cake or ADY. In some embodiments, the concentration of the yeast may be at least about 50% (w/v), at least about 60% (w/v), at least about 50% (w/v), at least about 70% (w/v), at least about 80% (w/v), or at least about 90% (w/v). In some embodiments, the concentration of the yeast may be at least about 90% (w/v).

The final yeast product may need to meet certain product specifications such as metal content (lead, cadmium, arsenic, selenium, mercury), contamination levels (e.g., *Salmonella, E. coli*, coliforms, *Lactobacillus*), viability count, appearance (e.g., color, odor), dry matter, viscosity, and shelf life. Scientific standards for testing content and contaminants have been established worldwide. Examples of testing methods include the FDA Bacteriological Analytical Manual, AOAC International analysis methods, and Compendium of Methods for the Microbiological Examination of Foods (CMMEF).

The fermentation medium for yeast production may contain various nutrients and/or micronutrients. Included among the nutrients and micronutrients typically used: nitrogen, minerals, trace elements, and vitamins, as well as other growth factors. In particular, micronutrients may include chromium, copper, iron, lithium, magnesium, manganese, molybdenum, potassium, vanadium, and zinc. Suitable growth factors include vitamins, purines, pyrimidines, nucleotides, nucleosides, amino acids, fatty acids, sterols, and polyamines. Nitrogen may be obtained from sources such as gaseous ammonia; ammonium salts such as ammonium sulfate or diammonium hydrogen phosphate; nitrates; urea; organic forms of nitrogen such as mixtures of peptides and amino acids (which may in turn be obtained from hydrolyzed plant protein material such as corn steep liquor, casein hydrolysate, soybean meal, barley malt, corn gluten meal, linseed meal, whey powder, beet and cane molasses, rice and wheat meal, and yeast extract); and peptones, which are protein hydrolysates derived from meat, casein, gelatin, keratin, peanuts, soybean meal, cottonseeds, and sunflower seeds. Suitable minerals and elements typically include phosphorus (e.g., $(NH_4)_2HPO_4$), potassium (e.g., KCl), magnesium, sulfur (e.g., $MgSO_4.7H_2O$) sodium, chlorine, cobalt, nickel (e.g., $NiCl_2$), iron (e.g., $FeCl_2.H_2O$), zinc (e.g., $ZnCl_2$), manganese, calcium (e.g., $CaCl_2$), copper (e.g., $CuSO_4 \cdot 5H_2O$), and molybdenum (e.g., $Na_2MoO_4$). Suitable vitamins typically include riboflavin, nicotinic acid, pantothenic acid, folic acid, choline, inositol, biotin, pyroxidine, and thiamin.

In addition, yeast production may be controlled by measuring and monitoring relevant conditions and variables which may include one or more of the following: temperature, pressure, gas flow rate, liquid inlet and outlet flow rates, culture level, culture volume, culture weight, culture viscosity, foaming, dissolved oxygen concentration, dissolved oxygen tension, dissolved $CO_2$ concentration, redox potential, pH, conductivity, ionic strength, dilution rate, carbohydrate concentration, total protein concentration, vitamin concentration, nucleic acid concentration, total cell count, viable cell count, biomass concentration, cell size, and age, doubling time, substrate uptake rate, or product formation rate. Measurement of reaction conditions and variables may be performed using analytical methods such as high performance liquid chromatography, nuclear magnetic resonance, flow cytometry, fluorometry, flow injection analysis, mass spectrometry or gas chromatography.

In some embodiments, antimicrobial agents may also be added to the fermentors to minimize contamination. Examples of antimicrobial agents include, but are not limited to, antibiotics such as erythromycin, tylosin, and virginiamycin, hops-derived antimicrobials such as IsoStab™ and LactoStab™, and/or disinfectants such as Wescodyne®, Virkon® S, Divosan®, and Sporocidine®. In some embodiments, the fermentation medium may be treated with antibiotics, hops-derived antimicrobials, disinfectants, acid treatment, ammonia, urea, hydrogen peroxide, and/or chlorine dioxide. In some embodiments, steam sterilization may be used to minimize contamination. In some embodiments, heat and/or filter sterilization may be used to minimize contamination.

For commercial-scale production of a yeast product as well as commercial-scale fermentation, numerous factors, for example, but not limited to, microbial physiology and metabolism (e.g., genetic switch), oxygen uptake rate (OUR), growth cycle, growth on carbon sources (e.g., molasses, sucrose, glucose, ethanol), growth rate (e.g., average growth rate, $\mu_{avg}$), fermentation medium, cell density propagation, fermentor configuration (e.g., fed-batch, continuous, profusion-coupled), and product production (e.g., alcohol) may be modified to improve yeast production and/or fermentation.

For example, prior to commercial-scale fermentation, yeast may be grown in order to achieve sufficient biomass to afford the yields and rates required for the commercial-scale fermentation. To achieve sufficient biomass, yeast may be grown utilizing a dual carbon source such as ethanol and glucose, ethanol and acetate, or acetate and glucose. Under these growth conditions, increased biomass yields as well as reduced byproduct accumulation may be attained. In some embodiments, for the production of a yeast product, yeast may be grown utilizing carbon-limited fed-batch fermentation.

Metabolic control of yeast propagation and production may be regulated by genetic switches. Certain promoters (e.g., genetic switches) are sensitive to one or more physiochemical differences such as dissolved oxygen concentration, glucose concentration, source of the fermentable carbon substrate, concentration of product (e.g., alcohol) in fermentation medium, pH, and temperature. For example, promoters for genes such as HXK2, IMA1, SLT2, YHR210c, YJL171c, PUN1, PRE8, PRE10, COS3, DIA1, YNR062C, AIM45, ZRT1, ZRT2, PH084, PCL1, ARG1, ZPS1, FIT2, FIT3, FRE5, CSM4, SAM3, and FDH2 may increase or decrease the expression of these genes under certain fermentation conditions. As an example, if a genetic switch provides preferential expression in high glucose conditions, the glucose concentration in propagation or production under which minimal expression is desired can be controlled so as to maintain minimal expression. As such, genetic switches may provide a means to improve yeast propagation and production. A description of genetic switches may be found in U.S. Patent Application Publication No. 2014/0004526, the entire contents of which are herein incorporated by reference.

Yeast propagation and production may also be improved by increased tolerance to certain fermentation condition. Trehalose is a disaccharide and plays a major role in yeast survival and tolerance to osmotic stress. Trehalose has multiple physiological roles including, for example, osmotolerance, heat shock response, and desiccation tolerance (see, e.g., Conlin, et al., Mol. Cell. Biol. 27:1505-1515, 2007). In addition, trehalose biosynthesis regulates glycolysis in yeast (Eastmond, et al., Curr. Opin. Plant Biol. 6:231-235, 2003), and it has also been postulated that trehalose may be a chemical co-chaperone during stress response. Therefore, trehalose can impact cell growth and survival to adverse stress conditions.

Alcohols such as ethanol and butanol are known to alter membrane fluidity, potentially resulting in lower tolerance to stress conditions. It has been shown that microorganisms capable of producing isobutanol (i.e., isobutanologen) with intracellular trehalose concentrations greater than 70 mM during aerobic growth in the presence of excess glucose and nitrogen source have higher intrinsic growth rate and higher glucose consumption rates. This observation suggests that the level of trehalose can impact cell growth and isobutanol production rate of an isobutanologen. Further, genes that regulate trehalose biosynthesis could also impact cell growth and isobutanol production rate.

Therefore, yeast may be engineered to exhibit improved tolerance, improved cell viability, and/or improved productivity through the expression and/or activity of one or more components of trehalose biosynthesis pathway. In some embodiments, yeast may comprise one or more alterations in one or more components of trehalose biosynthesis pathway. In some embodiments, the one or more components of trehalose biosynthesis pathway may be LSM1, MSN2, NTH1 (e.g., neutral trehalase), TPS1 (e.g., trehalose-6-phosphate synthase), TPS2 (e.g., trehalose-6-phosphate synthase/phosphatase), or combinations thereof. In some embodiments, the alteration of one or more components of trehalose biosynthesis pathway may be overexpression of MSN2, TPS1, TPS2, or combinations thereof. In some embodiments, the alteration of one or more components of trehalose biosynthesis pathway may be deletion of LSM1, NTH1, or combinations thereof. In some embodiments, the trehalose content of a yeast population may be at least about 5%.

In some embodiments, yeast may comprise one or more modifications that alter expression and/or activity of one or more components of trehalose biosynthesis, and a butanol biosynthetic pathway. In some embodiments, yeast may comprise one or more modifications that alter expression and/or activity of LSM1, MSN2, NTH1, TPS1, TPS2, or combinations thereof, and a butanol biosynthetic pathway. In some embodiments, the butanol biosynthetic pathway may be a 1-butanol biosynthetic pathway, 2-butanol biosynthetic pathway, 2-butanone biosynthetic pathway, or isobutanol biosynthetic pathway.

Definitions

In order to further define this invention, the following terms and definitions are herein provided.

"Biomass" as used herein refers to a natural product containing hydrolyzable polysaccharides that provide fermentable sugars including any sugars and starch derived from natural resources such as corn, sugar cane, wheat, cellulosic or lignocellulosic material and materials comprising cellulose, hemicellulose, lignin, starch, oligosaccharides, disaccharides and/or monosaccharides, and mixtures thereof. Biomass may also comprise additional components such as protein and/or lipids. Biomass may be derived from a single source or biomass may comprise a mixture derived from more than one source. For example, biomass may comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste (e.g., forest thinnings). Examples of biomass include, but are not limited to, corn grain, corn cobs, crop residues such as corn husks, corn stover, grasses, wheat, rye, wheat straw, spelt, triticale, barley, barley straw, oats, hay, rice, rice straw, switchgrass, potato, sweet potato, cassava, Jerusalem artichoke, waste paper, sugar cane bagasse, sorghum, sugar cane, sugar beet, fodder beet, soy, palm, coconut, rapeseed, safflower, sunflower, millet, *eucalyptus, miscanthus*, components obtained from milling of grains, trees, branches, roots, leaves, wood chips, sawdust, shrubs and bushes, vegetables, fruits, flowers, animal manure, and mixtures thereof. For example, mash, juice, molasses, or hydrolysate may be formed from biomass by any processing known in the art for processing biomass for purposes of fermentation such as by milling, treating, and/or liquefying, and treated biomass may comprise fermentable sugar and may comprise water. For example, cellulosic and/or lignocellulosic biomass may be processed to obtain a hydrolysate containing fermentable sugars by any method known to one skilled in the art. A low ammonia pretreatment is disclosed in U.S. Patent Application Publication No. 2007/0031918A1, the entire contents of which are herein incorporated by reference. Enzymatic saccharification of cellulosic and/or lignocellulosic biomass typically makes use of enzyme mixtures for hydrolysis of cellulose and hemicellulose to produce a hydrolysate containing sugars including glucose, xylose, and arabinose. Saccharification enzymes suitable for cellulosic and/or lignocellulosic biomass are reviewed in Lynd, et al. (Microbiol. Mol. Biol. Rev. 66:506-577, 2002).

"Carbon substrate" or "fermentable carbon substrate" as used herein refers to a carbon source capable of being metabolized by microorganisms. Suitable fermentable carbon sources include, but are not limited to, monosaccharides such as glucose or fructose; disaccharides such as lactose or sucrose; oligosaccharides; polysaccharides such as starch or cellulose; ethanol, lactate, succinate, glycerol, carbon dioxide, methanol, one carbon substrates; and mixtures thereof.

"Fermentable sugar" as used herein refers to one or more sugars capable of being metabolized by microorganisms for the production of fermentative products such as alcohols.

"Feedstock" as used herein refers to a feed in a fermentation process, the feed containing a fermentable carbon source with or without undissolved solids and oil, and where applicable, the feed containing a fermentable carbon source before or after the fermentable carbon source has been liberated from starch or obtained from the hydrolysis of complex sugars by further processing such as by liquefaction, saccharification, or other process. Feedstock includes or is derived from a biomass. Suitable feedstocks include, but are not limited to, rye, wheat, corn, corn mash, cane, cane mash, barley, cellulosic material, lignocellulosic material, or mixtures thereof. Where reference is made to "feedstock oil," it will be appreciated that the term encompasses the oil produced from a given feedstock.

"Fermentation medium" as used herein refers to the mixture of water, fermentable carbon sources (e.g., sugars, starch), dissolved solids, optionally microorganisms producing alcohol, product alcohol, undissolved solids, and all other constituents of the material held in the fermentor in which product alcohol is being made by the metabolism of fermentable carbon sources by the microorganisms to form alcohol, water, and carbon dioxide ($CO_2$). From time to time as used herein, the term "fermentation broth" and "fermented mixture" can be used synonymously with "fermentation medium."

"Fermentor" or "fermentation vessel" as used herein refers to a vessel or tank in which the fermentation reaction is carried out whereby product alcohol such as ethanol or butanol is made from fermentable carbon sources. Fermentor may also refer to a vessel or tank in which growth of microorganism occurs. In some instances, both microbial growth and fermentation may occur in a fermentor. The term "fermentor" can be used synonymously herein with "fermentation vessel."

"Sugar" as used herein refers to oligosaccharides, disaccharides, monosaccharides, and/or mixtures thereof. The term "saccharide" also includes carbohydrates including starches, dextrans, glycogens, cellulose, pentosans, as well as sugars.

"Alcohol" as used herein refers to any alcohol that may be produced by a microorganism in a fermentation process that utilizes biomass as a fermentable carbon source. Product alcohols include, but are not limited to, $C_1$ to $C_8$ alkyl alcohols. In some embodiments, the product alcohols are $C_2$ to $C_8$ alkyl alcohols. In other embodiments, the product alcohols are $C_2$ to $C_5$ alkyl alcohols. It will be appreciated that $C_1$ to $C_8$ alkyl alcohols include, but are not limited to, methanol, ethanol, propanol, butanol, pentanol, and isomers thereof. Likewise, $C_2$ to $C_8$ alkyl alcohols include, but are not limited to, ethanol, propanol, butanol, pentanol, and isomers thereof "Alcohol" is also used herein with reference to a product alcohol.

"Butanol" as used herein refers to butanol isomers: 1-butanol (1-BuOH), 2-butanol (2-BuOH), tertiary-butanol (tert-BuOH), and/or isobutanol (iBuOH, i-BuOH, or I-BUOH), either individually or as mixtures thereof.

"Propanol" as used herein refers to the propanol isomers: isopropanol or 1-propanol.

"Pentanol" as used herein refers to the pentanol isomers: 1-pentanol, 3-methyl-1-butanol, 2-methyl-1-butanol, 2,2-dimethyl-1-propanol, 3-pentanol, 2-pentanol, 3-methyl-2-butanol, or 2-methyl-2-butanol.

The term "microaerobic conditions" as used herein means growth conditions with low levels of dissolved oxygen. For example, the oxygen level may be less than about 1% of air-saturation.

The term "anaerobic conditions" as used herein means growth conditions in the absence of oxygen.

Biosynthetic Pathways

In some embodiments, the yeast cell may comprise a butanol biosynthetic pathway as described herein. In some embodiments, the yeast cell may comprise an isobutanol biosynthetic pathway, a 1-butanol biosynthetic pathway, a 2-butanol biosynthetic pathway, or a 2-butanone biosynthetic pathway. In some embodiments, the yeast cell may comprise one or more polynucleotides encoding one or more polypeptides that catalyzes substrate to product conversions of these biosynthetic pathway. The substrate to product conversions of the isobutanol biosynthetic pathway, a 1-butanol biosynthetic pathway, a 2-butanol biosynthetic pathway, and a 2-butanone biosynthetic pathway are described herein.

Biosynthetic pathways for the production of isobutanol that may be used include those described in U.S. Pat. No. 7,851,188, the entire contents of which are herein incorporated by reference. In some embodiments, the isobutanol biosynthetic pathway comprises the following substrate to product conversions:
 a) pyruvate to acetolactate, which may be catalyzed, for example, by acetolactate synthase;
 b) acetolactate to 2,3-dihydroxyisovalerate, which may be catalyzed, for example, by acetohydroxy acid reductoisomerase;
 c) 2,3-dihydroxyisovalerate to α-ketoisovalerate, which may be catalyzed, for example, by acetohydroxy acid dehydratase;
 d) α-ketoisovalerate to isobutyraldehyde, which may be catalyzed, for example, by a branched-chain α-keto acid decarboxylase; and
 e) isobutyraldehyde to isobutanol, which may be catalyzed, for example, by a branched-chain alcohol dehydrogenase.

In some embodiments, the isobutanol biosynthetic pathway comprises the following substrate to product conversions:
 a) pyruvate to acetolactate, which may be catalyzed, for example, by acetolactate synthase;
 b) acetolactate to 2,3-dihydroxyisovalerate, which may be catalyzed, for example, by ketol-acid reductoisomerase;
 c) 2,3-dihydroxyisovalerate to a-ketoisovalerate, which may be catalyzed, for example, by dihydroxyacid dehydratase;
 d) α-ketoisovalerate to valine, which may be catalyzed, for example, by transaminase or valine dehydrogenase;
 e) valine to isobutylamine, which may be catalyzed, for example, by valine decarboxylase;
 f) isobutylamine to isobutyraldehyde, which may be catalyzed by, for example, omega transaminase; and
 g) isobutyraldehyde to isobutanol, which may be catalyzed, for example, by a branched-chain alcohol dehydrogenase.

In some embodiments, the isobutanol biosynthetic pathway comprises the following substrate to product conversions:
 a) pyruvate to acetolactate, which may be catalyzed, for example, by acetolactate synthase;
 b) acetolactate to 2,3-dihydroxyisovalerate, which may be catalyzed, for example, by acetohydroxy acid reductoisomerase;
 c) 2,3-dihydroxyisovalerate to α-ketoisovalerate, which may be catalyzed, for example, by acetohydroxy acid dehydratase;
 d) α-ketoisovalerate to isobutyryl-CoA, which may be catalyzed, for example, by branched-chain keto acid dehydrogenase;
 e) isobutyryl-CoA to isobutyraldehyde, which may be catalyzed, for example, by acelylating aldehyde dehydrogenase; and
 f) isobutyraldehyde to isobutanol, which may be catalyzed, for example, by a branched-chain alcohol dehydrogenase.

Biosynthetic pathways for the production of 1-butanol that may be used include those described in U.S. Patent Application Publication No. 2008/0182308, the entire contents of which are herein incorporated by reference. In some embodiments, the 1-butanol biosynthetic pathway comprises the following substrate to product conversions:
 a) acetyl-CoA to acetoacetyl-CoA, which may be catalyzed, for example, by acetyl-CoA acetyltransferase;
 b) acetoacetyl-CoA to 3-hydroxybutyryl-CoA, which may be catalyzed, for example, by 3-hydroxybutyryl-CoA dehydrogenase;
 c) 3-hydroxybutyryl-CoA to crotonyl-CoA, which may be catalyzed, for example, by crotonase;
 d) crotonyl-CoA to butyryl-CoA, which may be catalyzed, for example, by butyryl-CoA dehydrogenase;
 e) butyryl-CoA to butyraldehyde, which may be catalyzed, for example, by butyraldehyde dehydrogenase; and
 f) butyraldehyde to 1-butanol, which may be catalyzed, for example, by butanol dehydrogenase.

Biosynthetic pathways for the production of 2-butanol that may be used include those described in U.S. Patent Application Publication No. 2007/0259410 and U.S. Patent Application Publication No. 2009/0155870, the entire contents of which are herein incorporated by reference. In some embodiments, the 2-butanol biosynthetic pathway comprises the following substrate to product conversions:
 a) pyruvate to alpha-acetolactate, which may be catalyzed, for example, by acetolactate synthase;
 b) alpha-acetolactate to acetoin, which may be catalyzed, for example, by acetolactate decarboxylase;
 c) acetoin to 3-amino-2-butanol, which may be catalyzed, for example, acetonin aminase;
 d) 3-amino-2-butanol to 3-amino-2-butanol phosphate, which may be catalyzed, for example, by aminobutanol kinase;
 e) 3-amino-2-butanol phosphate to 2-butanone, which may be catalyzed, for example, by aminobutanol phosphate phosphorylase; and
 f) 2-butanone to 2-butanol, which may be catalyzed, for example, by butanol dehydrogenase.

In some embodiments, the 2-butanol biosynthetic pathway comprises the following substrate to product conversions:
 a) pyruvate to alpha-acetolactate, which may be catalyzed, for example, by acetolactate synthase;
 b) alpha-acetolactate to acetoin, which may be catalyzed, for example, by acetolactate decarboxylase;
 c) acetoin to 2,3-butanediol, which may be catalyzed, for example, by butanediol dehydrogenase;
 d) 2,3-butanediol to 2-butanone, which may be catalyzed, for example, by dial dehydratase; and
 e) 2-butanone to 2-butanol, which may be catalyzed, for example, by butanol dehydrogenase.

Biosynthetic pathways for the production of 2-butanone that may be used include those described in U.S. Patent Application Publication No. 2007/0259410 and U.S. Patent Application Publication No. 2009/0155870, the entire contents of which are herein incorporated by reference. In some embodiments, the 2-butanone biosynthetic pathway comprises the following substrate to product conversions:
 a) pyruvate to alpha-acetolactate, which may be catalyzed, for example, by acetolactate synthase;
 b) alpha-acetolactate to acetoin, which may be catalyzed, for example, by acetolactate decarboxylase;
 c) acetoin to 3-amino-2-butanol, which may be catalyzed, for example, acetonin aminase;

d) 3-amino-2-butanol to 3-amino-2-butanol phosphate, which may be catalyzed, for example, by aminobutanol kinase; and, e) 3-amino-2-butanol phosphate to 2-butanone, which may be catalyzed, for example, by aminobutanol phosphate phosphorylase.

In some embodiments, the 2-butanone biosynthetic pathway comprises the following substrate to product conversions:

a) pyruvate to alpha-acetolactate, which may be catalyzed, for example, by acetolactate synthase;

b) alpha-acetolactate to acetoin which may be catalyzed, for example, by acetolactate decarboxylase;

c) acetoin to 2,3-butanediol, which may be catalyzed, for example, by butanediol dehydrogenase; and d) 2,3-butanediol to 2-butanone, which may be catalyzed, for example, by diol dehydratase.

In some embodiments, the invention produces butanol from plant-derived carbon sources, avoiding the negative environmental impact associated with standard petrochemical processes for butanol production. In some embodiments, the invention provides a method for the production of butanol using recombinant industrial host cells comprising a butanol pathway.

In some embodiments, the butanol biosynthetic pathways may comprise at least one polynucleotide, at least two polynucleotides, at least three polynucleotides, at least four polynucleotides, at least five polynucleotides, at least six polynucleotides, or at least seven polynucleotides that is/are heterologous to the host cell. In some embodiments, each substrate to product conversion of a butanol biosynthetic pathway in a recombinant host cell may be catalyzed by a heterologous polypeptide. In some embodiments, the polypeptide catalyzing the substrate to product conversions of acetolactate to 2,3-dihydroxyisovalerate and/or the polypeptide catalyzing the substrate to product conversion of isobutyraldehyde to isobutanol are capable of utilizing NADH (reduced nicotinamide adenine dinucleotide) as a cofactor.

The term "acetohydroxyacid synthase," "acetolactate synthase," and "acetolactate synthetase" (abbreviated "ALS"), and in some instances, may be used interchangeably herein, refer to a polypeptide (or polypeptides) having enzyme activity that catalyzes the conversion of pyruvate to acetolactate and $CO_2$. Example acetolactate synthases are known by the EC number 2.2.1.6 (Enzyme Nomenclature 1992, Academic Press, San Diego). These unmodified enzymes are available from a number of sources including, but not limited to, *Bacillus subtilis* (GenBank Nos: CAB15618 (SEQ ID NO: 1), Z99122 (SEQ ID NO: 2), NCBI (National Center for Biotechnology Information) amino acid sequence, NCBI nucleotide sequence, respectively), *Klebsiella pneumoniae* (GenBank Nos: AAA25079 (SEQ ID NO: 3), M73842 (SEQ ID NO: 4)), and *Lactococcus lactis* (GenBank Nos: AAA25161 (SEQ ID NO: 5), L16975 (SEQ ID NO: 6)).

The term "ketol-acid reductoisomerase" ("KARI"), "acetohydroxy acid isomeroreductase," and "acetohydroxy acid reductoisomerase," and in some instances, may be used interchangeably herein, refer to a polypeptide (or polypeptides) having enzyme activity that catalyzes the reaction of (S)-acetolactate to 2,3-dihydroxyisovalerate. Example KARI enzymes may be classified as EC number EC 1.1.1.86 (Enzyme Nomenclature 1992, Academic Press, San Diego), and are available from a vast array of microorganisms, including, but not limited to, *Escherichia coli* (GenBank Nos: NP_418222 (SEQ ID NO: 7), NC_000913 (SEQ ID NO: 8)), *Saccharomyces cerevisiae* (GenBank Nos: NP_013459 (SEQ ID NO: 9), NC_001144 (SEQ ID NO: 10)), *Methanococcus maripaludis* (GenBank Nos: CAF30210 (SEQ ID NO: 11), BX957220 (SEQ ID NO: 12)), and *Bacillus subtilis* (GenBank Nos: CAB14789 (SEQ ID NO: 13), Z99118 (SEQ ID NO: 14)). KARIs include *Anaerostipes caccae* KARI variants "K9G9" and "K9D3" (SEQ ID NOs: 15 and 16, respectively). Ketol-acid reductoisomerase (KARI) enzymes are described in U.S. Patent Application Publication Nos. 2008/0261230, 2009/0163376, and 2010/0197519, and PCT Application Publication No. WO/2011/041415, the entire contents of which are herein incorporated by reference. Examples of KARIs disclosed therein are those from *Lactococcus lactis*, *Vibrio cholera*, *Pseudomonas aeruginosa* PAO1, and *Pseudomonas fluorescens* PF5 mutants. In some embodiments, the KARI may utilize NADH. In some embodiments, the KARI may utilize NADPH (reduced nicotinamide adenine dinucleotide phosphate).

The term "acetohydroxy acid dehydratase" and "dihydroxyacid dehydratase" ("DHAD"), and in some instances, may be used interchangeably herein, refer to a polypeptide (or polypeptides) having enzyme activity that catalyzes the conversion of 2,3-dihydroxyisovalerate to α-ketoisovalerate. Example acetohydroxy acid dehydratases are known by the EC number 4.2.1.9. Such enzymes are available from a vast array of microorganisms including, but not limited to, *E. coli* (GenBank Nos: YP_026248 (SEQ ID NO: 17), NC000913 (SEQ ID NO: 18)), *Saccharomyces cerevisiae* (GenBank Nos: NP_012550 (SEQ ID NO: 19), NC 001142 (SEQ ID NO: 20)), *M. maripaludis* (GenBank Nos: CAF29874 (SEQ ID NO: 21), BX957219 (SEQ ID NO: 22)), *B. subtilis* (GenBank Nos: CAB14105 (SEQ ID NO: 23), Z99115 (SEQ ID NO: 24)), *Lactococcus lactis*, *Streptococcus mutans*, and *N. crassa*. U.S. Patent Application Publication No. 2010/0081154 and U.S. Pat. No. 7,851,188, the entire contents of which are herein incorporated by reference, describe dihydroxyacid dehydratases (DHADs).

The term "branched-chain α-keto acid decarboxylase," "α-ketoacid decarboxylase," "α-ketoisovalerate decarboxylase," or "2-ketoisovalerate decarboxylase" ("KIVD"), and in some instances, may be used interchangeably herein, refer to a polypeptide (or polypeptides) having enzyme activity that catalyzes the conversion of α-ketoisovalerate to isobutyraldehyde and $CO_2$. Example branched-chain α-keto acid decarboxylases are known by the EC number 4.1.1.72 and are available from a number of sources including, but not limited to, *Lactococcus lactis* (GenBank Nos: AAS49166 (SEQ ID NO: 25), AY548760 (SEQ ID NO: 26); CAG34226 (SEQ ID NO: 27), AJ746364 (SEQ ID NO: 28), *Salmonella typhimurium* (GenBank Nos: NP_461346 (SEQ ID NO: 29), NC_003197 (SEQ ID NO: 30)), *Clostridium acetobutylicum* (GenBank Nos: NP_149189 (SEQ ID NO: 31), NC_001988 (SEQ ID NO: 32)), *M. caseolyticus* (SEQ ID NO: 33), and *Listeria. grayi* (SEQ ID NO: 34).

The term "branched-chain alcohol dehydrogenase" ("ADH") refers to a polypeptide (or polypeptides) having enzyme activity that catalyzes the conversion of isobutyraldehyde to isobutanol. Example branched-chain alcohol dehydrogenases are known by the EC number 1.1.1.265, but may also be classified under other alcohol dehydrogenases (specifically, EC 1.1.1.1 or 1.1.1.2). Alcohol dehydrogenases may be NADPH dependent or NADH dependent. Such enzymes are available from a number of sources including, but not limited to, *S. cerevisiae* (GenBank Nos: NP_010656 (SEQ ID NO: 35), NC_001136 (SEQ ID NO: 36), NP_014051 (SEQ ID NO: 37), NC_001145 (SEQ ID NO: 38)), *E. coli* (GenBank Nos: NP_417484 (SEQ ID NO:

39), NC_000913 (SEQ ID NO: 40)), *C. acetobutylicum* (GenBank Nos: NP_349892 (SEQ ID NO: 41), NC_003030 (SEQ ID NO: 42); NP_349891 (SEQ ID NO: 43), NC_003030 (SEQ ID NO: 44)). U.S. Patent Application Publication No. 2009/0269823 describes SadB, an alcohol dehydrogenase (ADH) from *Achromobacter xylosoxidans*. Alcohol dehydrogenases also include horse liver ADH and *Beijerinkia indica* ADH (as described by U.S. Patent Application Publication No. 2011/0269199, the entire contents of which are herein incorporated by reference).

The term "butanol dehydrogenase" refers to a polypeptide (or polypeptides) having enzyme activity that catalyzes the conversion of isobutyraldehyde to isobutanol or the conversion of 2-butanone and 2-butanol. Butanol dehydrogenases are a subset of a broad family of alcohol dehydrogenases. Butanol dehydrogenase may be NAD- or NADP-dependent. The NAD-dependent enzymes are known as EC 1.1.1.1 and are available, for example, from *Rhodococcus ruber* (GenBank Nos: CAD36475, AJ491307). The NADP-dependent enzymes are known as EC 1.1.1.2 and are available, for example, from *Pyrococcus furiosus* (GenBank Nos: AAC25556, AF013169). Additionally, a butanol dehydrogenase is available from *Escherichia coli* (GenBank Nos: NP 417484, NC_000913) and a cyclohexanol dehydrogenase is available from *Acinetobacter* sp. (GenBank Nos: AAG10026, AF282240). The term "butanol dehydrogenase" also refers to a polypeptide (or polypeptides) having enzyme activity that catalyzes the conversion of butyraldehyde to 1-butanol, using either NADH or NADPH as cofactor. Butanol dehydrogenases are available from, for example, *C. acetobutylicum* (GenBank Nos: NP_149325, NC_001988; this enzyme possesses both aldehyde and alcohol dehydrogenase activity); NP_349891, NC_003030; and NP_349892, NC_003030) and *E. coli* (GenBank Nos: NP_417-484, NC_000913).

The term "branched-chain keto acid dehydrogenase" refers to a polypeptide (or polypeptides) having enzyme activity that catalyzes the conversion of α-ketoisovalerate to isobutyryl-CoA (isobutyryl-coenzyme A), typically using $NAD^+$ (nicotinamide adenine dinucleotide) as an electron acceptor. Example branched-chain keto acid dehydrogenases are known by the EC number 1.2.4.4. Such branched-chain keto acid dehydrogenases are comprised of four subunits and sequences from all subunits are available from a vast array of microorganisms including, but not limited to, *B. subtilis* (GenBank Nos: CAB14336 (SEQ ID NO: 45), Z99116 (SEQ ID NO: 46); CAB14335 (SEQ ID NO: 47), Z99116 (SEQ ID NO: 48); CAB14334 (SEQ ID NO: 49), Z99116 (SEQ ID NO: 50); and CAB14337 (SEQ ID NO: 51), Z99116 (SEQ ID NO: 52)) and *Pseudomonas putida* (GenBank Nos: AAA65614 (SEQ ID NO: 53), M57613 (SEQ ID NO: 54); AAA65615 (SEQ ID NO: 55), M57613 (SEQ ID NO: 56); AAA65617 (SEQ ID NO: 57), M57613 (SEQ ID NO: 58); and AAA65618 (SEQ ID NO: 59), M57613 (SEQ ID NO: 60)).

The term "acylating aldehyde dehydrogenase" refers to a polypeptide (or polypeptides) having enzyme activity that catalyzes the conversion of isobutyryl-CoA to isobutyraldehyde, typically using either NADH or NADPH as an electron donor. Example acylating aldehyde dehydrogenases are known by the EC numbers 1.2.1.10 and 1.2.1.57. Such enzymes are available from multiple sources including, but not limited to, *Clostridium beijerinckii* (GenBank Nos: AAD31841 (SEQ ID NO: 61), AF157306 (SEQ ID NO: 62)), *C. acetobutylicum* (GenBank Nos: NP_149325 (SEQ ID NO: 63), NC_001988 (SEQ ID NO: 64); NP_149199 (SEQ ID NO: 65), NC_001988 (SEQ ID NO: 66)), *P. putida* (GenBank Nos: AAA89106 (SEQ ID NO: 67), U13232 (SEQ ID NO: 68)), and *Thermus thermophilus* (GenBank Nos: YP_145486 (SEQ ID NO: 69), NC_006461 (SEQ ID NO: 70)).

The term "transaminase" refers to a polypeptide (or polypeptides) having enzyme activity that catalyzes the conversion of α-ketoisovalerate to L-valine, using either alanine or glutamate as an amine donor. Example transaminases are known by the EC numbers 2.6.1.42 and 2.6.1.66. Such enzymes are available from a number of sources. Examples of sources for alanine-dependent enzymes include, but are not limited to, *E. coli* (GenBank Nos: YP_026231 (SEQ ID NO: 71), NC_000913 (SEQ ID NO: 72)) and *Bacillus licheniformis* (GenBank Nos: YP_093743 (SEQ ID NO: 73), NC_006322 (SEQ ID NO: 74)). Examples of sources for glutamate-dependent enzymes include, but are not limited to, *E. coli* (GenBank Nos: YP_026247 (SEQ ID NO: 75), NC_000913 (SEQ ID NO: 76)), *Saccharomyces cerevisiae* (GenBank Nos: NP_012682 (SEQ ID NO: 77), NC_001142 (SEQ ID NO: 78)) and *Methanobacterium thermoautotrophicum* (GenBank Nos: NP_276546 (SEQ ID NO: 79), NC_000916 (SEQ ID NO: 80)).

The term "valine dehydrogenase" refers to a polypeptide (or polypeptides) having enzyme activity that catalyzes the conversion of α-ketoisovalerate to L-valine, typically using NAD(P)H as an electron donor and ammonia as an amine donor. Example valine dehydrogenases are known by the EC numbers 1.4.1.8 and 1.4.1.9 and such enzymes are available from a number of sources including, but not limited to, *Streptomyces coelicolor* (GenBank Nos: NP_628270 (SEQ ID NO: 81), NC_003888 (SEQ ID NO: 82)) and *B. subtilis* (GenBank Nos: CAB14339 (SEQ ID NO: 83), Z99116 (SEQ ID NO: 84)).

The term "valine decarboxylase" refers to a polypeptide (or polypeptides) having enzyme activity that catalyzes the conversion of L-valine to isobutylamine and $CO_2$. Example valine decarboxylases are known by the EC number 4.1.1.14. Such enzymes are found in *Streptomyces* such as, for example, *Streptomyces viridifaciens* (GenBank Nos: AAN10242 (SEQ ID NO: 85), AY116644 (SEQ ID NO: 86)).

The term "omega transaminase" refers to a polypeptide (or polypeptides) having enzyme activity that catalyzes the conversion of isobutylamine to isobutyraldehyde using a suitable amino acid as an amine donor. Example omega transaminases are known by the EC number 2.6.1.18 and are available from a number of sources including, but not limited to, *Alcaligenes denitrificans* (AAP92672 (SEQ ID NO: 87), AY330220 (SEQ ID NO: 88)), *Ralstonia eutropha* (GenBank Nos: YP_294474 (SEQ ID NO: 89), NC_007347 (SEQ ID NO: 90)), *Shewanella oneidensis* (GenBank Nos: NP_719046 (SEQ ID NO: 91), NC_004347 (SEQ ID NO: 92)), and *P. putida* (GenBank Nos: AAN66223 (SEQ ID NO: 93), AE016776 (SEQ ID NO: 94)).

The term "acetyl-CoA acetyltransferase" refers to a polypeptide (or polypeptides) having enzyme activity that catalyzes the conversion of two molecules of acetyl-CoA to acetoacetyl-CoA and coenzyme A (CoA). Example acetyl-CoA acetyltransferases are acetyl-CoA acetyltransferases with substrate preferences (reaction in the forward direction) for a short chain acyl-CoA and acetyl-CoA and are classified as E.C. 2.3.1.9 [Enzyme Nomenclature 1992, Academic Press, San Diego]; although, enzymes with a broader substrate range (E.C. 2.3.1.16) will be functional as well. Acetyl-CoA acetyltransferases are available from a number of sources, for example, *Escherichia coli* (GenBank Nos:

NP_416728, NC_000913; NCBI amino acid sequence, NCBI nucleotide sequence)), *Clostridium acetobutylicum* (GenBank Nos: NP_349476.1, NC_003030; NP_149242, NC_001988, *Bacillus subtilis* (GenBank Nos: NP_390297, NC_000964), and *Saccharomyces cerevisiae* (GenBank Nos: NP_015297, NC_001148).

The term "3-hydroxybutyryl-CoA dehydrogenase" refers to a polypeptide (or polypeptides) having enzyme activity that catalyzes the conversion of acetoacetyl-CoA to 3-hydroxybutyryl-CoA. Example 3-hydroxybutyryl-CoA dehydrogenases may be reduced nicotinamide adenine dinucleotide (NADH)-dependent, with a substrate preference for (S)-3-hydroxybutyryl-CoA or (R)-3-hydroxybutyryl-CoA. Examples may be classified as E.C. 1.1.1.35 and E.C. 1.1.1.30, respectively. Additionally, 3-hydroxybutyryl-CoA dehydrogenases may be reduced nicotinamide adenine dinucleotide phosphate (NADPH)-dependent, with a substrate preference for (S)-3-hydroxybutyryl-CoA or (R)-3-hydroxybutyryl-CoA and are classified as E.C. 1.1.1.157 and E.C. 1.1.1.36, respectively. 3-Hydroxybutyryl-CoA dehydrogenases are available from a number of sources, for example, *C. acetobutylicum* (GenBank Nos: NP_349314, NC_003030), *B. subtilis* (GenBank Nos: AAB09614, U29084), *Ralstonia eutropha* (GenBank Nos: YP_294481, NC_007347), and *Alcaligenes eutrophus* (GenBank Nos: AAA21973, J04987).

The term "crotonase" refers to a polypeptide (or polypeptides) having enzyme activity that catalyzes the conversion of 3-hydroxybutyryl-CoA to crotonyl-CoA and $H_2O$. Example crotonases may have a substrate preference for (S)-3-hydroxybutyryl-CoA or (R)-3-hydroxybutyryl-CoA and may be classified as E.C. 4.2.1.17 and E.C. 4.2.1.55, respectively. Crotonases are available from a number of sources, for example, *E. coli* (GenBank Nos: NP_415911, NC_000913), *C. acetobutylicum* (GenBank Nos: NP_349318, NC_003030), *B. subtilis* (GenBank Nos: CAB13705, Z99113), and *Aeromonas caviae* (GenBank Nos: BAA21816, D88825).

The term "butyryl-CoA dehydrogenase" refers to a polypeptide (or polypeptides) having enzyme activity that catalyzes the conversion of crotonyl-CoA to butyryl-CoA. Example butyryl-CoA dehydrogenases may be NADH-dependent, NADPH-dependent, or flavin-dependent and may be classified as E.C. 1.3.1.44, E.C. 1.3.1.38, and E.C. 1.3.99.2, respectively. Butyryl-CoA dehydrogenases are available from a number of sources, for example, *C. acetobutylicum* (GenBank Nos: NP_347102, NC_003030), *Euglena gracilis* (GenBank Nos: Q5EU90), AY741582), *Streptomyces collinus* (GenBank Nos: AAA92890, U37135), and *Streptomyces coelicolor* (GenBank Nos: CAA22721, AL939127).

The term "butyraldehyde dehydrogenase" refers to a polypeptide (or polypeptides) having enzyme activity that catalyzes the conversion of butyryl-CoA to butyraldehyde, using NADH or NADPH as cofactor. Butyraldehyde dehydrogenases with a preference for NADH are known as E.C. 1.2.1.57 and are available from, for example, *Clostridium beijerinckii* (GenBank Nos: AAD31841, AF157306) and *C. acetobutylicum* (GenBank Nos: NP.sub.—149325, NC.sub.—001988).

The term "isobutyryl-CoA mutase" refers to a polypeptide (or polypeptides) having enzyme activity that catalyzes the conversion of butyryl-CoA to isobutyryl-CoA. This enzyme uses coenzyme $B_{12}$ as cofactor. Example isobutyryl-CoA mutases are known by the EC number 5.4.99.13. These enzymes are found in a number of *Streptomyces* including, but not limited to, *Streptomyces cinnamonensis* (GenBank Nos: AAC08713 (SEQ ID NO: 95), U67612 (SEQ ID NO: 96); CAB59633 (SEQ ID NO: 97), AJ246005 (SEQ ID NO: 98)), *S. coelicolor* (GenBank Nos: CAB70645 (SEQ ID NO: 99), AL939123 (SEQ ID NO: 100); CAB92663 (SEQ ID NO: 101), AL939121 (SEQ ID NO: 102)), and *Streptomyces avermitilis* (GenBank Nos: NP_824008 (SEQ ID NO: 103), NC_003155 (SEQ ID NO: 104); NP_824637 (SEQ ID NO: 105), NC_003155 (SEQ ID NO: 106)).

The term "acetolactate decarboxylase" refers to a polypeptide (or polypeptides) having enzyme activity that catalyzes the conversion of alpha-acetolactate to acetoin. Example acetolactate decarboxylases are known as EC 4.1.1.5 and are available, for example, from *Bacillus subtilis* (GenBank Nos: AAA22223, L04470), *Klebsiella terrigena* (GenBank Nos: AAA25054, L04507), and *Klebsiella pneumoniae* (GenBank Nos: AAU43774, AY722056).

The term "acetoin aminase" or "acetoin transaminase," and in some instances, may be used interchangeably herein, refer to a polypeptide (or polypeptides) having enzyme activity that catalyzes the conversion of acetoin to 3-amino-2-butanol. Acetoin aminase may utilize the cofactor pyridoxal 5'-phosphate or NADH or NADPH. The resulting product may have (R) or (S) stereochemistry at the 3-position. The pyridoxal phosphate-dependent enzyme may use an amino acid such as alanine or glutamate as the amino donor. The NADH- and NADPH-dependent enzymes may use ammonia as a second substrate. A suitable example of an NADH dependent acetoin aminase, also known as amino alcohol dehydrogenase, is described by Ito, et al. (U.S. Pat. No. 6,432,688). An example of a pyridoxal-dependent acetoin aminase is the amine:pyruvate aminotransferase (also called amine:pyruvate transaminase) described by Shin and Kim (J. Org. Chem. 67:2848-2853, 2002).

The term "acetoin kinase" refers to a polypeptide (or polypeptides) having enzyme activity that catalyzes the conversion of acetoin to phosphoacetoin. Acetoin kinase may utilize ATP (adenosine triphosphate) or phosphoenolpyruvate as the phosphate donor in the reaction. Enzymes that catalyze the analogous reaction on the similar substrate dihydroxyacetone, for example, include enzymes known as EC 2.7.1.29 (Garcia-Alles, et al., Biochemistry 43:13037-13046, 2004).

The term "acetoin phosphate aminase" refers to a polypeptide (or polypeptides) having enzyme activity that catalyzes the conversion of phosphoacetoin to 3-amino-2-butanol 0-phosphate. Acetoin phosphate aminase may use the cofactor pyridoxal 5'-phosphate, NADH, or NADPH. The resulting product may have (R) or (S) stereochemistry at the 3-position. The pyridoxal phosphate-dependent enzyme may use an amino acid such as alanine or glutamate. The NADH and NADPH-dependent enzymes may use ammonia as a second substrate. Although there are no reports of enzymes catalyzing this reaction on phosphoacetoin, there is a pyridoxal phosphate-dependent enzyme that is proposed to carry out the analogous reaction on the similar substrate serinol phosphate (Yasuta, et al., Appl. Environ. Microbial. 67:4999-5009, 2001).

The term "aminobutanol phosphate phospholyase," also called "amino alcohol 0-phosphate lyase," and in some instances, may be used interchangeably herein, refers to a polypeptide (or polypeptides) having enzyme activity that catalyzes the conversion of 3-amino-2-butanol 0-phosphate to 2-butanone. Amino butanol phosphate phospho-lyase may utilize the cofactor pyridoxal 5'-phosphate. There are reports of enzymes that catalyze the analogous reaction on the similar substrate 1-amino-2-propanol phosphate (Jones, et al., Biochem. J. 134:167-182, 1973). U.S. Patent Application Publication No. 2007/0259410 describes an aminobutanol phosphate phospho-lyase from the organism *Erwinia carotovora*.

The term "aminobutanol kinase" refers to a polypeptide (or polypeptides) having enzyme activity that catalyzes the conversion of 3-amino-2-butanol to 3-amino-2-butanol 0-phosphate. Amino butanol kinase may utilize ATP as the phosphate donor. Although there are no reports of enzymes catalyzing this reaction on 3-amino-2-butanol, there are reports of enzymes that catalyze the analogous reaction on the similar substrates ethanolamine and 1-amino-2-propanol (Jones, et al., supra). U.S. Patent Application Publication No. 2009/0155870 describes, in Example 14, an amino alcohol kinase of *Erwinia carotovora* subsp. *Atroseptica*.

The term "butanediol dehydrogenase," also known as "acetoin reductase," and in some instances, may be used interchangeably herein, refers to a polypeptide (or polypeptides) having enzyme activity that catalyzes the conversion of acetoin to 2,3-butanediol. Butanedial dehydrogenases are a subset of the broad family of alcohol dehydrogenases. Butanediol dehydrogenase enzymes may have specificity for production of (R)- or (S)-stereochemistry in the alcohol product. (S)-specific butanediol dehydrogenases are known as EC 1.1.1.76 and are available, for example, from *Klebsiella pneumoniae* (GenBank Nos: BBA13085, D86412). (R)-specific butanediol dehydrogenases are known as EC 1.1.1.4 and are available, for example, from *Bacillus cereus* (GenBank Nos. NP 830481, NC_004722; AAP07682, AE017000), and *Lactococcus lactis* (GenBank Nos. AAK04995, AE006323).

The term "butanediol dehydratase," also known as "dial dehydratase" or "propanediol dehydratase," and in some instances, may be used interchangeably herein, refers to a polypeptide (or polypeptides) having an enzyme activity that catalyzes the conversion of 2,3-butanediol to 2-butanone. Butanediol dehydratase may utilize the cofactor adenosyl cobalamin (also known as coenzyme Bw or vitamin B12; although vitamin B12 may refer also to other forms of cobalamin that are not coenzyme B12). Adenosyl cobalamin-dependent enzymes are known as EC 4.2.1.28 and are available, for example, from *Klebsiella oxytoca* [(GenBank Nos: AA08099 (alpha subunit), D45071; BAA08100 (beta subunit), D45071; and BBA08101 (gamma subunit), D45071 (Note all three subunits are required for activity)], and *Klebsiella pneumonia* (GenBank Nos: AAC98384 (alpha subunit), AF102064; GenBank Nos: AAC98385 (beta subunit), AF102064, GenBank Nos: AAC98386 (gamma subunit), AF102064). Other suitable dial dehydratases include, but are not limited to, B12-dependent dial dehydratases available from *Salmonella typhimurium* (GenBank Nos: AAB84102 (large subunit), AF026270; GenBank Nos: AAB84103 (medium subunit), AF026270; GenBank Nos: AAB84104 (small subunit), AF026270); and *Lactobacillus collinoides* (GenBank Nos: CAC82541 (large subunit), AJ297723; GenBank Nos: CAC82542 (medium subunit); AJ297723; GenBank Nos: CAD01091 (small subunit), AJ297723); and enzymes from *Lactobacillus brevis* (particularly strains CNRZ 734 and CNRZ 735, Speranza, et al., J. Agric. Food Chem. 45:3476-3480, 1997), and nucleotide sequences that encode the corresponding enzymes. Methods of dial dehydratase gene isolation are well known in the art (e.g., U.S. Pat. No. 5,686,276).

The term "pyruvate decarboxylase" refers to a polypeptide (or polypeptides) having an enzyme activity that catalyzes the decarboxylation of pyruvic acid to acetaldehyde and carbon dioxide. Pyruvate dehydrogenases are known by the EC number 4.1.1.1. These enzymes are found in a number of yeast including *Saccharomyces cerevisiae* (GenBank Nos: CAA97575 (SEQ ID NO: 107), CAA97705 (SEQ ID NO: 109), CAA97091 (SEQ ID NO: 111)).

It will be appreciated that host cells comprising a butanol biosynthetic pathway as provided herein may further comprise one or more additional modifications. U.S. Patent Application Publication No. 2009/0305363, the entire contents of which are herein incorporated by reference, discloses increased conversion of pyruvate to acetolactate by engineering yeast for expression of a cytosol-localized acetolactate synthase and substantial elimination of pyruvate decarboxylase activity. In some embodiments, the host cells comprise modifications to reduce glycerol-3-phosphate dehydrogenase activity and/or disruption in at least one gene encoding a polypeptide having pyruvate decarboxylase activity or a disruption in at least one gene encoding a regulatory element controlling pyruvate decarboxylase gene expression as described in U.S. Patent Application Publication No. 2009/0305363, modifications to a host cell that provide for increased carbon flux through an Entner-Doudoroff Pathway or reducing equivalents balance as described in U.S. Patent Application Publication No. 2010/0120105, the entire contents of which are herein incorporated by reference. Other modifications include integration of at least one polynucleotide encoding a polypeptide that catalyzes a step in a pyruvate-utilizing biosynthetic pathway. Other modifications include at least one deletion, mutation, insertion, and/or substitution in an endogenous polynucleotide encoding a polypeptide having acetolactate reductase activity. As used herein, "acetolactate reductase activity" refers to the activity of any polypeptide having the ability to catalyze the conversion of acetolactate to 2,3-dihydroxy-2-methyl butyrate (DHMB). Such polypeptides can be determined by methods well known in the art and disclosed herein. DHMB includes "fast DHMB," which has the 2S, 3S configuration, and "slow DHMB," which has the 2S, 3R configurate (Kaneko, et al., Phytochemistry 39:115-120, 1995, which is herein incorporated by reference in its entirety and refers to fast DHMB as anglyceric acid and slow DHMB as tiglyceric acid). In some embodiments, the polypeptide having acetolactate reductase activity is YMR226C (SEQ ID NOs: 127, 128) of *Saccharomyces cerevisiae* or a homolog thereof.

Additional modifications include a deletion, mutation, insertion, and/or substitution in an endogenous polynucleotide encoding a polypeptide having aldehyde dehydrogenase and/or aldehyde oxidase activity. As used herein, "aldehyde dehydrogenase activity" refers to any polypeptide having a biological function of an aldehyde dehydrogenase. Such polypeptides include a polypeptide that catalyzes the oxidation (dehydrogenation) of aldehydes. Such polypeptides include a polypeptide that catalyzes the conversion of isobutyraldehyde to isobutyric acid. Such polypeptides also include a polypeptide that corresponds to EC 1.2.1.3, EC 1.2.1.4 or EC 1.2.1.5. Such polypeptides can be determined by methods well known in the art and disclosed herein. As used herein, "aldehyde oxidase activity" refers to any polypeptide having a biological function of an aldehyde oxidase. Such polypeptides include a polypeptide that catalyzes carboxylic acids from aldehydes. Such polypeptides include a polypeptide that catalyzes the conversion of isobutyraldehyde to isobutyric acid. Such polypeptides also include a polypeptide that corresponds to EC 1.2.3.1. Such polypeptides can be determined by methods well known in the art and disclosed herein. In some embodiments, the polypeptide having aldehyde dehydrogenase activity is ALD6 from *Saccharomyces cerevisiae* or a homolog thereof.

A genetic modification which has the effect of reducing glucose repression wherein the yeast production host cell is pdc- is described in U.S. Patent Application Publication No. 2011/0124060, the entire contents of which are herein incorporated by reference. In some embodiments, the pyruvate decarboxylase that is deleted or down-regulated is PDC1, PDC5, PDC6, or combinations thereof. In some embodiments, the pyruvate decarboxylase is selected from those enzymes in Table 7. In some embodiments, host cells may contain a deletion or down-regulation of a polynucleotide encoding a polypeptide that catalyzes the conversion of glyceraldehyde-3-phosphate to glycerate 1,3, bisphosphate. In some embodiments, the enzyme that catalyzes this reaction is glyceraldehyde-3-phosphate dehydrogenase.

TABLE 1

SEQ ID Numbers of PDC Target Gene coding regions and Proteins

| Description | SEQ ID NO: Amino Acid | SEQ ID NO: Nucleic Acid |
|---|---|---|
| PDC1 pyruvate decarboxylase from Saccharomyces cerevisiae | 107 | 108 |
| PDC5 pyruvate decarboxylase from Saccharomyces cerevisiae | 109 | 110 |
| PDC6 pyruvate decarboxylase Saccharomyces cerevisiae | 111 | 112 |
| pyruvate decarboxylase from Candida glabrata | 113 | 114 |
| PDC1 pyruvate decarboxylase from Pichia stipitis | 115 | 116 |
| PDC2 pyruvate decarboxylase from Pichia stipitis | 117 | 118 |
| pyruvate decarboxylase from Kluyveromyces lactis | 119 | 120 |
| pyruvate decarboxylase from Yarrowia lipolytica | 121 | 122 |
| pyruvate decarboxylase from Schizosaccharomyces pombe | 123 | 124 |
| pyruvate decarboxylase from Zygosaccharomyces rouxii | 125 | 126 |

Yeasts may have one or more genes encoding pyruvate decarboxylase. For example, there is one gene encoding pyruvate decarboxylase in Candida glabrata and Schizosaccharomyces pombe, while there are three isozymes of pyruvate decarboxylase encoded by the PDC1, PCD5, and PDC6 genes in Saccharomyces. In some embodiments, at least one PDC gene may be inactivated. If the yeast cell used has more than one expressed (active) PDC gene, then each of the active PDC genes may be modified or inactivated thereby producing a pdc-cell. For example, in Saccharomyces cerevisiae, the PDC1, PDC5, and PDC6 genes may be modified or inactivated. If a PDC gene is not active under the fermentation conditions to be used, then such a gene would not need to be modified or inactivated.

Other target genes, such as those encoding pyruvate decarboxylase proteins having at least about 70% to at least about 75%, at least about 75% to at least about 80%, at least about 80% to at least about 85%, at least about 85% to at least about 90%, at least about 90% to at least about 95%, at least about 96%, at least about 97%, at least about 98%, or at least about 99% sequence identity to the pyruvate decarboxylases of SEQ ID NOs: 107, 109, 111, 113, 115, 117, 119, 121, 123, or 125 may be identified in the literature and in bioinformatics databases well known to the skilled person. In some embodiments, target genes, such as those encoding pyruvate decarboxylase proteins having at least about 70%, at least about 75%, at least about 80%, at least about 85%, at least about 90%, at least about 95%, at least about 96%, at least about 97%, at least about 98%, or at least about 99% sequence identity to the pyruvate decarboxylases of SEQ ID NOs: 108, 110, 112, 114, 116, 118, 120, 122, 124, or 126 may be identified in the literature and in bioinformatics databases well known to the skilled person.

Recombinant host cells may further comprise (a) at least one heterologous polynucleotide encoding a polypeptide having dihydroxy-acid dehydratase activity; and (b)(i) at least one deletion, mutation, insertion, and/or substitution in an endogenous gene encoding a polypeptide affecting Fe—S cluster biosynthesis; and/or (ii) at least one heterologous polynucleotide encoding a polypeptide affecting Fe—S cluster biosynthesis. In some embodiments, the polypeptide affecting Fe—S cluster biosynthesis may be encoded by AFT1, AFT2, FRA2, GRX3 or CCC1. AFT1 and AFT2 are described in PCT Application Publication No. WO 2001/103300, the entire contents of which are herein incorporated by reference. In some embodiments, the polypeptide affecting Fe—S cluster biosynthesis may be constitutive mutant AFT1 L99A, AFT1 L102A, AFT1 C291F, or AFT1 C293F. In some embodiments, the recombinant host cell may further comprise a deletion, mutation, insertion, and/or substitution in glycerol dehydrogenase (GPD2) or phosphodiesterase (PDE1). In some embodiments, the recombinant host cell may further comprise reduced or eliminated Gpd2 activity. In some embodiments, the recombinant host cell may further comprise reduced or eliminated Pde1 activity.

Additionally, recombinant host cells may comprise heterologous polynucleotides encoding a polypeptide with phosphoketolase activity and/or a heterologous polynucleotide encoding a polypeptide with phosphotransacetylase activity as described in U.S. Patent Application Publication No. 2012/0156735, incorporated herein by reference.

Carbon Substrates

Suitable carbon substrates may include, but are not limited to, monosaccharides such as fructose or glucose; oligosaccharides such as lactose, maltose, galactose, or sucrose; polysaccharides such as starch or cellulose; and mixtures thereof, and unpurified mixtures from renewable feedstocks such as cheese whey permeate, cornsteep liquor, sugar beet molasses, and barley malt. Other carbon substrates may include ethanol, lactate, succinate, or glycerol.

"Sugar" includes monosaccharides such as fructose or glucose; oligosaccharides such as lactose, maltose, galactose, or sucrose; polysaccharides such as starch or cellulose; C5 sugars such as xylose and arabinose; and mixtures thereof.

Additionally, the carbon substrate may also be one-carbon substrates such as carbon dioxide or methanol for which metabolic conversion into key biochemical intermediates has been demonstrated. In addition to one and two carbon substrates, methylotrophic organisms are also known to utilize a number of other carbon containing compounds such as methylamine, glucosamine, and a variety of amino acids for metabolic activity. For example, methylotrophic yeasts are known to utilize the carbon from methylamine to form trehalose or glycerol (Bellion, et al., *Microb. Growth C1 Compd.*, [Int. Symp.], 7th (1993), 415-32, Editor(s): Murrell, J. Collin; Kelly, Don P. Publisher: Intercept, Andover, UK). Similarly, various species of Candida will metabolize alanine or oleic acid (Sulter, et al., Arch. Microbiol. 153: 485-489, 1990). Hence, it is contemplated that the source of carbon utilized in the present invention may encompass a wide variety of carbon containing substrates and will only be limited by the choice of organism.

Although it is contemplated that the carbon substrates described herein and mixtures thereof are suitable in the present invention, in some embodiments, the carbon substrates may be glucose, fructose, and sucrose, or mixtures of these with C5 sugars such as xylose and arabinose for yeasts cells modified to use C5 sugars. Sucrose may be derived from renewable sugar sources such as sugar cane, sugar beets, cassava, sweet sorghum, and mixtures thereof. Glucose and dextrose may be derived from renewable grain sources through saccharification of starch based feedstocks including grains such as corn, wheat, rye, barley, oats, and mixtures thereof. In addition, fermentable sugars may be derived from renewable cellulosic or lignocellulosic biomass through processes of pretreatment and saccharification, as described, for example, in U.S. Patent Application Publication No. 2007/0031918, the entire contents of which are herein incorporated by reference. Biomass includes materials comprising cellulose, and optionally further comprising hemicellulose, lignin, starch, oligosaccharides, and/or monosaccharides. Biomass may also comprise additional components such as protein and/or lipid. Biomass may be derived from a single source or biomass may comprise a mixture derived from more than one source; for example, biomass may comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers, animal manure, and mixtures thereof.

In some embodiments, the carbon substrate may be glucose derived from corn. In some embodiments, the carbon substrate may be glucose derived from wheat. In some embodiments, the carbon substrate may be sucrose derived from sugar cane.

In addition to an appropriate carbon source, fermentation media may contain suitable minerals, salts, cofactors, buffers, and other components, known to those skilled in the art, suitable for the growth of the cultures and promotion of an enzymatic pathway described herein.

Fermentation Conditions

Typically, cells are grown at a temperature in the range of at least about 20° C. to at least about 40° C. in an appropriate medium. In some embodiments, cells may be grown at least about 20° C., at least about 22° C., at least about 25° C., at least about 27° C., at least about 30° C., at least about 32° C., at least about 35° C., at least about 37° C., or at least about 40° C. In some embodiments, the cells may be grown in the range of at least about 25° C. to at least about 40° C. Suitable growth media in the present invention include common commercially prepared media such as Sabouraud Dextrose (SD) broth, Yeast Medium (YM) broth, or broth that includes yeast nitrogen base, ammonium sulfate, and dextrose (as the carbon/energy source) or YPD Medium, a blend of peptone, yeast extract, and dextrose in optimal proportions for growing most Saccharomyces cerevisiae strains. Other defined or synthetic growth media may also be used, and the appropriate medium for growth of the particular microorganism will be known by one skilled in the art of microbiology or fermentation science. The use of agents known to modulate catabolite repression directly or indirectly, for example, cyclic adenosine 2':3'-monophosphate, may also be incorporated into the fermentation medium.

Suitable pH ranges for the fermentation may be from at least about pH 5.0 to at least about pH 9.0. In some embodiments, at least about pH 6.0 to at least about pH 8.0 may be used for the initial condition. Suitable pH ranges for the fermentation of yeast are typically from at least about pH 3.0 to at least about pH 9.0. In some embodiments, at least about pH 5.0 to at least about pH 8.0 may be used for the initial condition. Suitable pH ranges for the fermentation of other microorganisms are from at least about pH 3.0 to at least about pH 7.5. In some embodiments, at least about pH 4.5 to at least about pH 6.5 may be used for the initial condition.

Fermentations may be performed under aerobic or anaerobic conditions. In some embodiments, anaerobic or microaerobic conditions are used for fermentations. In some embodiments, the culture conditions are such that the fermentation occurs without respiration.

Industrial Batch and Continuous Fermentations

Butanol, or other products, may be produced using a batch method of fermentation. A classical batch fermentation is a closed system where the composition of the medium is set at the beginning of the fermentation and not subject to artificial alterations during the fermentation. A variation on the standard batch system is the fed-batch system. Fed-batch fermentation processes are also suitable in the present invention and comprise a typical batch system with the exception that the substrate is added in increments as the fermentation progresses. Fed-batch systems are useful when catabolite repression is apt to inhibit the metabolism of the cells and where it is desirable to have limited amounts of substrate in the media. Batch and fed-batch fermentations are common and well known in the art and examples may be found in Thomas D. Brock in *Biotechnology: A Textbook of Industrial Microbiology*, Second Edition (1989) Sinauer Associates, Inc., Sunderland, Mass., or Deshpande, Appl. Biochem. Biotechnol. 36:227, 1992.

Butanol, or other products, may also be produced using continuous fermentation methods. Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth. Continuous fermentation allows for the modulation of one factor or any number of factors that affect cell growth or end product concentration. Methods of modulating nutrients and growth factors for continuous fermentation processes as well as techniques for maximizing the rate of product formation are well known in the art of industrial microbiology and a variety of methods are detailed by Brock, supra.

It is contemplated that the production of butanol, or other products, may be practiced using batch, fed-batch, or continuous processes and that any known mode of fermentation would be suitable. Additionally, it is contemplated that cells may be immobilized on a substrate as whole cell catalysts and subjected to fermentation conditions for isobutanol production.

Methods for Isobutanol Isolation from the Fermentation Medium

Bioproduced isobutanol may be isolated from the fermentation medium using methods known in the art, for example, ABE fermentations (see, e.g., Dune, Appl. Microbiol. Biotechnol. 49:639-648, 1998, Groot, et al., Process. Biochem. 27:61-75, 1992, and references therein). For example, solids may be removed from the fermentation medium by centrifugation, filtration, decantation, or the like (see, e.g., U.S.

Patent Application Publication No. 2012/0164302, the entire contents of which are herein incorporated by reference). Isobutanol may be isolated from the fermentation medium using methods such as distillation, azeotropic distillation, liquid-liquid extraction, adsorption, gas stripping, membrane evaporation, or pervaporation.

Because isobutanol forms a low boiling point, azeotropic mixture with water, distillation may be used to separate the mixture up to its azeotropic composition. Distillation may be used in combination with another separation method to obtain separation of the azeotrope. Methods that may be used in combination with distillation to isolate and purify isobutanol include, but are not limited to, decantation, liquid-liquid extraction, adsorption, and membrane-based techniques. Additionally, isobutanol may be isolated using azeotropic distillation using an entrainer (see, e.g., Doherty and Malone, *Conceptual Design of Distillation Systems*, McGraw Hill, New York, 2001).

The isobutanol-water mixture forms a heterogeneous azeotrope so that distillation may be used in combination with decantation to isolate and purify isobutanol. In this method, isobutanol-containing fermentation broth is distilled to near the azeotropic composition. Then, the azeotropic mixture is condensed, and isobutanol is separated from the fermentation medium by decantation. The decanted aqueous phase may be returned to the first distillation column as reflux. The isobutanol-rich decanted organic phase may be further purified by distillation in a second distillation column. Examples of distillation methods are described in U.S. Patent Application Publication No. 2011/0162953, U.S. Patent Application Publication No. 2011/0162954; U.S. Patent Application Publication No. 2011/0288345; and U.S. Patent Application Publication No. 2011/0288344; the entire contents of which are herein incorporated by reference.

Isobutanol may also be isolated from the fermentation medium using liquid-liquid extraction in combination with distillation. In this method, isobutanol is extracted from the fermentation broth using liquid-liquid extraction with a suitable solvent. The isobutanol-containing organic phase is then distilled to separate isobutanol from the solvent.

Distillation in combination with adsorption may also be used to isolate isobutanol from the fermentation medium. In this method, the fermentation broth containing isobutanol is distilled to near the azeotropic composition and then the remaining water is removed by use of an adsorbent, such as molecular sieves (Aden, et al., *Lignocellulosic Biomass to Ethanol Process Design and Economics Utilizing Co-Current Dilute Acid Prehydrolysis and Enzymatic Hydrolysis for Corn Stover*, Report NREL/TP-510-32438, National Renewable Energy Laboratory, June 2002).

Additionally, distillation in combination with pervaporation may be used to isolate and purify isobutanol from the fermentation medium. In this method, the fermentation broth containing isobutanol is distilled to near the azeotropic composition, and then the remaining water is removed by pervaporation through a hydrophilic membrane (Guo, et al., J. Membr. Sci. 245:199-210, 2004).

In situ product removal (ISPR) (also referred to as extractive fermentation) may be used to remove isobutanol (or other fermentative alcohol) from the fermentation vessel as it is produced, thereby allowing the microorganism to produce isobutanol at high yields. One method for ISPR for removing fermentative alcohol that has been described in the art is liquid-liquid extraction. In general, with regard to isobutanol fermentation, for example, the fermentation medium, which includes the microorganism, is contacted with an organic extractant at a time before the isobutanol concentration reaches a toxic level. The organic extractant and the fermentation medium form a biphasic mixture. Isobutanol partitions into the organic extractant phase, decreasing the concentration in the aqueous phase containing the microorganism, thereby limiting the exposure of the microorganism to the inhibitory isobutanol.

Liquid-liquid extraction may be performed, for example, according to the processes described in U.S. Patent Application Publication No. 2009/0305370, the disclosure of which is hereby incorporated in its entirety. U.S. Patent Application Publication No. 2009/0305370 describes methods for producing and recovering isobutanol from a fermentation broth using liquid-liquid extraction, the methods comprising the step of contacting the fermentation broth with a water immiscible extractant to form a two-phase mixture comprising an aqueous phase and an organic phase. Typically, the extractant may be an organic extractant selected from the group consisting of saturated, mono-unsaturated, poly-unsaturated (and mixtures thereof) $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, and mixtures thereof. The extractant(s) for ISPR may be non-alcohol extractants. The ISPR extractant may be an exogenous organic extractant such as oleyl alcohol, behenyl alcohol, cetyl alcohol, lauryl alcohol, myristyl alcohol, stearyl alcohol, alkyl alkanols, 1-undecanol, oleic acid, lauric acid, linoleic acid, linolenic acid, myristic acid, stearic acid, octanoic acid, decanoic acid, undecanoic acid, methyl myristate, methyl oleate, 1-nonanol, 1-decanol, 2-undecanol, 1-nonanal, 1-undecanol, undecanal, lauric aldehyde, 2-methylundecanal, oleamide, linoleamide, palmitamide, stearylamide, 2-ethyl-1-hexanol, 2-hexyl-1-decanol, 2-octyl-1-dodecanol, trioctyl phosphine oxide, and mixtures thereof.

In some embodiments, an ester may be formed by contacting the alcohol in a fermentation medium with an organic acid (e.g., fatty acids) and a catalyst capable of esterifying the alcohol with the organic acid. In some embodiments, the organic acid may serve as an ISPR extractant into which the alcohol esters partition. The organic acid may be supplied to the fermentation vessel and/or derived from the biomass supplying fermentable carbon fed to the fermentation vessel. Lipids present in the feedstock may be catalytically hydrolyzed to organic acid, and the same catalyst (e.g., enzymes) can esterify the organic acid with the alcohol. The catalyst may be supplied to the feedstock prior to fermentation, or may be supplied to the fermentation vessel before or contemporaneously with the supplying of the feedstock. When the catalyst is supplied to the fermentation vessel, alcohol esters may be obtained by hydrolysis of the lipids into organic acid and substantially simultaneous esterification of the organic acid with isobutanol present in the fermentation vessel. Organic acid and/or native oil not derived from the feedstock may also be fed to the fermentation vessel, with the native oil being hydrolyzed into organic acid. Any organic acid not esterified with the alcohol may serve as part of the ISPR extractant. The extractant containing alcohol esters may be separated from the fermentation medium, and the alcohol can be recovered from the extractant. The extractant may be recycled to the fermentation vessel. Thus, in the case of isobutanol production, for example, the conversion of isobutanol to an ester reduces the free isobutanol concentration in the fermentation medium, shielding the microorganism from the toxic effect of increasing isobutanol concentration. In addition, unfractionated grain may be used as feedstock without separation of lipids therein, since the lipids can be catalytically hydrolyzed to organic acid, thereby decreasing the rate of build-up of lipids in the ISPR extractant. Other isobutanol product recovery and/or ISPR methods may be employed, including those described in U.S. Patent Application Publication No. 2009/0305370; U.S. Patent Application Publication No. 2011/0097773; U.S. Patent Application Publication No. 2012/0156738; the entire contents of which are herein incorporated by reference.

In situ product removal may be carried out in a batch mode or a continuous mode. In a continuous mode of in situ product removal, product is continually removed from the reactor. In a batchwise mode of in situ product removal, a volume of organic extractant is added to the fermentation vessel and the extractant is not removed during the process. For in situ product removal, the organic extractant may contact the fermentation medium at the start of the fermentation forming a biphasic fermentation medium. Alternatively, the organic extractant may contact the fermentation medium after the microorganism has achieved a desired amount of growth, which may be determined by measuring the optical density of the culture. Further, the organic extractant may contact the fermentation medium at a time at which the product level in the fermentation medium reaches a preselected level. In the case of isobutanol production according to some embodiments of the present invention, the organic acid extractant may contact the fermentation medium at a time before the isobutanol concentration reaches a toxic level, so as to esterify isobutanol with the organic acid to produce isobutanol esters and consequently reduce the concentration of isobutanol in the fermentation vessel. The ester-containing organic phase may then be removed from the fermentation vessel (and separated from the fermentation broth which constitutes the aqueous phase) after a desired effective titer of the isobutanol esters is achieved. In some embodiments, the ester-containing organic phase is separated from the aqueous phase after fermentation of the available fermentable sugar in the fermentation vessel is substantially complete.

Isobutanol titer in any phase may be determined by methods known in the art, such as via high performance liquid chromatography (HPLC) or gas chromatography, as described, for example in U.S. Patent Application Publication No. 2009/0305370, which is incorporated herein by reference.

EXAMPLES

The present invention is further defined in the following Examples. It should be understood that these Examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

Standard recombinant DNA, molecular cloning techniques, and transformation protocols used in the Examples are well known in the art and are described by Sambrook, et al. (Molecular Cloning: A Laboratory Manual; Cold Spring Harbor Laboratory Press, Cold Spring Harbor, 1989), Ausubel, et al. (Current Protocols in Molecular Biology, Greene Publishing Assoc. and Wiley-Interscience, 1987), and Amberg, et al. (Methods in Yeast Genetics: A Cold Spring Harbor Laboratory Course Manual, Cold Spring Harbor Press, 2005). Materials and methods suitable for the maintenance and growth of bacterial cultures are well known in the art. Techniques suitable for use in the following examples may be found as set out in Manual of Methods for General Bacteriology (Phillipp, et al., eds., American Society for Microbiology, Washington, D.C., 1994) or Thomas D. Brock (Biotechnology: A Textbook of Industrial Microbiology, Second Edition, Sinauer Associates, Inc., Sunderland, Mass. 1989). All reagents, restriction enzymes, and materials used for the growth and maintenance of bacterial cells were obtained from Sigma-Aldrich Chemicals (St. Louis, Mo.), BD Diagnostic Systems (Sparks, Md.), Invitrogen (Carlsbad, Calif.), HiMedia (Mumbai, India), SD Fine Chemicals (India), or Takara Bio Inc. (Shiga, Japan), unless otherwise specified.

The meaning of abbreviations is as follows: "sec" means second(s), "min" means minute(s), "h" means hour(s), "nm" means nanometers, "uL" means microliter(s), "mL" means milliliter(s), "mg/mL" means milligram per milliliter, "L" means liter(s), "nm" means nanometers, "mM" means millimolar, "M" means molar, "mmol" means millimole(s), "µmole" means micromole(s), "kg" means kilogram, "g" means gram(s), "µg" means microgram(s) and "ng" means nanogram(s), "PCR" means polymerase chain reaction, "OD" means optical density, "OD600" means the optical density measured at a wavelength of 600 nm, "kDa" means kilodaltons, "g" can also mean the gravitation constant, "bp" means base pair(s), "kbp" means kilobase pair(s), "kb" means kilobase, "%" means percent, "% w/v" means weight/volume percent, "% v/v" means volume/volume percent, "HPLC" means high performance liquid chromatography, "g/L" means gram per liter, "µg/L" means microgram per liter, "ng/µL" means nanogram per microliter, "pmol/µL" means picomol per microliter, "RPM" means rotation per minute, "µmol/min/mg" means micromole per minute per milligram, "w/v" means weight per volume, "v/v" means volume per volume.

Example 1

Construction of Isobutanologen Strains

Construction of Strain PNY1621

Strain PNY1621 was constructed from strain PNY2145. Strain PNY2145 has the genotype: MATa ura3Δ::loxP his3Δ pdc5Δ::P[FBA(L8)]-XPK|xpk1_Lp-CYCt-loxP66/71 fra2Δ 2-micron plasmid (CEN.PK2) pdc1Δ::P[PDC1]-ALS|alsS_Bs-CYC1t-loxP71/66 pdc6Δ::(UAS)PGK1-P[FBA1]-KIVD|Lg(y)-TDH3t-loxP71/66 adh1Δ::P[ADH1]-ADH|Bi(y)-ADHt-loxP71/66 fra2Δ::P[ILV5]-ADH|Bi(y)-ADHt-loxP71/66 gpd2Δ::loxP71/66 amn1Δ::AMN1(y). The chimeric gene on chromosome XII in PNY2145 consisting of the PDC1 promoter, alsS coding region, CYC1 terminator, and loxP71/66 site was deleted from 750 bp upstream of the alsS coding region to the first base of native PDC1 3' UTR region. The region was deleted using CRE-lox mediated marker removal. The region was replaced with a chimeric gene comprised of the FBA1::HXT1_331 promoter and the alsS coding region from *Bacillus subtilis*. The native PDC1 terminator was used to complete the chimeric gene. A loxP71/66 site flanked by two priming sites remained upstream of the promoter after CRE-mediated marker removal. For expression of an isobutanol biosynthetic pathway, plasmids were introduced into PNY1620 for expression of KARI and DHAD (pLH804::L2V4, plasmid SEQ ID NO: 129), and KivD and ADH (pRS413::BiADH-kivD_Lg(y), plasmid SEQ ID NO: 130).

Construction of Strain PNY2289

Strain PNY2289 was constructed from PNY2056 having the genotype: MATa ura3Δ::loxP-kanMX4-loxP his3Δ pdc1Δ::loxP71/66 pdc5Δ::loxP71/66 fra2Δ 2-micron gpd2Δ, and was further modified by integrating a phosphoketolase and phosphotransacetylase expression cassette at the pdc5Δ::loxP locus. In addition, a glucose-regulated hybrid promoter was constructed by cloning a glucose repressor sequence from the *Saccharomyces cerevisiae* HXT1 promoter into the *Saccharomyces cerevisiae* FBA1 promoter generating a cassette, URA3::P[FBA1::HXT1-331]-alsS, for integration into the Δpdc1::loxP71/66 locus. For expression of an isobutanol biosynthetic pathway, plasmids were introduced for expression of KARI (pHR81::ILV5p-K9JB4P, SEQ ID NO: 131) and DHAD/KivD/ADH (pLA84, SEQ ID NO: 132).

Example 2

Fed-batch Fermentation Using Strains PNY2289 and PNY1621

Cells of the engineered yeast strains PNY2289 or PNY1621 were inoculated in 20 mL synthetic complete medium (1× Yeast Nitrogen Base without Amino Acids (Becton, Dickinson and Company, San Jose, Calif.), 1× amino acid drop-out without histidine and uracil (Clontech; Mountain View, Calif.) containing 2 g/L glucose (Sigma-Aldrich Chemicals, St. Louis, Mo.) and 2 g/L ethanol) in 125 mL flask. Cells were grown at 30° C. for 24 hr with agitation at 200 rpm. This culture was used to inoculate 90 mL fresh synthetic complete medium (with 2 g/L ethanol and 2 g/L glucose) in 250 mL flask and grown for 24 hr at 30° C. and 200 rpm. After 24 hr, cells were harvested by centrifugation at 4000 rpm for 5 min and re-suspended at an initial $OD_{600}$ of 20 in synthetic complete medium containing 2 g/L ethanol and 20% v/v glycerol (Sigma-Aldrich Chemicals, St. Louis, Mo.). The cells were distributed in aliquots of 1 mL in screw cap tubes and frozen using slow freezers and stored at −80° C. (glycerol stocks) until use.

Seed culture was prepared in three stages: pre-seed, seed 1, and seed 2. The pre-seed culture was started by inoculating vials of glycerol stock in 100 mL filter sterilized pre-seed medium in 500 mL flask and grown at 30° C. and 250 rpm for 24 hr.

| Pre-Seed Medium | | |
| --- | --- | --- |
| Components | UOM | Amount |
| Amino acid dropout without histidine, uracil and leucine | g/L | 0.65 |
| Leucine | mg/L | 60.0 |
| Yeast nitrogen base without amino acids | g/L | 6.5 |
| Glucose | g/L | 20.0 |
| Ethanol | g/L | 5.0 |
| 4-Morpholineethane-sulphonic acid | g/L | 19.5 |
| Ampicillin | mg/L | 50.0 | pH adjusted to 5.5 using 1M $H_2SO_4$

The Seed 1 stage was initiated by adding pre-seed culture in filter sterilized seed flask medium to a 1 L flask and incubated at 30° C. and 250 rpm for 24 hr. In the Seed 2 stage, Seed 1 culture was inoculated in 500 mL fresh seed flask medium in 2.8 L Fernbach flasks and incubated at 30° C. and 250 rpm for 24 hr.

| Seed Flask Medium | | |
| --- | --- | --- |
| Components | UOM | Amount |
| Yeast nitrogen base without amino acids | g/L | 6.7 |
| Amino acid dropout without histidine, uracil and leucine | g/L | 2.8 |
| Leucine | mg/L | 200 |
| Tryptophan | mg/L | 40.0 |
| Yeast extract | g/L | 2.0 |
| Peptone | g/L | 4.0 |
| 4-Morpholineethane-sulphonic acid | g/L | 19.5 |
| Glucose | g/L | 20.0 |
| Ethanol | g/L | 5.0 |
| Ampicillin | mg/L | 50.0 | pH adjusted to 5.5 using 1M $H_2SO_4$

The fed-batch fermentation was initiated by inoculating a 14 L vessel fermentor containing seed tank medium with 950 mL inoculum from Fernbach flasks.

Components added initially and included in the steam-in-place sterilization of the tank:

| Seed Tank Medium | | |
| --- | --- | --- |
| Components | UOM | Amount |
| Potassium phosphate, monobasic ($KH_2PO_4$) | g/kg | 8.00 |
| Ammonium phosphate, monobasic ($NH_4H_2PO_4$) | g/kg | 4.00 |
| Ammonium sulfate [$(NH_4)_2SO_4$] | g/kg | 1.00 |
| Magnesium sulfate, heptahydrate ($MgSO_4 \cdot 7H_2O$) | g/kg | 2.50 |
| Ferrous sulfate, heptahydrate ($FeSO_4 \cdot 7H_2O$) | g/kg | 0.03 |
| Yeast Extract | g/kg | 2.00 |
| Foam Blast ® 882 | g/kg | 0.20 |
| Delft Trace Elements 1000X | g/kg | 1.00 |

Components added to the tank after sterilization

| Seed Tank Medium (after sterilization) | | |
| --- | --- | --- |
| Components | UOM | Amount |
| Delft+ Vitamin Solution 1000X | g/kg | 1.00 |
| Calcium Chloride, dehydrate ($CaCl_2 \cdot H_2O$) | g/kg | 0.40 |
| 50% (w/v) DE99 grade dextrose | g/kg | — |
| Ethanol 200 proof | g/kg | — |

| Delft+ Vitamin Solution 1000x | | |
| --- | --- | --- |
| Components | Stock (g/L) | Final (mg/L) |
| EDTA Disodium Salt ($C_{10}H_{14}N_2Na_2O_8 \cdot 2H_2O$) | 15.0 | 15.0 |
| Zinc sulfate heptahydrate ($ZnSO_4 \cdot 7H_2O$) | 4.5 | 4.5 |
| Manganese Chloride 4-hydrate ($MnCl_2 \cdot 4H_2O$) | 1.0 | 1.0 |
| Cobalt (II) chloride hexahydrate ($CoCl_2 \cdot 6H_2O$) | 0.3 | 0.3 |
| Copper (II) sulfate pentahydrate ($CuSO_4 \cdot 5H_2O$) | 0.3 | 0.3 |

-continued

Delft+ Vitamin Solution 1000x

| Components | Stock (g/L) | Final (mg/L) |
|---|---|---|
| Di-sodium molybdenum dihydrate ($Na_2MoO_4 \cdot 2H_2O$) | 0.4 | 0.4 |
| Calcium chloride dihydrate ($CaCl_2 \cdot 2H_2O$) | 4.5 | 4.5 |
| Iron sulfate heptahydrate ($FeSO_4 \cdot 7H_2O$) | 3.0 | 3.0 |
| Boric acid ($H_3BO_3$) | 1.0 | 1.0 |
| Potassium iodide (KI) | 0.1 | 0.1 |

Delft Trace Elements 1000x

| Components | Stock (g/L) | Final (mg/L) |
|---|---|---|
| Ca-panthothenate ($C_{18}H_{32}CaN_2O_{10}$) | 1.00 | 1.00 |
| Thiamine HCl | 1.00 | 1.00 |
| Riboflavin | 4.50 | 4.50 |
| Nicotinic acid | 1.00 | 1.00 |
| Pyridoxine HCl | 1.00 | 1.00 |
| D-biotin | 0.05 | 0.05 |
| p-Aminobenzoic acid | 0.20 | 0.20 |
| Myo-inositol (microbiology grade) | 25.00 | 25.00 |

Feed medium consisted of: dextrose in the range of 10-60% w/w; ethanol in the range of 0-30% w/w; and yeast extract at 8 g/kg. The concentration of dextrose and ethanol were varied to accommodate the feed rates.

Fermentation control settings were as follows: airflow=2 SLPM, pressure=0.5 barg, agitation=300 rpm, DO %>=30%, pH=5.5, and temperature=30° C. The dissolved oxygen (DO %) was automatically maintained above 30% by increasing the agitation as needed. Control of pH was accomplished by addition of base as either 28% ammonia hydroxide or 20% sodium hydroxide (for nitrogen limitation). Addition of feed medium was started when the initial batched glucose was depleted. The initial feed rate was based on known tank mass and cell concentration and estimated glucose yield. The feed rate was on an exponentially increasing ramp, based on a desired profile corresponding to a 6 hr doubling time. Partly based upon manual measurements of residual glucose, the feed rate was adjusted at 24 hr and set to a profile corresponding to an 11.4 hr doubling time. The run was terminated at 44 hr.

In selected fermentations, the biomass at the end of the intended growth phase was subjected to a "wind down" process where the feed rate of feed medium was allowed to become limiting. In all wind down experiments, the feed rate of glucose and ethanol components were reduced (to produce carbon limitation), and optionally ammonium sulfate (to produce nitrogen limitation).

Samples were extracted during the course of fermentation at 4 hr intervals and immediately prior to termination. Samples were used to measured OD, dry cell weight, glucose concentration, ammonium concentration, phosphate concentration, and additional metabolites (maltotriose, maltose, phosphate, glucose, pyruvic acid, ketoisovalerate (KIV), dihydroxyisovalerate (DHIV), succinic acid, lactic acid, glycerol, formic acid, acetic acid, acetoin, 2R,3R-butanediol, isobutyric acid, ethanol, isobutyraldehyde, and isobutanol) by HPLC.

Intracellular trehalose was measured using an HPLC assay or using an enzymatic assay (Analytical Biochem. 248:186-188, 1997). For the HPLC assay, 1 g cell suspension was treated with 5 μL 5N NaOH and added to a PCR tube filled with glass beads. Cells were lysed by mixing for two cycles for 2 min each and centrifuged. The supernatant was diluted 10-fold in running buffer (9 mM $H_2SO_4$), filtered to remove any particulates, and injected onto a ROA-organic acid H+ column using a flow rate of 0.6 mL/min, temperature of 65° C., and 20 min run time. Trehalose concentration was quantitated using a known standard curve. The effect of the wind down process using limiting glucose/ethanol in strain PNY2289 is shown in Table 2, and the effect of the wind down process using limiting glucose/ethanol/ammonia in strain PNY2289 is shown in Table 3.

TABLE 2

| Sample | Seed tank media components | Intracellular trehalose (% w/v) | | % Improvement using wind down |
|---|---|---|---|---|
| | | End of growth phase | After 4 hr wind down | |
| A | | 1.0 | 2.1 | 210% |
| B | | 2.3 | 2.7 | 117% |
| C | | 1.5 | 1.9 | 127% |
| D | 3 g/kg glucose + 3 g/kg ethanol | 1.1 | 2.6 | 236% |
| E | 3 g/kg glucose + 3 g/kg ethanol | 3.0 | 3.6 | 120% |
| F | 3 g/kg glucose + 3 g/kg ethanol | 3.2 | 3.8 | 119% |

TABLE 3

| Sample | Seed tank media components | Intracellular trehalose (% w/v) | | % Improvement |
|---|---|---|---|---|
| | | End of growth phase | After 4 hr wind down | |
| G | 3 g/kg glucose + 3 g/kg ethanol | 6.6 | 8.3 | 126% |
| H | 3 g/kg glucose + 3 g/kg ethanol | 6.8 | 9.1 | 134% |

Example 3

Dual Carbon Source for Yeast Production

Figure 2:
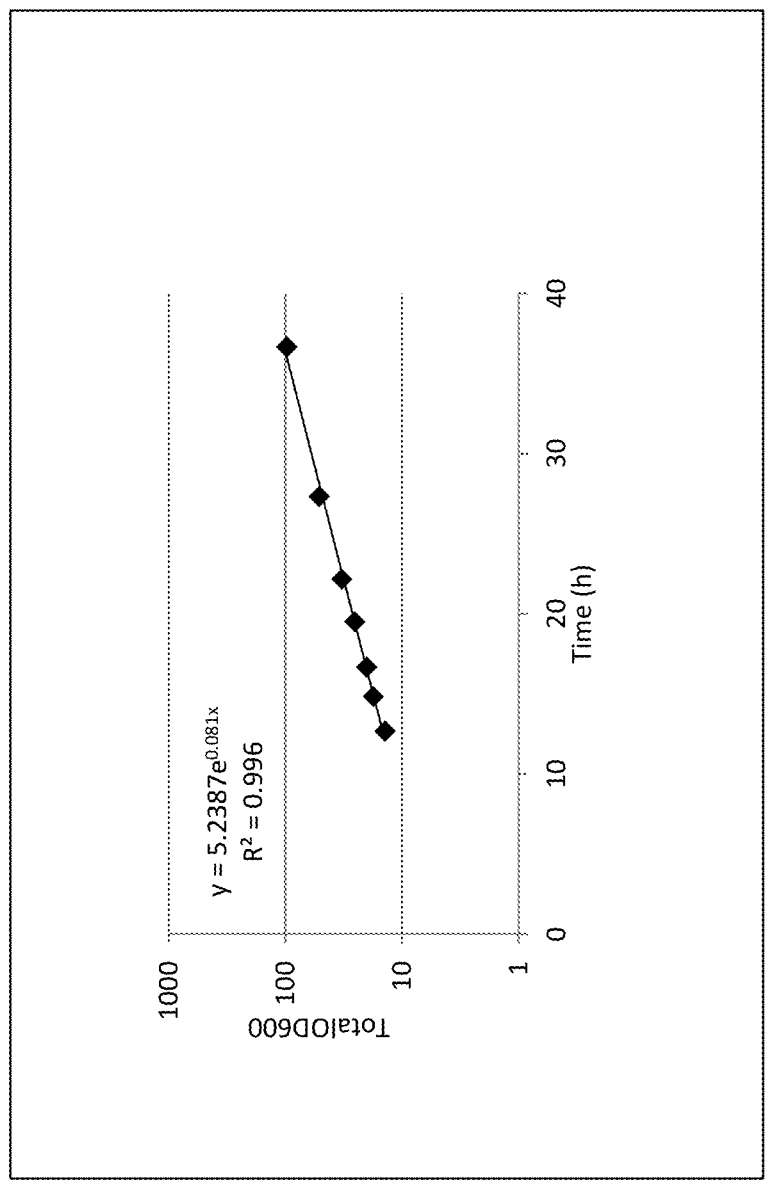
FIG. 2 shows the growth with a glucose feed exponent of 0.08/h.
Figure 3:
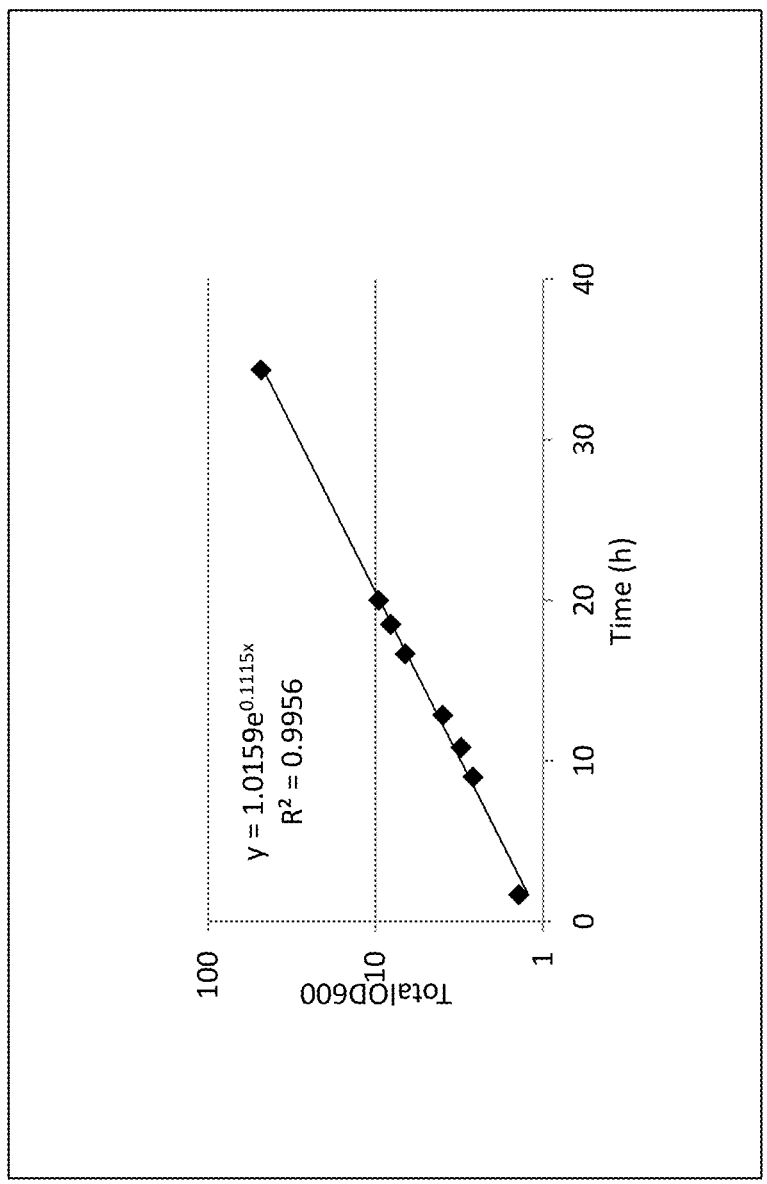
FIG. 3 shows the growth with a glucose feed exponent of 0.11/h.
Figure 4:
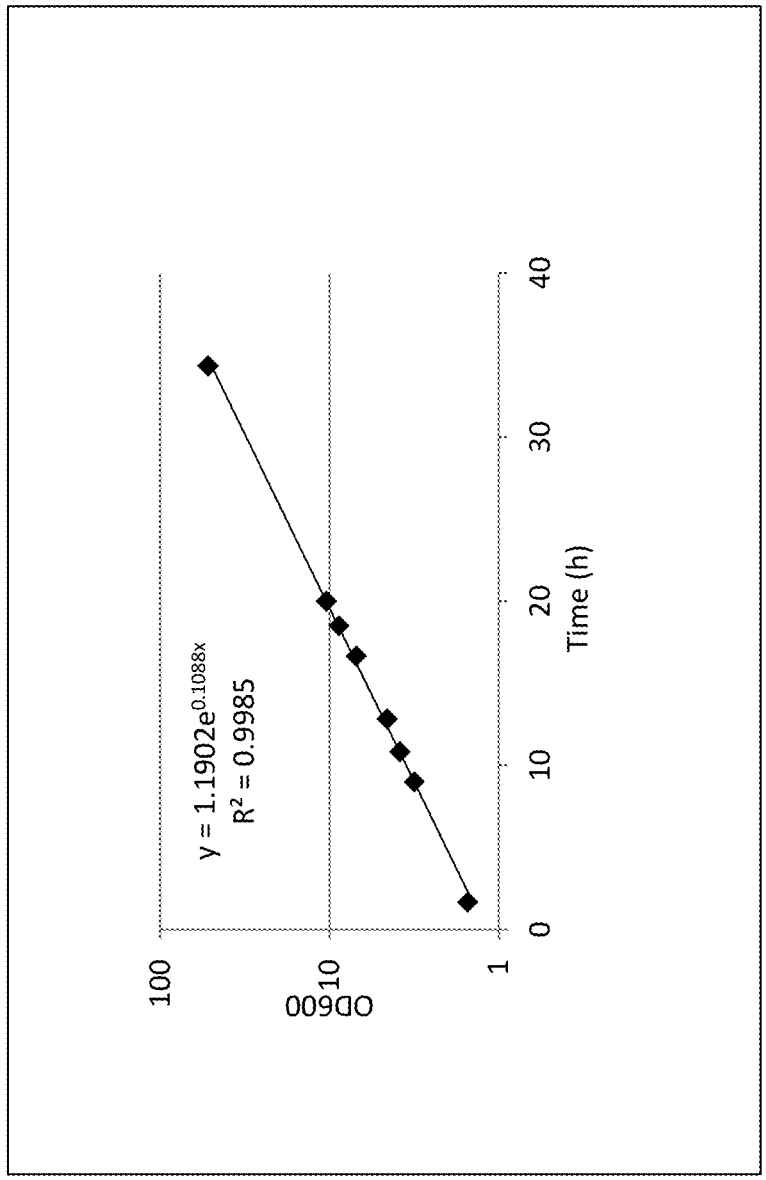
FIG. 4 shows the growth with a glucose feed exponent of 0.13/h

Yeast were grown in a glucose limited fed-batch process with excess ethanol under the following conditions: 1) glucose feed with a feed exponent of 0.08/h; 2) glucose feed with a feed exponent of 0.11/h; and 3) glucose feed with a feed exponent of 0.13/h. A critical feed exponent (or growth rate, $\mu_{crit}$) was observed. That is, above the critical feed exponent, increased glucose consumption had no effect on growth, but did result in increased byproduct accumulation. Results are shown in Table 4 and FIGS. 2-4. FIG. 2 shows the growth with a glucose feed exponent of 0.08/h, FIG. 3 shows the growth with a glucose feed exponent of 0.11/h, and FIG. 4 shows the growth with a glucose feed exponent of 0.13/h.

TABLE 4

| Exponent of glucose feed | 0.08 | 0.11 | 0.13 |
|---|---|---|---|
| Growth rate µ (/h) | 0.08 | 0.11 | 0.11 |
| Biomass produced (g/L) | 49 | 40 | 42 |
| Glucose consumed (g/L) | 33 | 52 | 95 |
| Ethanol consumed (g/L) | 49 | 13 | 12 |
| Glucose consumed/biomass (g/g) | 0.7 | 1.3 | 2.3 |
| Ethanol consumed/biomass (g/g) | 1.0 | 0.33 | 0.29 |

The results demonstrate that there is a critical glucose feed exponent (µ) below which growth was controlled by feed, and this critical glucose feed exponent is 0.11. Glucose feed below the critical glucose feed exponent resulted in decreased consumption of glucose and increased consumption of ethanol. Above the critical point, ethanol consumption was not significantly decreased, and glucose consumption was increased with no effect on biomass production. Glucose feed above the critical glucose feed exponent resulted in higher accumulation of byproducts as compared to the critical glucose feed exponent and feed below the critical glucose feed exponent.

Example 4

Construction of *Saccharomyces cerevisiae* Strain with TPS1 Overexpression

A *Saccharomyces cerevisiae* strain is constructed by transformation of plasmids pRS413::TPS1up and pLH804::L2V4 into host strain PNY1620. Plasmid pRS413::TPS1up is constructed using standard methodology using the pRS413 vector backbone (ATCC No. 87518) and contains the *Saccharomyces cerevisiae* TPS1 (SEQ ID NO: 133) coding sequence with the TDH3 promoter and TDH3 terminator. Plasmid pLH804::L2V4 is constructed using the pHR81 vector backbone (ATCC No. 87541) and contains the *Anaerostipes caccae* K9JB4P KARI with the ILV5 promoter and ILV5 terminator, and the *Streptococcus mutans* L2V4 DHAD with the TEF1(M7) promoter and FBA1 terminator. Plasmids are introduced by a lithium acetate transformation method (Methods in Yeast Genetics: A Cold Spring Harbor Laboratory Course Manual, Cold Spring Harbor Press, 2005), and transformants are selected on synthetic complete medium minus histidine and uracil with 1% ethanol as carbon source. Transformants are then transferred to plates containing synthetic complete medium minus histidine and uracil with 2% glucose as carbon source and optionally ethanol (0.05%) or acetate (2 mM) as a C2 supplement. Freezer vials are made by dilution of log-phase cultures with 45% glycerol to a final glycerol concentration of 15% (w/v).

Example 5

Construction of *Saccharomyces cerevisiae* Strain with TPS2 Overexpression

A *Saccharomyces cerevisiae* strain is constructed by transformation of plasmids pRS413::TPS2up and pLH804::L2V4 into the host strain PNY1620. Plasmid pRS413::TPS2up is constructed using standard methodology using the pRS413 vector backbone (ATCC No. 87518) and contains the *Saccharomyces cerevisiae* TPS2 (SEQ ID NO: 134) coding sequence with the TDH3 promoter and TDH3 terminator. Plasmids are introduced by the lithium acetate transformation method and transformants are selected on synthetic complete medium minus histidine and uracil with 1% ethanol as carbon source. Transformants are then transferred to plates containing synthetic complete medium minus histidine and uracil with 2% glucose as carbon source and optionally ethanol (0.05%) or acetate (2 mM) as a C2 supplement. Freezer vials are made by dilution of log-phase cultures with 45% glycerol to a final glycerol concentration of 15% (w/v).

Example 6

Construction of *Saccharomyces cerevisiae* Strain with TPS1 and TPS2 Overexpression A *Saccharomyces cerevisiae* strain is constructed by transformation of plasmids pRS413::TPS1+TPS2up and pLH804::L2V4 into the host strain PNY1620. Plasmid pRS413::TPS1+TPS2up is derived from the pRS413 vector backbone (ATCC No. 87518) and contains: the *Saccharomyces cerevisiae* TPS1 coding sequence driven by the ADH1 promoter and ADH1 terminator, and the *Saccharomyces cerevisiae* TPS2 coding sequence driven by the TDH3 promoter and TDH3 terminator. Plasmid pLH804::L2V4 is derived from the pHR81 vector backbone (ATCC No. 87541) and contains: the *Anaerostipes caccae* K9JB4P KARI driven by the ILV5 promoter and ILV5 terminator, and the *Streptococcus mutans* L2V4 DHAD driven by the TEF1(M7) promoter and FBA1 terminator. Plasmids are introduced by lithium acetate transformation method (Methods in Yeast Genetics: A Cold Spring Harbor Laboratory Course Manual, Cold Spring Harbor Press, 2005), and transformants are selected on synthetic complete medium, minus histidine and uracil, with 1% ethanol as carbon source. Transformants are then transferred to plates containing synthetic complete medium, minus histidine and uracil, with 2% glucose as carbon source and optionally ethanol (0.05%) or acetate (2 mM) as a C2 supplement. Freezer vials are made by dilution of log-phase cultures with 45% glycerol to a final glycerol concentration of 15% (w/v).

Example 7

Construction of *Saccharomyces cerevisiae* Strain with MSN2 Overexpression

A *Saccharomyces cerevisiae* strain is constructed by transformation of plasmids pRS413::MSN2up and pLH804::L2V4 into the host strain PNY1620. Plasmid pRS413::MSN2up is constructed using standard methodology from the pRS413 vector backbone (ATCC No. 87518) and contains: the *Saccharomyces cerevisiae* MSN2 (SEQ ID NO: 135) coding sequence driven by the ADH1 promoter and ADH1 terminator. Plasmid pLH804::L2V4 is constructed as described herein. Plasmids are introduced by lithium acetate transformation method (Methods in Yeast Genetics: A Cold Spring Harbor Laboratory Course Manual, Cold Spring Harbor Press, 2005), and transformants are selected on synthetic complete medium, minus histidine and uracil, with 1% ethanol as carbon source. Transformants are then transferred to plates containing synthetic complete medium, minus histidine and uracil, with 2% glucose as carbon source and optionally ethanol (0.05%) or acetate (2 mM) as a C2 supplement. Freezer vials are made by dilution of log-phase cultures with 45% glycerol to a final glycerol concentration of 15% (w/v).

Example 8

Construction of *Saccharomyces cerevisiae* Strain with LSM1 Deletion

A *Saccharomyces cerevisiae* strain is constructed by deletion of the LSM1 gene (SEQ ID NO: 136) and by transformation of plasmid pLH804::L2V4 into the host strain PNY1620. The LSM1 deletion is made using standard yeast deletions known to those of skill in the art using a kanMX4 cassette (see, e.g., Brachmann, et al., Yeast 14:115-132, 1998). Plasmid pLH804::L2V4 is constructed as described herein. Plasmids are introduced by lithium acetate transformation method (Methods in Yeast Genetics: A Cold Spring Harbor Laboratory Course Manual, Cold Spring Harbor Press, 2005), and transformants are selected on synthetic complete medium minus uracil, with 1% ethanol as carbon source. Transformants are then transferred to plates containing synthetic complete medium, minus uracil, with 2% glucose as carbon source and optionally ethanol (0.05%) or acetate (2 mM) as a C2 supplement. Freezer vials are made by dilution of log-phase cultures with 45% glycerol to a final glycerol concentration of 15% (w/v).

Example 9

Construction of Saccharomyces cerevisiae Strain with NTH1 Deletion

A Saccharomyces cerevisiae strain is constructed by deletion of the NTH1 gene (SEQ ID NO: 137) and by transformation of plasmid pLH804::L2V4 into the host strain PNY1620. The NTH1 deletion is made using standard yeast deletions known to those of skill in the art using a kanMX4 cassette (see, e.g., Brachmann, et al., Yeast 14:115-132, 1998). Plasmid pLH804::L2V4 is constructed as described herein. Plasmids are introduced by lithium acetate transformation method (Methods in Yeast Genetics: A Cold Spring Harbor Laboratory Course Manual, Cold Spring Harbor Press, 2005), and transformants are selected on synthetic complete medium minus uracil, with 1% ethanol as carbon source. Transformants are then transferred to plates containing synthetic complete medium, minus uracil, with 2% glucose as carbon source and optionally ethanol (0.05%) or acetate (2 mM) as a C2 supplement. Freezer vials are made by dilution of log-phase cultures with 45% glycerol to a final glycerol concentration of 15% (w/v).

Example 10

Increased Trehalose Production with Modified Strains

The strains described in Examples 4-9 are inoculated into 10 mL synthetic complete media minus uracil with 2% glucose as carbon source and optionally ethanol (0.05%) or acetate (2 mM) as a C2 supplement in 125 mL shake flasks, and incubated aerobically at 225 rpm at 30° C. for 18 hr.

From the flasks, 10 mL culture broth is used to inoculate 100 mL synthetic complete media uracil with 2% glucose as carbon source and optionally ethanol (0.05%) or acetate (2 mM) as a C2 supplement in 125 mL shake flasks, and incubated aerobically at 225 rpm at 30° C. for 24 hr. Cells are harvested and assayed for trehalose.

A portion of the cells (5 mL) is filtered onto a 50 mm nylon membrane filter (Millipore Corporation, Billerica, Mass.) resting on top of the glass filter holder (Thermo Fisher Scientific, Inc., Waltham, Mass.). Immediately after filtering, the filter is removed from the holder and transferred to 1.3 mL pre-cooled (−20° C.) extraction solvent (40:40:20 acetonitrile/methanol/water) in petri dishes. Cells are placed face down in the solvent. Cells are extracted for 15 minutes at −20° C. Briefly, the filter is turned over (i.e., cells or debris facing up), and cell debris is washed with extraction solvent in the petri dish about 10 times. The resulting extract (about 1 mL extract) is transferred to Eppendorf tubes (Eppendorf North America, Hauppauge, N.Y.) and centrifuged at about 15000 g under 4° C. for 5 min. The supernatant is transferred to clean microfuge tubes and stored overnight.

Cell extracts are stored at −20° C. until analyzed. About 400 μL extract is transferred to a new Eppendorf tube and the solvent is dried under nitrogen in the hood. The resulting pellet is re-suspended in 150 μL HPLC grade water and transferred to HPLC vials. Samples are analyzed by reversed phase ion-pairing liquid chromatography (LC) coupled with an electrospray ionization (ESI) (negative mode) to a high-resolution, high-accuracy Exactive™ mass spectrometer (Thermo Fisher Scientific, Inc., Waltham, Mass.) operated in full scan mode at 1 s scan time, $10^5$ resolution. The system consists of an Accela U-HPLC system with quaternary pumps, an HTC PAL autosampler, and an Exactive™ Orbitrap mass spectrometer, controlled by Xcalibur 2.1 software. Liquid chromatography separation was achieved on a Synergy™ Hydro-RP column (100 mm×2 mm, 2.5 μm particle size; Phenomenex Inc., Torrance, Calif.) using reversed-phase chromatography with the ion pairing agent tributylamine in the aqueous mobile phase to enhance retention and separation. The total run time is 20 min. Solvent A is 97:3 water/methanol with 10 mM tributylamine and 15 mM acetic acid; solvent B is methanol. The gradient is 0 min, 0% B, flow rate 200 μL/min; 2.5 min, 0% B, flow rate 200 μL/min; 5 min, 20% B, flow rate 250 μL/min; 12 min, 95% B, flow rate 250 μL/min; 14.5 min, 95% B, flow rate 250 μL/min; 15 min, 0% B, flow rate 250 μL/min; 19 min, 0% B, flow rate 200 μL/min; 20 min, 0% B, flow rate 200 μL/min. Scan range is m/z 75-1000 in negative ion mode at a frequency of 1 Hz.

Increased trehalose concentrations are observed in strains with modifications relative to the parental strains.

What is claimed is:

1. A method of producing a yeast product comprising:
   a) culturing a population of yeast in the presence of a carbon substrate, nitrogen substrate, and ethanol whereby the feed rate of carbon substrate and ethanol is ramped such that concentration of carbon substrate and ethanol maintains the growth rate of the population at less than $\mu_{crit}$ and whereby the population reaches a cell density;
   b) ceasing the ramping of the feed rate whereby the concentration of carbon substrate, nitrogen substrate, and ethanol decreases over a period of time; and
   c) subjecting the population of yeast to a feed rate which is ramped down to less than half of the maximum feed rate of (a).

2. The method of claim 1, wherein the carbon substrate is glucose, acetate, or a mixture thereof.

3. The method of claim 1, wherein the carbon substrate is a dual carbon source.

4. The method of claim 3, wherein the dual carbon source is glucose and acetate.

5. The method of claim 1, wherein the yeast is a butanologen.

6. The method of claim 1 further comprising concentrating the population of yeast to at least about 16% (w/v).

7. The method of claim 1 further comprising concentrating the population of yeast to at least about 30% (w/v).

8. The method of claim 6, wherein the concentrating is carried out in a centrifuge.

9. The method of claim 6, wherein (b) and (c) increase the trehalose concentration of the population of yeast by at least 100%.

10. The method of claim 6, wherein (b) and (c) increase the trehalose concentration of the population of yeast by at least 500%.

11. The method of claim 6, wherein the trehalose content of the population of yeast is at least about 5%.

12. The method of claim 6, wherein the population of yeast is further concentrated to at least about 90% (w/v).

13. The method of claim 12, wherein the population of yeast is further concentrated to at least about 90% (w/v) by drying.

14. The method of claim 7, wherein the concentrating is carried out in a centrifuge.

15. The method of claim 7, wherein (b) and (c) increase the trehalose concentration of the population of yeast by at least 100% or by at least 500%.

16. The method of claim 7, wherein the population of yeast is further concentrated to at least about 90% (w/v).

* * * * *

SEQUENCE LISTING

```
<160> NUMBER OF SEQ ID NOS: 137

<210> SEQ ID NO 1
<211> LENGTH: 570
<212> TYPE: PRT
<213> ORGANISM: Bacillus subtilis

<400> SEQUENCE: 1

Met Thr Lys Ala Thr Lys Glu Gln Lys Ser Leu Val Lys Asn Arg Gly
1               5                   10                  15

Ala Glu Leu Val Val Asp Cys Leu Val Glu Gln Gly Val Thr His Val
```

-continued

```
                20                  25                  30
Phe Gly Ile Pro Gly Ala Lys Ile Asp Ala Val Phe Asp Ala Leu Gln
            35                  40                  45
Asp Lys Gly Pro Glu Ile Ile Val Ala Arg His Glu Gln Asn Ala Ala
        50                  55                  60
Phe Met Ala Gln Ala Val Gly Arg Leu Thr Gly Lys Pro Gly Val Val
65                  70                  75                  80
Leu Val Thr Ser Gly Pro Gly Ala Ser Asn Leu Ala Thr Gly Leu Leu
                85                  90                  95
Thr Ala Asn Thr Glu Gly Asp Pro Val Val Ala Leu Ala Gly Asn Val
            100                 105                 110
Ile Arg Ala Asp Arg Leu Lys Arg Thr His Gln Ser Leu Asp Asn Ala
        115                 120                 125
Ala Leu Phe Gln Pro Ile Thr Lys Tyr Ser Val Glu Val Gln Asp Val
    130                 135                 140
Lys Asn Ile Pro Glu Ala Val Thr Asn Ala Phe Arg Ile Ala Ser Ala
145                 150                 155                 160
Gly Gln Ala Gly Ala Ala Phe Val Ser Phe Pro Gln Asp Val Val Asn
                165                 170                 175
Glu Val Thr Asn Thr Lys Asn Val Arg Ala Val Ala Ala Pro Lys Leu
            180                 185                 190
Gly Pro Ala Ala Asp Asp Ala Ile Ser Ala Ala Ile Ala Lys Ile Gln
        195                 200                 205
Thr Ala Lys Leu Pro Val Val Leu Val Gly Met Lys Gly Gly Arg Pro
    210                 215                 220
Glu Ala Ile Lys Ala Val Arg Lys Leu Leu Lys Lys Val Gln Leu Pro
225                 230                 235                 240
Phe Val Glu Thr Tyr Gln Ala Ala Gly Thr Leu Ser Arg Asp Leu Glu
                245                 250                 255
Asp Gln Tyr Phe Gly Arg Ile Gly Leu Phe Arg Asn Gln Pro Gly Asp
            260                 265                 270
Leu Leu Leu Glu Gln Ala Asp Val Val Leu Thr Ile Gly Tyr Asp Pro
        275                 280                 285
Ile Glu Tyr Asp Pro Lys Phe Trp Asn Ile Asn Gly Asp Arg Thr Ile
    290                 295                 300
Ile His Leu Asp Glu Ile Ile Ala Asp Ile Asp His Ala Tyr Gln Pro
305                 310                 315                 320
Asp Leu Glu Leu Ile Gly Asp Ile Pro Ser Thr Ile Asn His Ile Glu
                325                 330                 335
His Asp Ala Val Lys Val Glu Phe Ala Glu Arg Glu Gln Lys Ile Leu
            340                 345                 350
Ser Asp Leu Lys Gln Tyr Met His Glu Gly Glu Gln Val Pro Ala Asp
        355                 360                 365
Trp Lys Ser Asp Arg Ala His Pro Leu Glu Ile Val Lys Glu Leu Arg
    370                 375                 380
Asn Ala Val Asp Asp His Val Thr Val Thr Cys Asp Ile Gly Ser His
385                 390                 395                 400
Ala Ile Trp Met Ser Arg Tyr Phe Arg Ser Tyr Glu Pro Leu Thr Leu
                405                 410                 415
Met Ile Ser Asn Gly Met Gln Thr Leu Gly Val Ala Leu Pro Trp Ala
            420                 425                 430
Ile Gly Ala Ser Leu Val Lys Pro Gly Glu Lys Val Val Ser Val Ser
        435                 440                 445
```

```
Gly Asp Gly Gly Phe Leu Phe Ser Ala Met Glu Leu Glu Thr Ala Val
    450                 455                 460

Arg Leu Lys Ala Pro Ile Val His Ile Val Trp Asn Asp Ser Thr Tyr
465                 470                 475                 480

Asp Met Val Ala Phe Gln Gln Leu Lys Lys Tyr Asn Arg Thr Ser Ala
                485                 490                 495

Val Asp Phe Gly Asn Ile Asp Ile Val Lys Tyr Ala Glu Ser Phe Gly
            500                 505                 510

Ala Thr Gly Leu Arg Val Glu Ser Pro Asp Gln Leu Ala Asp Val Leu
        515                 520                 525

Arg Gln Gly Met Asn Ala Glu Gly Pro Val Ile Ile Asp Val Pro Val
    530                 535                 540

Asp Tyr Ser Asp Asn Ile Asn Leu Ala Ser Asp Lys Leu Pro Lys Glu
545                 550                 555                 560

Phe Gly Glu Leu Met Lys Thr Lys Ala Leu
                565                 570

<210> SEQ ID NO 2
<211> LENGTH: 1716
<212> TYPE: DNA
<213> ORGANISM: Bacillus subtilis

<400> SEQUENCE: 2
atgttgacaa agcaacaaa agaacaaaaa tcccttgtga aaaacagagg ggcggagctt      60
gttgttgatt gcttagtgga gcaaggtgtc acacatgtat ttggcattcc aggtgcaaaa     120
attgatgcgg tatttgacgc tttacaagat aaaggacctg aaattatcgt tgcccggcac     180
gaacaaaacg cagcattcat ggcccaagca gtcggccgtt aactggaaa accgggagtc      240 gtgttagtca catcaggacc gggtgcctct aacttggcaa caggcctgct gacagcgaac     300
actgaaggag accctgtcgt tgcgcttgct ggaaacgtga tccgtgcaga tcgtttaaaa     360
cggacacatc aatctttgga taatgcggcg ctattccagc cgattacaaa atacagtgta     420
gaagttcaag atgtaaaaaa tataccggaa gctgttacaa atgcatttag gatagcgtca     480
gcagggcagg ctggggccgc ttttgtgagc tttccgcaag atgttgtgaa tgaagtcaca     540
aatacgaaaa acgtgcgtgc tgttgcagcg ccaaaactcg gtcctgcagc agatgatgca     600
atcagtgcgg ccatagcaaa aatccaaaca gcaaaacttc ctgtcgtttt ggtcggcatg     660
aaaggcggaa gaccggaagc aattaaagcg gttcgcaagc ttttgaaaaa ggttcagctt     720
ccatttgttg aaacatatca agctgccggt acccttctca gagatttaga ggatcaatat     780
tttggccgta tcggtttgtt ccgcaaccag cctggcgatt tactgctaga gcaggcagat     840
gttgttctga cgatcggcta tgacccgatt gaatatgatc cgaaattctg gaatatcaat     900
ggagaccgga caattatcca tttagacgag attatcgctg acattgatca tgcttaccag     960
cctgatcttg aattgatcgg tgacattccg tccacgatca atcatatcga acacgatgct    1020
gtgaaagtgg aatttgcaga gcgtgagcag aaaatccttt ctgatttaaa acaatatatg    1080
catgaaggtg agcaggtgcc tgcagattgg aaatcagaca gagcgcaccc tcttgaaatc    1140
gttaaagagt tgcgtaatgc agtcgatgat catgttacag taacttgcga tatcggttcg    1200
cacgccattt ggatgtcacg ttatttccgc agctacgagc cgttaacatt aatgatcagt    1260
aacggtatgc aaacactcgg cgttgcgctt cctgggcaa tcggcgcttc attggtgaaa    1320
ccgggagaaa aagtggtttc tgtctctggt gacggcggtt tcttattctc agcaatggaa    1380
```

-continued

```
ttagagacag cagttcgact aaaagcacca attgtacaca ttgtatggaa cgacagcaca    1440
tatgacatgg ttgcattcca gcaattgaaa aaatataacc gtacatctgc ggtcgatttc    1500
ggaaatatcg atatcgtgaa atatgcggaa agcttcggag caactggctt gcgcgtagaa    1560
tcaccagacc agctggcaga tgttctgcgt caaggcatga acgctgaagg tcctgtcatc    1620
atcgatgtcc cggttgacta cagtgataac attaatttag caagtgacaa gcttccgaaa    1680
gaattcgggg aactcatgaa aacgaaagct ctctag                              1716

<210> SEQ ID NO 3
<211> LENGTH: 559
<212> TYPE: PRT
<213> ORGANISM: Klebsiella pneumoniae

<400> SEQUENCE: 3

Met Asp Lys Gln Tyr Pro Val Arg Gln Trp Ala His Gly Ala Asp Leu
1               5                   10                  15

Val Val Ser Gln Leu Glu Ala Gln Gly Val Arg Gln Val Phe Gly Ile
                20                  25                  30

Pro Gly Ala Lys Ile Asp Lys Val Phe Asp Ser Leu Leu Asp Ser Ser
            35                  40                  45

Ile Arg Ile Ile Pro Val Arg His Glu Ala Asn Ala Ala Phe Met Ala
        50                  55                  60

Ala Ala Val Gly Arg Ile Thr Gly Lys Ala Gly Val Ala Leu Val Thr
65                  70                  75                  80

Ser Gly Pro Gly Cys Ser Asn Leu Ile Thr Gly Met Ala Thr Ala Asn
                85                  90                  95

Ser Glu Gly Asp Pro Val Val Ala Leu Gly Gly Ala Val Lys Arg Ala
            100                 105                 110

Asp Lys Ala Lys Gln Val His Gln Ser Met Asp Thr Val Ala Met Phe
        115                 120                 125

Ser Pro Val Thr Lys Tyr Ala Ile Glu Val Thr Ala Pro Asp Ala Leu
    130                 135                 140

Ala Glu Val Val Ser Asn Ala Phe Arg Ala Ala Glu Gln Gly Arg Pro
145                 150                 155                 160

Gly Ser Ala Phe Val Ser Leu Pro Gln Asp Val Asp Gly Pro Val
                165                 170                 175

Ser Gly Lys Val Leu Pro Ala Ser Gly Ala Pro Gln Met Gly Ala Ala
            180                 185                 190

Pro Asp Asp Ala Ile Asp Gln Val Ala Lys Leu Ile Ala Gln Ala Lys
        195                 200                 205

Asn Pro Ile Phe Leu Leu Gly Leu Met Ala Ser Gln Pro Glu Asn Ser
    210                 215                 220

Lys Ala Leu Arg Arg Leu Leu Glu Thr Ser His Ile Pro Val Thr Ser
225                 230                 235                 240

Thr Tyr Gln Ala Ala Gly Ala Val Asn Gln Asp Asn Phe Ser Arg Phe
                245                 250                 255

Ala Gly Arg Val Gly Leu Phe Asn Asn Gln Ala Gly Asp Arg Leu Leu
            260                 265                 270

Gln Leu Ala Asp Leu Val Ile Cys Ile Gly Tyr Ser Pro Val Glu Tyr
        275                 280                 285

Glu Pro Ala Met Trp Asn Ser Gly Asn Ala Thr Leu Val His Ile Asp
    290                 295                 300

Val Leu Pro Ala Tyr Glu Glu Arg Asn Tyr Thr Pro Asp Val Glu Leu
305                 310                 315                 320
```

```
Val Gly Asp Ile Ala Gly Thr Leu Asn Lys Leu Ala Gln Asn Ile Asp
                325                 330                 335

His Arg Leu Val Leu Ser Pro Gln Ala Ala Glu Ile Leu Arg Asp Arg
            340                 345                 350

Gln His Gln Arg Glu Leu Leu Asp Arg Arg Gly Ala Gln Leu Asn Gln
        355                 360                 365

Phe Ala Leu His Pro Leu Arg Ile Val Arg Ala Met Gln Asp Ile Val
    370                 375                 380

Asn Ser Asp Val Thr Leu Thr Val Asp Met Gly Ser Phe His Ile Trp
385                 390                 395                 400

Ile Ala Arg Tyr Leu Tyr Thr Phe Arg Ala Arg Gln Val Met Ile Ser
                405                 410                 415

Asn Gly Gln Gln Thr Met Gly Val Ala Leu Pro Trp Ala Ile Gly Ala
            420                 425                 430

Trp Leu Val Asn Pro Glu Arg Lys Val Val Ser Val Ser Gly Asp Gly
        435                 440                 445

Gly Phe Leu Gln Ser Ser Met Glu Leu Glu Thr Ala Val Arg Leu Lys
    450                 455                 460

Ala Asn Val Leu His Leu Ile Trp Val Asp Asn Gly Tyr Asn Met Val
465                 470                 475                 480

Ala Ile Gln Glu Glu Lys Lys Tyr Gln Arg Leu Ser Gly Val Glu Phe
                485                 490                 495

Gly Pro Met Asp Phe Lys Ala Tyr Ala Glu Ser Phe Gly Ala Lys Gly
            500                 505                 510

Phe Ala Val Glu Ser Ala Glu Ala Leu Glu Pro Thr Leu Arg Ala Ala
        515                 520                 525

Met Asp Val Asp Gly Pro Ala Val Val Ala Ile Pro Val Asp Tyr Arg
    530                 535                 540

Asp Asn Pro Leu Leu Met Gly Gln Leu His Leu Ser Gln Ile Leu
545                 550                 555

<210> SEQ ID NO 4
<211> LENGTH: 2055
<212> TYPE: DNA
<213> ORGANISM: Klebsiella pneumoniae

<400> SEQUENCE: 4
tcgaccacgg ggtgctgacc ttcggcgaaa ttcacaagct gatgatcgac ctgcccgccg      60
acagcgcgtt cctgcaggct aatctgcatc cgataatctc gatgccgcc atccgttccg     120 tagaaagtta aggggtcac atggacaaac agtatccggt acgccagtgg gcgcacggcg     180
ccgatctcgt cgtcagtcag ctggaagctc agggagtacg ccaggtgttc ggcatccccg     240
gcgccaaaat cgacaaggtc tttgattcac tgctggattc ctccattcgc attattccgg     300
tacgccacga agccaacgcc gcatttatgg ccgccgccgt cggacgcatt accggcaaag     360
cgggcgtggc gctggtcacc tccggtccgg gctgttccaa cctgatcacc ggcatggcca     420
ccgcgaacag cgaaggcgac ccggtggtgg ccctgggcgg cgcggtaaaa cgcgccgata     480
aagcgaagca ggtccaccag agtatggata cggtggcgat gttcagcccg gtcaccaaat     540
acgccatcga ggtgacggcg ccggatgcgc tggcggaagt ggtctccaac gccttccgcg     600
ccgccgagca gggccggccg ggcagcgcgt tcgttagcct gccgcaggat gtggtcgatg     660
gcccggtcag cggcaaagtg ctgccggcca gcggggcccc gcagatgggc gccgcgccgg     720
atgatgccat cgaccaggtg gcgaagctta tcgcccaggc gaagaacccg atcttcctgc     780
```

-continued

```
tcggcctgat ggccagccag ccggaaaaca gcaaggcgct cgcccgtttg ctggagacca    840
gccatattcc agtcaccagc acctatcagg ccgccggagc ggtgaatcag gataacttct    900
ctcgcttcgc cggccgggtt gggctgttta acaaccaggc cggggaccgt ctgctgcagc    960
tcgccgacct ggtgatctgc atcggctaca gcccggtgga atacgaaccg gcgatgtgga   1020
acagcggcaa cgcgacgctg gtgcacatcg acgtgctgcc cgcctatgaa gagcgcaact   1080
acaccccgga tgtcgagctg gtgggcgata tcgccggcac tctcaacaag ctggcgcaaa   1140
atatcgatca tcggctggtg ctctccccgc aggcggcgga gatcctccgc gaccgccagc   1200
accagcgcga gctgctggac cgccgcgcg cgcagctcaa ccagtttgcc ctgcatcccc    1260
tgcgcatcgt tcgcgccatg caggatatcg tcaacagcga cgtcacgttg accgtggaca   1320
tgggcagctt ccatatctgg attgcccgct acctgtacac gttccgcgcc cgtcaggtga   1380
tgatctccaa cggccagcag accatgggcg tcgccctgcc ctgggctatc ggcgcctggc   1440
tggtcaatcc tgagcgcaaa gtggtctccg tctccggcga cggcggcttc ctgcagtcga   1500
gcatggagct ggagaccgcc gtccgcctga agccaacgt gctgcatctt atctgggtcg    1560
ataacggcta caacatggtc gctatccagg aagagaaaaa atatcagcgc ctgtccggcg   1620
tcgagtttgg gccgatggat tttaaagcct atgccgaatc cttcggcgcg aaagggtttg   1680
ccgtggaaag cgccgaggcg ctggagccga ccctgcgcgc ggcgatggac gtcgacggcc   1740
cggcggtagt ggccatcccg gtggattatc gcgataaccc gctgctgatg ggccagctgc   1800
atctgagtca gattctgtaa gtcatcacaa taaggaaaga aaatgaaaa aagtcgcact    1860
tgttaccggc gccggccagg ggattggtaa agctatcgcc cttcgtctgg tgaaggatgg   1920
atttgccgtg gccattgccg attataacga cgccaccgcc aaagcggtcg cctccgaaat   1980
caaccaggcc ggcggccgcg ccatggcggt gaaagtggat gtttctgacc gcgaccaggt   2040
atttgccgcc gtcga                                                   2055
```

<210> SEQ ID NO 5
<211> LENGTH: 554
<212> TYPE: PRT
<213> ORGANISM: Lactococcus lactis

<400> SEQUENCE: 5

```
Met Ser Glu Lys Gln Phe Gly Ala Asn Leu Val Val Asp Ser Leu Ile
1               5                   10                  15

Asn His Lys Val Lys Tyr Val Phe Gly Ile Pro Gly Ala Lys Ile Asp
            20                  25                  30

Arg Val Phe Asp Leu Leu Glu Asn Glu Glu Gly Pro Gln Met Val Val
        35                  40                  45

Thr Arg His Glu Gln Gly Ala Ala Phe Met Ala Gln Ala Val Gly Arg
    50                  55                  60

Leu Thr Gly Glu Pro Gly Val Val Val Thr Ser Gly Pro Gly Val
65                  70                  75                  80

Ser Asn Leu Ala Thr Pro Leu Leu Thr Ala Thr Ser Glu Gly Asp Ala
                85                  90                  95

Ile Leu Ala Ile Gly Gly Gln Val Lys Arg Ser Asp Arg Leu Lys Arg
            100                 105                 110

Ala His Gln Ser Met Asp Asn Ala Gly Met Met Gln Ser Ala Thr Lys
        115                 120                 125

Tyr Ser Ala Glu Val Leu Asp Pro Asn Thr Leu Ser Glu Ser Ile Ala
    130                 135                 140
```

```
Asn Ala Tyr Arg Ile Ala Lys Ser Gly His Pro Gly Ala Thr Phe Leu
145                 150                 155                 160

Ser Ile Pro Gln Asp Val Thr Asp Ala Glu Val Ser Ile Lys Ala Ile
            165                 170                 175

Gln Pro Leu Ser Asp Pro Lys Met Gly Asn Ala Ser Ile Asp Asp Ile
            180                 185                 190

Asn Tyr Leu Ala Gln Ala Ile Lys Asn Ala Val Leu Pro Val Ile Leu
            195                 200                 205

Val Gly Ala Gly Ala Ser Asp Ala Lys Val Ala Ser Ser Leu Arg Asn
210                 215                 220

Leu Leu Thr His Val Asn Ile Pro Val Val Glu Thr Phe Gln Gly Ala
225                 230                 235                 240

Gly Val Ile Ser His Asp Leu Glu His Thr Phe Tyr Gly Arg Ile Gly
            245                 250                 255

Leu Phe Arg Asn Gln Pro Gly Asp Met Leu Leu Lys Arg Ser Asp Leu
            260                 265                 270

Val Ile Ala Val Gly Tyr Asp Pro Ile Glu Tyr Glu Ala Arg Asn Trp
            275                 280                 285

Asn Ala Glu Ile Asp Ser Arg Ile Ile Val Ile Asp Asn Ala Ile Ala
290                 295                 300

Glu Ile Asp Thr Tyr Tyr Gln Pro Glu Arg Glu Leu Ile Gly Asp Ile
305                 310                 315                 320

Ala Ala Thr Leu Asp Asn Leu Leu Pro Ala Val Arg Gly Tyr Lys Ile
            325                 330                 335

Pro Lys Gly Thr Lys Asp Tyr Leu Asp Gly Leu His Glu Val Ala Glu
            340                 345                 350

Gln His Glu Phe Asp Thr Glu Asn Thr Glu Glu Gly Arg Met His Pro
            355                 360                 365

Leu Asp Leu Val Ser Thr Phe Gln Glu Ile Val Lys Asp Asp Glu Thr
            370                 375                 380

Val Thr Val Asp Val Gly Ser Leu Tyr Ile Trp Met Ala Arg His Phe
385                 390                 395                 400

Lys Ser Tyr Glu Pro Arg His Leu Leu Phe Ser Asn Gly Met Gln Thr
            405                 410                 415

Leu Gly Val Ala Leu Pro Trp Ala Ile Thr Ala Ala Leu Leu Arg Pro
            420                 425                 430

Gly Lys Lys Val Tyr Ser His Ser Gly Asp Gly Gly Phe Leu Phe Thr
            435                 440                 445

Gly Gln Glu Leu Glu Thr Ala Val Arg Leu Asn Leu Pro Ile Val Gln
            450                 455                 460

Ile Ile Trp Asn Asp Gly His Tyr Asp Met Val Lys Phe Gln Glu Glu
465                 470                 475                 480

Met Lys Tyr Gly Arg Ser Ala Ala Val Asp Phe Gly Tyr Val Asp Tyr
            485                 490                 495

Val Lys Tyr Ala Glu Ala Met Arg Ala Lys Gly Tyr Arg Ala His Ser
            500                 505                 510

Lys Glu Glu Leu Ala Glu Ile Leu Lys Ser Ile Pro Asp Thr Thr Gly
            515                 520                 525

Pro Val Val Ile Asp Val Pro Leu Asp Tyr Ser Asp Asn Ile Lys Leu
530                 535                 540

Ala Glu Lys Leu Leu Pro Glu Glu Phe Tyr
545                 550
```

<210> SEQ ID NO 6
<211> LENGTH: 3220
<212> TYPE: DNA
<213> ORGANISM: Lactococcus lactis

<400> SEQUENCE: 6

| | |
|---|---|
| tagatccgga aacaactgat tacctgagtt aacttagcag aaattgcaga agataacggt | 60 |
| aatttggatg aagcattaaa ttacctttat caaattccgg tgaatgatga aaattatatt | 120 |
| gctgctttaa tcaaaattgc tgacttatat caatttgaag ttgattttga aacagcaatt | 180 |
| tctaagttag aagaagcaag agaattatcg gattctcctc tgattacttt tgctttggct | 240 |
| gagtcctact ttgaacaagg tgattattca gctgccatta ccgaatatgc aaaactttca | 300 |
| gaacgaaaaa ttttacatga aacaaaaatt tctatttatc aaagaattgg tgactcttat | 360 |
| gcccaattag gtaattttga gaatgccata tcatttcttg aaaaatcact tgaatttgat | 420 |
| gaaaaaccgg aaaccttgta taaaattgct cttctttatg agaaactca taatgaaaca | 480 |
| agagccattg ctaatttcaa acggttagaa aaaatggatt tgaatttttt gaactatgaa | 540 |
| ttagcctatg cccaaaccct agaagctaat caagaattta agctgcact agaaatggca | 600 |
| aagaaaggga tgaaaaaaaa tcctaatgcc gttcctctct acacttcgc ttcaaaaatt | 660 |
| tgtttcaaac ttaaggacaa agctgcagca gaacgttatc tcgtggatgc tttaaattta | 720 |
| ccagaattac atgacgaaac agtctttttg cttgctaatt tatacttcaa cgaagaagat | 780 |
| tttgaagctg tcattaatct tgaagagctt ttagaagatg aacatttatt agctaaatgg | 840 |
| cttttttgcag gagcacataa agctttggaa atgattctg aagcggctgc tttgtatgaa | 900 |
| gaactcattc aaaccaatct gtcagagaat ccagagtttt tagaagacta tattgatttt | 960 |
| cttaaagaaa ttggtcaaat ttctaaaaca gaaccaatta ttgaacaata tttggaactt | 1020 |
| gttccagatg atgaaaatat gagaaattta ctgacagact aaaaaataa ttactgacaa | 1080 |
| agctgtcagt aattattttt attgtaagct agaaaattca aaaacttgcg tcaaaataat | 1140 |
| tgtaaaaggt tctattatct gataaaatga ttgtgaagta atccaagaga ttatgaaata | 1200 |
| tgaattagaa caaatagagg taaaataaaa aatgtctgag aaacaatttg gggcgaactt | 1260 |
| ggttgtcgat agtttgatta accataaagt gaagtatgta tttgggattc caggagcaaa | 1320 |
| aattgaccgg gttttttgatt tattagaaaa tgaagaaggc cctcaaatgg tcgtgactcg | 1380 |
| tcatgagcaa ggagctgctt tcatggctca agctgtcggt cgtttaactg gcgaacctgg | 1440 |
| tgtagtagtt gttacgagtg ggcctggtgt atcaaacctt gcgactccgc ttttgaccgc | 1500 |
| gacatcagaa ggtgatgcta ttttggctat cggtggacaa gttaaacgaa gtgaccgtct | 1560 |
| taaacgtgcg caccaatcaa tggataatgc tggaatgatg caatcagcaa caaaatattc | 1620 |
| agcagaagtt cttgacccta atacactttc tgaatcaatt gccaacgctt atcgtattgc | 1680 |
| aaaatcagga catccaggtg caactttctt atcaatcccc caagatgtaa cggatgccga | 1740 |
| agtatcaatc aaagccattc aaccactttc agaccctaaa atggggaatg cctctattga | 1800 |
| tgacattaat tatttagcac aagcaattaa aaatgctgta ttgccagtaa ttttggttgg | 1860 |
| agctggtgct tcagatgcta agtcgcttc atccttgcgt aatctattga ctcatgttaa | 1920 |
| tattcctgtc gttgaaacat ccaaggtgc agggtattt tcacatgatt tagaacatac | 1980 |
| tttttatgga cgtatcggtc ttttccgcaa tcaaccaggc gatatgcttc tgaaacgttc | 2040 |
| tgaccttgtt attgctgttg gttatgaccc aattgaatat gaagctcgta actggaatgc | 2100 |
| agaaattgat agtcgaatta tcgttattga taatgccatt gctgaaattg atacttacta | 2160 |

-continued

```
ccaaccagag cgtgaattaa ttggtgatat cgcagcaaca ttggataatc ttttaccagc   2220
tgttcgtggc tacaaaattc caaaaggaac aaaagattat ctcgatggcc ttcatgaagt   2280
tgctgagcaa cacgaatttg atactgaaaa tactgaagaa ggtagaatgc accctcttga   2340
tttggtcagc actttccaag aaatcgtcaa ggatgatgaa acagtaaccg ttgacgtagg   2400
ttcactctac atttggatgg cacgtcattt caaatcatac gaaccacgtc atctcctctt   2460
ctcaaacgga atgcaaacac tcggagttgc acttccttgg caattacag ccgcattgtt   2520 gcgcccaggt aaaaagttt attcacactc tggtgatgga ggcttccttt tcacagggca   2580
agaattggaa acagctgtac gtttgaatct tccaatcgtt caaattatct ggaatgacgg   2640
ccattatgat atggttaaat tccaagaaga aatgaaatat ggtcgttcag cagccgttga   2700
ttttggctat gttgattacg taaaatatgc tgaagcaatg agagcaaaag gttaccgtgc   2760
acacagcaaa gaagaacttg ctgaaattct caaatcaatc ccagatacta ctggaccggt   2820
ggtaattgac gttcctttgg actattctga taacattaaa ttagcagaaa aattattgcc   2880
tgaagagttt tattgattac aatcaagcaa tttgtggcat aacaaaataa agaagaagg    2940 ccttgaacac ctaagcgttc agggcctttt tttgtgaaat aaattagatg aaatttacaa   3000
tgagttttgt gaaactagct tctagtttgt gaaaaattgc ctataattgc cgaataaaaa   3060
tacccattta ccactccaag aggatgcttc aaattagcta atacccgtt ttagaggatg    3120 cgtaaaaaca acaaaagagg atgagtatag aacgataaaa cttttttatg ataggttgag   3180
agaattgaat ataaaatata ataagtagaa ggcagcaatt                          3220
```

<210> SEQ ID NO 7
<211> LENGTH: 491
<212> TYPE: PRT
<213> ORGANISM: Escherichia coli

<400> SEQUENCE: 7

```
Met Ala Asn Tyr Phe Asn Thr Leu Asn Leu Arg Gln Gln Leu Ala Gln
1               5                   10                  15

Leu Gly Lys Cys Arg Phe Met Gly Arg Asp Glu Phe Ala Asp Gly Ala
            20                  25                  30

Ser Tyr Leu Gln Gly Lys Lys Val Ile Val Gly Cys Gly Ala Gln
        35                  40                  45

Gly Leu Asn Gln Gly Leu Asn Met Arg Asp Ser Gly Leu Asp Ile Ser
    50                  55                  60

Tyr Ala Leu Arg Lys Glu Ala Ile Ala Glu Lys Arg Ala Ser Trp Arg
65                  70                  75                  80

Lys Ala Thr Glu Asn Gly Phe Lys Val Gly Thr Tyr Glu Glu Leu Ile
                85                  90                  95

Pro Gln Ala Asp Leu Val Ile Asn Leu Thr Pro Asp Lys Gln His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140

Lys Asp Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Gly Glu Gly Met Ala Ile Ala Lys
```

```
                180              185                  190
Ala Trp Ala Ala Thr Gly Gly His Arg Ala Gly Val Leu Glu Ser
            195                  200                 205
Ser Phe Val Ala Glu Val Lys Ser Asp Leu Met Gly Glu Gln Thr Ile
            210                  215                 220
Leu Cys Gly Met Leu Gln Ala Gly Ser Leu Leu Cys Phe Asp Lys Leu
225                  230                  235                 240
Val Glu Glu Gly Thr Asp Pro Ala Tyr Ala Glu Lys Leu Ile Gln Phe
                245                  250                 255
Gly Trp Glu Thr Ile Thr Glu Ala Leu Lys Gln Gly Gly Ile Thr Leu
                260                  265                 270
Met Met Asp Arg Leu Ser Asn Pro Ala Lys Leu Arg Ala Tyr Ala Leu
                275                  280                 285
Ser Glu Gln Leu Lys Glu Ile Met Ala Pro Leu Phe Gln Lys His Met
                290                  295                 300
Asp Asp Ile Ile Ser Gly Glu Phe Ser Ser Gly Met Met Ala Asp Trp
305                  310                  315                 320
Ala Asn Asp Asp Lys Lys Leu Leu Thr Trp Arg Glu Glu Thr Gly Lys
                325                  330                 335
Thr Ala Phe Glu Thr Ala Pro Gln Tyr Glu Gly Lys Ile Gly Glu Gln
                340                  345                 350
Glu Tyr Phe Asp Lys Gly Val Leu Met Ile Ala Met Val Lys Ala Gly
                355                  360                 365
Val Glu Leu Ala Phe Glu Thr Met Val Asp Ser Gly Ile Ile Glu Glu
            370                  375                 380
Ser Ala Tyr Tyr Glu Ser Leu His Glu Leu Pro Leu Ile Ala Asn Thr
385                  390                  395                 400
Ile Ala Arg Lys Arg Leu Tyr Glu Met Asn Val Ile Ser Asp Thr
                405                  410                 415
Ala Glu Tyr Gly Asn Tyr Leu Phe Ser Tyr Ala Cys Val Pro Leu Leu
                420                  425                 430
Lys Pro Phe Met Ala Glu Leu Gln Pro Gly Asp Leu Gly Lys Ala Ile
                435                  440                 445
Pro Glu Gly Ala Val Asp Asn Gly Gln Leu Arg Asp Val Asn Glu Ala
            450                  455                 460
Ile Arg Ser His Ala Ile Glu Gln Val Gly Lys Lys Leu Arg Gly Tyr
465                  470                  475                 480
Met Thr Asp Met Lys Arg Ile Ala Val Ala Gly
                485                  490

<210> SEQ ID NO 8
<211> LENGTH: 1476
<212> TYPE: DNA
<213> ORGANISM: Escherichia coli

<400> SEQUENCE: 8
atggctaact acttcaatac actgaatctg cgccagcagc tggcacagct gggcaaatgt      60
cgctttatgg ccgcgatga attcgccgat ggcgcgagct accttcaggg taaaaaagta     120
gtcatcgtcg gctgtggcgc acagggtctg aaccagggcc tgaacatgcg tgattctggt     180
ctcgatatct cctacgctct gcgtaaagaa gcgattgccg agaagcgcgc gtcctggcgt     240
aaagcgaccg aaaatggttt taaagtgggt acttacgaag aactgatccc acaggcggat     300
ctggtgatta acctgacgcc ggacaagcag cactctgatg tagtgcgcac cgtacagcca     360
```

-continued

```
ctgatgaaag acggcgcggc gctgggctac tcgcacggtt tcaacatcgt cgaagtgggc      420
gagcagatcc gtaaagatat caccgtagtg atggttgcgc cgaaatgccc aggcaccgaa      480
gtgcgtgaag agtacaaacg tgggttcggc gtaccgacgc tgattgccgt tcacccggaa      540
aacgatccga aggcgaagg catggcgatt gccaaagcct gggcggctgc aaccggtggt       600
caccgtgcgg gtgtgctgga atcgtccttc gttgcggaag tgaaatctga cctgatgggc      660
gagcaaacca tcctgtgcgg tatgttcag gctggctctc tgctgtgctt cgacaagctg       720
gtggaagaag gtaccgatcc agcatacgca gaaaaactga ttcagttcgg ttgggaaacc      780
atcaccgaag cactgaaaca gggcggcatc accctgatga tggaccgtct ctctaacccg      840
gcgaaactgc gtgcttatgc gctttctgaa cagctgaaag agatcatggc acccctgttc      900
cagaaacata tggacgacat catctccggc gaattctctt ccggtatgat ggcggactgg      960
gccaacgatg ataagaaact gctgacctgg cgtgaagaga ccggcaaaac cgcgtttgaa     1020
accgcgccgc agtatgaagg caaaatcggc gagcaggagt acttcgataa aggcgtactg     1080
atgattgcga tggtgaaagc gggcgttgaa ctggcgttcg aaaccatggt cgattccggc     1140
atcattgaag agtctgcata ttatgaatca ctgcacgagc tgccgctgat tgccaacacc     1200
atcgcccgta agcgtctgta cgaaatgaac gtggttatct ctgataccgc tgagtacggt     1260
aactatctgt ctcttacgc ttgtgtgccg ttgctgaaac cgtttatggc agagctgcaa      1320
ccgggcgacc tgggtaaagc tattccggaa ggcgcggtag ataacgggca actgcgtgat     1380
gtgaacgaag cgattcgcag ccatgcgatt gagcaggtag gtaagaaact gcgcggctat     1440
atgacagata tgaaacgtat tgctgttgcg ggttaa                               1476
```

<210> SEQ ID NO 9
<211> LENGTH: 395
<212> TYPE: PRT
<213> ORGANISM: Saccharomyces cerevisiae

<400> SEQUENCE: 9

```
Met Leu Arg Thr Gln Ala Ala Arg Leu Ile Cys Asn Ser Arg Val Ile
1               5                   10                  15

Thr Ala Lys Arg Thr Phe Ala Leu Ala Thr Arg Ala Ala Ala Tyr Ser
            20                  25                  30

Arg Pro Ala Ala Arg Phe Val Lys Pro Met Ile Thr Thr Arg Gly Leu
        35                  40                  45

Lys Gln Ile Asn Phe Gly Gly Thr Val Glu Thr Val Tyr Glu Arg Ala
    50                  55                  60

Asp Trp Pro Arg Glu Lys Leu Leu Asp Tyr Phe Lys Asn Asp Thr Phe
65                  70                  75                  80

Ala Leu Ile Gly Tyr Gly Ser Gln Gly Tyr Gly Gln Gly Leu Asn Leu
                85                  90                  95

Arg Asp Asn Gly Leu Asn Val Ile Ile Gly Val Arg Lys Asp Gly Ala
            100                 105                 110

Ser Trp Lys Ala Ala Ile Glu Asp Gly Trp Val Pro Gly Lys Asn Leu
        115                 120                 125

Phe Thr Val Glu Asp Ala Ile Lys Arg Gly Ser Tyr Val Met Asn Leu
    130                 135                 140

Leu Ser Asp Ala Ala Gln Ser Glu Thr Trp Pro Ala Ile Lys Pro Leu
145                 150                 155                 160

Leu Thr Lys Gly Lys Thr Leu Tyr Phe Ser His Gly Phe Ser Pro Val
                165                 170                 175
```

```
Phe Lys Asp Leu Thr His Val Glu Pro Pro Lys Asp Leu Asp Val Ile
                180                 185                 190
Leu Val Ala Pro Lys Gly Ser Gly Arg Thr Val Arg Ser Leu Phe Lys
            195                 200                 205
Glu Gly Arg Gly Ile Asn Ser Ser Tyr Ala Val Trp Asn Asp Val Thr
        210                 215                 220
Gly Lys Ala His Glu Lys Ala Gln Ala Leu Ala Val Ala Ile Gly Ser
225                 230                 235                 240
Gly Tyr Val Tyr Gln Thr Thr Phe Glu Arg Glu Val Asn Ser Asp Leu
                245                 250                 255
Tyr Gly Glu Arg Gly Cys Leu Met Gly Gly Ile His Gly Met Phe Leu
            260                 265                 270
Ala Gln Tyr Asp Val Leu Arg Glu Asn Gly His Ser Pro Ser Glu Ala
        275                 280                 285
Phe Asn Glu Thr Val Glu Glu Ala Thr Gln Ser Leu Tyr Pro Leu Ile
290                 295                 300
Gly Lys Tyr Gly Met Asp Tyr Met Tyr Asp Ala Cys Ser Thr Thr Ala
305                 310                 315                 320
Arg Arg Gly Ala Leu Asp Trp Tyr Pro Ile Phe Lys Asn Ala Leu Lys
                325                 330                 335
Pro Val Phe Gln Asp Leu Tyr Glu Ser Thr Lys Asn Gly Thr Glu Thr
            340                 345                 350
Lys Arg Ser Leu Glu Phe Asn Ser Gln Pro Asp Tyr Arg Glu Lys Leu
        355                 360                 365
Glu Lys Glu Leu Asp Thr Ile Arg Asn Met Glu Ile Trp Lys Val Gly
370                 375                 380
Lys Glu Val Arg Lys Leu Arg Pro Glu Asn Gln
385                 390                 395

<210> SEQ ID NO 10
<211> LENGTH: 1188
<212> TYPE: DNA
<213> ORGANISM: Saccharomyces cerevisiae

<400> SEQUENCE: 10
atgttgagaa ctcaagccgc cagattgatc tgcaactccc gtgtcatcac tgctaagaga      60
acctttgctt tggccacccg tgctgctgct tacagcagac cagctgcccg tttcgttaag     120
ccaatgatca ctacccgtgg tttgaagcaa atcaacttcg gtggtactgt tgaaaccgtc     180
tacgaaagag ctgactggcc aagagaaaag ttgttggact acttcaagaa cgacactttt     240
gctttgatcg gttacggttc ccaaggttac ggtcaaggtt tgaacttgag agacaacggt     300
ttgaacgtta tcattggtgt ccgtaaagat ggtgcttctt ggaaggctgc catcgaagac     360
ggttgggttc aggcaagaa cttgttcact gttgaagatg ctatcaagag aggtagttac     420
gttatgaact gttgtccga tgccgctcaa tcagaaacct ggcctgctat caagccattg     480
ttgaccaagg gtaagacttt gtacttctcc cacggtttct ccccagtctt caaggacttg     540
actcacgttg aaccaccaaa ggacttagat gttatcttgg ttgctccaaa gggttccggt     600
agaactgtca gatctttgtt caaggaaggt cgtggtatta actcttctta cgccgtctgg     660
aacgatgtca ccggtaaggc tcacgaaaag gcccaagctt tggccgttgc cattggttcc     720
ggttacgttt accaaaccac tttcgaagag aagtcaact ctgacttgta cggtgaaaga     780
ggttgtttaa tgggtggtat ccacggtatg ttccttggct caatacgacgt cttgagagaa     840 aacggtcact ccccatctga agctttcaac gaaaccgtcg aagaagctac ccaatctcta     900
```

```
tacccattga tcggtaagta cggtatggat tacatgtacg atgcttgttc caccaccgcc      960
agaagaggtg ctttggactg gtacccaatc ttcaagaatg ctttgaagcc tgttttccaa     1020
gacttgtacg aatctaccaa gaacggtacc gaaaccaaga gatctttgga attcaactct     1080
caacctgact acagagaaaa gctagaaaag gaattagaca ccatcagaaa catggaaatc     1140
tggaaggttg gtaaggaagt cagaaagttg agaccagaaa accaataa                  1188
```

<210> SEQ ID NO 11
<211> LENGTH: 330
<212> TYPE: PRT
<213> ORGANISM: Methanococcus maripaludis

<400> SEQUENCE: 11

```
Met Lys Val Phe Tyr Asp Ser Asp Phe Lys Leu Asp Ala Leu Lys Glu
1               5                   10                  15

Lys Thr Ile Ala Val Ile Gly Tyr Gly Ser Gln Gly Arg Ala Gln Ser
            20                  25                  30

Leu Asn Met Lys Asp Ser Gly Leu Asn Val Val Gly Leu Arg Lys
        35                  40                  45

Asn Gly Ala Ser Trp Asn Asn Ala Lys Ala Asp Gly His Asn Val Met
    50                  55                  60

Thr Ile Glu Glu Ala Ala Glu Lys Ala Asp Ile Ile His Ile Leu Ile
65                  70                  75                  80

Pro Asp Glu Leu Gln Ala Glu Val Tyr Glu Ser Gln Ile Lys Pro Tyr
                85                  90                  95

Leu Lys Glu Gly Lys Thr Leu Ser Phe Ser His Gly Phe Asn Ile His
            100                 105                 110

Tyr Gly Phe Ile Val Pro Pro Lys Gly Val Asn Val Val Leu Val Ala
        115                 120                 125

Pro Lys Ser Pro Gly Lys Met Val Arg Arg Thr Tyr Glu Glu Gly Phe
    130                 135                 140

Gly Val Pro Gly Leu Ile Cys Ile Glu Ile Asp Ala Thr Asn Asn Ala
145                 150                 155                 160

Phe Asp Ile Val Ser Ala Met Ala Lys Gly Ile Gly Leu Ser Arg Ala
                165                 170                 175

Gly Val Ile Gln Thr Thr Phe Lys Glu Glu Thr Glu Thr Asp Leu Phe
            180                 185                 190

Gly Glu Gln Ala Val Leu Cys Gly Gly Val Thr Glu Leu Ile Lys Ala
        195                 200                 205

Gly Phe Glu Thr Leu Val Glu Ala Gly Tyr Ala Pro Glu Met Ala Tyr
    210                 215                 220

Phe Glu Thr Cys His Glu Leu Lys Leu Ile Val Asp Leu Ile Tyr Gln
225                 230                 235                 240

Lys Gly Phe Lys Asn Met Trp Asn Asp Val Ser Asn Thr Ala Glu Tyr
                245                 250                 255

Gly Gly Leu Thr Arg Arg Ser Arg Ile Val Thr Ala Asp Ser Lys Ala
            260                 265                 270

Ala Met Lys Glu Ile Leu Arg Glu Ile Gln Asp Gly Arg Phe Thr Lys
        275                 280                 285

Glu Phe Leu Leu Glu Lys Gln Val Ser Tyr Ala His Leu Lys Ser Met
    290                 295                 300

Arg Arg Leu Glu Gly Asp Leu Gln Ile Glu Glu Val Gly Ala Lys Leu
305                 310                 315                 320
```

```
           Arg Lys Met Cys Gly Leu Glu Lys Glu Glu
                       325                 330
```

<210> SEQ ID NO 12
<211> LENGTH: 993
<212> TYPE: DNA
<213> ORGANISM: Methanococcus maripaludis

<400> SEQUENCE: 12

```
atgaaggtat tctatgactc agattttaaa ttagatgctt taaaagaaaa aacaattgca    60
gtaatcggtt atggaagtca aggtagggca cagtccttaa acatgaaaga cagcggatta   120
aacgttgttg ttggtttaag aaaaaacggt gcttcatgga caacgctaa agcagacggt    180
cacaatgtaa tgaccattga gaagctgct gaaaaagcgg acatcatcca catcttaata   240
cctgatgaat acaggcaga gtttatgaa agccagataa aaccataccta aaagaagga    300
aaaacactaa gcttttcaca tggttttaac atccactatg gattcattgt tccaccaaaa   360
ggagttaacg tggttttagt tgctccaaaa tcacctggaa aaatggttag aagaacatac   420
gaagaaggtt tcggtgttcc aggtttaatc tgtattgaaa ttgatgcaac aaacaacgca   480
tttgatattg tttcagcaat ggcaaaagga atcggtttat caagagctgg agttatccag   540
acaactttca agaagaaac agaaactgac cttttcggtg aacaagctgt tttatgcggt   600
ggagttaccg aattaatcaa ggcaggattt gaaacactcg ttgaagcagg atacgcacca   660
gaaatggcat actttgaaac ctgccacgaa ttgaaattaa tcgttgactt aatctaccaa   720
aaaggattca aaacatgtg gaacgatgta agtaacactg cagaatacgg cggacttaca   780
agaagaagca gaatcgttac agctgattca aaagctgcaa tgaaagaaat cttaagagaa   840
atccaagatg gaagattcac aaaagaattc cttctcgaaa acaggtaag ctatgctcat    900
ttaaaatcaa tgagaagact cgaaggagac ttacaaatcg aagaagtcgg cgcaaaatta   960
agaaaaatgt gcggtcttga aaagaagaa taa                                 993
```

<210> SEQ ID NO 13
<211> LENGTH: 342
<212> TYPE: PRT
<213> ORGANISM: Bacillus subtilis

<400> SEQUENCE: 13

```
Met Val Lys Val Tyr Tyr Asn Gly Asp Ile Lys Glu Asn Val Leu Ala
  1               5                  10                  15

Gly Lys Thr Val Ala Val Ile Gly Tyr Gly Ser Gln Gly His Ala His
                 20                  25                  30

Ala Leu Asn Leu Lys Glu Ser Gly Val Asp Val Ile Gly Val Arg
             35                  40                  45

Gln Gly Lys Ser Phe Thr Gln Ala Gln Glu Asp Gly His Lys Val Phe
         50                  55                  60

Ser Val Lys Glu Ala Ala Ala Gln Ala Glu Ile Ile Met Val Leu Leu
 65                  70                  75                  80

Pro Asp Glu Gln Gln Gln Lys Val Tyr Glu Ala Glu Ile Lys Asp Glu
                 85                  90                  95

Leu Thr Ala Gly Lys Ser Leu Val Phe Ala His Gly Phe Asn Val His
                100                 105                 110

Phe His Gln Ile Val Pro Pro Ala Asp Val Asp Val Phe Leu Val Ala
            115                 120                 125

Pro Lys Gly Pro Gly His Leu Val Arg Arg Thr Tyr Glu Gln Gly Ala
        130                 135                 140
```

Gly Val Pro Ala Leu Phe Ala Ile Tyr Gln Asp Val Thr Gly Glu Ala
145                 150                 155                 160

Arg Asp Lys Ala Leu Ala Tyr Ala Lys Gly Ile Gly Gly Ala Arg Ala
            165                 170                 175

Gly Val Leu Glu Thr Thr Phe Lys Glu Thr Glu Thr Asp Leu Phe
        180                 185                 190

Gly Glu Gln Ala Val Leu Cys Gly Leu Ser Ala Leu Val Lys Ala
        195                 200                 205

Gly Phe Glu Thr Leu Thr Glu Ala Gly Tyr Gln Pro Glu Leu Ala Tyr
        210                 215                 220

Phe Glu Cys Leu His Glu Leu Lys Leu Ile Val Asp Leu Met Tyr Glu
225                 230                 235                 240

Glu Gly Leu Ala Gly Met Arg Tyr Ser Ile Ser Asp Thr Ala Gln Trp
                245                 250                 255

Gly Asp Phe Val Ser Gly Pro Arg Val Val Asp Ala Lys Val Lys Glu
            260                 265                 270

Ser Met Lys Glu Val Leu Lys Asp Ile Gln Asn Gly Thr Phe Ala Lys
        275                 280                 285

Glu Trp Ile Val Glu Asn Gln Val Asn Arg Pro Arg Phe Asn Ala Ile
        290                 295                 300

Asn Ala Ser Glu Asn Glu His Gln Ile Glu Val Val Gly Arg Lys Leu
305                 310                 315                 320

Arg Glu Met Met Pro Phe Val Lys Gly Lys Lys Glu Ala Val
                325                 330                 335

Val Ser Val Ala Gln Asn
            340

<210> SEQ ID NO 14
<211> LENGTH: 1476
<212> TYPE: DNA
<213> ORGANISM: Bacillus subtilis

<400> SEQUENCE: 14
atggctaact acttcaatac actgaatctg cgccagcagc tggcacagct gggcaaatgt     60
cgctttatgg ccgcgatga attcgccgat ggcgcgagct accttcaggg taaaaaagta    120
gtcatcgtcg gctgtggcgc acagggtctg aaccagggcc tgaacatgcg tgattctggt    180
ctcgatatct cctacgctct gcgtaaagaa gcgattgccg agaagcgcgc gtcctggcgt    240
aaagcgaccg aaaatggttt taaagtgggt acttacgaag aactgatccc acaggcggat    300
ctggtgatta acctgacgcc ggacaagcag cactctgatg tagtgcgcac cgtacagcca    360
ctgatgaaag acggcgcggc gctgggctac tcgcacggtt tcaacatcgt cgaagtgggc    420
gagcagatcc gtaaagatat caccgtagtg atggttgcgc cgaaatgccc aggcaccgaa    480
gtgcgtgaag agtacaaacg tgggttcggc gtaccgacgc tgattgccgt tcacccggaa    540
aacgatccga aggcgaagg catggcgatt gccaaagcct gggcggctgc aaccggtggt    600
caccgtgcgg gtgtgctgga atcgtccttc gttgcggaag tgaaatctga cctgatgggc    660
gagcaaacca tcctgtgcgg tatgttgcag gctggctctc tgctgtgctt cgacaagctg    720
gtggaagaag gtaccgatcc agcatacgca gaaaaactga ttcagttcgg ttgggaaacc    780
atcaccgaag cactgaaaca gggcggcatc accctgatga tggaccgtct ctctaacccg    840
gcgaaactgc gtgcttatgc gctttctgaa cagctgaaag agatcatggc accccctgttc    900 cagaaaacata tggacgacat catctccggc gaattctctt ccggtatgat ggcggactgg    960

```
gccaacgatg ataagaaact gctgacctgg cgtgaagaga ccggcaaaac cgcgtttgaa    1020
accgcgccgc agtatgaagg caaaatcggc gagcaggagt acttcgataa aggcgtactg    1080
atgattgcga tggtgaaagc gggcgttgaa ctggcgttcg aaaccatggt cgattccggc    1140
atcattgaag agtctgcata ttatgaatca ctgcacgagc tgccgctgat tgccaacacc    1200
atcgcccgta agcgtctgta cgaaatgaac gtggttatct ctgataccgc tgagtacggt    1260
aactatctgt tctcttacgc ttgtgtgccg ttgctgaaac cgtttatggc agagctgcaa    1320
ccgggcgacc tgggtaaagc tattccggaa ggcgcggtag ataacgggca actgcgtgat    1380
gtgaacgaag cgattcgcag ccatgcgatt gagcaggtag gtaagaaact gcgcggctat    1440
atgacagata tgaaacgtat tgctgttgcg ggttaa                              1476
```

<210> SEQ ID NO 15
<211> LENGTH: 343
<212> TYPE: PRT
<213> ORGANISM: Anaerostipes caccae

<400> SEQUENCE: 15

```
Met Glu Glu Cys Lys Met Ala Lys Ile Tyr Tyr Gln Glu Asp Cys Asn
1               5                   10                  15

Leu Ser Leu Leu Asp Gly Lys Thr Ile Ala Val Ile Gly Tyr Gly Ser
            20                  25                  30

Gln Gly His Ala His Ala Leu Asn Ala Lys Glu Ser Gly Cys Asn Val
        35                  40                  45

Ile Ile Gly Leu Tyr Glu Gly Ala Lys Glu Trp Lys Arg Ala Glu Glu
    50                  55                  60

Gln Gly Phe Glu Val Tyr Thr Ala Ala Glu Ala Lys Lys Ala Asp
65                  70                  75                  80

Ile Ile Met Ile Leu Ile Asn Asp Glu Lys Gln Ala Thr Met Tyr Lys
                85                  90                  95

Asn Asp Ile Glu Pro Asn Leu Glu Ala Gly Asn Met Leu Met Phe Ala
            100                 105                 110

His Gly Phe Asn Ile His Phe Gly Cys Ile Val Pro Pro Lys Asp Val
        115                 120                 125

Asp Val Thr Met Ile Ala Pro Lys Gly Pro Gly His Thr Val Arg Ser
    130                 135                 140

Glu Tyr Glu Glu Gly Lys Gly Val Pro Cys Leu Val Ala Val Glu Gln
145                 150                 155                 160

Asp Ala Thr Gly Lys Ala Leu Asp Met Ala Leu Ala Tyr Ala Leu Ala
                165                 170                 175

Ile Gly Gly Ala Arg Ala Gly Val Leu Glu Thr Thr Phe Arg Thr Glu
            180                 185                 190

Thr Glu Thr Asp Leu Phe Gly Glu Gln Ala Val Leu Cys Gly Gly Val
        195                 200                 205

Cys Ala Leu Met Gln Ala Gly Phe Glu Thr Leu Val Glu Ala Gly Tyr
    210                 215                 220

Asp Pro Arg Asn Ala Tyr Phe Glu Cys Ile His Glu Met Lys Leu Ile
225                 230                 235                 240

Val Asp Leu Ile Tyr Gln Ser Gly Phe Ser Gly Met Arg Tyr Ser Ile
                245                 250                 255

Ser Asn Thr Ala Glu Tyr Gly Asp Tyr Ile Thr Gly Pro Lys Ile Ile
            260                 265                 270

Thr Glu Asp Thr Lys Lys Ala Met Lys Lys Ile Leu Ser Asp Ile Gln
```

```
                275                 280                 285
Asp Gly Thr Phe Ala Lys Asp Phe Leu Val Asp Met Ser Asp Ala Gly
        290                 295                 300
Ser Gln Val His Phe Lys Ala Met Arg Lys Leu Ala Ser Glu His Pro
305                 310                 315                 320
Ala Glu Val Val Gly Glu Ile Arg Ser Leu Tyr Ser Trp Ser Asp
                325                 330                 335
Glu Asp Lys Leu Ile Asn Asn
        340

<210> SEQ ID NO 16
<211> LENGTH: 343
<212> TYPE: PRT
<213> ORGANISM: Anaerostipes caccae

<400> SEQUENCE: 16

Met Glu Glu Cys Lys Met Ala Lys Ile Tyr Tyr Gln Glu Asp Cys Asn
1               5                   10                  15
Leu Ser Leu Leu Asp Gly Lys Thr Ile Ala Val Ile Gly Tyr Gly Ser
                20                  25                  30
Gln Gly His Ala His Ala Leu Asn Ala Lys Glu Ser Gly Cys Asn Val
            35                  40                  45
Ile Ile Gly Leu Tyr Glu Gly Ala Lys Asp Trp Lys Arg Ala Glu Glu
        50                  55                  60
Gln Gly Phe Glu Val Tyr Thr Ala Ala Glu Ala Lys Lys Ala Asp
65                  70                  75                  80
Ile Ile Met Ile Leu Ile Asn Asp Glu Lys Gln Ala Thr Met Tyr Lys
                85                  90                  95
Asn Asp Ile Glu Pro Asn Leu Glu Ala Gly Asn Met Leu Met Phe Ala
                100                 105                 110
His Gly Phe Asn Ile His Phe Gly Cys Ile Val Pro Pro Lys Asp Val
            115                 120                 125
Asp Val Thr Met Ile Ala Pro Lys Gly Pro Gly His Thr Val Arg Ser
        130                 135                 140
Glu Tyr Glu Glu Gly Lys Gly Val Pro Cys Leu Val Ala Val Glu Gln
145                 150                 155                 160
Asp Ala Thr Gly Lys Ala Leu Asp Met Ala Leu Ala Tyr Ala Leu Ala
                165                 170                 175
Ile Gly Gly Ala Arg Ala Gly Val Leu Glu Thr Thr Phe Arg Thr Glu
            180                 185                 190
Thr Glu Thr Asp Leu Phe Gly Glu Gln Ala Val Leu Cys Gly Gly Val
        195                 200                 205
Cys Ala Leu Met Gln Ala Gly Phe Glu Thr Leu Val Glu Ala Gly Tyr
210                 215                 220
Asp Pro Arg Asn Ala Tyr Phe Glu Cys Ile His Glu Met Lys Leu Ile
225                 230                 235                 240
Val Asp Leu Ile Tyr Gln Ser Gly Phe Ser Gly Met Arg Tyr Ser Ile
                245                 250                 255
Ser Asn Thr Ala Glu Tyr Gly Asp Tyr Ile Thr Gly Pro Lys Ile Ile
            260                 265                 270
Thr Glu Asp Thr Lys Lys Ala Met Lys Lys Ile Leu Ser Asp Ile Gln
        275                 280                 285
Asp Gly Thr Phe Ala Lys Asp Phe Leu Val Asp Met Ser Asp Ala Gly
        290                 295                 300
```

```
Ser Gln Val His Phe Lys Ala Met Arg Lys Leu Ala Ser Glu His Pro
305                 310                 315                 320

Ala Glu Val Val Gly Glu Ile Arg Ser Leu Tyr Ser Trp Ser Asp
                325                 330                 335

Glu Asp Lys Leu Ile Asn Asn
            340
```

<210> SEQ ID NO 17
<211> LENGTH: 616
<212> TYPE: PRT
<213> ORGANISM: Escherichia coli

<400> SEQUENCE: 17

```
Met Pro Lys Tyr Arg Ser Ala Thr Thr Thr His Gly Arg Asn Met Ala
1               5                   10                  15

Gly Ala Arg Ala Leu Trp Arg Ala Thr Gly Met Thr Asp Ala Asp Phe
            20                  25                  30

Gly Lys Pro Ile Ile Ala Val Val Asn Ser Phe Thr Gln Phe Val Pro
        35                  40                  45

Gly His Val His Leu Arg Asp Leu Gly Lys Leu Val Ala Glu Gln Ile
    50                  55                  60

Glu Ala Ala Gly Gly Val Ala Lys Glu Phe Asn Thr Ile Ala Val Asp
65                  70                  75                  80

Asp Gly Ile Ala Met Gly His Gly Gly Met Leu Tyr Ser Leu Pro Ser
                85                  90                  95

Arg Glu Leu Ile Ala Asp Ser Val Glu Tyr Met Val Asn Ala His Cys
            100                 105                 110

Ala Asp Ala Met Val Cys Ile Ser Asn Cys Asp Lys Ile Thr Pro Gly
        115                 120                 125

Met Leu Met Ala Ser Leu Arg Leu Asn Ile Pro Val Ile Phe Val Ser
    130                 135                 140

Gly Gly Pro Met Glu Ala Gly Lys Thr Lys Leu Ser Asp Gln Ile Ile
145                 150                 155                 160

Lys Leu Asp Leu Val Asp Ala Met Ile Gln Gly Ala Asp Pro Lys Val
                165                 170                 175

Ser Asp Ser Gln Ser Asp Gln Val Glu Arg Ser Ala Cys Pro Thr Cys
            180                 185                 190

Gly Ser Cys Ser Gly Met Phe Thr Ala Asn Ser Met Asn Cys Leu Thr
        195                 200                 205

Glu Ala Leu Gly Leu Ser Gln Pro Gly Asn Gly Ser Leu Leu Ala Thr
    210                 215                 220

His Ala Asp Arg Lys Gln Leu Phe Leu Asn Ala Gly Lys Arg Ile Val
225                 230                 235                 240

Glu Leu Thr Lys Arg Tyr Tyr Glu Gln Asn Asp Glu Ser Ala Leu Pro
                245                 250                 255

Arg Asn Ile Ala Ser Lys Ala Ala Phe Glu Asn Ala Met Thr Leu Asp
            260                 265                 270

Ile Ala Met Gly Gly Ser Thr Asn Thr Val Leu His Leu Leu Ala Ala
        275                 280                 285

Ala Gln Glu Ala Glu Ile Asp Phe Thr Met Ser Asp Ile Asp Lys Leu
    290                 295                 300

Ser Arg Lys Val Pro Gln Leu Cys Lys Val Ala Pro Ser Thr Gln Lys
305                 310                 315                 320

Tyr His Met Glu Asp Val His Arg Ala Gly Gly Val Ile Gly Ile Leu
                325                 330                 335
```

Gly Glu Leu Asp Arg Ala Gly Leu Leu Asn Arg Asp Val Lys Asn Val
            340                 345                 350

Leu Gly Leu Thr Leu Pro Gln Thr Leu Glu Gln Tyr Asp Val Met Leu
        355                 360                 365

Thr Gln Asp Asp Ala Val Lys Asn Met Phe Arg Ala Gly Pro Ala Gly
    370                 375                 380

Ile Arg Thr Thr Gln Ala Phe Ser Gln Asp Cys Arg Trp Asp Thr Leu
385                 390                 395                 400

Asp Asp Asp Arg Ala Asn Gly Cys Ile Arg Ser Leu Glu His Ala Tyr
                405                 410                 415

Ser Lys Asp Gly Gly Leu Ala Val Leu Tyr Gly Asn Phe Ala Glu Asn
            420                 425                 430

Gly Cys Ile Val Lys Thr Ala Gly Val Asp Asp Ser Ile Leu Lys Phe
        435                 440                 445

Thr Gly Pro Ala Lys Val Tyr Glu Ser Gln Asp Asp Ala Val Glu Ala
    450                 455                 460

Ile Leu Gly Gly Lys Val Val Ala Gly Asp Val Val Ile Arg Tyr
465                 470                 475                 480

Glu Gly Pro Lys Gly Gly Pro Gly Met Gln Glu Met Leu Tyr Pro Thr
                485                 490                 495

Ser Phe Leu Lys Ser Met Gly Leu Gly Lys Ala Cys Ala Leu Ile Thr
            500                 505                 510

Asp Gly Arg Phe Ser Gly Gly Thr Ser Gly Leu Ser Ile Gly His Val
        515                 520                 525

Ser Pro Glu Ala Ala Ser Gly Ser Ile Gly Leu Ile Glu Asp Gly
    530                 535                 540

Asp Leu Ile Ala Ile Asp Ile Pro Asn Arg Gly Ile Gln Leu Gln Val
545                 550                 555                 560

Ser Asp Ala Glu Leu Ala Ala Arg Arg Glu Ala Gln Asp Ala Arg Gly
                565                 570                 575

Asp Lys Ala Trp Thr Pro Lys Asn Arg Glu Arg Gln Val Ser Phe Ala
            580                 585                 590

Leu Arg Ala Tyr Ala Ser Leu Ala Thr Ser Ala Asp Lys Gly Ala Val
        595                 600                 605

Arg Asp Lys Ser Lys Leu Gly Gly
    610                 615

<210> SEQ ID NO 18
<211> LENGTH: 1851
<212> TYPE: DNA
<213> ORGANISM: Escherichia coli

<400> SEQUENCE: 18
atgcctaagt accgttccgc caccaccact catggtcgta atatggcggg tgctcgtgcg     60
ctgtggcgcg ccaccggaat gaccgacgcc gatttcggta agccgattat cgcggttgtg    120
aactcgttca cccaatttgt accgggtcac gtccatctgc gcgatctcgg taaactggtc    180
gccgaacaaa ttgaagcggc tggcggcgtt gccaaagagt tcaacaccat tgcggtggat    240
gatgggattg ccatgggcca cggggggatg ctttattcac tgcctatctcg cgaactgatc    300 gctgattccg ttgagtatat ggtcaacgcc cactgcgccg acgccatggt ctgcatctct    360
aactgcgaca aaatcacccc gggggatgctg atggcttccc tgcgcctgaa tattccggtg    420
atctttgttt ccggcggccc gatggaggcc gggaaaacca aactttccga tcagatcatc    480

```
aagctcgatc tggttgatgc gatgatccag ggcgcagacc cgaaagtatc tgactcccag    540
agcgatcagg ttgaacgttc cgcgtgtccg acctgcggtt cctgctccgg atgtttacc     600
gctaactcaa tgaactgcct gaccgaagcg ctgggcctgt cgcagccggg caacggctcg    660
ctgctggcaa cccacgccga ccgtaagcag ctgttcctta atgctggtaa acgcattgtt    720
gaattgacca aacgttatta cgagcaaaac gacgaaagtg cactgccgcg taatatcgcc    780
agtaaggcgg cgtttgaaaa cgccatgacg ctggatatcg cgatgggtgg atcgactaac    840
accgtacttc acctgctggc ggcggcgcag gaagcggaaa tcgacttcac catgagtgat    900
atcgataagc tttcccgcaa ggttccacag ctgtgtaaag ttgcgccgag cacccagaaa    960
taccatatgg aagatgttca ccgtgctggt ggtgttatcg gtattctcgg cgaactggat    1020
cgcgcggggt tactgaaccg tgatgtgaaa aacgtacttg gcctgacgtt gccgcaaacg    1080
ctggaacaat acgacgttat gctgacccag gatgacgcgg taaaaaatat gttccgcgca    1140
ggtcctgcag gcattcgtac cacacaggca ttctcgcaag attgccgttg ggatacgctg    1200
gacgacgatc gcgccaatgg ctgtatccgc tcgctggaac acgcctacag caaagacggc    1260
ggcctggcgg tgctctacgg taactttgcg gaaaacggct gcatcgtgaa acggcaggc    1320
gtcgatgaca gcatcctcaa attcaccggc ccggcgaaag tgtacgaaag ccaggacgat    1380
gcggtagaag cgattctcgg cggtaaagtt gtcgccggag atgtggtagt aattcgctat    1440
gaaggcccga aaggcggtcc ggggatgcag gaaatgctct acccaaccag cttcctgaaa    1500
tcaatgggtc tcggcaaagc ctgtgcgctg atcaccgacg tcgtttctc tggtggcacc     1560
tctggtcttt ccatcggcca cgtctcaccg gaagcggcaa gcggcggcag cattggcctg    1620
attgaagatg gtgacctgat cgctatcgac atcccgaacc gtggcattca gttacaggta    1680
agcgatgccg aactggcggc gcgtcgtgaa gcgcaggacg ctcgaggtga caaagcctgg    1740
acgccgaaaa atcgtgaacg tcaggtctcc tttgccctgc gtgcttatgc cagcctggca    1800
accagcgccg acaaaggcgc ggtgcgcgat aaatcgaaac tggggggtta a             1851
```

<210> SEQ ID NO 19
<211> LENGTH: 585
<212> TYPE: PRT
<213> ORGANISM: Saccharomyces cerevisiae

<400> SEQUENCE: 19

```
Met Gly Leu Leu Thr Lys Val Ala Thr Ser Arg Gln Phe Ser Thr Thr
1               5                   10                  15

Arg Cys Val Ala Lys Lys Leu Asn Lys Tyr Ser Tyr Ile Ile Thr Glu
            20                  25                  30

Pro Lys Gly Gln Gly Ala Ser Gln Ala Met Leu Tyr Ala Thr Gly Phe
        35                  40                  45

Lys Lys Glu Asp Phe Lys Lys Pro Gln Val Gly Val Gly Ser Cys Trp
    50                  55                  60

Trp Ser Gly Asn Pro Cys Asn Met His Leu Leu Asp Leu Asn Asn Arg
65                  70                  75                  80

Cys Ser Gln Ser Ile Glu Lys Ala Gly Leu Lys Ala Met Gln Phe Asn
                85                  90                  95

Thr Ile Gly Val Ser Asp Gly Ile Ser Met Gly Thr Lys Gly Met Arg
            100                 105                 110

Tyr Ser Leu Gln Ser Arg Glu Ile Ile Ala Asp Ser Phe Glu Thr Ile
        115                 120                 125

Met Met Ala Gln His Tyr Asp Ala Asn Ile Ala Ile Pro Ser Cys Asp
```

-continued

```
            130                 135                 140
Lys Asn Met Pro Gly Val Met Ala Met Gly Arg His Asn Arg Pro
145                 150                 155                 160

Ser Ile Met Val Tyr Gly Thr Ile Leu Pro Gly His Pro Thr Cys
                165                 170                 175

Gly Ser Ser Lys Ile Ser Lys Asn Ile Asp Ile Val Ser Ala Phe Gln
            180                 185                 190

Ser Tyr Gly Glu Tyr Ile Ser Lys Gln Phe Thr Glu Glu Arg Glu
                195                 200                 205

Asp Val Val Glu His Ala Cys Pro Gly Pro Ser Cys Gly Gly Met
            210                 215                 220

Tyr Thr Ala Asn Thr Met Ala Ser Ala Ala Glu Val Leu Gly Leu Thr
225                 230                 235                 240

Ile Pro Asn Ser Ser Phe Pro Ala Val Ser Lys Glu Lys Leu Ala
                245                 250                 255

Glu Cys Asp Asn Ile Gly Glu Tyr Ile Lys Lys Thr Met Glu Leu Gly
                260                 265                 270

Ile Leu Pro Arg Asp Ile Leu Thr Lys Glu Ala Phe Glu Asn Ala Ile
                275                 280                 285

Thr Tyr Val Val Ala Thr Gly Gly Ser Thr Asn Ala Val Leu His Leu
290                 295                 300

Val Ala Val Ala His Ser Ala Gly Val Lys Leu Ser Pro Asp Asp Phe
305                 310                 315                 320

Gln Arg Ile Ser Asp Thr Thr Pro Leu Ile Gly Asp Phe Lys Pro Ser
                325                 330                 335

Gly Lys Tyr Val Met Ala Asp Leu Ile Asn Val Gly Gly Thr Gln Ser
                340                 345                 350

Val Ile Lys Tyr Leu Tyr Glu Asn Asn Met Leu His Gly Asn Thr Met
                355                 360                 365

Thr Val Thr Gly Asp Thr Leu Ala Glu Arg Ala Lys Lys Ala Pro Ser
370                 375                 380

Leu Pro Glu Gly Gln Glu Ile Ile Lys Pro Leu Ser His Pro Ile Lys
385                 390                 395                 400

Ala Asn Gly His Leu Gln Ile Leu Tyr Gly Ser Leu Ala Pro Gly Gly
                405                 410                 415

Ala Val Gly Lys Ile Thr Gly Lys Glu Gly Thr Tyr Phe Lys Gly Arg
                420                 425                 430

Ala Arg Val Phe Glu Glu Gly Ala Phe Ile Glu Ala Leu Glu Arg
                435                 440                 445

Gly Glu Ile Lys Lys Gly Glu Lys Thr Val Val Ile Arg Tyr Glu
450                 455                 460

Gly Pro Arg Gly Ala Pro Gly Met Pro Glu Met Leu Lys Pro Ser Ser
465                 470                 475                 480

Ala Leu Met Gly Tyr Gly Leu Gly Lys Asp Val Ala Leu Leu Thr Asp
                485                 490                 495

Gly Arg Phe Ser Gly Gly Ser His Gly Phe Leu Ile Gly His Ile Val
                500                 505                 510

Pro Glu Ala Ala Glu Gly Gly Pro Ile Gly Leu Val Arg Asp Gly Asp
                515                 520                 525

Glu Ile Ile Ile Asp Ala Asp Asn Asn Lys Ile Asp Leu Leu Val Ser
530                 535                 540

Asp Lys Glu Met Ala Gln Arg Lys Gln Ser Trp Val Ala Pro Pro Pro
545                 550                 555                 560
```

Arg Tyr Thr Arg Gly Thr Leu Ser Lys Tyr Ala Lys Leu Val Ser Asn
                565                 570                 575

Ala Ser Asn Gly Cys Val Leu Asp Ala
            580                 585

<210> SEQ ID NO 20
<211> LENGTH: 1131
<212> TYPE: DNA
<213> ORGANISM: Saccharomyces cerevisiae

<400> SEQUENCE: 20

| | | |
|---|---|---|
| atgaccttgg caccoctaga cgcctccaaa gttaagataa ctaccacaca acatgcatct | 60 |
| aagccaaaac cgaacagtga gttagtgttt ggcaagagct tcacggacca catgttaact | 120 |
| gcggaatgga cagctgaaaa agggtggggt accccagaga ttaaacctta tcaaaatctg | 180 |
| tctttagacc cttccgcggt ggttttccat tatgcttttg agctattcga agggatgaag | 240 |
| gcttacagaa cggtggacaa caaaattaca atgtttcgtc cagatatgaa tatgaagcgc | 300 |
| atgaataagt ctgctcagag aatctgtttg ccaacgttcg acccagaaga gttgattacc | 360 |
| ctaattggga aactgatcca gcaagataag tgcttagttc ctgaaggaaa aggttactct | 420 |
| ttatatatca ggcctacatt aatcggcact acggccggtt taggggtttc cacgcctgat | 480 |
| agagccttgc tatatgtcat ttgctgccct gtgggtcctt attacaaaac tggatttaag | 540 |
| gcggtcagac tggaagccac tgattatgcc acaagagctt ggccaggagg ctgtggtgac | 600 |
| aagaaactag gtgcaaacta cgcccccctgc gtcctgccac aattgcaagc tgcttcaagg | 660 |
| ggttaccaac aaaatttatg gctatttggt ccaaataaca acattactga agtcggcacc | 720 |
| atgaatgctt ttttcgtgtt taaagatagt aaaacgggca agaaggaact agttactgct | 780 |
| ccactagacg gtaccatttt ggaaggtgtt actagggatt ccattttaaa tcttgctaaa | 840 |
| gaaagactcg aaccaagtga atggaccatt agtgaacgct acttcactat aggcgaagtt | 900 |
| actgagagat ccaagaacgg tgaactactt gaagcctttg gttctggtac tgctgcgatt | 960 |
| gtttctccca ttaaggaaat cggctggaaa ggcgaacaaa ttaatattcc gttgttgccc | 1020 |
| ggcgaacaaa ccggtccatt ggccaaagaa gttgcacaat ggattaatgg aatccaatat | 1080 |
| ggcgagactg agcatggcaa ttggtcaagg gttgttactg atttgaactg a | 1131 |

<210> SEQ ID NO 21
<211> LENGTH: 550
<212> TYPE: PRT
<213> ORGANISM: Methanococcus maripaludis

<400> SEQUENCE: 21

Met Ile Ser Asp Asn Val Lys Lys Gly Val Ile Arg Thr Pro Asn Arg
1               5                   10                  15

Ala Leu Leu Lys Ala Cys Gly Tyr Thr Asp Glu Asp Met Glu Lys Pro
            20                  25                  30

Phe Ile Gly Ile Val Asn Ser Phe Thr Glu Val Pro Gly His Ile
            35                  40                  45

His Leu Arg Thr Leu Ser Glu Ala Ala Lys His Gly Val Tyr Ala Asn
        50                  55                  60

Gly Gly Thr Pro Phe Glu Phe Asn Thr Ile Gly Ile Cys Asp Gly Ile
65                  70                  75                  80

Ala Met Gly His Glu Gly Met Lys Tyr Ser Leu Pro Ser Arg Glu Ile
                85                  90                  95

```
Ile Ala Asp Ala Val Glu Ser Met Ala Arg Ala His Gly Phe Asp Gly
                100                 105                 110

Leu Val Leu Ile Pro Thr Cys Asp Lys Ile Val Pro Gly Met Ile Met
            115                 120                 125

Gly Ala Leu Arg Leu Asn Ile Pro Phe Ile Val Thr Gly Gly Pro
130                 135                 140

Met Leu Pro Gly Glu Phe Gln Gly Lys Lys Tyr Glu Leu Ile Ser Leu
145                 150                 155                 160

Phe Glu Gly Val Gly Glu Tyr Gln Val Gly Lys Ile Thr Glu Glu
                165                 170                 175

Leu Lys Cys Ile Glu Asp Cys Ala Cys Ser Gly Ala Gly Ser Cys Ala
            180                 185                 190

Gly Leu Tyr Thr Ala Asn Ser Met Ala Cys Leu Thr Glu Ala Leu Gly
                195                 200                 205

Leu Ser Leu Pro Met Cys Ala Thr Thr His Ala Val Asp Ala Gln Lys
210                 215                 220

Val Arg Leu Ala Lys Lys Ser Gly Ser Lys Ile Val Asp Met Val Lys
225                 230                 235                 240

Glu Asp Leu Lys Pro Thr Asp Ile Leu Thr Lys Glu Ala Phe Glu Asn
                245                 250                 255

Ala Ile Leu Val Asp Leu Ala Leu Gly Gly Ser Thr Asn Thr Thr Leu
            260                 265                 270

His Ile Pro Ala Ile Ala Asn Glu Ile Glu Asn Lys Phe Ile Thr Leu
        275                 280                 285

Asp Asp Phe Asp Arg Leu Ser Asp Glu Val Pro His Ile Ala Ser Ile
290                 295                 300

Lys Pro Gly Gly Glu His Tyr Met Ile Asp Leu His Asn Ala Gly Gly
305                 310                 315                 320

Ile Pro Ala Val Leu Asn Val Leu Lys Glu Lys Ile Arg Asp Thr Lys
                325                 330                 335

Thr Val Asp Gly Arg Ser Ile Leu Glu Ile Ala Glu Ser Val Lys Tyr
            340                 345                 350

Ile Asn Tyr Asp Val Ile Arg Lys Val Glu Ala Pro Val His Glu Thr
            355                 360                 365

Ala Gly Leu Arg Val Leu Lys Gly Asn Leu Ala Pro Asn Gly Cys Val
370                 375                 380

Val Lys Ile Gly Ala Val His Pro Lys Met Tyr Lys His Asp Gly Pro
385                 390                 395                 400

Ala Lys Val Tyr Asn Ser Glu Asp Glu Ala Ile Ser Ala Ile Leu Gly
                405                 410                 415

Gly Lys Ile Val Glu Gly Asp Val Ile Val Ile Arg Tyr Glu Gly Pro
            420                 425                 430

Ser Gly Gly Pro Gly Met Arg Glu Met Leu Ser Pro Thr Ser Ala Ile
        435                 440                 445

Cys Gly Met Gly Leu Asp Asp Ser Val Ala Leu Ile Thr Asp Gly Arg
450                 455                 460

Phe Ser Gly Gly Ser Arg Gly Pro Cys Ile Gly His Val Ser Pro Glu
465                 470                 475                 480

Ala Ala Ala Gly Gly Val Ile Ala Ile Glu Asn Gly Asp Ile Ile
                485                 490                 495

Lys Ile Asp Met Ile Glu Lys Glu Ile Asn Val Asp Leu Asp Glu Ser
            500                 505                 510

Val Ile Lys Glu Arg Leu Ser Lys Leu Gly Glu Phe Glu Pro Lys Ile
```

```
              515                 520                 525
        Lys Lys Gly Tyr Leu Ser Arg Tyr Ser Lys Leu Val Ser Ser Ala Asp
                530                 535                 540

Glu Gly Ala Val Leu Lys
        545                 550
```

<210> SEQ ID NO 22
<211> LENGTH: 1653
<212> TYPE: DNA
<213> ORGANISM: Methanococcus maripaludis

<400> SEQUENCE: 22

```
atgataagtg ataacgtcaa aaagggagtt ataagaactc aaaccgagc tcttttaaag     60
gcttgcggat atacgacga agacatggaa aaccattta ttggaattgt aaacagcttt    120
acagaagttg ttcccggcca cattcactta agaacattat cagaagcggc taaacatggt    180
gtttatgcaa acgtggaac accatttgaa tttaatacca ttggaattttg cgacggtatt    240
gcaatgggcc acgaaggtat gaaatactct ttaccttcaa gagaaattat tgcagacgct    300
gttgaatcaa tggcaagagc acatggattt gatggtcttg ttttaattcc tacgtgtgat    360
aaaatcgttc ctggaatgat aatgggtgct ttaagactaa acattccatt tattgtagtt    420
actggaggac caatgcttcc cggagaattc caaggtaaaa aatacgaact tatcagcctt    480
tttgaaggtg tcggagaata ccaagttgga aaaattactg aagaagagtt aaagtgcatt    540
gaagactgtg catgttcagg tgctggaagt tgtgcagggc tttacactgc aaacagtatg    600
gcctgcctta cagaagcttt gggactctct cttccaatgt gtgcaacaac gcatgcagtt    660
gatgcccaaa aagttaggct tgctaaaaaa agtggctcaa aaattgttga tatggtaaaa    720
gaagacctaa aaccaacaga catattaaca aaagaagctt tgaaaatgc tattttagtt    780
gaccttgcac ttggtggatc aacaaacaca acattacaca ttcctgcaat gcaaatgaa    840
attgaaaata aattcataac tctcgatgac tttgacaggt taagcgatga agttccacac    900
attgcatcaa tcaaaccagg tggagaacac tacatgattg atttacacaa tgctggaggt    960
attcctgcgg tattgaacgt tttaaaagaa aaaattagag atacaaaaac agttgatgga   1020
agaagcattt tggaaatcgc agaatctgtt aaatacataa attacgacgt tataagaaaa   1080
gtggaagctc cggttcacga aactgctggt ttaagggttt taagggggaaa tcttgctcca   1140
aacggttgcg ttgtaaaaat cggtgcagta catccgaaaa tgtacaaaca cgatggacct   1200
gcaaaagttt acaattccga agatgaagca atttctgcga tacttggcgg aaaaattgta   1260
gaagggacg ttatagtaat cagatacgaa ggaccatcag gaggccctgg aatgagagaa   1320
atgctctccc caacttcagc aatctgtgga atgggtcttg atgacagcgt tgcattgatt   1380
actgatggaa gattcagtgg tggaagtagg ggcccatgta tcggacacgt ttctccagaa   1440
gctgcagctg gcggagtaat tgctgcaatt gaaacggggg atatcatcaa aatcgacatg   1500
attgaaaaag aaataaatgt tgatttagat gaatcagtca ttaaagaaag actctcaaaa   1560
ctgggagaat ttgagcctaa aatcaaaaaa ggctatttat caagatactc aaaacttgtc   1620
tcatctgctg acgaaggggc agttttaaaa taa                                1653
```

<210> SEQ ID NO 23
<211> LENGTH: 558
<212> TYPE: PRT
<213> ORGANISM: Bacillus subtilis

<400> SEQUENCE: 23

```
Met Ala Glu Leu Arg Ser Asn Met Ile Thr Gln Gly Ile Asp Arg Ala
1               5                  10                 15

Pro His Arg Ser Leu Leu Arg Ala Ala Gly Val Lys Glu Glu Asp Phe
            20                  25                 30

Gly Lys Pro Phe Ile Ala Val Cys Asn Ser Tyr Ile Asp Ile Val Pro
            35                  40                 45

Gly His Val His Leu Gln Glu Phe Gly Lys Ile Val Lys Glu Ala Ile
            50                  55                 60

Arg Glu Ala Gly Gly Val Pro Phe Glu Phe Asn Thr Ile Gly Val Asp
65                  70                  75                 80

Asp Gly Ile Ala Met Gly His Ile Gly Met Arg Tyr Ser Leu Pro Ser
                85                  90                 95

Arg Glu Ile Ile Ala Asp Ser Val Thr Val Val Ser Ala His Trp
                    100                 105                110

Phe Asp Gly Met Val Cys Ile Pro Asn Cys Asp Lys Ile Thr Pro Gly
            115                 120                 125

Met Leu Met Ala Ala Met Arg Ile Asn Ile Pro Thr Ile Phe Val Ser
    130                 135                 140

Gly Gly Pro Met Ala Ala Gly Arg Thr Ser Asp Gly Arg Lys Ile Ser
145                 150                 155                160

Leu Ser Ser Val Phe Glu Gly Val Gly Ala Tyr Gln Ala Gly Lys Ile
                165                 170                 175

Asn Glu Asn Glu Leu Gln Glu Leu Glu Gln Phe Gly Cys Pro Thr Cys
            180                 185                 190

Gly Ser Cys Ser Gly Met Phe Thr Ala Asn Ser Met Asn Cys Leu Ser
        195                 200                 205

Glu Ala Leu Gly Leu Ala Leu Pro Gly Asn Gly Thr Ile Leu Ala Thr
    210                 215                 220

Ser Pro Glu Arg Lys Glu Phe Val Arg Lys Ser Ala Ala Gln Leu Met
225                 230                 235                 240

Glu Thr Ile Arg Lys Asp Ile Lys Pro Arg Asp Ile Val Thr Val Lys
                245                 250                 255

Ala Ile Asp Asn Ala Phe Ala Leu Asp Met Ala Leu Gly Gly Ser Thr
            260                 265                 270

Asn Thr Val Leu His Thr Leu Ala Leu Ala Asn Glu Ala Gly Val Glu
        275                 280                 285

Tyr Ser Leu Glu Arg Ile Asn Glu Val Ala Glu Arg Val Pro His Leu
    290                 295                 300

Ala Lys Leu Ala Pro Ala Ser Asp Val Phe Ile Glu Asp Leu His Glu
305                 310                 315                 320

Ala Gly Gly Val Ser Ala Ala Leu Asn Glu Leu Ser Lys Lys Glu Gly
                325                 330                 335

Ala Leu His Leu Asp Ala Leu Thr Val Thr Gly Lys Thr Leu Gly Glu
        340                 345                 350

Thr Ile Ala Gly His Glu Val Lys Asp Tyr Asp Val Ile His Pro Leu
    355                 360                 365

Asp Gln Pro Phe Thr Glu Lys Gly Gly Leu Ala Val Leu Phe Gly Asn
    370                 375                 380

Leu Ala Pro Asp Gly Ala Ile Ile Lys Thr Gly Gly Val Gln Asn Gly
385                 390                 395                 400

Ile Thr Arg His Glu Gly Pro Ala Val Val Phe Asp Ser Gln Asp Glu
                405                 410                 415
```

```
Ala Leu Asp Gly Ile Ile Asn Arg Lys Val Lys Glu Gly Asp Val Val
            420                 425                 430

Ile Ile Arg Tyr Glu Gly Pro Lys Gly Gly Pro Gly Met Pro Glu Met
            435                 440                 445

Leu Ala Pro Thr Ser Gln Ile Val Gly Met Gly Leu Gly Pro Lys Val
        450                 455                 460

Ala Leu Ile Thr Asp Gly Arg Phe Ser Gly Ala Ser Arg Gly Leu Ser
465                 470                 475                 480

Ile Gly His Val Ser Pro Glu Ala Ala Glu Gly Pro Leu Ala Phe
                485                 490                 495

Val Glu Asn Gly Asp His Ile Ile Val Asp Ile Glu Lys Arg Ile Leu
            500                 505                 510

Asp Val Gln Val Pro Glu Glu Trp Glu Lys Arg Lys Ala Asn Trp
        515                 520                 525

Lys Gly Phe Glu Pro Lys Val Lys Thr Gly Tyr Leu Ala Arg Tyr Ser
        530                 535                 540

Lys Leu Val Thr Ser Ala Asn Thr Gly Gly Ile Met Lys Ile
545                 550                 555
```

<210> SEQ ID NO 24
<211> LENGTH: 1677
<212> TYPE: DNA
<213> ORGANISM: Bacillus subtilis

<400> SEQUENCE: 24

| | | | |
|---|---|---|---|
| atggcagaat tacgcagtaa tatgatcaca caaggaatcg atagagctcc gcaccgcagt | 60 |
| ttgcttcgtg cagcagggt aaaagaagag gatttcggca agccgtttat tgcggtgtgt | 120 |
| aattcataca ttgatatcgt tcccggtcat gttcacttgc aggagtttgg gaaaatcgta | 180 |
| aaagaagcaa tcagagaagc aggggggcgtt ccgtttgaat taataccat tggggtagat | 240 |
| gatggcatcg caatgggca tcggtatg agatattcgc tgccaagccg tgaaattatc | 300 |
| gcagactctg tggaaacggt tgtatccgca cactggtttg acggaatggt ctgtattccg | 360 |
| aactgcgaca aaatcacacc gggaatgctt atggcggcaa tgcgcatcaa cattccgacg | 420 |
| attttttgtca gcggcggacc gatggcggca ggaagaacaa gttacgggcg aaaaatctcc | 480 |
| ctttcctcag tattcgaagg ggtaggcgcc taccaagcag ggaaaatcaa cgaaaacgag | 540 |
| cttcaagaac tagagcagtt cggatgccca acgtgcgggt cttgctcagg catgtttacg | 600 |
| gcgaactcaa tgaactgtct gtcagaagca cttggtcttg ctttgccggg taatggaacc | 660 |
| attctggcaa catctccgga acgcaaagag tttgtgagaa aatcggctgc gcaattaatg | 720 |
| gaaacgattc gcaaagatat caaaccgcgt gatattgtta cagtaaaagc gattgataac | 780 |
| gcgtttgcac tcgatatggc gctcggaggt tctacaaata ccgttcttca tacccttgcc | 840 |
| cttgcaaacg aagccggcgt tgaatactct ttagaacgca ttaacgaagt cgctgagcgc | 900 |
| gtgccgcact ggctaagct ggcgcctgca tcggatgtgt ttattgaaga tcttcacgaa | 960 |
| gcgggcggcg tttcagcggc tctgaatgag ctttcgaaga agaaggagc gcttcattta | 1020 |
| gatgcgctga ctgttacagg aaaaactctt ggagaaacca ttgccggaca tgaagtaaag | 1080 |
| gattatgacg tcattcaccc gctggatcaa ccattcactg aaaagggagg ccttgctgtt | 1140 |
| ttattcggta atctagctcc ggacggcgct atcattaaaa caggcggcgt acagaatggg | 1200 |
| attacaagac acgaagggcc ggctgtcgta ttcgattctc aggacgaggc gcttgacggc | 1260 |
| attatcaacc gaaaagtaaa agaaggcgac gttgtcatca tcagatacga agggccaaaa | 1320 |

-continued

```
ggcggacctg gcatgccgga aatgctggcg ccaacatccc aaatcgttgg aatgggactc    1380
gggccaaaag tggcattgat tacgacgga cgttttccg gagcctcccg tggcctctca      1440
atcggccacg tatcacctga ggccgctgag ggcgggccgc ttgcctttgt tgaaaacgga    1500
gaccatatta tcgttgatat tgaaaaacgc atcttggatg tacaagtgcc agaagaagag    1560
tgggaaaaac gaaaagcgaa ctggaaaggt tttgaaccga aagtgaaaac cggctacctg    1620
gcacgttatt ctaaacttgt gacaagtgcc aacaccggcg gtattatgaa aatctag       1677
```

<210> SEQ ID NO 25
<211> LENGTH: 547
<212> TYPE: PRT
<213> ORGANISM: Lactococcus lactis

<400> SEQUENCE: 25

```
Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser Arg Glu Asp Met Lys Trp Ile Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Ile
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Asp Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Tyr
    130                 135                 140

Glu Ile Asp Arg Val Leu Ser Gln Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ala Leu Ser Leu Glu Lys Glu Ser Ser Thr Thr Asn Thr Thr Glu Gln
            180                 185                 190

Val Ile Leu Ser Lys Ile Glu Glu Ser Leu Lys Asn Ala Gln Lys Pro
        195                 200                 205

Val Val Ile Ala Gly His Glu Val Ile Ser Phe Gly Leu Glu Lys Thr
    210                 215                 220

Val Thr Gln Phe Val Ser Glu Thr Lys Leu Pro Ile Thr Thr Leu Asn
225                 230                 235                 240

Phe Gly Lys Ser Ala Val Asp Glu Ser Leu Pro Ser Phe Leu Gly Ile
                245                 250                 255

Tyr Asn Gly Lys Leu Ser Glu Ile Ser Leu Lys Asn Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asp Glu Asn Lys Met Ile Ser Leu Asn
    290                 295                 300

Ile Asp Glu Gly Ile Ile Phe Asn Lys Val Val Glu Asp Phe Asp Phe
305                 310                 315                 320
```

```
Arg Ala Val Val Ser Ser Leu Ser Glu Leu Lys Gly Ile Glu Tyr Glu
            325                 330                 335

Gly Gln Tyr Ile Asp Lys Gln Tyr Glu Glu Phe Ile Pro Ser Ser Ala
        340                 345                 350

Pro Leu Ser Gln Asp Arg Leu Trp Gln Ala Val Glu Ser Leu Thr Gln
    355                 360                 365

Ser Asn Glu Thr Ile Val Ala Glu Gln Gly Thr Ser Phe Phe Gly Ala
370                 375                 380

Ser Thr Ile Phe Leu Lys Ser Asn Ser Arg Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ser Ile Arg Glu Lys Leu Asn
        435                 440                 445

Pro Ile Cys Phe Ile Ile Asn Asn Asp Gly Tyr Thr Val Glu Arg Glu
    450                 455                 460

Ile His Gly Pro Thr Gln Ser Tyr Asn Asp Ile Pro Met Trp Asn Tyr
465                 470                 475                 480

Ser Lys Leu Pro Glu Thr Phe Gly Ala Thr Glu Asp Arg Val Val Ser
                485                 490                 495

Lys Ile Val Arg Thr Glu Asn Glu Phe Val Ser Val Met Lys Glu Ala
            500                 505                 510

Gln Ala Asp Val Asn Arg Met Tyr Trp Ile Glu Leu Val Leu Glu Lys
        515                 520                 525

Glu Asp Ala Pro Lys Leu Leu Lys Lys Met Gly Lys Leu Phe Ala Glu
    530                 535                 540

Gln Asn Lys
545

<210> SEQ ID NO 26
<211> LENGTH: 1828
<212> TYPE: DNA
<213> ORGANISM: Lactococcus lactis

<400> SEQUENCE: 26
tttaaataag tcaatatcgt tgacttattt agaagaaaga gttattcttt aaatgtcaag      60
ttagttgact aaattaaata taaaatatgg aggaatgtga tgtatacagt aggagattac     120
ctgttagacc gattacacga gttgggaatt gaagaaattt ttggagttcc tggtgactat     180
aacttacaat ttttagatca aattatttca cgcgaagata tgaaatggat tggaaatgct     240
aatgaattaa atgcttctta tatggctgat ggttatgctc gtactaaaaa agctgccgca     300
tttctcacca catttggagt cggcgaattg agtgcgatca atggactggc aggaagttat     360
gccgaaaatt taccagtagt agaaattgtt ggttcaccaa cttcaaaagt acaaatgac      420 ggaaaatttg tccatcatac actagcagat ggtgatttta acactttat gaagatgcat      480 gaacctgtta cagcagcgcg gactttactg acagcagaaa atgccacata tgaaattgac     540
cgagtacttt ctcaattact aaaagaaaga aaaccagtct atattaactt accagtcgat     600
gttgctgcag caaaagcaga gaagcctgca ttatctttag aaaagaaag ctctacaaca      660 aatacaactg aacaagtgat tttgagtaag attgaagaaa gtttgaaaaa tgcccaaaaa     720
ccagtagtga ttgcaggaca cgaagtaatt agttttggtt tagaaaaaac ggtaactcag     780
```

```
tttgtttcag aaacaaaact accgattacg acactaaatt ttggtaaaag tgctgttgat    840
gaatctttgc cctcattttt aggaatatat aacgggaaac tttcagaaat cagtcttaaa    900
aattttgtgg agtccgcaga ctttatccta atgcttggag tgaagcttac ggactcctca    960
acaggtgcat tcacacatca tttagatgaa aataaaatga tttcactaaa catagatgaa   1020
ggaataattt tcaataaagt ggtagaagat tttgatttta gagcagtggt ttcttcttta   1080
tcagaattaa aaggaataga atatgaagga caatatattg ataagcaata tgaagaattt   1140
attccatcaa gtgctccctt atcacaagac cgtctatggc aggcagttga agtttgact    1200 caaagcaatg aaacaatcgt tgctgaacaa ggaacctcat tttttggagc ttcaacaatt   1260
ttcttaaaat caaatagtcg ttttattgga caacctttat ggggttctat ggatatact    1320 tttccagcgg ctttaggaag ccaaattgcg gataaagaga gcagacacct tttatttatt   1380
ggtgatggtt cacttcaact taccgtacaa gaattaggac tatcaatcag agaaaaactc   1440
aatccaattt gttttatcat aaataatgat ggttatacag ttgaaagaga atccacgga    1500 cctactcaaa gttataacga cattccaatg tggaattact cgaaattacc agaaacattt   1560
ggagcaacag aagatcgtgt agtatcaaaa attgttagaa cagagaatga atttgtgtct   1620
gtcatgaaag aagcccaagc agatgtcaat agaatgtatt ggatagaact agttttggaa   1680
aaagaagatg cgccaaaatt actgaaaaaa atgggtaaat tatttgctga gcaaaataaa   1740
tagatatcaa cggatgatga aaagtaaaat agacaaagtc caataatttt ataaaaagta   1800
aaaacattag gattttccta atgttttt                                     1828
```

<210> SEQ ID NO 27
<211> LENGTH: 548
<212> TYPE: PRT
<213> ORGANISM: Lactococcus lactis

<400> SEQUENCE: 27

```
Met Tyr Thr Val Gly Asp Tyr Leu Leu Asp Arg Leu His Glu Leu Gly
 1               5                  10                  15

Ile Glu Glu Ile Phe Gly Val Pro Gly Asp Tyr Asn Leu Gln Phe Leu
            20                  25                  30

Asp Gln Ile Ile Ser His Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
           100                 105                 110

His Thr Leu Ala Asp Gly Asp Phe Lys His Phe Met Lys Met His Glu
       115                 120                 125

Pro Val Thr Ala Ala Arg Thr Leu Leu Thr Ala Glu Asn Ala Thr Val
   130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
               165                 170                 175

Ser Leu Pro Leu Lys Lys Glu Asn Ser Thr Ser Asn Thr Ser Asp Gln
```

```
                    180             185             190
Glu Ile Leu Asn Lys Ile Gln Glu Ser Leu Lys Asn Ala Lys Lys Pro
            195                 200                 205

Ile Val Ile Thr Gly His Glu Ile Ile Ser Phe Gly Leu Glu Lys Thr
            210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Thr Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
            275                 280                 285

Gly Ala Phe Thr His His Leu Asn Glu Asn Lys Met Ile Ser Leu Asn
            290                 295                 300

Ile Asp Glu Gly Lys Ile Phe Asn Glu Arg Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
            355                 360                 365

Ser Asn Glu Thr Ile Val Ala Glu Gln Gly Thr Ser Phe Phe Gly Ala
370                 375                 380

Ser Ser Ile Phe Leu Lys Ser Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ala Ile Arg Glu Lys Ile Asn
            435                 440                 445

Pro Ile Cys Phe Ile Ile Asn Asn Asp Gly Tyr Thr Val Glu Arg Glu
            450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Asp Arg Val Val Ser
                485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
            515                 520                 525

Glu Gly Ala Pro Lys Val Leu Lys Lys Met Gly Lys Leu Phe Ala Glu
            530                 535                 540

Gln Asn Lys Ser
545

<210> SEQ ID NO 28
<211> LENGTH: 1954
<212> TYPE: DNA
<213> ORGANISM: Lactococcus lactis

<400> SEQUENCE: 28
```

```
ctagagtttt ctttagtcat aattcactcc ttttattagt ctattatact tgataattca      60
aataagtcaa tatcgttgac ttatttaaag aaaagcgtta ttctataaat gtcaagttga     120
ttgaccaata tataataaaa tatggaggaa tgcgatgtat acagtaggag attacctatt    180
agaccgatta cacgagttag gaattgaaga aatttttgga gtccctggag actataactt    240
acaatttta gatcaaatta tttcccacaa ggatatgaaa tgggtcggaa atgctaatga    300
attaaatgct tcatatatgg ctgatggcta tgctcgtact aaaaaagctg ccgcatttct    360
tacaaccttt ggagtaggtg aattgagtgc agttaatgga ttagcaggaa gttacgccga    420
aaatttacca gtagtagaaa tagtgggatc acctacatca aaagttcaaa atgaaggaaa    480
atttgttcat catacgctgg ctgacggtga ttttaaacac tttatgaaaa tgcacgaacc    540
tgttacagca gctcgaactt tactgacagc agaaaatgca accgttgaaa ttgaccgagt    600
actttctgca ctattaaaag aaagaaaacc tgtctatatc aacttaccag ttgatgttgc    660
tgctgcaaaa gcagagaaac cctcactccc tttgaaaaag gaaaactcaa cttcaaatac    720
aagtgaccaa gaaattttga acaaaattca gaaagcttg aaaaatgcca aaaaccaat    780
cgtgattaca ggacatgaaa taattagttt tggcttagaa aaaacagtca ctcaatttat    840
ttcaaagaca aaactaccta ttacgacatt aaactttggt aaaagttcag ttgatgaagc    900
cctcccttca tttttaggaa tctataatgg tacactctca gagcctaatc ttaaagaatt    960
cgtggaatca gccgacttca tcttgatgct tggagttaaa ctcacagact cttcaacagg   1020
agccttcact catcatttaa atgaaaataa aatgatttca ctgaatatag atgaaggaaa   1080
aatatttaac gaaagaatcc aaaatttga ttttgaatcc ctcatctcct ctctcttaga   1140
cctaagcgaa atagaataca aggaaaata tatcgataaa aagcaagaag actttgttcc   1200
atcaaatgcg cttttatcac aagaccgcct atggcaagca gttgaaaacc taactcaaag   1260
caatgaaaca atcgttgctg aacaagggac atcattcttt ggcgcttcat caattttctt   1320
aaaatcaaag agtcattta ttggtcaacc cttatgggga tcaattggat atacattccc   1380
agcagcatta ggaagccaaa ttgcagataa agaaagcaga caccttttat ttattggtga   1440
tggttcactt caacttacag tgcaagaatt aggattagca atcagagaaa aaattaatcc   1500
aatttgcttt attatcaata atgatggtta tacagtcgaa agagaaattc atggaccaaa   1560
tcaaagctac aatgatattc caatgtggaa ttactcaaaa ttaccagaat cgttggagc   1620
aacagaagat cgagtagtct caaaaatcgt tagaactgaa aatgaatttg tgtctgtcat   1680
gaaagaagct caagcagatc caaatagaat gtactggatt gagttaattt tggcaaaaga   1740
aggtgcacca aagtactga aaaaatgggg caaactattt gctgaacaaa ataaatcata   1800
atttataaat agtaaaaaac attaggaaat acctaatgtt tttttgttga ctaaatcaat   1860
ccctctttat atagaaaacc ttagtttctc aaagacaact taattaagcc tgccaaattg   1920
gaactcgcaa atgtaatct atcctctgct ccta                                 1954
```

<210> SEQ ID NO 29
<211> LENGTH: 550
<212> TYPE: PRT
<213> ORGANISM: Salmonella typhimurium

<400> SEQUENCE: 29

```
Met Gln Asn Pro Tyr Thr Val Ala Asp Tyr Leu Leu Asp Arg Leu Ala
1               5                   10                  15

Gly Cys Gly Ile Gly His Leu Phe Gly Val Pro Gly Asp Tyr Asn Leu
            20                  25                  30
```

```
Gln Phe Leu Asp His Val Ile Asp His Pro Thr Leu Arg Trp Val Gly
         35                  40                  45

Cys Ala Asn Glu Leu Asn Ala Ala Tyr Ala Ala Asp Gly Tyr Ala Arg
 50                  55                  60

Met Ser Gly Ala Gly Leu Leu Thr Thr Phe Gly Val Gly Glu Leu
 65                  70                  75                  80

Ser Ala Ile Asn Gly Ile Ala Gly Ser Tyr Ala Glu Tyr Val Pro Val
                 85                  90                  95

Leu His Ile Val Gly Ala Pro Cys Ser Ala Ala Gln Gln Arg Gly Glu
                100                 105                 110

Leu Met His His Thr Leu Gly Asp Gly Asp Phe Arg His Phe Tyr Arg
        115                 120                 125

Met Ser Gln Ala Ile Ser Ala Ala Ser Ala Ile Leu Asp Glu Gln Asn
130                 135                 140

Ala Cys Phe Glu Ile Asp Arg Val Leu Gly Glu Met Leu Ala Ala Arg
145                 150                 155                 160

Arg Pro Gly Tyr Ile Met Leu Pro Ala Asp Val Ala Lys Lys Thr Ala
                165                 170                 175

Ile Pro Pro Thr Gln Ala Leu Ala Leu Pro Val His Glu Ala Gln Ser
                180                 185                 190

Gly Val Glu Thr Ala Phe Arg Tyr His Ala Arg Gln Cys Leu Met Asn
        195                 200                 205

Ser Arg Arg Ile Ala Leu Leu Ala Asp Phe Leu Ala Gly Arg Phe Gly
        210                 215                 220

Leu Arg Pro Leu Leu Gln Arg Trp Met Ala Glu Thr Pro Ile Ala His
225                 230                 235                 240

Ala Thr Leu Leu Met Gly Lys Gly Leu Phe Asp Glu Gln His Pro Asn
                245                 250                 255

Phe Val Gly Thr Tyr Ser Ala Gly Ala Ser Ser Lys Glu Val Arg Gln
                260                 265                 270

Ala Ile Glu Asp Ala Asp Arg Val Ile Cys Val Gly Thr Arg Phe Val
        275                 280                 285

Asp Thr Leu Thr Ala Gly Phe Thr Gln Gln Leu Pro Ala Glu Arg Thr
        290                 295                 300

Leu Glu Ile Gln Pro Tyr Ala Ser Arg Ile Gly Glu Thr Trp Phe Asn
305                 310                 315                 320

Leu Pro Met Ala Gln Ala Val Ser Thr Leu Arg Glu Leu Cys Leu Glu
                325                 330                 335

Cys Ala Phe Ala Pro Pro Thr Arg Ser Ala Gly Gln Pro Val Arg
                340                 345                 350

Ile Asp Lys Gly Glu Leu Thr Gln Glu Ser Phe Trp Gln Thr Leu Gln
                355                 360                 365

Gln Tyr Leu Lys Pro Gly Asp Ile Ile Leu Val Asp Gln Gly Thr Ala
        370                 375                 380

Ala Phe Gly Ala Ala Leu Ser Leu Pro Asp Gly Ala Glu Val Val
385                 390                 395                 400

Leu Gln Pro Leu Trp Gly Ser Ile Gly Tyr Ser Leu Pro Ala Ala Phe
                405                 410                 415

Gly Ala Gln Thr Ala Cys Pro Asp Arg Arg Val Ile Leu Ile Ile Gly
                420                 425                 430

Asp Gly Ala Ala Gln Leu Thr Ile Gln Glu Met Gly Ser Met Leu Arg
                435                 440                 445
```

| | | | | | | | | | | | |
|---|---|---|---|---|---|---|---|---|---|---|---|
|Asp|Gly|Gln|Ala|Pro|Val|Ile|Leu|Leu|Asn|Asn|Asp|Gly|Tyr|Thr|
| |450| | | |455| | | |460| | | | | |
|Val|Glu|Arg|Ala|Ile|His|Gly|Ala|Ala|Gln|Arg|Tyr|Asn|Asp|Ile|Ala|
|465| | | | |470| | | | |475| | | | |480|
|Ser|Trp|Asn|Trp|Thr|Gln|Ile|Pro|Pro|Ala|Leu|Asn|Ala|Ala|Gln|Gln|
| | | | |485| | | | |490| | | | |495| |
|Ala|Glu|Cys|Trp|Arg|Val|Thr|Gln|Ala|Ile|Gln|Leu|Ala|Glu|Val|Leu|
| | | |500| | | | |505| | | | |510| | |
|Glu|Arg|Leu|Ala|Arg|Pro|Gln|Arg|Leu|Ser|Phe|Ile|Glu|Val|Met|Leu|
| | | |515| | | | |520| | | | |525| | |
|Pro|Lys|Ala|Asp|Leu|Pro|Glu|Leu|Leu|Arg|Thr|Val|Thr|Arg|Ala|Leu|
| |530| | | | |535| | | | |540| | | | |
|Glu|Ala|Arg|Asn|Gly|Gly|
|545| | | |550| |

<210> SEQ ID NO 30
<211> LENGTH: 1653
<212> TYPE: DNA
<213> ORGANISM: Salmonella typhimurium

<400> SEQUENCE: 30

```
ttatccccg ttgcgggctt ccagcgcccg ggtcacggta cgcagtaatt ccggcagatc      60
ggcttttggc aacatcactt caataaatga cagacgttgt gggcgcgcca accgttcgag     120
gacctctgcc agttggatag cctgcgtcac ccgccagcac tccgcctgtt gcgccgcgtt     180
tagcgccggt ggtatctgcg tccagttcca gctcgcgatg tcgttatacc gctgggccgc     240
gccgtgaatg gcgcgctcta cggtatagcc gtcattgttg agcagcagga tgaccggcgc     300
ctgcccgtcg cgtaacatcg agcccatctc ctgaatcgtg agctgcgccg cgccatcgcc     360
gataatcaga atcacccgcc gatcgggaca ggcggtttgc gcgccaaacg cggcgggcaa     420
ggaatagccg atagacccc acagcggctg taacacaact tccgcgccgt caggaagcga     480
cagcgcggca gcgccaaaag ctgctgtccc ctggtcgaca aggataatat ctccgggttt     540
gagatactgc tgtaaggttt gccagaagct ttcctgggtc agttctcctt tatcaatccg     600
cactggctgt ccggcggaac gcgtcggcgg cggcgcaaaa gcgcattcca ggcacagttc     660
gcgcagcgta gacaccgcct gcgccatcgg gaggttgaac caggtttcgc cgatgcgcga     720
cgcgtaaggc tgaatctcca gcgtgcgttc cgccggtaat tgttgggtaa atccggccgt     780
aagggtatcg acaaaacggg tgccgacgca gataaccctc tcggcgtcct ctatggcctg     840
acgcacttct ttgctgctgg cgccagcgct ataggtgcca acgaagttcg ggtgctgttc     900
atcaaaaagc cccttcccca tcagtagtgt cgcatgagcg atgggcgttt ccgccatcca     960
gcgctgcaac agtggtcgta aaccaaaacg cccggcaaga agtcggcca atagcgcaat    1020
gcgccgactg ttcatcaggc actgacgggc gtgataacga aaggccgtct ccacgccgct    1080
ttgcgcttca tgcacgggca acgccagcgc ctgcgtaggt gggatggccg ttttttttcgc   1140
cacatcggcg ggcaacatga tgtatcctgg cctgcgtgcg gcaagcattt cacccaacac    1200
gcggtcaatc tcgaaacagg cgttctgttc atctaatatt gcgctggcag cggatatcgc    1260
ctgactcatg cgataaaaat gacgaaaatc gccgtcaccg agggtatggt gcatcaattc    1320
gccacgctgc tgcgcagcgc tacagggcgc gccgacgata tgcaagaccg ggacatattc    1380
cgcgtaactg cccgcgatac cgttaatagc gctaagttct cccacgccaa aggtggtgag    1440
tagcgctcca gcgcccgaca tgcgcgcata gccgtccgcg gcataagcgg cgttcagctc    1500
```

```
attggcgcat cccacccaac gcagggtcgg gtggtcaatc acatggtcaa gaaactgcaa    1560
gttataatcg cccggtacgc caaaaagatg gccaatgccg catcctgcca gtctgtccag    1620
caaatagtcg gccacggtat aggggttttg cat                                 1653
```

<210> SEQ ID NO 31
<211> LENGTH: 554
<212> TYPE: PRT
<213> ORGANISM: Clostridium acetobutylicum

<400> SEQUENCE: 31

```
Met Lys Ser Glu Tyr Thr Ile Gly Arg Tyr Leu Leu Asp Arg Leu Ser
1               5                   10                  15

Glu Leu Gly Ile Arg His Ile Phe Gly Val Pro Gly Asp Tyr Asn Leu
            20                  25                  30

Ser Phe Leu Asp Tyr Ile Met Glu Tyr Lys Gly Ile Asp Trp Val Gly
        35                  40                  45

Asn Cys Asn Glu Leu Asn Ala Gly Tyr Ala Ala Asp Gly Tyr Ala Arg
    50                  55                  60

Ile Asn Gly Ile Gly Ala Ile Leu Thr Thr Phe Gly Val Gly Glu Leu
65                  70                  75                  80

Ser Ala Ile Asn Ala Ile Ala Gly Ala Tyr Ala Glu Gln Val Pro Val
                85                  90                  95

Val Lys Ile Thr Gly Ile Pro Thr Ala Lys Val Arg Asp Asn Gly Leu
            100                 105                 110

Tyr Val His His Thr Leu Gly Asp Gly Arg Phe Asp His Phe Phe Glu
        115                 120                 125

Met Phe Arg Glu Val Thr Val Ala Glu Ala Leu Leu Ser Glu Glu Asn
    130                 135                 140

Ala Ala Gln Glu Ile Asp Arg Val Leu Ile Ser Cys Trp Arg Gln Lys
145                 150                 155                 160

Arg Pro Val Leu Ile Asn Leu Pro Ile Asp Val Tyr Asp Lys Pro Ile
                165                 170                 175

Asn Lys Pro Leu Lys Pro Leu Leu Asp Tyr Thr Ile Ser Ser Asn Lys
            180                 185                 190

Glu Ala Ala Cys Glu Phe Val Thr Glu Ile Val Pro Ile Ile Asn Arg
        195                 200                 205

Ala Lys Lys Pro Val Ile Leu Ala Asp Tyr Gly Val Tyr Arg Tyr Gln
    210                 215                 220

Val Gln His Val Leu Lys Asn Leu Ala Glu Lys Thr Gly Phe Pro Val
225                 230                 235                 240

Ala Thr Leu Ser Met Gly Lys Gly Val Phe Asn Glu Ala His Pro Gln
                245                 250                 255

Phe Ile Gly Val Tyr Asn Gly Asp Val Ser Ser Pro Tyr Leu Arg Gln
            260                 265                 270

Arg Val Asp Glu Ala Asp Cys Ile Ile Ser Val Gly Val Lys Leu Thr
        275                 280                 285

Asp Ser Thr Thr Gly Gly Phe Ser His Gly Phe Ser Lys Arg Asn Val
    290                 295                 300

Ile His Ile Asp Pro Phe Ser Ile Lys Ala Lys Gly Lys Lys Tyr Ala
305                 310                 315                 320

Pro Ile Thr Met Lys Asp Ala Leu Thr Glu Leu Thr Ser Lys Ile Glu
                325                 330                 335

His Arg Asn Phe Glu Asp Leu Asp Ile Lys Pro Tyr Lys Ser Asp Asn
            340                 345                 350
```

Gln Lys Tyr Phe Ala Lys Glu Lys Pro Ile Thr Gln Lys Arg Phe Phe
        355                 360                 365
Glu Arg Ile Ala His Phe Ile Lys Glu Lys Asp Val Leu Leu Ala Glu
    370                 375                 380
Gln Gly Thr Cys Phe Phe Gly Ala Ser Thr Ile Gln Leu Pro Lys Asp
385                 390                 395                 400
Ala Thr Phe Ile Gly Gln Pro Leu Trp Gly Ser Ile Gly Tyr Thr Leu
                405                 410                 415
Pro Ala Leu Leu Gly Ser Gln Leu Ala Asp Gln Lys Arg Arg Asn Ile
                420                 425                 430
Leu Leu Ile Gly Asp Gly Ala Phe Gln Met Thr Ala Gln Glu Ile Ser
            435                 440                 445
Thr Met Leu Arg Leu Gln Ile Lys Pro Ile Ile Phe Leu Ile Asn Asn
    450                 455                 460
Asp Gly Tyr Thr Ile Glu Arg Ala Ile His Gly Arg Glu Gln Val Tyr
465                 470                 475                 480
Asn Asn Ile Gln Met Trp Arg Tyr His Asn Val Pro Lys Val Leu Gly
                485                 490                 495
Pro Lys Glu Cys Ser Leu Thr Phe Lys Val Gln Ser Gly Thr Glu Leu
                500                 505                 510
Glu Lys Ala Leu Leu Val Ala Asp Lys Asp Cys Glu His Leu Ile Phe
            515                 520                 525
Ile Glu Val Val Met Asp Arg Tyr Asp Lys Pro Glu Pro Leu Glu Arg
    530                 535                 540
Leu Ser Lys Arg Phe Ala Asn Gln Asn Asn
545                 550

<210> SEQ ID NO 32
<211> LENGTH: 1665
<212> TYPE: DNA
<213> ORGANISM: Clostridium acetobutylicum

<400> SEQUENCE: 32
ttgaagagtg aatacacaat tggaagatat ttgttagacc gtttatcaga gttgggtatt      60
cggcatatct ttggtgtacc tggagattac aatctatcct ttttagacta tataatggag     120
tacaaaggga tagattgggt tggaaattgc aatgaattga atgctgggta tgctgctgat     180
ggatatgcaa gaataaatgg aattggagcc atacttacaa catttggtgt ggagaatta      240 agtgccatta cgcaattgc tggggcatac gctgagcaag ttccagttgt taaaattaca      300
ggtatcccca cagcaaaagt tagggacaat ggattatatg tacaccacac attaggtgac     360
ggaaggtttg atcactttt tgaaatgttt agagaagtaa cagttgctga ggcattacta     420
agcgaagaaa atgcagcaca agaaattgat cgtgttctta tttcatgctg agacaaaaa     480 cgtcctgttc ttataaattt accgattgat gtatatgata aaccaattaa caaaccatta     540
aagccattac tcgattatac tatttcaagt aacaaagagg ctgcatgtga atttgttaca     600
gaaatagtac ctataataaa tagggcaaaa aagcctgtta ttcttgcaga ttatggagta     660
tatcgttacc aagttcaaca tgtgcttaaa aacttggccg aaaaaaccgg atttcctgtg     720
gctacactaa gtatgggaaa aggtgttttc aatgaagcac accctcaatt tattggtgtt     780
tataatggtg atgtaagttc tccttattta aggcagcgag ttgatgaagc agactgcatt     840
attagcgttg gtgtaaaatt gacgattca accacagggg gatttctca tggatttct      900 aaaaggaatg taattcacat tgatcctttt tcaataaagg caaaaggtaa aaaatatgca     960

```
cctattacga tgaaagatgc tttaacagaa ttaacaagta aaattgagca tagaaacttt    1020
gaggatttag atataaagcc ttacaaatca gataatcaaa agtattttgc aaaagagaag    1080
ccaattacac aaaaacgttt ttttgagcgt attgctcact ttataaaaga aaaagatgta    1140
ttattagcag aacagggtac atgctttttt ggtgcgtcaa ccatacaact acccaaagat    1200
gcaactttta ttggtcaacc tttatgggga tctattggat acacacttcc tgctttatta    1260
ggttcacaat tagctgatca aaaaaggcgt aatattcttt taattgggga tggtgcattt    1320
caaatgacag cacaagaaat ttcaacaatg cttcgtttac aaatcaaacc tattattttt    1380
ttaattaata cgatggtta tacaattgaa cgtgctattc atggtagaga caagtatat    1440 aacaatattc aaatgtggcg atatcataat gttccaaagg ttttaggtcc taaagaatgc    1500
agcttaacct ttaaagtaca agtgaaact gaacttgaaa aggctctttt agtggcagat    1560
aaggattgtg aacatttgat ttttatagaa gttgttatgg atcgttatga taaacccgag    1620
cctttagaac gtctttcgaa acgttttgca aatcaaaata attag                   1665
```

<210> SEQ ID NO 33  
<211> LENGTH: 1641  
<212> TYPE: DNA  
<213> ORGANISM: Clostridium acetobutylicum

<400> SEQUENCE: 33

```
atgaaacaac gtatcgggca atacttgatc gatgccctac acgttaatgg tgtcgataag    60
atctttggag tcccaggtga tttcacttta gccttttttgg acgatatcat aagacatgac    120
aacgtggaat gggtgggaaa tactaatgag ttgaacgccg cttacgccgc tgatggttac    180
gctagagtta atggattagc cgctgtatct accactttg gggttggcga gttatctgct    240
gtgaatggta ttgctggaag ttacgcagag cgtgttcctg taatcaaaat ctcaggcggt    300
ccttcatcag ttgctcaaca gagggtaga tatgtccacc attcattggg tgaaggaatc    360
tttgattcat attcaaagat gtacgctcac ataaccgcaa caactacaat cttatccgtt    420
gacaacgcag tcgacgaaat tgatagagtt attcattgtg ctttgaagga aaagaggcca    480
gtgcatattc atttgcctat tgacgtagcc ttaactgaga ttgaaatccc tcatgcacca    540
aaagtttaca cacacgaatc ccagaacgtc gatgcttaca ttcaagctgt tgagaaaaag    600
ttaatgtctg caaaacaacc agtaatcata gcaggtcatg aaatcaattc attcaagttg    660
cacgaacaac tggaacagtt tgtcaatcag acaaacatcc ctgttgcaca actttccttg    720
ggtaagtctg ctttcaatga agagaatgaa cattaccttg gtatctacga tggcaaaatc    780
gcaaaggaaa atgtgagaga gtacgtcgac aatgctgatg tcatattgaa cataggtgcc    840
aaactgactg attctgctac agctggattt tcctacaagt tcgatacaaa aacataatc    900 tacattaacc ataatgactt caaagctgaa gatgtgattt ctgataatgt ttcactgatt    960
gatcttgtga tggcctgaa ttctattgac tatagaaatg aaacacacta cccatcttat    1020
caaagatctg atatgaaata cgaattgaat gacgcaccac ttacacaatc taactatttc    1080
aaaatgatga acgcttttct agaaaaagat gacatcctac tagctgaaca aggtacatcc    1140 ttttttcggcg catatgactt atccctatac aagggaaatc agtttatcgg tcagccttta    1200
tgggggtcaa tagggtatac ttttccatct ttactaggaa gtcaactagc agacatgcat    1260
aggagaaaca ttttgcttat aggcgatggt agtttacaac ttactgttca agccctaagt    1320
acaatgatta gaaaggatat caaaccaatc atttttcgtta tcaataacga cggttacacc    1380
```

```
gtcgaaagac ttatccacgg catggaagag ccatacaatg atatccaaat gtggaactac      1440
aagcaattgc cagaagtatt tggtggaaaa gatactgtaa aagttcatga tgctaaaacc      1500
tccaacgaac tgaaaactgt aatggattct gttaaagcag acaagatca catgcatttc       1560 attgaagtgc atatggcagt agaggacgcc ccaaagaagt tgattgatat agctaaagcc      1620
tttagtgatg ctaacaagta a                                                1641

<210> SEQ ID NO 34
<211> LENGTH: 1647
<212> TYPE: DNA
<213> ORGANISM: Listeria grayi

<400> SEQUENCE: 34
atgtacaccg tcggccaata cttagtagac cgcttagaag agatcggcat cgataaggtt       60
tttggtgtcc cgggtgacta caacctgacc tttttggact acatccagaa ccacgaaggt      120
ctgagctggc aagtaatac gaatgaactg aatgccgcgt acgcagctga tggctatgct       180
cgtgaacgcg gtgttagcgc tttggtcacg accttcggcg ttggtgagct gtccgcaatc      240
aatggcaccg caggtagctt cgcggagcaa gttccggtga ttcatatcgt gggcagcccg      300
accatgaatg ttcagagcaa caagaaactg gttcatcaca gcctgggtat gggcaacttt      360
cacaacttca gcgagatggc gaaagaagtc accgccgcaa ccacgatgct gacggaagag      420
aatgcggcgt cggagattga tcgtgttctg gaaaccgccc tgctggagaa cgcccagtg       480 tacatcaatc tgccgatcga cattgctcac aaggcgatcg tcaagccggc gaaagccctg      540
caaaccgaga gagctctgg cgagcgtgag gcacaactgg cggagatcat tctgagccat       600
ctggagaagg ctgcacagcc gattgtgatt gcgggtcacg agatcgcgcg cttccagatc      660
cgtgagcgtt tcgagaattg gattaatcaa acgaaactgc cggtgaccaa tctggcctac      720
ggcaagggta gcttcaacga agaaaacgag catttcattg gtacctatta tcctgcattt      780
agcgataaga acgtgctgga ctacgtggat aactccgact ttgtcctgca ctttggtggt      840
aaaatcattg ataacagcac ctccagcttc tcccaaggct tcaaaaccga aacaccctg       900 actgcggcga acgatatcat tatgctgccg gacggtagca cgtattctgg tattagcctg      960
aatggcctgc tggccgagct ggaaaaactg aatttcacgt ttgccgacac cgcagcaaag     1020
caggcggagt tggcggtgtt tgagccgcag gctgaaaccc cgttgaaaca ggaccgtttt     1080
caccaggcgg tgatgaattt tctgcaagct gacgatgtcc tggttacgga acagggcacc     1140 tcttctttg gcttgatgct ggcgcctctg aaaaagggta tgaacttgat ctcgcaaacg      1200
ctgtggggta gcattggtta cacgttgccg gcgatgattg gtagccaaat tgcggcaccg     1260
gagcgtcgtc atatcctgag cattggtgat ggtagctttc agctgactgc gcaggaaatg     1320
agcaccattt ccgtgagaa actgaccca gtcatcttca tcattaacaa tgatggctat       1380
accgttgagc gtgcgatcca tggcgaagat gaaagctata cgacattcc gacgtggaac      1440 ttgcaactgg tggcggaaac cttcggtggt gacgccgaaa ccgtcgacac tcacaatgtg     1500
ttcacggaga ctgatttcgc caacaccctg gcggcaattg acgcgacgcc gcagaaagca     1560
cacgttgtgg aagttcacat ggaacaaatg gatatgccgg agagcctgcg ccagatcggt     1620
ctggcactgt ccaagcagaa tagctaa                                         1647

<210> SEQ ID NO 35
<211> LENGTH: 312
<212> TYPE: PRT
<213> ORGANISM: Saccharomyces cerevisiae
```

<400> SEQUENCE: 35

```
Met Pro Ala Thr Leu Lys Asn Ser Ser Ala Thr Leu Lys Leu Asn Thr
1               5                   10                  15
Gly Ala Ser Ile Pro Val Leu Gly Phe Gly Thr Trp Arg Ser Val Asp
            20                  25                  30
Asn Asn Gly Tyr His Ser Val Ile Ala Ala Leu Lys Ala Gly Tyr Arg
        35                  40                  45
His Ile Asp Ala Ala Ile Tyr Leu Asn Glu Glu Glu Val Gly Arg
    50                  55                  60
Ala Ile Lys Asp Ser Gly Val Pro Arg Glu Glu Ile Phe Ile Thr Thr
65                  70                  75                  80
Lys Leu Trp Gly Thr Glu Gln Arg Asp Pro Glu Ala Ala Leu Asn Lys
                85                  90                  95
Ser Leu Lys Arg Leu Gly Leu Asp Tyr Val Asp Leu Tyr Leu Met His
            100                 105                 110
Trp Pro Val Pro Leu Lys Thr Asp Arg Val Thr Asp Gly Asn Val Leu
        115                 120                 125
Cys Ile Pro Thr Leu Glu Asp Gly Thr Val Asp Ile Asp Thr Lys Glu
    130                 135                 140
Trp Asn Phe Ile Lys Thr Trp Glu Leu Met Gln Glu Leu Pro Lys Thr
145                 150                 155                 160
Gly Lys Thr Lys Ala Val Gly Val Ser Asn Phe Ser Ile Asn Asn Ile
                165                 170                 175
Lys Glu Leu Leu Glu Ser Pro Asn Asn Lys Val Val Pro Ala Thr Asn
            180                 185                 190
Gln Ile Glu Ile His Pro Leu Leu Pro Gln Asp Glu Leu Ile Ala Phe
        195                 200                 205
Cys Lys Glu Lys Gly Ile Val Val Glu Ala Tyr Ser Pro Phe Gly Ser
    210                 215                 220
Ala Asn Ala Pro Leu Leu Lys Glu Gln Ala Ile Ile Asp Met Ala Lys
225                 230                 235                 240
Lys His Gly Val Glu Pro Ala Gln Leu Ile Ile Ser Trp Ser Ile Gln
                245                 250                 255
Arg Gly Tyr Val Val Leu Ala Lys Ser Val Asn Pro Glu Arg Ile Val
            260                 265                 270
Ser Asn Phe Lys Ile Phe Thr Leu Pro Glu Asp Asp Phe Lys Thr Ile
        275                 280                 285
Ser Asn Leu Ser Lys Val His Gly Thr Lys Arg Val Val Asp Met Lys
    290                 295                 300
Trp Gly Ser Phe Pro Ile Phe Gln
305                 310
```

<210> SEQ ID NO 36
<211> LENGTH: 939
<212> TYPE: DNA
<213> ORGANISM: Saccharomyces cerevisiae

<400> SEQUENCE: 36

```
atgcctgcta cgttaaagaa ttcttctgct acattaaaac taaatactgg tgcctccatt      60
ccagtgttgg gtttcggcac ttggcgttcc gttgacaata acggttacca ttctgtaatt     120
gcagctttga aagctggata cagacacatt gatgctgcgg ctatctattt gaatgaagaa     180
gaagttggca gggctattaa agattccgga gtccctcgtg aggaaatttt tattactact     240
```

```
aagctttggg gtacggaaca acgtgatccg gaagctgctc taaacaagtc tttgaaaaga    300
ctaggcttgg attatgttga cctatatctg atgcattggc cagtgccttt gaaaaccgac    360
agagttactg atggtaacgt tctgtgcatt ccaacattag aagatggcac tgttgacatc    420
gatactaagg aatggaattt tatcaagacg tgggagttga tgcaagagtt gccaagacg     480
ggcaaaacta agccgttggt tgtctctaat ttttctatta acaacattaa agaattatta    540
gaatctccaa ataacaaggt ggtaccagct actaatcaaa ttgaaattca tccattgcta    600
ccacaagacg aattgattgc cttttgtaag gaaaagggta ttgttgttga agcctactca    660
ccatttggga gtgctaatgc tcctttacta aagagcaag caattattga tatggctaaa    720
aagcacggcg ttgagccagc acagcttatt atcagttgga gtattcaaag aggctacgtt    780
gttctggcca aatcggttaa tcctgaaaga attgtatcca atttaagat tttcactctg     840
cctgaggatg atttcaagac tattagtaac ctatccaaag tgcatggtac aaagagagtc    900
gttgatatga agtggggatc cttcccaatt ttccaatga                           939
```

```
<210> SEQ ID NO 37
<211> LENGTH: 360
<212> TYPE: PRT
<213> ORGANISM: Saccharomyces cerevisiae

<400> SEQUENCE: 37

Met Ser Tyr Pro Glu Lys Phe Glu Gly Ile Ala Ile Gln Ser His Glu
1               5                   10                  15

Asp Trp Lys Asn Pro Lys Lys Thr Lys Tyr Asp Pro Lys Pro Phe Tyr
            20                  25                  30

Asp His Asp Ile Asp Ile Lys Ile Glu Ala Cys Gly Val Cys Gly Ser
        35                  40                  45

Asp Ile His Cys Ala Ala Gly His Trp Gly Asn Met Lys Met Pro Leu
    50                  55                  60

Val Val Gly His Glu Ile Val Gly Lys Val Val Lys Leu Gly Pro Lys
65                  70                  75                  80

Ser Asn Ser Gly Leu Lys Val Gly Gln Arg Val Gly Val Gly Ala Gln
                85                  90                  95

Val Phe Ser Cys Leu Glu Cys Asp Arg Cys Lys Asn Asp Asn Glu Pro
            100                 105                 110

Tyr Cys Thr Lys Phe Val Thr Thr Tyr Ser Gln Pro Tyr Glu Asp Gly
        115                 120                 125

Tyr Val Ser Gln Gly Gly Tyr Ala Asn Tyr Val Arg Val His Glu His
    130                 135                 140

Phe Val Val Pro Ile Pro Glu Asn Ile Pro Ser His Leu Ala Ala Pro
145                 150                 155                 160

Leu Leu Cys Gly Gly Leu Thr Val Tyr Ser Pro Leu Val Arg Asn Gly
                165                 170                 175

Cys Gly Pro Gly Lys Lys Val Gly Ile Val Gly Leu Gly Gly Ile Gly
            180                 185                 190

Ser Met Gly Thr Leu Ile Ser Lys Ala Met Gly Ala Glu Thr Tyr Val
        195                 200                 205

Ile Ser Arg Ser Ser Arg Lys Arg Glu Asp Ala Met Lys Met Gly Ala
    210                 215                 220

Asp His Tyr Ile Ala Thr Leu Glu Glu Gly Asp Trp Gly Glu Lys Tyr
225                 230                 235                 240

Phe Asp Thr Phe Asp Leu Ile Val Val Cys Ala Ser Ser Leu Thr Asp
                245                 250                 255
```

Ile Asp Phe Asn Ile Met Pro Lys Ala Met Lys Val Gly Gly Arg Ile
                260                 265                 270

Val Ser Ile Ser Ile Pro Glu Gln His Glu Met Leu Ser Leu Lys Pro
            275                 280                 285

Tyr Gly Leu Lys Ala Val Ser Ile Ser Tyr Ser Ala Leu Gly Ser Ile
        290                 295                 300

Lys Glu Leu Asn Gln Leu Leu Lys Leu Val Ser Glu Lys Asp Ile Lys
305                 310                 315                 320

Ile Trp Val Glu Thr Leu Pro Val Gly Glu Ala Gly Val His Glu Ala
                325                 330                 335

Phe Glu Arg Met Glu Lys Gly Asp Val Arg Tyr Arg Phe Thr Leu Val
            340                 345                 350

Gly Tyr Asp Lys Glu Phe Ser Asp
        355                 360

<210> SEQ ID NO 38
<211> LENGTH: 1083
<212> TYPE: DNA
<213> ORGANISM: Saccharomyces cerevisiae

<400> SEQUENCE: 38
ctagtctgaa aattctttgt cgtagccgac taaggtaaat ctatatctaa cgtcacccatt      60
ttccatcctt tcgaaggctt catggacgcc ggcttcacca acaggtaatg tttccaccca     120
aattttgata tcttttcag agactaattt caagagttgg ttcaattctt tgatggaacc      180
taaagcactg taagaaatgg agacagcctt taagccatat ggctttagcg ataacatttc     240
gtgttgttct ggtatagaga ttgagacaat tctaccacca accttcatag cctttggcat     300
aatgttgaag tcaatgtcgg taagggagga agcacagact acaatcaggt cgaaggtgtc     360
aaagtacttt tcaccccaat caccttcttc taatgtagca atgtagtgat cggcgcccat     420
cttcattgca tcttctcttt ttctcgaaga acgagaaata acatacgtct ctgccccat     480
ggctttggaa atcaatgtac ccatactgcc gataccacca agaccaacta taccaacttt     540
tttacctgga ccgcaaccgt tacgaaccaa tggagagtac acagtcaaac caccacataa     600
tagtggagca gccaaatgtg atggaatatt ctctgggata ggcaccacaa aatgttcatg     660
aactctgacg tagtttgcat agccaccctg cgacacatag ccgtcttcat aaggctgact     720
gtatgtggta acaaacttgg tgcagtatgg ttcattatca ttcttacaac ggtcacattc     780
caagcatgaa aagacttgag cacctacacc aacacgttga ccgactttca acccactgtt     840
tgacttgggc cctagcttga caactttacc aacgatttca tgaccaacga ctagcggcat     900
cttcatattg ccccaatgac cagctgcaca atgaatatca ctaccgcaga caccacatgc     960
ttcgatctta atgtcaatgt catgatcgta aaatggtttt gggtcatact tgtcttcctt    1020
tgggttttttc caatcttcgt gtgattgaat agcgatacct tcaaatttct caggataaga    1080
cat                                                                  1083

<210> SEQ ID NO 39
<211> LENGTH: 387
<212> TYPE: PRT
<213> ORGANISM: Escherichia coli

<400> SEQUENCE: 39

Met Asn Asn Phe Asn Leu His Thr Pro Thr Arg Ile Leu Phe Gly Lys
1               5                   10                  15

```
Gly Ala Ile Ala Gly Leu Arg Glu Gln Ile Pro His Asp Ala Arg Val
             20                  25                  30

Leu Ile Thr Tyr Gly Gly Ser Val Lys Lys Thr Gly Val Leu Asp
         35                  40                  45

Gln Val Leu Asp Ala Leu Lys Gly Met Asp Val Leu Glu Phe Gly Gly
 50                  55                  60

Ile Glu Pro Asn Pro Ala Tyr Glu Thr Leu Met Asn Ala Val Lys Leu
 65                  70                  75                  80

Val Arg Glu Gln Lys Val Thr Phe Leu Leu Ala Val Gly Gly Gly Ser
                 85                  90                  95

Val Leu Asp Gly Thr Lys Phe Ile Ala Ala Ala Asn Tyr Pro Glu
                100                 105                 110

Asn Ile Asp Pro Trp His Ile Leu Gln Thr Gly Gly Lys Glu Ile Lys
            115                 120                 125

Ser Ala Ile Pro Met Gly Cys Val Leu Thr Leu Pro Ala Thr Gly Ser
130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
                180                 185                 190

Val Asp Ala Phe Val His Thr Val Glu Gln Tyr Val Thr Lys Pro Val
                195                 200                 205

Asp Ala Lys Ile Gln Asp Arg Phe Ala Glu Gly Ile Leu Leu Thr Leu
210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
                260                 265                 270

Leu Thr Ala Met His Gly Leu Asp His Ala Gln Thr Leu Ala Ile Val
            275                 280                 285

Leu Pro Ala Leu Trp Asn Glu Lys Arg Asp Thr Lys Arg Ala Lys Leu
290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
                340                 345                 350

Ile Pro Ala Leu Leu Lys Lys Leu Glu Glu His Gly Met Thr Gln Leu
            355                 360                 365

Gly Glu Asn His Asp Ile Thr Leu Asp Val Ser Arg Arg Ile Tyr Glu
370                 375                 380

Ala Ala Arg
385

<210> SEQ ID NO 40
<211> LENGTH: 387
<212> TYPE: PRT
<213> ORGANISM: Escherichia coli

<400> SEQUENCE: 40
```

Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Ser Val Lys Lys Thr Gly Val Leu Asp
        35                  40                  45

Gln Val Leu Asp Ala Leu Lys Gly Met Asp Val Leu Glu Phe Gly Gly
50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Asn Tyr Pro Glu
                100                 105                 110

Asn Ile Asp Pro Trp His Ile Leu Gln Thr Gly Gly Lys Glu Ile Lys
            115                 120                 125

Ser Ala Ile Pro Met Gly Cys Val Leu Thr Leu Pro Ala Thr Gly Ser
130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
            195                 200                 205

Asp Ala Lys Ile Gln Asp Arg Phe Ala Glu Gly Ile Leu Leu Thr Leu
210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
            275                 280                 285

Leu Pro Ala Leu Trp Asn Glu Lys Arg Asp Thr Lys Arg Ala Lys Leu
            290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
            355                 360                 365

Gly Glu Asn His Asp Ile Thr Leu Asp Val Ser Arg Arg Ile Tyr Glu
370                 375                 380

Ala Ala Arg
385

<210> SEQ ID NO 41
<211> LENGTH: 389

<212> TYPE: PRT
<213> ORGANISM: Clostridium acetobutylicum

<400> SEQUENCE: 41

```
Met Leu Ser Phe Asp Tyr Ser Ile Pro Thr Lys Val Phe Phe Gly Lys
1               5                   10                  15

Gly Lys Ile Asp Val Ile Gly Glu Glu Ile Lys Lys Tyr Gly Ser Arg
            20                  25                  30

Val Leu Ile Val Tyr Gly Gly Gly Ser Ile Lys Arg Asn Gly Ile Tyr
        35                  40                  45

Asp Arg Ala Thr Ala Ile Leu Lys Glu Asn Asn Ile Ala Phe Tyr Glu
    50                  55                  60

Leu Ser Gly Val Glu Pro Asn Pro Arg Ile Thr Thr Val Lys Lys Gly
65                  70                  75                  80

Ile Glu Ile Cys Arg Glu Asn Asn Val Asp Leu Val Leu Ala Ile Gly
                85                  90                  95

Gly Gly Ser Ala Ile Asp Cys Ser Lys Val Ile Ala Ala Gly Val Tyr
            100                 105                 110

Tyr Asp Gly Asp Thr Trp Asp Met Val Lys Asp Pro Ser Lys Ile Thr
        115                 120                 125

Lys Val Leu Pro Ile Ala Ser Ile Leu Thr Leu Ser Ala Thr Gly Ser
130                 135                 140

Glu Met Asp Gln Ile Ala Val Ile Ser Asn Met Glu Thr Asn Glu Lys
145                 150                 155                 160

Leu Gly Val Gly His Asp Asp Met Arg Pro Lys Phe Ser Val Leu Asp
                165                 170                 175

Pro Thr Tyr Thr Phe Thr Val Pro Lys Asn Gln Thr Ala Ala Gly Thr
            180                 185                 190

Ala Asp Ile Met Ser His Thr Phe Glu Ser Tyr Phe Ser Gly Val Glu
        195                 200                 205

Gly Ala Tyr Val Gln Asp Gly Ile Ala Glu Ala Ile Leu Arg Thr Cys
    210                 215                 220

Ile Lys Tyr Gly Lys Ile Ala Met Glu Lys Thr Asp Asp Tyr Glu Ala
225                 230                 235                 240

Arg Ala Asn Leu Met Trp Ala Ser Ser Leu Ala Ile Asn Gly Leu Leu
                245                 250                 255

Ser Leu Gly Lys Asp Arg Lys Trp Ser Cys His Pro Met Glu His Glu
            260                 265                 270

Leu Ser Ala Tyr Tyr Asp Ile Thr His Gly Val Gly Leu Ala Ile Leu
        275                 280                 285

Thr Pro Asn Trp Met Glu Tyr Ile Leu Asn Asp Asp Thr Leu His Lys
    290                 295                 300

Phe Val Ser Tyr Gly Ile Asn Val Trp Gly Ile Asp Lys Asn Lys Asp
305                 310                 315                 320

Asn Tyr Glu Ile Ala Arg Glu Ala Ile Lys Asn Thr Arg Glu Tyr Phe
                325                 330                 335

Asn Ser Leu Gly Ile Pro Ser Lys Leu Arg Glu Val Gly Ile Gly Lys
            340                 345                 350

Asp Lys Leu Glu Leu Met Ala Lys Gln Ala Val Arg Asn Ser Gly Gly
        355                 360                 365

Thr Ile Gly Ser Leu Arg Pro Ile Asn Ala Glu Asp Val Leu Glu Ile
    370                 375                 380

Phe Lys Lys Ser Tyr
385
```

<210> SEQ ID NO 42
<211> LENGTH: 1170
<212> TYPE: DNA
<213> ORGANISM: Clostridium acetobutylicum

<400> SEQUENCE: 42

```
ttaataagat ttttaaaata tctcaagaac atcctctgca tttattggtc ttaaacttcc      60
tattgttcct ccagaatttc taacagcttg ctttgccatt agttctagtt tatcttttcc    120
tattccaact tctctaagct ttgaaggaat acccaatgaa ttaaagtatt ctctcgtatt    180
tttaatagcc tctcgtgcta tttcatagtt atctttgttc ttgtctattc cccaaacatt    240
tattccataa gaaacaaatt tatgaagtgt atcgtcattt agaatatatt ccatccaatt    300
aggtgttaaa attgcaagtc ctacaccatg tgttatatca taatatgcac ttaactcgtg    360
ttccatagga tgacaactcc attttctatc cttaccaagt gataatagac catttatagc    420
taaacttgaa gcccacatca aattagctct agcctcgtaa tcatcagtct tctccattgc    480
tattttcca tactttatac atgttcttaa gattgcttct gctataccgt cctgcacata     540
agcaccttca acaccactaa agtaagattc aaaggtgtga ctcataatgt cagctgttcc    600
cgctgctgtt tgattttag gtactgtaaa agtatatgta ggatctaaca ctgaaaattt    660
aggtctcata tcatcatgtc ctactccaag cttttcatta gtctccatat ttgaaattac    720
tgcaatttga tccatttcag accctgttgc tgaaagagta agtatacttg caattggaag    780
aactttagtt attttagatg gatctttaac catgtcccat gtatcgccat cataataaac    840
tccagctgca attaccttag aacagtctat tgcacttcct cccctattg ctaatactaa     900
atccacatta ttttctctac atatttctat gcctttttt actgttgtta tcctaggatt    960
tggctctact cctgaaagtt catagaaagc tatattgttt tcttttaata tagctgttgc   1020
tctatcatat ataccgttcc ttttatact tcctccgcca taaactataa gcactcttga    1080
gccatatttc ttaatttctt ctccaattac gtctattttt cctttccaa aaaaaacttt    1140
agttggtatt gaataatcaa aacttagcat                                     1170
```

<210> SEQ ID NO 43
<211> LENGTH: 390
<212> TYPE: PRT
<213> ORGANISM: Clostridium acetobutylicum

<400> SEQUENCE: 43

```
Met Val Asp Phe Glu Tyr Ser Ile Pro Thr Arg Ile Phe Phe Gly Lys
1               5                   10                  15

Asp Lys Ile Asn Val Leu Gly Arg Glu Leu Lys Lys Tyr Gly Ser Lys
            20                  25                  30

Val Leu Ile Val Tyr Gly Gly Gly Ser Ile Lys Arg Asn Gly Ile Tyr
        35                  40                  45

Asp Lys Ala Val Ser Ile Leu Glu Lys Asn Ser Ile Lys Phe Tyr Glu
    50                  55                  60

Leu Ala Gly Val Glu Pro Asn Pro Arg Val Thr Thr Val Glu Lys Gly
65                  70                  75                  80

Val Lys Ile Cys Arg Glu Asn Gly Val Glu Val Leu Ala Ile Gly
                85                  90                  95

Gly Gly Ser Ala Ile Asp Cys Ala Lys Val Ile Ala Ala Ala Cys Glu
            100                 105                 110

Tyr Asp Gly Asn Pro Trp Asp Ile Val Leu Asp Gly Ser Lys Ile Lys
```

115                 120                 125
Arg Val Leu Pro Ile Ala Ser Ile Leu Thr Ile Ala Ala Thr Gly Ser
    130                 135                 140

Glu Met Asp Thr Trp Ala Val Ile Asn Asn Met Asp Thr Asn Glu Lys
145                 150                 155                 160

Leu Ile Ala Ala His Pro Asp Met Ala Pro Lys Phe Ser Ile Leu Asp
                165                 170                 175

Pro Thr Tyr Thr Tyr Thr Val Pro Thr Asn Gln Thr Ala Ala Gly Thr
            180                 185                 190

Ala Asp Ile Met Ser His Ile Phe Glu Val Tyr Phe Ser Asn Thr Lys
        195                 200                 205

Thr Ala Tyr Leu Gln Asp Arg Met Ala Glu Ala Leu Leu Arg Thr Cys
    210                 215                 220

Ile Lys Tyr Gly Gly Ile Ala Leu Glu Lys Pro Asp Asp Tyr Glu Ala
225                 230                 235                 240

Arg Ala Asn Leu Met Trp Ala Ser Ser Leu Ala Ile Asn Gly Leu Leu
                245                 250                 255

Thr Tyr Gly Lys Asp Thr Asn Trp Ser Val His Leu Met Glu His Glu
            260                 265                 270

Leu Ser Ala Tyr Tyr Asp Ile Thr His Gly Val Gly Leu Ala Ile Leu
        275                 280                 285

Thr Pro Asn Trp Met Glu Tyr Ile Leu Asn Asn Asp Thr Val Tyr Lys
    290                 295                 300

Phe Val Glu Tyr Gly Val Asn Val Trp Gly Ile Asp Lys Glu Lys Asn
305                 310                 315                 320

His Tyr Asp Ile Ala His Gln Ala Ile Gln Lys Thr Arg Asp Tyr Phe
                325                 330                 335

Val Asn Val Leu Gly Leu Pro Ser Arg Leu Arg Asp Val Gly Ile Glu
            340                 345                 350

Glu Glu Lys Leu Asp Ile Met Ala Lys Glu Ser Val Lys Leu Thr Gly
        355                 360                 365

Gly Thr Ile Gly Asn Leu Arg Pro Val Asn Ala Ser Glu Val Leu Gln
    370                 375                 380

Ile Phe Lys Lys Ser Val
385                 390

<210> SEQ ID NO 44
<211> LENGTH: 1173
<212> TYPE: DNA
<213> ORGANISM: Clostridium acetobutylicum

<400> SEQUENCE: 44
gtggttgatt tcgaatattc aataccaact agaatttttt tcggtaaaga taagataaat     60
gtacttggaa gagagcttaa aaaatatggt tctaaagtgc ttatagttta tggtggagga    120
agtataaaga gaaatggaat atatgataaa gctgtaagta tacttgaaaa aacagtatt    180 aaattttatg aacttgcagg agtagagcca atccaagag taactacagt tgaaaaagga    240
gttaaaatat gtagagaaaa tggagttgaa gtagtactag ctataggtgg aggaagtgca    300
atagattgcg caaaggttat agcagcagca tgtgaatatg atggaaatcc atgggatatt    360
gtgttagatg gctcaaaaat aaaaagggtg cttcctatag ctagtatatt aaccattgct    420
gcaacaggat cagaaatgga tacgtgggca gtaataaata tatgggatac aaacgaaaaa    480
ctaattgcgg cacatccaga tatggctcct aagttttcta tattagatcc aacgtatacg    540

```
tataccgtac ctaccaatca aacagcagca ggaacagctg atattatgag tcatatattt      600
gaggtgtatt ttagtaatac aaaaacagca tatttgcagg atagaatggc agaagcgtta      660
ttaagaactt gtattaaata tggaggaata gctcttgaga agccggatga ttatgaggca      720
agagccaatc taatgtgggc ttcaagtctt gcgataaatg gacttttaac atatggtaaa      780
gacactaatt ggagtgtaca cttaatggaa catgaattaa gtgcttatta cgacataaca      840
cacggcgtag ggcttgcaat tttaacaccct aattggatgg agtatatttt aaataatgat      900
acagtgtaca agtttgttga atatggtgta aatgtttggg gaatagacaa agaaaaaaat      960
cactatgaca tagcacatca agcaatacaa aaaacaagag attactttgt aaatgtacta      1020
ggtttaccat ctagactgag agatgttgga attgaagaag aaaaattgga cataatggca      1080
aaggaatcag taaagcttac aggaggaacc ataggaaacc taagaccagt aaacgcctcc      1140
gaagtcctac aaatattcaa aaaatctgtg taa                                   1173
```

<210> SEQ ID NO 45
<211> LENGTH: 330
<212> TYPE: PRT
<213> ORGANISM: Bacillus subtilis

<400> SEQUENCE: 45

```
Met Ser Thr Asn Arg His Gln Ala Leu Gly Leu Thr Asp Gln Glu Ala
1               5                   10                  15

Val Asp Met Tyr Arg Thr Met Leu Leu Ala Arg Lys Ile Asp Glu Arg
            20                  25                  30

Met Trp Leu Leu Asn Arg Ser Gly Lys Ile Pro Phe Val Ile Ser Cys
        35                  40                  45

Gln Gly Gln Glu Ala Ala Gln Val Gly Ala Ala Phe Ala Leu Asp Arg
    50                  55                  60

Glu Met Asp Tyr Val Leu Pro Tyr Tyr Arg Asp Met Gly Val Val Leu
65                  70                  75                  80

Ala Phe Gly Met Thr Ala Lys Asp Leu Met Met Ser Gly Phe Ala Lys
                85                  90                  95

Ala Ala Asp Pro Asn Ser Gly Gly Arg Gln Met Pro Gly His Phe Gly
            100                 105                 110

Gln Lys Lys Asn Arg Ile Val Thr Gly Ser Ser Pro Val Thr Thr Gln
        115                 120                 125

Val Pro His Ala Val Gly Ile Ala Leu Ala Gly Arg Met Glu Lys Lys
    130                 135                 140

Asp Ile Ala Ala Phe Val Thr Phe Gly Glu Gly Ser Ser Asn Gln Gly
145                 150                 155                 160

Asp Phe His Glu Gly Ala Asn Phe Ala Ala Val His Lys Leu Pro Val
                165                 170                 175

Ile Phe Met Cys Glu Asn Asn Lys Tyr Ala Ile Ser Val Pro Tyr Asp
            180                 185                 190

Lys Gln Val Ala Cys Glu Asn Ile Ser Asp Arg Ala Ile Gly Tyr Gly
        195                 200                 205

Met Pro Gly Val Thr Val Asn Gly Asn Asp Pro Leu Glu Val Tyr Gln
    210                 215                 220

Ala Val Lys Glu Ala Arg Glu Arg Ala Arg Gly Glu Gly Pro Thr
225                 230                 235                 240

Leu Ile Glu Thr Ile Ser Tyr Arg Leu Thr Pro His Ser Ser Asp
                245                 250                 255

Asp Asp Ser Ser Tyr Arg Gly Arg Glu Glu Val Glu Glu Ala Lys Lys
```

```
              260                 265                 270
Ser Asp Pro Leu Leu Thr Tyr Gln Ala Tyr Leu Lys Glu Thr Gly Leu
            275                 280                 285

Leu Ser Asp Glu Ile Glu Gln Thr Met Leu Asp Glu Ile Met Ala Ile
            290                 295                 300

Val Asn Glu Ala Thr Asp Ala Glu Asn Ala Pro Tyr Ala Ala Pro
305                 310                 315                 320

Glu Ser Ala Leu Asp Tyr Val Tyr Ala Lys
            325                 330

<210> SEQ ID NO 46
<211> LENGTH: 993
<212> TYPE: DNA
<213> ORGANISM: Bacillus subtilis

<400> SEQUENCE: 46
atgagtacaa accgacatca agcactaggg ctgactgatc aggaagccgt tgatatgtat      60
agaaccatgc tgttagcaag aaaaatcgat gaaagaatgt ggctgttaaa ccgttctggc     120
aaaattccat ttgtaatctc ttgtcaagga caggaagcag cacaggtagg agcggctttc     180
gcacttgacc gtgaaatgga ttatgtattg ccgtactaca gagacatggg tgtcgtgctc     240
gcgtttggca tgacagcaaa ggacttaatg atgtccgggt tgcaaaagc agcagatccg      300
aactcaggag gccgccagat gccgggacat ttcggacaaa agaaaaaccg cattgtgacg     360
ggatcatctc cggttacaac gcaagtgccg cacgcagtcg gtattgcgct gcgggacgt      420
atggagaaaa aggatatcgc agcctttgtt acattcgggg aagggtcttc aaaccaaggc     480
gatttccatg aaggggcaaa ctttgccgct gtccataagc tgccggttat tttcatgtgt     540
gaaaacaaca aatacgcaat ctcagtgcct tacgataagc aagtcgcatg tgagaacatt     600
tccgaccgtg ccataggcta tgggatgcct ggcgtaactg tgaatggaaa tgatccgctg     660
gaagtttatc aagcggttaa agaagcacgc gaaagggcac gcagaggaga aggcccgaca     720
ttaattgaaa cgatttctta ccgccttaca ccacattcca gtgatgacga tgacagcagc     780
tacagaggcc gtgaagaagt agaggaagcg aaaaaagtg atcccctgct tacttatcaa      840
gcttacttaa aggaaacagg cctgctgtcc gatgagatag aacaaaccat gctggatgaa     900
attatggcaa tcgtaaatga agcgacggat gaagcggaga acgccccata tgcagctcct     960
gagtcagcgc ttgattatgt ttatgcgaag tag                                   993

<210> SEQ ID NO 47
<211> LENGTH: 327
<212> TYPE: PRT
<213> ORGANISM: Bacillus subtilis

<400> SEQUENCE: 47

Met Ser Val Met Ser Tyr Ile Asp Ala Ile Asn Leu Ala Met Lys Glu
1               5                   10                  15

Glu Met Glu Arg Asp Ser Arg Val Phe Val Leu Gly Glu Asp Val Gly
            20                  25                  30

Arg Lys Gly Gly Val Phe Lys Ala Thr Ala Gly Leu Tyr Glu Gln Phe
        35                  40                  45

Gly Glu Glu Arg Val Met Asp Thr Pro Leu Ala Glu Ser Ala Ile Ala
    50                  55                  60

Gly Val Gly Ile Gly Ala Ala Met Tyr Gly Met Arg Pro Ile Ala Glu
65                  70                  75                  80
```

```
Met Gln Phe Ala Asp Phe Ile Met Pro Ala Val Asn Gln Ile Ile Ser
                85                  90                  95

Glu Ala Ala Lys Ile Arg Tyr Arg Ser Asn Asn Asp Trp Ser Cys Pro
            100                 105                 110

Ile Val Val Arg Ala Pro Tyr Gly Gly Gly Val His Gly Ala Leu Tyr
            115                 120                 125

His Ser Gln Ser Val Glu Ala Ile Phe Ala Asn Gln Pro Gly Leu Lys
            130                 135                 140

Ile Val Met Pro Ser Thr Pro Tyr Asp Ala Lys Gly Leu Leu Lys Ala
145                 150                 155                 160

Ala Val Arg Asp Glu Asp Pro Val Leu Phe Phe Glu His Lys Arg Ala
                165                 170                 175

Tyr Arg Leu Ile Lys Gly Glu Val Pro Ala Asp Asp Tyr Val Leu Pro
            180                 185                 190

Ile Gly Lys Ala Asp Val Lys Arg Glu Gly Asp Asp Ile Thr Val Ile
            195                 200                 205

Thr Tyr Gly Leu Cys Val His Phe Ala Leu Gln Ala Ala Glu Arg Leu
            210                 215                 220

Glu Lys Asp Gly Ile Ser Ala His Val Val Asp Leu Arg Thr Val Tyr
225                 230                 235                 240

Pro Leu Asp Lys Glu Ala Ile Ile Glu Ala Ala Ser Lys Thr Gly Lys
                245                 250                 255

Val Leu Leu Val Thr Glu Asp Thr Lys Glu Gly Ser Ile Met Ser Glu
            260                 265                 270

Val Ala Ala Ile Ile Ser Glu His Cys Leu Phe Asp Leu Asp Ala Pro
            275                 280                 285

Ile Lys Arg Leu Ala Gly Pro Asp Ile Pro Ala Met Pro Tyr Ala Pro
            290                 295                 300

Thr Met Glu Lys Tyr Phe Met Val Asn Pro Asp Lys Val Glu Ala Ala
305                 310                 315                 320

Met Arg Glu Leu Ala Glu Phe
                325

<210> SEQ ID NO 48
<211> LENGTH: 984
<212> TYPE: DNA
<213> ORGANISM: Bacillus subtilis

<400> SEQUENCE: 48
atgtcagtaa tgtcatatat tgatgcaatc aatttggcga tgaaagaaga atggaacga        60 gattctcgcg ttttcgtcct tggggaagat gtaggaagaa aaggcggtgt gtttaaagcg       120
acagcgggac tctatgaaca atttggggaa gagcgcgtta tggatacgcc gcttgctgaa       180
tctgcaatcg caggagtcgg tatcggagcg gcaatgtacg gaatgagacc gattgctgaa       240
atgcagtttg ctgatttcat tatgccggca gtcaaccaaa ttatttctga agcggctaaa       300
atccgctacc gcagcaacaa tgactggagc tgtccgattg tcgtcagagc gccatacggc       360
ggaggcgtgc acggagcccct gtatcattct caatcagtcg aagcaatttt cgccaaccag       420
cccggactga aaattgtcat gccatcaaca ccatatgacg cgaaagggct cttaaaagcc       480
gcagttcgtg acgaagaccc cgtgctgttt tttgagcaca agcgggcata ccgtctgata       540
aagggcgagg ttccggctga tgattatgtc ctgccaatcg gcaaggcgga cgtaaaaagg       600
gaaggcgacg acatcacagt gatcacatac ggcctgtgtg tccacttcgc cttacaagct       660
gcagaacgtc tcgaaaaaga tggcatttca gcgcatgtgg tggatttaag aacagtttac       720
```

```
ccgcttgata aagaagccat catcgaagct gcgtccaaaa ctggaaaggt tcttttggtc    780
acagaagata caaaagaagg cagcatcatg agcgaagtag ccgcaattat atccgagcat    840
tgtctgttcg acttagacgc gccgatcaaa cggcttgcag gtcctgatat tccggctatg    900
ccttatgcgc cgacaatgga aaatacttt atggtcaacc ctgataaagt ggaagcggcg    960
atgagagaat tagcggagtt ttaa    984
```

<210> SEQ ID NO 49
<211> LENGTH: 424
<212> TYPE: PRT
<213> ORGANISM: Bacillus subtilis

<400> SEQUENCE: 49

```
Met Ala Ile Glu Gln Met Thr Met Pro Gln Leu Gly Glu Ser Val Thr
1               5                   10                  15

Glu Gly Thr Ile Ser Lys Trp Leu Val Ala Pro Gly Asp Lys Val Asn
            20                  25                  30

Lys Tyr Asp Pro Ile Ala Glu Val Met Thr Asp Lys Val Asn Ala Glu
        35                  40                  45

Val Pro Ser Ser Phe Thr Gly Thr Ile Thr Glu Leu Val Gly Glu Glu
    50                  55                  60

Gly Gln Thr Leu Gln Val Gly Glu Met Ile Cys Lys Ile Glu Thr Glu
65                  70                  75                  80

Gly Ala Asn Pro Ala Glu Gln Lys Gln Glu Gln Pro Ala Ala Ser Glu
                85                  90                  95

Ala Ala Glu Asn Pro Val Ala Lys Ser Ala Gly Ala Ala Asp Gln Pro
            100                 105                 110

Asn Lys Lys Arg Tyr Ser Pro Ala Val Leu Arg Leu Ala Gly Glu His
        115                 120                 125

Gly Ile Asp Leu Asp Gln Val Thr Gly Thr Gly Ala Gly Gly Arg Ile
    130                 135                 140

Thr Arg Lys Asp Ile Gln Arg Leu Ile Glu Thr Gly Gly Val Gln Glu
145                 150                 155                 160

Gln Asn Pro Glu Glu Leu Lys Thr Ala Ala Pro Ala Pro Lys Ser Ala
                165                 170                 175

Ser Lys Pro Glu Pro Lys Glu Glu Thr Ser Tyr Pro Ala Ser Ala Ala
            180                 185                 190

Gly Asp Lys Glu Ile Pro Val Thr Gly Val Arg Lys Ala Ile Ala Ser
        195                 200                 205

Asn Met Lys Arg Ser Lys Thr Glu Ile Pro His Ala Trp Thr Met Met
    210                 215                 220

Glu Val Asp Val Thr Asn Met Val Ala Tyr Arg Asn Ser Ile Lys Asp
225                 230                 235                 240

Ser Phe Lys Lys Thr Glu Gly Phe Asn Leu Thr Phe Ala Phe Phe
                245                 250                 255

Val Lys Ala Val Ala Gln Ala Leu Lys Glu Phe Pro Gln Met Asn Ser
            260                 265                 270

Met Trp Ala Gly Asp Lys Ile Ile Gln Lys Lys Asp Ile Asn Ile Ser
        275                 280                 285

Ile Ala Val Ala Thr Glu Asp Ser Leu Phe Val Pro Val Ile Lys Asn
    290                 295                 300

Ala Asp Glu Lys Thr Ile Lys Gly Ile Ala Lys Asp Ile Thr Gly Leu
305                 310                 315                 320
```

```
Ala Lys Lys Val Arg Asp Gly Lys Leu Thr Ala Asp Asp Met Gln Gly
            325                 330                 335

Gly Thr Phe Thr Val Asn Asn Thr Gly Ser Phe Gly Ser Val Gln Ser
            340                 345                 350

Met Gly Ile Ile Asn Tyr Pro Gln Ala Ala Ile Leu Gln Val Glu Ser
            355                 360                 365

Ile Val Lys Arg Pro Val Val Met Asp Asn Gly Met Ile Ala Val Arg
            370                 375                 380

Asp Met Val Asn Leu Cys Leu Ser Leu Asp His Arg Val Leu Asp Gly
385                 390                 395                 400

Leu Val Cys Gly Arg Phe Leu Gly Arg Val Lys Gln Ile Leu Glu Ser
            405                 410                 415

Ile Asp Glu Lys Thr Ser Val Tyr
            420
```

```
<210> SEQ ID NO 50
<211> LENGTH: 1275
<212> TYPE: DNA
<213> ORGANISM: Bacillus subtilis

<400> SEQUENCE: 50
atggcaattg aacaaatgac gatgccgcag cttggagaaa gcgtaacaga ggggacgatc      60
agcaaatggc ttgtcgcccc cggtgataaa gtgaacaaat acgatccgat cgcggaagtc     120
atgacagata aggtaaatgc agaggttccg tcttctttta ctggtacgat aacagagctt     180
gtgggagaag aaggccaaac cctgcaagtc ggagaaatga tttgcaaaat tgaaacagaa     240
ggcgcgaatc cggctgaaca aaaacaagaa cagccagcag catcagaagc cgctgagaac     300
cctgttgcaa aaagtgctgg agcagccgat cagcccaata aaaagcgcta ctcgccagct     360
gttctccgtt tggccggaga gcacggcatt gacctcgatc aagtgacagg aactggtgcc     420
ggcgggcgca tcacacgaaa agatattcag cgcttaattg aaacaggcgg cgtgcaagaa     480
cagaatcctg aggagctgaa aacagcagct cctgcaccga gtctgcatc aaaacctgag      540
ccaaaagaag agacgtcata tcctgcgtct gcagccggtg ataaagaaat ccctgtcaca     600
ggtgtaagaa aagcaattgc ttccaatatg aagcgaagca aacagaaat tccgcatgct      660
tggacgatga tggaagtcga cgtcacaaat atggttgcat atcgcaacag tataaaagat     720
tcttttaaga agacagaagg cttaattta acgttcttcg cctttttgt aaaagcggtc       780
gctcaggcgt taaagaatt cccgcaaatg aatagcatgt gggcggggga caaaattatt     840
cagaaaaagg atatcaatat ttcaattgca gttgccacag aggattcttt atttgttccg     900
gtgattaaaa acgctgatga aaaaacaatt aaaggcattg cgaaagacat taccggccta     960
gctaaaaaag taagagacgg aaaactcact gcagatgaca tgcagggagg cacgtttacc    1020
gtcaacaaca caggttcgtt cgggtctgtt cagtcgatgg cattatcaa ctaccctcag     1080
gctgcgattc ttcaagtaga atccatcgtc aaacgcccgg ttgtcatgga caatggcatg    1140
attgctgtca gagacatggt taatctgtgc ctgtcattag atcacagagt gcttgacggt    1200
ctcgtgtgcg gacgattcct cggacgagtg aaacaaattt tagaatcgat tgacgagaag    1260
acatctgttt actaa                                                     1275

<210> SEQ ID NO 51
<211> LENGTH: 474
<212> TYPE: PRT
<213> ORGANISM: Bacillus subtilis
```

<400> SEQUENCE: 51

```
Met Ala Thr Glu Tyr Asp Val Val Ile Leu Gly Gly Thr Gly Gly
1               5                   10                  15

Tyr Val Ala Ala Ile Arg Ala Ala Gln Leu Gly Leu Lys Thr Ala Val
            20                  25                  30

Val Glu Lys Glu Lys Leu Gly Gly Thr Cys Leu His Lys Gly Cys Ile
        35                  40                  45

Pro Ser Lys Ala Leu Leu Arg Ser Ala Glu Val Tyr Arg Thr Ala Arg
50                  55                  60

Glu Ala Asp Gln Phe Gly Val Glu Thr Ala Gly Val Ser Leu Asn Phe
65                  70                  75                  80

Glu Lys Val Gln Gln Arg Lys Gln Ala Val Val Asp Lys Leu Ala Ala
                85                  90                  95

Gly Val Asn His Leu Met Lys Lys Gly Lys Ile Asp Val Tyr Thr Gly
            100                 105                 110

Tyr Gly Arg Ile Leu Gly Pro Ser Ile Phe Ser Pro Leu Pro Gly Thr
        115                 120                 125

Ile Ser Val Glu Arg Gly Asn Gly Glu Glu Asn Asp Met Leu Ile Pro
130                 135                 140

Lys Gln Val Ile Ile Ala Thr Gly Ser Arg Pro Arg Met Leu Pro Gly
145                 150                 155                 160

Leu Glu Val Asp Gly Lys Ser Val Leu Thr Ser Asp Glu Ala Leu Gln
                165                 170                 175

Met Glu Glu Leu Pro Gln Ser Ile Ile Ile Val Gly Gly Gly Val Ile
            180                 185                 190

Gly Ile Glu Trp Ala Ser Met Leu His Asp Phe Gly Val Lys Val Thr
        195                 200                 205

Val Ile Glu Tyr Ala Asp Arg Ile Leu Pro Thr Glu Asp Leu Glu Ile
210                 215                 220

Ser Lys Glu Met Glu Ser Leu Leu Lys Lys Lys Gly Ile Gln Phe Ile
225                 230                 235                 240

Thr Gly Ala Lys Val Leu Pro Asp Thr Met Thr Lys Thr Ser Asp Asp
                245                 250                 255

Ile Ser Ile Gln Ala Glu Lys Asp Gly Glu Thr Val Thr Tyr Ser Ala
            260                 265                 270

Glu Lys Met Leu Val Ser Ile Gly Arg Gln Ala Asn Ile Glu Gly Ile
        275                 280                 285

Gly Leu Glu Asn Thr Asp Ile Val Thr Glu Asn Gly Met Ile Ser Val
290                 295                 300

Asn Glu Ser Cys Gln Thr Lys Glu Ser His Ile Tyr Ala Ile Gly Asp
305                 310                 315                 320

Val Ile Gly Gly Leu Gln Leu Ala His Val Ala Ser His Glu Gly Ile
                325                 330                 335

Ile Ala Val Glu His Phe Ala Gly Leu Asn Pro His Pro Leu Asp Pro
            340                 345                 350

Thr Leu Val Pro Lys Cys Ile Tyr Ser Ser Pro Glu Ala Ala Ser Val
        355                 360                 365

Gly Leu Thr Glu Asp Glu Ala Lys Ala Asn Gly His Asn Val Lys Ile
370                 375                 380

Gly Lys Phe Pro Phe Met Ala Ile Gly Lys Ala Leu Val Tyr Gly Glu
385                 390                 395                 400

Ser Asp Gly Phe Val Lys Ile Val Ala Asp Arg Asp Thr Asp Asp Ile
                405                 410                 415
```

Leu Gly Val His Met Ile Gly Pro His Val Thr Asp Met Ile Ser Glu
            420                 425                 430

Ala Gly Leu Ala Lys Val Leu Asp Ala Thr Pro Trp Glu Val Gly Gln
        435                 440                 445

Thr Ile His Pro His Pro Thr Leu Ser Glu Ala Ile Gly Glu Ala Ala
    450                 455                 460

Leu Ala Ala Asp Gly Lys Ala Ile His Phe
465                 470

<210> SEQ ID NO 52
<211> LENGTH: 1425
<212> TYPE: DNA
<213> ORGANISM: Bacillus subtilis

<400> SEQUENCE: 52

```
atggcaactg agtatgacgt agtcattctg gcggcggta ccggcggtta tgttgcggcc      60
atcagagccg ctcagctcgg cttaaaaaca gccgttgtgg aaaaggaaaa actcggggga     120
acatgtctgc ataaaggctg tatcccgagt aaagcgctgc ttagaagcgc agaggtatac    180
cggacagctc gtgaagccga tcaattcgga gtggaaacgg ctggcgtgtc cctcaacttt    240
gaaaaagtgc agcagcgtaa gcaagccgtt gttgataagc ttgcagcggg tgtaaatcat    300
ttaatgaaaa aaggaaaaat tgacgtgtac accggatatg acgtatcct ggaccgtca     360
atcttctctc cgctgccggg aacaatttct gttgagcggg gaaatggcga agaaaatgac    420
atgctgatcc cgaaacaagt gatcattgca acaggatcaa gaccgagaat gcttccgggt    480
cttgaagtgg acggtaagtc tgtactgact tcagatgagg cgctccaaat ggaggagctg    540
ccacagtcaa tcatcattgt cggcggaggg gttatcggta tcgaatgggc gtctatgctt    600
catgattttg gcgttaaggt aacggttatt gaatacgcgg atcgcatatt gccgactgaa    660
gatctagaga tttcaaaaga aatggaaagt cttcttaaga aaaaggcat ccagttcata     720
acagggcaa aagtgctgcc tgacacaatg acaaaaacat cagacgatat cagcatacaa    780
gcggaaaaag acggagaaac cgttacctat tctgctgaga aaatgcttgt ttccatcggc    840
agacaggcaa atatcgaagg catcggccta gagaacaccg atattgttac tgaaaatggc    900
atgatttcag tcaatgaaag ctgccaaacg aaggaatctc atatttatgc aatcggagac    960
gtaatcggtg gcctgcagtt agctcacgtt gcttcacatg agggaattat tgctgttgag   1020
cattttgcag gtctcaatcc gcatccgctt gatccgacgc ttgtgccgaa gtgcatttac   1080
tcaagccctg aagctgccag tgtcggctta accgaagacg aagcaaaggc gaacgggcat   1140
aatgtcaaaa tcggcaagtt cccatttatg gcgattggaa aagcgcttgt atacggtgaa   1200
agcgacggtt ttgtcaaaat cgtggctgac cgagatacag atgatattct cggcgttcat   1260
atgattggcc cgcatgtcac cgacatgatt tctgaagcgg tcttgccaa agtgctggac    1320
gcaacaccgt gggaggtcgg gcaaacgatt caccgcatc caacgctttc tgaagcaatt   1380
ggagaagctg cgcttgccgc agatggcaaa gccattcatt tttaa                   1425
```

<210> SEQ ID NO 53
<211> LENGTH: 410
<212> TYPE: PRT
<213> ORGANISM: Pseudomonas putida

<400> SEQUENCE: 53

Met Asn Glu Tyr Ala Pro Leu Arg Leu His Val Pro Glu Pro Thr Gly
1               5                   10                  15

Arg Pro Gly Cys Gln Thr Asp Phe Ser Tyr Leu Arg Leu Asn Asp Ala
            20                  25                  30

Gly Gln Ala Arg Lys Pro Pro Val Asp Val Asp Ala Ala Asp Thr Ala
        35                  40                  45

Asp Leu Ser Tyr Ser Leu Val Arg Val Leu Asp Glu Gln Gly Asp Ala
50                      55                  60

Gln Gly Pro Trp Ala Glu Asp Ile Asp Pro Gln Ile Leu Arg Gln Gly
65                      70                  75                  80

Met Arg Ala Met Leu Lys Thr Arg Ile Phe Asp Ser Arg Met Val Val
                85                  90                  95

Ala Gln Arg Gln Lys Lys Met Ser Phe Tyr Met Gln Ser Leu Gly Glu
            100                 105                 110

Glu Ala Ile Gly Ser Gly Gln Ala Leu Ala Leu Asn Arg Thr Asp Met
            115                 120                 125

Cys Phe Pro Thr Tyr Arg Gln Gln Ser Ile Leu Met Ala Arg Asp Val
130                 135                 140

Ser Leu Val Glu Met Ile Cys Gln Leu Leu Ser Asn Glu Arg Asp Pro
145                 150                 155                 160

Leu Lys Gly Arg Gln Leu Pro Ile Met Tyr Ser Val Arg Glu Ala Gly
                165                 170                 175

Phe Phe Thr Ile Ser Gly Asn Leu Ala Thr Gln Phe Val Gln Ala Val
                180                 185                 190

Gly Trp Ala Met Ala Ser Ala Ile Lys Gly Asp Thr Lys Ile Ala Ser
            195                 200                 205

Ala Trp Ile Gly Asp Gly Ala Thr Ala Glu Ser Asp Phe His Thr Ala
210                 215                 220

Leu Thr Phe Ala His Val Tyr Arg Ala Pro Val Ile Leu Asn Val Val
225                 230                 235                 240

Asn Asn Gln Trp Ala Ile Ser Thr Phe Gln Ala Ile Ala Gly Gly Glu
            245                 250                 255

Ser Thr Thr Phe Ala Gly Arg Gly Val Gly Cys Gly Ile Ala Ser Leu
            260                 265                 270

Arg Val Asp Gly Asn Asp Phe Val Ala Val Tyr Ala Ala Ser Arg Trp
            275                 280                 285

Ala Ala Glu Arg Ala Arg Arg Gly Leu Gly Pro Ser Leu Ile Glu Trp
            290                 295                 300

Val Thr Tyr Arg Ala Gly Pro His Ser Thr Ser Asp Pro Ser Lys
305                 310                 315                 320

Tyr Arg Pro Ala Asp Asp Trp Ser His Phe Pro Leu Gly Asp Pro Ile
            325                 330                 335

Ala Arg Leu Lys Gln His Leu Ile Lys Ile Gly His Trp Ser Glu Glu
            340                 345                 350

Glu His Gln Ala Thr Thr Ala Glu Phe Glu Ala Ala Val Ile Ala Ala
            355                 360                 365

Gln Lys Glu Ala Glu Gln Tyr Gly Thr Leu Ala Asn Gly His Ile Pro
            370                 375                 380

Ser Ala Ala Ser Met Phe Glu Asp Val Tyr Lys Glu Met Pro Asp His
385                 390                 395                 400

Leu Arg Arg Gln Arg Gln Glu Leu Gly Val
            405                 410

<210> SEQ ID NO 54
<211> LENGTH: 6643

<212> TYPE: DNA
<213> ORGANISM: Pseudomonas putida

<400> SEQUENCE: 54

```
gcatgcctgc aggccgccga tgaaatggtg gaaggtatcg gtaggctggc cctgctcatc    60
gctgaacacg ttacgcccgc tgccggtatc gaccaggctc tggtgaatat gcatggaact   120
gccaggcgtg cgcgccagcg gtttggccat gcacaccacg gtcagcccgt gcttgagtgc   180
cacttccttg agcaggtgtt tgaacaggaa ggtctggtcg ccagcagca gcgggtcgcc    240
atgtagcaag ttgatctcga actggctgac gcccatttcg tgcatgaagg tgtcgcgcgg   300
caggccgagc gcggccatgc actggtacac ctcattgaag aacgggcgca ggccgttgtt   360
ggaactgaca ctgaacgccg aatggcccag ctcgcggcgg ccgtcggtgc cagcggtgg    420
ctggaacggt gctgcgggt cactgttggg ggcaaacacg aagaactcaa gctcggtcgc   480
cactaccggt gccagaccca cgctgcgta gcggcgatc acggccttca gctggccccg     540
ggtggacagt gccgagggcc ggccatccag ttcattggca tcgcagatgg ccagggcgcg   600
accgtcatcg ctccagggca agcgatgaac ctggctgggt tccgctacca acgccaggtc   660
gccgtcgtcg cagccgtaga atttcgccgg cgggtagccg cccatgatgc attgcagcag   720
caccccacgg gccatctgca ggcggcggcc ttcgagaaag ccttcggcgg tcatcacctt   780
gccgcgtggg acgccgttga ggtcggggggt gacgcattcg atttcatcga tgccctggag   840
ctgagcgatg ctcatgacgc ttgtccttgt tgttgtaggc tgacaacaac ataggctggg    900
ggtgtttaaa atatcaagca gcctctcgaa cgcctgggc ctcttctatt cgcgcaaggt     960
catgccattg gccggcaacg gcaaggctgt cttgtagcgc acctgtttca aggcaaaact   1020
cgagcggata ttcgccacac ccggcaaccg ggtcaggtaa tcgagaaacc gctccagcgc   1080
ctggatactc ggcagcagta cccgcaacag gtagtccggg tcgcccgtca tcaggtagca   1140
ctccatcacc tcgggccgtt cggcaatttc ttcctcgaag cggtgcagcg actgctctac   1200
ctgtttttcc aggctgacat ggatgaacac attcacatcc agccccaacg cctcgggcga   1260
caacaaggtc acctgctggc ggatcacccc cagttcttcc atggcccgca cccggttgaa   1320
acagggcgtg ggcgacaggt tgaccgagcg tgccagctcg gcgttggtga tgcgggcgtt   1380
ttcctgcagg ctgttgagaa tgccgatatc ggtacgatcg agtttgcgca tgagacaaaa   1440
tcaccggttt tttgtgttta tgcggaatgt ttatctgccc cgctcggcaa aggcaatcaa   1500
cttgagagaa aaattctcct gccggaccac taagatgtag gggacgctga cttaccagtc   1560
acaagccggt actcagcggc ggccgcttca gagctcacaa aaacaaatac ccgagcgagc   1620
gtaaaaagca tgaacgagta cgcccccctg cgtttgcatg tgcccgagcc caccggccgg   1680
ccaggctgcc agaccgattt ttcctacctg cgcctgaacg atgcaggtca agcccgtaaa   1740
cccccctgtcg atgtcgacgc tgccgacacc gccgacctgt cctacagcct ggtccgcgtg   1800
ctcgacgagc aaggcgacgc ccaaggcccg tgggctgaag acatcgaccc gcagatcctg   1860
cgccaaggca tgcgcgccat gctcaagacg cggatcttcg acagccgcat ggtggttgcc   1920
cagcgccaga agaagatgtc cttctacatg cagagcctgg gcgaagaagc catcggcagc   1980
ggccaggcgc tggcgcttaa ccgcaccgac atgtgcttcc ccacctaccg tcagcaaagc   2040
atcctgatgg cccgcgacgt gtcgctggtg gagatgatct gccagttgct gtccaacgaa   2100
cgcgacccc tcaagggccg ccagctgccg atcatgtact cggtacgcga ggccggcttc   2160
ttcaccatca gcggcaacct ggcgacccag ttcgtgcagg cggtcggctg ggccatggcc   2220
```

-continued

```
tcggcgatca agggcgatac caagattgcc tcggcctgga tcggcgacgg cgccactgcc        2280
gaatcggact tccacaccgc cctcacctt gcccacgttt accgcgcccc ggtgatcctc         2340
aacgtggtca acaaccagtg ggccatctca accttccagg ccatcgccgg tggcgagtcg        2400
accaccttcg ccgccgtgg cgtgggctgc ggcatcgctt cgctgcgggt ggacggcaac        2460
gacttcgtcg ccgtttacgc cgcttcgcgc tgggctgccg aacgtgcccg ccgtggtttg       2520
ggcccgagcc tgatcgagtg ggtcacctac cgtgccggcc cgcactcgac ctcggacgac       2580
ccgtccaagt accgccctgc cgatgactgg agccacttcc cgctgggtga cccgatcgcc       2640
cgcctgaagc agcacctgat caagatcggc cactggtccg aagaagaaca ccaggccacc       2700
acggccgagt tcgaagcggc cgtgattgct gcgcaaaaag aagccgagca gtacggcacc       2760
ctggccaacg gtcacatccc gagcgccgcc tcgatgttcg aggacgtgta caaggagatg       2820
cccgaccacc tgcgccgcca acgccaggaa ctggggtt gagatgaacg accacaacaa         2880
cagcatcaac ccggaaaccg ccatggccac cactaccatg accatgatcc aggccctgcg       2940
ctcggccatg gatgtcatgc ttgagcgcga cgacaatgtg gtggtgtacg ccaggacgt        3000 cggctacttc ggcggcgtgt tccgctgcac cgaaggcctg cagaccaagt acggcaagtc       3060
ccgcgtgttc gacgcgccca tctctgaaag cggcatcgtc ggcaccgccg tgggcatggg       3120
tgcctacggc ctgcgcccgg tggtggaaat ccagttcgct gactacttct acccggcctc       3180
cgaccagatc gtttctgaaa tggcccgcct gcgctaccgt tcggccggcg agttcatcgc       3240
cccgctgacc ctgcgtatgc cctgcggtgg cggtatctat ggcggccaga cacacagcca       3300
gagcccggaa gcgatgttca ctcaggtgtg cggcctgcgc accgtaatgc catccaaccc       3360
gtacgacgcc aaaggcctgc tgattgcctc gatcgaatgc gacgacccgg tgatcttcct       3420
ggagcccaag cgcctgtaca acggcccgtt cgacggccac catgaccgcc cggttacgcc       3480
gtggtcgaaa cacccgcaca gcgccgtgcc cgatggctac tacaccgtgc cactggacaa       3540
ggccgccatc acccgccccg gcaatgacgt gagcgtgctc acctatggca ccaccgtgta       3600
cgtggcccag gtggccgccg aagaaagtgg cgtggatgcc gaagtgatcg acctgcgcag       3660 cctgtgccg ctagacctgg acaccatcgt cgagtcggtg aaaaagaccg gccgttgcgt       3720
ggtagtacac gaggccaccc gtacttgtgg cttggcgca gaactggtgt cgctggtgca      3780
ggagcactgc ttccaccacc tggaggcgcc gatcgagcgc gtcaccggtt gggacacccc       3840
ctaccctcac gcgcaggaat gggcttactt cccagggcct tcgcgggtag gtgcggcatt       3900
gaaaaaggtc atgaggtct gaatgggcac gcacgtcatc aagatgccgg acattggcga       3960
aggcatcgcg caggtcgaat tggtggaatg gttcgtcaag gtgggcgaca tcatcgccga       4020
ggaccaagtg gtagccgacg tcatgaccga caaggccacc gtggaaatcc cgtcgccggt       4080
cagcggcaag gtgctggccc tgggtggcca gccaggtgaa gtgatggcgg tcggcagtga       4140
gctgatccgc atcgaagtgg aaggcagcgg caaccatgtg gatgtgccgc aagccaagcc       4200
ggccgaagtg cctgcggcac cggtagccgc taaacctgaa ccacagaaag acgttaaacc       4260
ggcggcgtac caggcgtcag ccagccacga ggcagcgccc atcgtgccgc gccagccggg       4320
cgacaagccg ctgcctcgc cggcggtgcg caaacgcgcc ctcgatgccg gcatcgaatt       4380
gcgttatgtg cacggcagcg gcccggccgg gcgcatcctg cacgaagacc tcgacgcgtt       4440
catgagcaaa ccgcaaagcg ctgccgggca accccccaat ggctatgcca ggcgcaccga       4500
cagcgagcag gtgccggtga tcggcctgcg ccgcaagatc gcccagcgca tgcaggacgc       4560
caagcgccgg gtcgcgcact tcagctatgt ggaagaaatc gacgtcaccg ccctggaagc       4620
```

```
cctgcgccag cagctcaaca gcaagcacgg cgacagccgc ggcaagctga cactgctgcc    4680
gttcctggtg cgcgccctgg tcgtggcact gcgtgacttc ccgcagataa cgccaccta    4740 cgatgacgaa gcgcagatca tcacccgcca tggcgcggtg catgtgggca tcgccaccca    4800
aggtgacaac ggcctgatgg tacccgtgct gcgccacgcc gaagcgggca gcctgtgggc    4860
caatgccggt gagatttcac gcctggccaa cgctgcgcgc aacaacaagg ccagccgcga    4920
agagctgtcc ggttcgacca ttaccctgac cagcctcggc gccctgggcg catcgtcag    4980 cacgccggtg gtcaacaccc cggaagtggc gatcgtcggt gtcaaccgca tggttgagcg    5040
gcccgtggtg atcgacggcc agatcgtcgt gcgcaagatg atgaacctgt ccagctcgtt    5100
cgaccaccgc gtggtcgatg gcatggacgc cgccctgttc atccaggccg tgcgtggcct    5160
gctcgaacaa cccgcctgcc tgttcgtgga gtgagcatgc aacagactat ccagacaacc    5220
ctgttgatca tcggcggcgg ccctggcggc tatgtggcgg ccatccgcgc cgggcaactg    5280
ggcatcccta ccgtgctggt ggaaggccag gcgctgggcg gtacctgcct gaacatcggc    5340
tgcattccgt ccaaggcgct gatccatgtg gccgagcagt tccaccaggc ctcgcgcttt    5400
accgaaccct cgccgctggg catcagcgtg gcttcgccac gcctggacat cggccagagc    5460
gtggcctgga aagacggcat cgtcgatcgc ctgaccactg tgtcgccgc cctgctgaaa    5520 aagcacgggg tgaaggtggt gcacggctgg gccaaggtgc ttgatggcaa gcaggtcgag    5580
gtggatggcc agcgcatcca gtgcgagcac ctgttgctgg ccacgggctc cagcagtgtc    5640
gaactgccga tgctgccgtt gggtgggccg gtgatttcct cgaccgaggc cctggcaccg    5700
aaagccctgc cgcaacacct ggtggtggtg ggcggtggct acatcggcct ggagctgggt    5760
atcgcctacc gcaagctcgg cgcgcaggtc agcgtggtgg aagcgcgcga gcgcatcctg    5820
ccgacttacg acagcgaact gaccgccccg gtggccgagt cgctgaaaaa gctgggtatc    5880
gccctgcacc ttggccacag cgtcgaaggt tacgaaaatg gctgcctgct ggccaacgat    5940
ggcaagggcg gacaactgcg cctggaagcc gaccgggtgc tggtggccgt gggccgccgc    6000
ccacgcacca agggcttcaa cctggaatgc ctggacctga agatgaatgg tgccgcgatt    6060
gccatcgacg agcgctgcca gaccagcatg cacaacgtct gggccatcgg cgacgtggcc    6120
ggcgaaccga tgctggcgca ccgggccatg gcccagggcg agatggtggc cgagatcatc    6180
gccggcaagg cacgccgctt cgaacccgct gcgatagccg ccgtgtgctt caccgacccg    6240
gaagtggtcg tggtcggcaa gacgccggaa caggccagtc agcaaggcct ggactgcatc    6300
gtcgcgcagt tcccgttcgc cgccaacggc cgggccatga gcctggagtc gaaaagcggt    6360
ttcgtgcgcg tggtcgcgcg gcgtgacaac cacctgatcc tgggctggca gcggttggc    6420 gtggcggttt ccgagctgtc cacggcgttt gcccagtcgc tggagatggg tgcctgcctg    6480
gaggatgtgg ccggtaccat ccatgcccac ccgaccctgg tgaagcggt acaggaagcg    6540 gcactgcgtg ccctgggcca cgccctgcat atctgacact gaagcggccg aggccgattt    6600
ggcccgccgc gccgagaggc gctgcgggtc ttttttatac ctg    6643
```

<210> SEQ ID NO 55
<211> LENGTH: 352
<212> TYPE: PRT
<213> ORGANISM: Pseudomonas putida

<400> SEQUENCE: 55

Met Asn Asp His Asn Asn Ser Ile Asn Pro Glu Thr Ala Met Ala Thr
1               5                   10                  15

Thr Thr Met Thr Met Ile Gln Ala Leu Arg Ser Ala Met Asp Val Met
            20                  25                  30

Leu Glu Arg Asp Asp Asn Val Val Tyr Gly Gln Asp Val Gly Tyr
        35                  40                  45

Phe Gly Gly Val Phe Arg Cys Thr Glu Gly Leu Gln Thr Lys Tyr Gly
 50                  55                  60

Lys Ser Arg Val Phe Asp Ala Pro Ile Ser Glu Ser Gly Ile Val Gly
 65                  70                  75                  80

Thr Ala Val Gly Met Gly Ala Tyr Gly Leu Arg Pro Val Val Glu Ile
                 85                  90                  95

Gln Phe Ala Asp Tyr Phe Tyr Pro Ala Ser Asp Gln Ile Val Ser Glu
            100                 105                 110

Met Ala Arg Leu Arg Tyr Arg Ser Ala Gly Glu Phe Ile Ala Pro Leu
        115                 120                 125

Thr Leu Arg Met Pro Cys Gly Gly Ile Tyr Gly Gly Gln Thr His
130                 135                 140

Ser Gln Ser Pro Glu Ala Met Phe Thr Gln Val Cys Gly Leu Arg Thr
145                 150                 155                 160

Val Met Pro Ser Asn Pro Tyr Asp Ala Lys Gly Leu Leu Ile Ala Ser
                165                 170                 175

Ile Glu Cys Asp Asp Pro Val Ile Phe Leu Glu Pro Lys Arg Leu Tyr
            180                 185                 190

Asn Gly Pro Phe Asp Gly His His Asp Arg Pro Val Thr Pro Trp Ser
        195                 200                 205

Lys His Pro His Ser Ala Val Pro Asp Gly Tyr Tyr Thr Val Pro Leu
    210                 215                 220

Asp Lys Ala Ala Ile Thr Arg Pro Gly Asn Asp Val Ser Val Leu Thr
225                 230                 235                 240

Tyr Gly Thr Thr Val Tyr Val Ala Gln Val Ala Ala Glu Ser Gly
                245                 250                 255

Val Asp Ala Glu Val Ile Asp Leu Arg Ser Leu Trp Pro Leu Asp Leu
            260                 265                 270

Asp Thr Ile Val Glu Ser Val Lys Lys Thr Gly Arg Cys Val Val Val
        275                 280                 285

His Glu Ala Thr Arg Thr Cys Gly Phe Gly Ala Glu Leu Val Ser Leu
    290                 295                 300

Val Gln Glu His Cys Phe His His Leu Glu Ala Pro Ile Glu Arg Val
305                 310                 315                 320

Thr Gly Trp Asp Thr Pro Tyr Pro His Ala Gln Glu Trp Ala Tyr Phe
                325                 330                 335

Pro Gly Pro Ser Arg Val Gly Ala Ala Leu Lys Lys Val Met Glu Val
            340                 345                 350

<210> SEQ ID NO 56
<211> LENGTH: 6643
<212> TYPE: DNA
<213> ORGANISM: Pseudomonas putida

<400> SEQUENCE: 56
gcatgcctgc aggccgccga tgaaatggtg aaggtatcg gtaggctggc cctgctcatc        60
gctgaacacg ttacgcccgc tgccggtatc gaccaggctc tggtgaatat gcatggaact      120
gccaggcgtg cgcgccagcg gtttggccat gcacaccacg gtcagcccgt gcttgagtgc      180
cacttccttg agcaggtgtt tgaacaggaa ggtctggtcg gccagcagca gcgggtcgcc      240

```
atgtagcaag ttgatctcga actggctgac gcccatttcg tgcatgaagg tgtcgcgcgg    300
caggccgagc gcggccatgc actggtacac ctcattgaag aacgggcgca ggccgttgtt    360
ggaactgaca ctgaacgccg aatggcccag ctcgcggcgg ccgtcggtgc ccagcggtgg    420
ctggaacggc tgctgcgggt cactgttggg ggcaaacacg aagaactcaa gctcggtcgc    480
cactaccggt gccagaccca acgctgcgta gcgggcgatc acggccttca gctggccccg    540
ggtggacagt gccgagggcc ggccatccag ttcattggca tcgcagatgg ccagggcgcg    600
accgtcatcg ctccagggca agcgatgaac ctggctgggt tccgctacca acgccaggtc    660
gccgtcgtcg cagccgtaga atttcgccgg cgggtagccg cccatgatgc attgcagcag    720
caccccacgg gccatctgca ggcggcggcc ttcgagaaag ccttcggcgg tcatcacctt    780
gccgcgtggg acgccgttga ggtcgggggt gacgcattcg atttcatcga tgccctggag    840
ctgagcgatg ctcatgacgc ttgtccttgt tgttgtaggc tgacaacaac ataggctggg    900
ggtgtttaaa atatcaagca gcctctcgaa cgcctgggc ctcttctatt cgcgcaaggt     960
catgccattg gccggcaacg gcaaggctgt cttgtagcgc acctgtttca aggcaaaact   1020
cgagcggata ttcgccacac ccggcaaccg ggtcaggtaa tcgagaaacc gctccagcgc   1080
ctggatactc ggcagcagta cccgcaacag gtagtccggg tcgcccgtca tcaggtagca   1140
ctccatcacc tcgggccgtt cggcaatttc ttcctgaag cggtgcagcg actgctctac     1200 ctgttttttcc aggctgacat ggatgaacac attcacatcc agccccaacg cctcgggcga   1260
caacaaggtc acctgctggc ggatcacccc cagttcttcc atggcccgca cccggttgaa   1320
acagggcgtg ggcgacaggt tgaccgagcg tgccagctcg gcgttggtga tgcgggcgtt   1380
ttcctgcagg ctgttgagaa tgccgatatc ggtacgatcg agtttgcgca tgagacaaaa   1440
tcaccggttt tttgtgttta tgcggaatgt ttatctgccc cgctcggcaa aggcaatcaa   1500
cttgagagaa aaattctcct gccggaccac taagatgtag gggacgctga cttaccagtc   1560
acaagccggt actcagcggc ggccgcttca gagctcacaa aaacaaatac ccgagcgagc   1620
gtaaaaagca tgaacgagta cgccccctg cgtttgcatg tgcccgagcc caccggccgg    1680
ccaggctgcc agaccgattt ttcctacctg cgcctgaacg atgcaggtca agcccgtaaa   1740 cccctgtcg atgtcgacgc tgccgacacc gccgacctgt cctacagcct ggtccgcgtg    1800
ctcgacgagc aaggcgacgc ccaaggcccg tgggctgaag acatcgaccc gcagatcctg   1860
cgccaaggca tgcgcgccat gctcaagacg cggatcttcg acagccgcat ggtggttgcc   1920
cagcgccaga agaagatgtc cttctacatg cagagcctgg cgaagaagc catcggcagc    1980 ggccaggcgc tggcgcttaa ccgcaccgac atgtgcttcc ccacctaccg tcagcaaagc   2040
atcctgatgg cccgcgacgt gtcgctggtg gagatgatct gccagttgct gtccaacgaa   2100 cgcgacccc tcaagggccg ccagctgccg atcatgtact cggtacgcga ggccggcttc    2160
ttcaccatca gcgcaaacct ggcgaccagt tcgtgcaggg cggtcggctg gccatggcc    2220 tcggcgatca agggcgatac caagattgcc tcggcctgga tcgcgacgg cgccactgcc    2280 gaatcggact ccacaccgc cctcacctttt gcccacgttt accgcgcccc ggtgatcctc    2340
aacgtggtca caaccagtg ggccatctca accttccagg ccatcgccgg tggcgagtcg    2400
accaccttcg ccggccgtgg cgtgggctgc ggcatcgctt cgctgcgggt ggacggcaac   2460
gacttcgtcg ccgtttacgc cgcttcgcgc tgggctgccg aacgtgcccg ccgtggtttg    2520
ggcccgagcc tgatcgagtg ggtcacctac cgtgccggcc cgcactcgac ctcggacgac   2580
```

```
ccgtccaagt accgccctgc cgatgactgg agccacttcc cgctgggtga cccgatcgcc   2640
cgcctgaagc agcacctgat caagatcggc cactggtccg aagaagaaca ccaggccacc   2700
acggccgagt tcgaagcggc cgtgattgct gcgcaaaaag aagccgagca gtacggcacc   2760
ctggccaacg gtcacatccc gagcgccgcc tcgatgttcg aggacgtgta caaggagatg   2820
cccgaccacc tgcgccgcca acgccaggaa ctggggggttt gagatgaacg accacaacaa   2880
cagcatcaac ccgaaaccgg ccatggccac cactaccatg accatgatcc aggccctgcg   2940
ctcggccatg gatgtcatgc ttgagcgcga cgacaatgtg gtggtgtacg ccaggacgt    3000
cggctacttc ggcggcgtgt tccgctgcac cgaaggcctg cagaccaagt acggcaagtc   3060
ccgcgtgttc gacgcgccca tctctgaaag cggcatcgtc ggcaccgccg tgggcatggg   3120
tgcctacggc ctgcgcccgg tggtggaaat ccagttcgct gactacttct acccggcctc   3180
cgaccagatc gtttctgaaa tggcccgcct gcgctaccgt tcggccggcg agttcatcgc   3240
cccgctgacc ctgcgtatgc cctgcggtgg cggtatctat ggcggccaga cacacagcca   3300
gagcccggaa gcgatgttca ctcaggtgtg cggcctgcgc accgtaatgc catccaaccc   3360
gtacgacgcc aaaggcctgc tgattgcctc gatcgaatgc gacgacccgg tgatcttcct   3420
ggagcccaag cgcctgtaca acggcccgtt cgacggccac catgaccgcc cggttacgcc   3480
gtggtcgaaa cacccgcaca gcgccgtgcc cgatggctac tacaccgtgc cactggacaa   3540
ggccgccatc acccgccccg gcaatgacgt gagcgtgctc acctatggca ccaccgtgta   3600
cgtggcccag gtggccgccg aagaaagtgg cgtggatgcc gaagtgatcg acctgcgcag   3660
cctgtggccg ctagacctgg acaccatcgt cgagtcggtg aaaaagaccg gccgttgcgt   3720
ggtagtacac gaggccaccc gtacttgtgg ctttggcgca gaactggtgt cgctggtgca   3780
ggagcactgc ttccaccacc tggaggcgcc gatcgagcgc gtcaccggtt gggacacccc   3840
ctaccctcac gcgcaggaat gggcttactt cccagggcct tcgcgggtag gtgcggcatt   3900
gaaaaaggtc atggaggtct gaatgggcac gcacgtcatc aagatgccgg acattgcga   3960
aggcatcgcg caggtcgaat tggtggaatg gttcgtcaag gtgggcgaca tcatcgccga   4020
ggaccaagtg gtagccgacg tcatgaccga caaggccacc gtggaaatcc cgtcgccggt   4080
cagcggcaag gtgctggccc tgggtggcca gccaggtgaa gtgatggcgg tcggcagtga   4140
gctgatccgc atcgaagtgg aaggcagcgg caaccatgtg gatgtgccgc aagccaagcc   4200
ggccgaagtg cctgcggcac cggtagccgc taaacctgaa ccacagaaag acgttaaacc   4260
ggcggcgtac caggcgtcag ccagccacga ggcagcgccc atcgtgccgc gccagccggg   4320
cgacaagccg ctggcctcgc cggcggtgcg caaacgcgcc ctcgatgccg gcatcgaatt   4380
gcgttatgtg cacggcagcg gcccggccgg gcgcatcctg cacgaagacc tcgacgcgtt   4440
catgagcaaa ccgcaaagcg ctgccgggca accccccaat ggctatgcca ggcgcaccga   4500
cagcgagcag gtgccggtga tcggcctgcg ccgcaagatc gcccagcgca tgcaggacgc   4560
caagcgccgg gtcgcgcact tcagctatgt ggaagaaatc gacgtcaccg ccctggaagc   4620
cctgcgccag cagctcaaca gcaagcacgg cgacagccgc ggcaagctga cactgctgcc   4680
gttcctggtg cgcgccctgg tcgtggcact gcgtgacttc ccgcagataa acgccaccta   4740
cgatgacgaa gcgcagatca tcacccgcca tggcgcggtg catgtgggca tcgccaccca   4800
aggtgacaac ggcctgatgg taccgtgct cgccacgcc gaagcgggca gcctgtgggc   4860
caatgccggt gagatttcac gcctggccaa cgctgcgcgc aacaacaagg ccagccgcga   4920
agagctgtcc ggttcgacca ttaccctgac cagcctcggc gccctgggcg catcgtcag   4980
```

```
cacgccggtg tcaacacccc cggaagtggc gatcgtcggt gtcaaccgca tggttgagcg    5040
gcccgtggtg atcgacggcc agatcgtcgt gcgcaagatg atgaacctgt ccagctcgtt    5100
cgaccaccgc gtggtcgatg gcatggacgc cgccctgttc atccaggccg tgcgtggcct    5160
gctcgaacaa cccgcctgcc tgttcgtgga gtgagcatgc aacagactat ccagacaacc    5220
ctgttgatca tcggcggcgg ccctggcggt tatgtggcgg ccatccgcgc cgggcaactg    5280
ggcatcccta ccgtgctggt ggaaggccag gcgctgggcg gtacctgcct gaacatcggc    5340
tgcattccgt ccaaggcgct gatccatgtg gccgagcagt ccaccaggc ctcgcgcttt     5400 accgaaccct cgccgctggg catcagcgtg gcttcgccac gcctggacat cggccagagc    5460
gtggcctgga agacggcat cgtcgatcgc ctgaccactg tgtcgccgc cctgctgaaa      5520 aagcacgggg tgaaggtggt gcacggctgg gccaaggtgc ttgatggcaa gcaggtcgag    5580
gtggatggcc agcgcatcca gtgcgagcac ctgttgctgg ccacgggctc cagcagtgtc    5640
gaactgccga tgctgccgtt gggtgggccg gtgatttcct cgaccgaggc cctggcaccg    5700
aaagccctgc cgcaacacct ggtggtggtg gcggtggct acatcggcct ggagctgggt    5760
atcgcctacc gcaagctcgg cgcgcaggtc agcgtggtgg aagcgcgcga gcgcatcctg    5820
ccgacttacg acagcgaact gaccgccccg gtggccgagt cgctgaaaaa gctgggtatc    5880
gccctgcacc ttggccacag cgtcgaaggt tacgaaaatg gctgcctgct ggccaacgat    5940
ggcaagggcg gacaactgcg cctggaagcc gaccgggtgc tggtggccgt gggccgccgc    6000
ccacgcacca agggcttcaa cctggaatgc ctggacctga agatgaatgg tgccgcgatt    6060
gccatcgacg agcgctgcca gaccagcatg cacaacgtct gggccatcgg cgacgtggcc    6120
ggcgaaccga tgctggcgca ccgggccatg gcccagggcg agatggtggc cgagatcatc    6180
gccggcaagg cacgccgctt cgaacccgct gcgatagccg ccgtgtgctt caccgacccg    6240
gaagtggtcg tggtcggcaa gacgccggaa caggccagtc agcaaggcct ggactgcatc    6300
gtcgcgcagt tcccgttcgc cgccaacggc cgggccatga gcctggagtc gaaaagcggt    6360
ttcgtgcgcg tggtcgcgcg gcgtgacaac cacctgatcc tgggctggca gcggttggc     6420 gtggcggttt ccgagctgtc cacggcgttt gcccagtcgc tggagatggg tgcctgcctg    6480
gaggatgtgg ccggtaccat ccatgcccac ccgaccctgg gtgaagcggt acaggaagcg    6540
gcactgcgtg ccctgggcca cgccctgcat atctgacact gaagcggccg aggccgattt    6600
ggcccgccgc gccagagggc gctgcgggtc tttttttatac ctg                     6643
```

<210> SEQ ID NO 57
<211> LENGTH: 423
<212> TYPE: PRT
<213> ORGANISM: Pseudomonas putida

<400> SEQUENCE: 57

Met Gly Thr His Val Ile Lys Met Pro Asp Ile Gly Glu Gly Ile Ala
1               5                   10                  15

Gln Val Glu Leu Val Glu Trp Phe Val Lys Val Gly Asp Ile Ile Ala
                20                  25                  30

Glu Asp Gln Val Val Ala Asp Val Met Thr Asp Lys Ala Thr Val Glu
            35                  40                  45

Ile Pro Ser Pro Val Ser Gly Lys Val Leu Ala Leu Gly Gly Gln Pro
        50                  55                  60

Gly Glu Val Met Ala Val Gly Ser Glu Leu Ile Arg Ile Glu Val Glu
65                  70                  75                  80

Gly Ser Gly Asn His Val Asp Val Pro Gln Ala Lys Pro Ala Glu Val
                85                  90                  95

Pro Ala Ala Pro Val Ala Ala Lys Pro Glu Pro Gln Lys Asp Val Lys
            100                 105                 110

Pro Ala Ala Tyr Gln Ala Ser Ser His Glu Ala Ala Pro Ile Val
            115                 120                 125

Pro Arg Gln Pro Gly Asp Lys Pro Leu Ala Ser Pro Ala Val Arg Lys
        130                 135                 140

Arg Ala Leu Asp Ala Gly Ile Glu Leu Arg Tyr Val His Gly Ser Gly
145                 150                 155                 160

Pro Ala Gly Arg Ile Leu His Glu Asp Leu Asp Ala Phe Met Ser Lys
                165                 170                 175

Pro Gln Ser Ala Ala Gly Gln Thr Pro Asn Gly Tyr Ala Arg Arg Thr
            180                 185                 190

Asp Ser Glu Gln Val Pro Val Ile Gly Leu Arg Arg Lys Ile Ala Gln
        195                 200                 205

Arg Met Gln Asp Ala Lys Arg Arg Val Ala His Phe Ser Tyr Val Glu
    210                 215                 220

Glu Ile Asp Val Thr Ala Leu Glu Ala Leu Arg Gln Gln Leu Asn Ser
225                 230                 235                 240

Lys His Gly Asp Ser Arg Gly Lys Leu Thr Leu Leu Pro Phe Leu Val
                245                 250                 255

Arg Ala Leu Val Val Ala Leu Arg Asp Phe Pro Gln Ile Asn Ala Thr
            260                 265                 270

Tyr Asp Asp Glu Ala Gln Ile Ile Thr Arg His Gly Ala Val His Val
        275                 280                 285

Gly Ile Ala Thr Gln Gly Asp Asn Gly Leu Met Val Pro Val Leu Arg
    290                 295                 300

His Ala Glu Ala Gly Ser Leu Trp Ala Asn Ala Gly Glu Ile Ser Arg
305                 310                 315                 320

Leu Ala Asn Ala Ala Arg Asn Asn Lys Ala Ser Arg Glu Glu Leu Ser
                325                 330                 335

Gly Ser Thr Ile Thr Leu Thr Ser Leu Gly Ala Leu Gly Gly Ile Val
            340                 345                 350

Ser Thr Pro Val Val Asn Thr Pro Glu Val Ala Ile Val Gly Val Asn
        355                 360                 365

Arg Met Val Glu Arg Pro Val Val Ile Asp Gly Gln Ile Val Val Arg
    370                 375                 380

Lys Met Met Asn Leu Ser Ser Ser Phe Asp His Arg Val Val Asp Gly
385                 390                 395                 400

Met Asp Ala Ala Leu Phe Ile Gln Ala Val Arg Gly Leu Leu Glu Gln
                405                 410                 415

Pro Ala Cys Leu Phe Val Glu
            420

<210> SEQ ID NO 58
<211> LENGTH: 6643
<212> TYPE: DNA
<213> ORGANISM: Pseudomonas putida

<400> SEQUENCE: 58
gcatgcctgc aggccgccga tgaaatggtg gaaggtatcg gtaggctggc cctgctcatc     60
gctgaacacg ttacgcccgc tgccggtatc gaccaggctc tggtgaatat gcatggaact    120

```
gccaggcgtg cgcgccagcg gtttggccat gcacaccacg gtcagcccgt gcttgagtgc    180
cacttccttg agcaggtgtt tgaacaggaa ggtctggtcg ccagcagca gcgggtcgcc    240 atgtagcaag ttgatctcga actggctgac gcccatttcg tgcatgaagg tgtcgcgcgg    300
caggccgagc gcggccatgc actggtacac ctcattgaag aacgggcgca ggccgttgtt    360
ggaactgaca ctgaacgccg aatggcccag ctcgcggcgg ccgtcggtgc ccagcggtgg    420
ctggaacggc tgctgcgggt cactgttggg ggcaaacacg aagaactcaa gctcggtcgc    480
cactaccggt gccagaccca cgctgcgta gcgggcgatc acggccttca gctggccccg    540
ggtggacagt gccgagggcc ggccatccag ttcattggca tcgcagatgg ccagggcgcg    600
accgtcatcg ctccagggca agcgatgaac ctggctgggt tccgctacca acgccaggtc    660
gccgtcgtcg cagccgtaga atttcgccgg cgggtagccg cccatgatgc attgcagcag    720
caccccacgg gccatctgca ggcggcggcc ttcgagaaag ccttcggcgg tcatcacctt    780
gccgcgtggg acgccgttga ggtcgggggt gacgcattcg atttcatcga tgccctggag    840
ctgagcgatg ctcatgacgc ttgtccttgt tgttgtaggc tgacaacaac ataggctggg    900
ggtgtttaaa atatcaagca gcctctcgaa cgcctgggc ctcttctatt cgcgcaaggt    960
catgccattg gccggcaacg gcaaggctgt cttgtagcgc acctgtttca aggcaaaact   1020
cgagcggata ttcgccacac ccggcaaccg ggtcaggtaa tcgagaaacc gctccagcgc   1080
ctggatactc ggcagcagta cccgcaacag gtagtccggg tcgcccgtca tcaggtagca   1140
ctccatcacc tcgggccgtt cggcaatttc ttcctcgaag cggtgcagcg actgctctac   1200 ctgttttcc aggctgacat ggatgaacac attcacatcc agcccaacg cctcgggcga   1260 caacaaggtc acctgctggc ggatcacccc cagttcttcc atggcccgca cccggttgaa   1320
acagggcgtg ggcgacaggt tgaccgagcg tgccagctcg gcgttggtga tgcgggcgtt   1380
ttcctgcagg ctgttgagaa tgccgatatc ggtacgatcg agtttgcgca tgagacaaaa   1440
tcaccggttt tttgtgttta tgcggaatgt ttatctgccc cgctcggcaa aggcaatcaa   1500
cttgagagaa aaattctcct gccggaccac taagatgtag gggacgctga cttaccagtc   1560
acaagccggt actcagcggc ggccgcttca gagctcacaa aaacaaatac ccgagcgagc   1620
gtaaaaagca tgaacgagta cgccccctg cgtttgcatg tgcccgagcc caccggccgg   1680
ccaggctgcc agaccgattt ttcctacctg cgcctgaacg atgcaggtca agcccgtaaa   1740 cccctgtcg atgtcgacgc tgccgacacc gccgacctgt cctacagcct ggtccgcgtg   1800
ctcgacgagc aaggcgacgc ccaaggcccg tgggctgaag acatcgaccc gcagatcctg   1860
cgccaaggca tgcgcgccat gctcaagacg cggatcttcg acagccgcat ggtggtttgcc   1920 cagcgccaga gaagatgtc cttctacatg cagagcctgg gcgaagaagc catcggcagc   1980
ggccaggcgc tggcgcttaa ccgcaccgac atgtgcttcc ccacctaccg tcagcaaagc   2040
atcctgatgg cccgcgacgt gtcgctggtg gagatgatct gccagttgct gtccaacgaa   2100
cgcgaccccc tcaagggccg ccagctgccg atcatgtact cggtacgcga ggccggcttc   2160
ttcaccatca gcggcaacct ggcgacccag ttcgtgcagg cggtcggctg ggccatggcc   2220
tcggcgatca agggcgatac caagattgcc tcggcctgga tcgcgacgg cgccactgcc   2280 gaatcggact tccacaccgc cctcaccttt gcccacgttt accgcgcccc ggtgatcctc   2340
aacgtggtca caaccagtg ggccatctca accttccagg ccatcgccgg tggcgagtcg   2400
accaccttcg ccgccgtgg cgtgggctgc ggcatcgctt cgctgcgggt ggacggcaac   2460
gacttcgtcg ccgtttacgc cgcttcgcgc tgggctgccg aacgtgcccg ccgtggtttg   2520
```

```
ggcccgagcc tgatcgagtg ggtcacctac cgtgccggcc cgcactcgac ctcggacgac    2580
ccgtccaagt accgccctgc cgatgactgg agccacttcc cgctgggtga cccgatcgcc    2640
cgcctgaagc agcacctgat caagatcggc cactggtccg aagaagaaca ccaggccacc    2700
acggccgagt tcgaagcggc cgtgattgct gcgcaaaaag aagccgagca gtacggcacc    2760
ctggccaacg gtcacatccc gagcgccgcc tcgatgttcg aggacgtgta caaggagatg    2820
cccgaccacc tgcgccgcca acgccaggaa ctgggggttt gagatgaacg accacaacaa    2880
cagcatcaac ccggaaaccg ccatggccac cactaccatg accatgatcc aggccctgcg    2940
ctcggccatg gatgtcatgc ttgagcgcga cgacaatgtg gtggtgtacg ccaggacgt    3000 cggctacttc ggcggcgtgt tccgctgcac cgaaggcctg cagaccaagt acggcaagtc    3060
ccgcgtgttc gacgcgccca tctctgaaag cggcatcgtc ggcaccgccg tgggcatggg    3120
tgcctacggc ctgcgcccgg tggtggaaat ccagttcgct gactacttct acccggcctc    3180
cgaccagatc gtttctgaaa tggcccgcct gcgctaccgt tcggccggcg agttcatcgc    3240
cccgctgacc ctgcgtatgc cctgcggtgg cggtatctat ggcggccaga cacacagcca    3300
gagcccggaa gcgatgttca ctcaggtgtg cggcctgcgc accgtaatgc catccaaccc    3360
gtacgacgcc aaaggcctgc tgattgcctc gatcgaatgc gacgacccgg tgatcttcct    3420
ggagcccaag cgcctgtaca acggcccgtt cgacggccac catgaccgcc cggttacgcc    3480
gtggtcgaaa cacccgcaca cgccgtgcc cgatggctac tacaccgtgc cactggacaa    3540
ggccgccatc acccgccccg gcaatgacgt gagcgtgctc acctatggca ccaccgtgta    3600
cgtggcccag gtggccgccg aagaaagtgg cgtggatgcc gaagtgatcg acctgcgcag    3660
cctgtggccg ctagacctgg acaccatcgt cgagtcggtg aaaaagaccg gccgttgcgt    3720
ggtagtacac gaggccaccc gtacttgtgg cttttggcgca gaactggtgt cgctggtgca    3780
ggagcactgc ttccaccacc tggaggcgcc gatcgagcgc gtcaccggtt gggacacccc    3840
ctaccctcac gcgcaggaat gggcttactt cccagggcct tcgcgggtag gtgcggcatt    3900
gaaaaaggtc atggaggtct gaatgggcac gcacgtcatc aagatgccgg acattggcga    3960
aggcatcgcg caggtcgaat tggtggaatg gttcgtcaag gtgggcgaca tcatcgccga    4020
ggaccaagtg gtagccgacg tcatgaccga caaggccacc gtggaaatcc cgtcgccggt    4080
cagcggcaag gtgctggccc tgggtggcca gccaggtgaa gtgatggcgg tcggcagtga    4140
gctgatccgc atcgaagtgg aaggcagcgg caaccatgtg gatgtgccgc aagccaagcc    4200
ggccgaagtg cctgcggcac cggtagccgc taaacctgaa ccacagaaag acgttaaacc    4260
ggcggcgtac caggcgtcag ccagccacga ggcagcgccc atcgtgccgc gccagccggg    4320
cgacaagccg ctggcctcgc cggcggtgcg caaacgcgcc ctcgatgccg gcatcgaatt    4380
gcgttatgtg cacggcagcg gcccggccgg gcgcatcctg cacgaagacc tcgacgcgtt    4440
catgagcaaa ccgcaaagcg ctgccgggca aaccccaat ggctatgcca ggcgcaccga    4500
cagcgagcag gtgccggtga tcggcctgcg ccgcaagatc gcccagcgca tgcaggacgc    4560
caagcgccgg gtcgcgcact tcagctatgt ggaagaaatc gacgtcaccg ccctggaagc    4620
cctgcgccag cagctcaaca gcaagcacgg cgacagccgc ggcaagctga cactgctgcc    4680
gttcctggtg cgcgcccctgg tcgtggcact gcgtgacttc ccgcagataa acgccaccta    4740
cgatgacgaa gcgcagatca tcacccgcca tggcgcggtg catgtgggca tcgccaccca    4800
aggtgacaac ggcctgatgg tacccgtgct gcgccacgcc gaagcgggca gcctgtgggc    4860
```

| | |
|---|---:|
| caatgccggt gagatttcac gcctggccaa cgctgcgcgc aacaacaagg ccagccgcga | 4920 |
| agagctgtcc ggttcgacca ttaccctgac cagcctcggc gccctgggcg gcatcgtcag | 4980 |
| cacgccggtg gtcaacaccc cggaagtggc gatcgtcggt gtcaaccgca tggtttgagcg | 5040 |
| gcccgtggtg atcgacggcc agatcgtcgt gcgcaagatg atgaacctgt ccagctcgtt | 5100 |
| cgaccaccgc gtggtcgatg gcatggacgc cgccctgttc atccaggccg tgcgtggcct | 5160 |
| gctcgaacaa cccgcctgcc tgttcgtgga gtgagcatgc aacagactat ccagacaacc | 5220 |
| ctgttgatca tcggcggcgg ccctggcggc tatgtggcgg ccatccgcgc cgggcaactg | 5280 |
| ggcatcccta ccgtgctggt ggaaggccag gcgctgggcg gtacctgcct gaacatcggc | 5340 |
| tgcattccgt ccaaggcgct gatccatgtg gccgagcagt tccaccaggc ctcgcgcttt | 5400 |
| accgaaccct cgccgctggg catcagcgtg gcttcgccac gcctggacat cggccagagc | 5460 |
| gtggcctgga aagacggcat cgtcgatcgc ctgaccactg tgtcgccgc cctgctgaaa | 5520 |
| aagcacgggg tgaaggtggt gcacggctgg gccaaggtgc ttgatggcaa gcaggtcgag | 5580 |
| gtggatggcc agcgcatcca gtgcgagcac ctgttgctgg ccacgggctc cagcagtgtc | 5640 |
| gaactgccga tgctgccgtt gggtgggccg gtgatttcct cgaccgaggc cctggcaccg | 5700 |
| aaagccctgc cgcaacacct ggtggtggtg ggcggtggct acatcggcct ggagctgggt | 5760 |
| atcgcctacc gcaagctcgg cgcgcaggtc agcgtggtgg aagcgcgcga gcgcatcctg | 5820 |
| ccgacttacg acagcgaact gaccgccccg gtggccgagt cgctgaaaaa gctgggtatc | 5880 |
| gccctgcacc ttggccacag cgtcgaaggt tacgaaaatg gctgcctgct ggccaacgat | 5940 |
| ggcaagggcg gacaactgcg cctggaagcc gaccgggtgc tggtggccgt gggccgccgc | 6000 |
| ccacgcacca agggcttcaa cctggaatgc ctggacctga agatgaatgg tgccgcgatt | 6060 |
| gccatcgacg agcgctgcca gaccagcatg cacaacgtct gggccatcgg cgacgtggcc | 6120 |
| ggcgaaccga tgctggcgca ccgggccatg gcccagggcg agatggtggc cgagatcatc | 6180 |
| gccggcaagg cacgccgctt cgaacccgct gcgatagccg ccgtgtgctt caccgacccg | 6240 |
| gaagtggtcg tggtcggcaa gacgccggaa caggccagtc agcaaggcct ggactgcatc | 6300 |
| gtcgcgcagt tcccgttcgc cgccaacggc cgggccatga gcctggagtc gaaaagcggt | 6360 |
| ttcgtgcgcg tggtcgcgcg gcgtgacaac cacctgatcc tgggctggca gcggttggc | 6420 |
| gtggcggttt ccgagctgtc cacggcgttt gcccagtcgc tggagatggg tgcctgcctg | 6480 |
| gaggatgtgg ccggtaccat ccatgcccac ccgaccctgg gtgaagcggt acaggaagcg | 6540 |
| gcactgcgtg ccctgggcca cgccctgcat atctgacact gaagcggccg aggccgattt | 6600 |
| ggcccgccgc gccgagaggc gctgcgggtc ttttttatac ctg | 6643 |

<210> SEQ ID NO 59
<211> LENGTH: 459
<212> TYPE: PRT
<213> ORGANISM: Pseudomonas putida

<400> SEQUENCE: 59

Met Gln Gln Thr Ile Gln Thr Thr Leu Leu Ile Ile Gly Gly Gly Pro
1               5                   10                  15

Gly Gly Tyr Val Ala Ala Ile Arg Ala Gly Gln Leu Gly Ile Pro Thr
            20                  25                  30

Val Leu Val Glu Gly Gln Ala Leu Gly Gly Thr Cys Leu Asn Ile Gly
        35                  40                  45

Cys Ile Pro Ser Lys Ala Leu Ile His Val Ala Glu Gln Phe His Gln
    50                  55                  60

```
Ala Ser Arg Phe Thr Glu Pro Ser Pro Leu Gly Ile Ser Val Ala Ser
 65                  70                  75                  80

Pro Arg Leu Asp Ile Gly Gln Ser Val Ala Trp Lys Asp Gly Ile Val
                 85                  90                  95

Asp Arg Leu Thr Thr Gly Val Ala Ala Leu Leu Lys Lys His Gly Val
                100                 105                 110

Lys Val Val His Gly Trp Ala Lys Val Leu Asp Gly Lys Gln Val Glu
            115                 120                 125

Val Asp Gly Gln Arg Ile Gln Cys Glu His Leu Leu Leu Ala Thr Gly
        130                 135                 140

Ser Ser Ser Val Glu Leu Pro Met Leu Pro Leu Gly Gly Pro Val Ile
145                 150                 155                 160

Ser Ser Thr Glu Ala Leu Ala Pro Lys Ala Leu Pro Gln His Leu Val
                165                 170                 175

Val Val Gly Gly Gly Tyr Ile Gly Leu Glu Leu Gly Ile Ala Tyr Arg
            180                 185                 190

Lys Leu Gly Ala Gln Val Ser Val Val Glu Ala Arg Glu Arg Ile Leu
        195                 200                 205

Pro Thr Tyr Asp Ser Glu Leu Thr Ala Pro Val Ala Glu Ser Leu Lys
    210                 215                 220

Lys Leu Gly Ile Ala Leu His Leu Gly His Ser Val Glu Gly Tyr Glu
225                 230                 235                 240

Asn Gly Cys Leu Leu Ala Asn Asp Gly Lys Gly Gln Leu Arg Leu
                245                 250                 255

Glu Ala Asp Arg Val Leu Val Ala Val Gly Arg Arg Pro Arg Thr Lys
                260                 265                 270

Gly Phe Asn Leu Glu Cys Leu Asp Leu Lys Met Asn Gly Ala Ala Ile
            275                 280                 285

Ala Ile Asp Glu Arg Cys Gln Thr Ser Met His Asn Val Trp Ala Ile
        290                 295                 300

Gly Asp Val Ala Gly Glu Pro Met Leu Ala His Arg Ala Met Ala Gln
305                 310                 315                 320

Gly Glu Met Val Ala Glu Ile Ile Ala Gly Lys Ala Arg Arg Phe Glu
                325                 330                 335

Pro Ala Ala Ile Ala Ala Val Cys Phe Thr Asp Pro Glu Val Val Val
            340                 345                 350

Val Gly Lys Thr Pro Glu Gln Ala Ser Gln Gln Gly Leu Asp Cys Ile
        355                 360                 365

Val Ala Gln Phe Pro Phe Ala Ala Asn Gly Arg Ala Met Ser Leu Glu
    370                 375                 380

Ser Lys Ser Gly Phe Val Arg Val Val Ala Arg Arg Asp Asn His Leu
385                 390                 395                 400

Ile Leu Gly Trp Gln Ala Val Gly Val Ala Val Ser Glu Leu Ser Thr
                405                 410                 415

Ala Phe Ala Gln Ser Leu Glu Met Gly Ala Cys Leu Glu Asp Val Ala
            420                 425                 430

Gly Thr Ile His Ala His Pro Thr Leu Gly Glu Ala Val Gln Glu Ala
        435                 440                 445

Ala Leu Arg Ala Leu Gly His Ala Leu His Ile
    450                 455

<210> SEQ ID NO 60
<211> LENGTH: 6643
```

<212> TYPE: DNA
<213> ORGANISM: Pseudomonas putida

<400> SEQUENCE: 60

```
gcatgcctgc aggccgccga tgaaatggtg gaaggtatcg gtaggctggc cctgctcatc    60
gctgaacacg ttacgcccgc tgccggtatc gaccaggctc tggtgaatat gcatggaact   120
gccaggcgtg cgcgccagcg gtttggccat gcacaccacg gtcagcccgt gcttgagtgc   180
cacttccttg agcaggtgtt tgaacaggaa ggtctggtcg ccagcagca gcgggtcgcc    240
atgtagcaag ttgatctcga actggctgac gcccatttcg tgcatgaagg tgtcgcgcgg   300
caggccgagc gcggccatgc actggtacac ctcattgaag aacgggcgca ggccgttgtt   360
ggaactgaca ctgaacgccg aatggcccag ctcgcggcgg ccgtcggtgc ccagcggtgg   420
ctggaacggt gctgcgggt cactgttggg ggcaaacacg aagaactcaa gctcggtcgc    480
cactaccggt gccagaccca acgctgcgta gcggcgatc acggccttca gctggccccg     540
ggtggacagt gccgagggcc ggccatccag ttcattggca tcgcagatgg ccagggcgcg   600
accgtcatcg ctccagggca agcgatgaac ctggctgggt tccgctacca acgccaggtc   660
gccgtcgtcg cagccgtaga atttcgccgg cgggtagccg cccatgatgc attgcagcag   720
caccccacgg gccatctgca ggcggcggcc ttcgagaaag ccttcggcgg tcatcacctt    780
gccgcgtggg acgccgttga ggtcgggggt gacgcattcg atttcatcga tgccctggag   840
ctgagcgatg ctcatgacgc ttgtccttgt tgttgtaggc tgacaacaac ataggctggg    900
ggtgtttaaa atatcaagca gcctctcgaa cgcctgggc ctcttctatt cgcgcaaggt     960
catgccattg gccggcaacg gcaaggctgt cttgtagcgc acctgtttca aggcaaaact   1020
cgagcggata ttcgccacac ccggcaaccg ggtcaggtaa tcgagaaacc gctccagcgc   1080
ctggatactc ggcagcagta cccgcaacag gtagtccggg tcgcccgtca tcaggtagca   1140
ctccatcacc tcgggccgtt cggcaatttc ttcctcgaag cggtgcagcg actgctctac   1200
ctgttttcc aggctgacat ggatgaacac attcacatcc agccccaacg cctcgggcga    1260
caacaaggtc acctgctggc ggatcacccc cagttcttcc atggcccgca cccggttgaa   1320
acagggcgtg ggcgacaggt tgaccgagcg tgccagctcg gcgttggtga tgcgggcgtt   1380
ttcctgcagg ctgttgagaa tgccgatatc ggtacgatcg agtttgcgca tgagacaaaa   1440
tcaccggttt tttgtgttta tgcggaatgt ttatctgccc cgctcggcaa aggcaatcaa   1500
cttgagagaa aaattctcct gccggaccac taagatgtag gggacgctga cttaccagtc   1560
acaagccggt actcagcggc ggccgcttca gagctcacaa aaacaaatac ccgagcgagc   1620
gtaaaaagca tgaacgagta cgccccctg cgtttgcatg tgcccgagcc caccggccgg    1680
ccaggctgcc agaccgattt ttcctacctg cgcctgaacg atgcaggtca agcccgtaaa   1740
cccccctgtcg atgtcgacgc tgccgacacc gccgacctgt cctacagcct ggtccgcgtg   1800
ctcgacgagc aaggcgacgc ccaaggcccg tgggctgaag acatcgaccc gcagatcctg   1860
cgccaaggca tgcgcgccat gctcaagacg cggatcttcg acagccgcat ggtggttgcc   1920
cagcgccaga agaagatgtc cttctacatg cagagcctgg gcgaagaagc catcggcagc   1980
ggccaggcgc tggcgcttaa ccgcaccgac atgtgcttcc ccacctaccg tcagcaaagc   2040
atcctgatgg cccgcgacgt gtcgctggtg gagatgatct gccagttgct gtccaacgaa   2100
cgcgacccc tcaagggccg ccagctgccg atcatgtact cggtacgcga ggccggcttc    2160
ttcaccatca gcggcaacct ggcgacccag ttcgtgcagg cggtcggctg ggccatggcc   2220
```

```
tcggcgatca agggcgatac caagattgcc tcggcctgga tcggcgacgg cgccactgcc    2280
gaatcggact ccacaccgc cctcacctt gcccacgttt accgcgcccc ggtgatcctc    2340
aacgtggtca caaccagtg ggccatctca accttccagg ccatcgccgg tggcgagtcg    2400
accaccttcg ccgccgtgg cgtgggctgc ggcatcgctt cgctgcgggt ggacggcaac    2460
gacttcgtcg ccgtttacgc cgcttcgcgc tgggctgccg aacgtgcccg ccgtggtttg    2520
ggcccgagcc tgatcgagtg ggtcacctac cgtgccggcc cgcactcgac ctcggacgac    2580
ccgtccaagt accgccctgc cgatgactgg agccacttcc cgctgggtga cccgatcgcc    2640
cgcctgaagc agcacctgat caagatcggc cactggtccg aagaagaaca ccaggccacc    2700
acggccgagt tcgaagcggc cgtgattgct gcgcaaaaag aagccgagca gtacggcacc    2760
ctggccaacg gtcacatccc gagcgccgcc tcgatgttcg aggacgtgta caaggagatg    2820
cccgaccacc tgcgccgcca acgccaggaa ctggggggttt gagatgaacg accacaacaa    2880
cagcatcaac ccggaaaccg ccatggccac cactaccatg accatgatcc aggccctgcg    2940
ctcggccatg gatgtcatgc ttgagcgcga cgacaatgtg gtggtgtacg ccaggacgt    3000 cggctacttc ggcggcgtgt tccgctgcac cgaaggcctg cagaccaagt acggcaagtc    3060
ccgcgtgttc gacgcgccca tctctgaaag cggcatcgtc ggcaccgccg tgggcatggg    3120
tgcctacggc ctgcgcccgg tggtggaaat ccagttcgct gactacttct acccggcctc    3180
cgaccagatc gtttctgaaa tggcccgcct gcgctaccgt tcggccggcg agttcatcgc    3240
cccgctgacc ctgcgtatgc cctgcggtgg cggtatctat ggcggccaga cacacagcca    3300
gagcccggaa gcgatgttca ctcaggtgtg cggcctgcgc accgtaatgc catccaaccc    3360
gtacgacgcc aaaggcctgc tgattgcctc gatcgaatgc gacgaccgg tgatcttcct    3420 ggagcccaag cgcctgtaca acggcccgtt cgacggccac catgaccgcc cggttacgcc    3480
gtggtcgaaa cacccgcaca gcgccgtgcc cgatggctac tacaccgtgc cactggacaa    3540
ggccgccatc acccgccccg gcaatgacgt gagcgtgctc acctatggca ccaccgtgta    3600
cgtggcccag gtggccgccg aagaaagtgg cgtggatgcc gaagtgatcg acctgcgcag    3660 cctgtgccg ctagacctgg acaccatcgt cgagtcggtg aaaaagaccg gccgttgcgt    3720
ggtagtacac gaggccaccc gtacttgtgg cttttggcgca gaactggtgt cgctggtgca    3780
ggagcactgc ttccaccacc tggaggcgcc gatcgagcgc gtcaccggtt gggacacccc    3840
ctaccctcac gcgcaggaat gggcttactt cccagggcct tcgcgggtag gtgcggcatt    3900
gaaaaaggtc atgagggtct gaatgggcac gcacgtcatc aagatgccgg acattggcga    3960
aggcatcgcg caggtcgaat tggtggaatg gttcgtcaag gtgggcgaca tcatcgccga    4020
ggaccaagtg gtagccgacg tcatgaccga caaggccacc gtggaaatcc cgtcgccggt    4080
cagcggcaag gtgctggccc tgggtggcca gccaggtgaa gtgatggcgg tcggcagtga    4140
gctgatccgc atcgaagtgg aaggcagcgg caaccatgtg gatgtgccgc aagccaagcc    4200
ggccgaagtg cctgcggcac cggtagccgc taaacctgaa ccacagaaag acgttaaacc    4260
ggcggcgtac caggcgtcag ccagccacga ggcagcgccc atcgtgccgc gccagccggg    4320
cgacaagccg ctgcctcgc cggcggtgcg caaacgcgcc ctcgatgccg gcatcgaatt    4380
gcgttatgtg cacggcagcg gcccggccgg gcgcatcctg cacgaagacc tcgacgcgtt    4440
catgagcaaa ccgcaaagcg ctgccgggca accccccaat ggctatgcca ggcgcaccga    4500
cagcgagcag gtgccggtga tcggcctgcg ccgcaagatc gcccagcgca tgcaggacgc    4560
caagcgccgg gtcgcgcact tcagctatgt ggaagaaatc gacgtcaccg ccctggaagc    4620
```

```
cctgcgccag cagctcaaca gcaagcacgg cgacagccgc ggcaagctga cactgctgcc    4680
gttcctggtg cgcgccctgg tcgtggcact gcgtgacttc ccgcagataa acgccaccta    4740
cgatgacgaa gcgcagatca tcacccgcca tggcgcggtg catgtgggca tcgccaccca    4800
aggtgacaac ggcctgatgg tacccgtgct gcgccacgcc gaagcgggca gcctgtgggc    4860
caatgccggt gagatttcac gcctggccaa cgctgcgcgc aacaacaagg ccagccgcga    4920
agagctgtcc ggttcgacca ttaccctgac cagcctcggc ccctgggcg catcgtcag     4980
cacgccggtg gtcaacaccc cggaagtggc gatcgtcggt gtcaaccgca tggttgagcg    5040
gcccgtggtg atcgacggcc agatcgtcgt gcgcaagatg atgaacctgt ccagctcgtt    5100
cgaccaccgc gtggtcgatg gcatggacgc cgccctgttc atccaggccg tgcgtggcct    5160
gctcgaacaa cccgcctgcc tgttcgtgga gtgagcatgc aacagactat ccagacaacc    5220
ctgttgatca tcggcggcgg ccctggcggc tatgtggcgg ccatccgcgc cgggcaactg    5280
ggcatcccta ccgtgctggt ggaaggccag gcgctgggcg gtacctgcct gaacatcggc    5340
tgcattccgt ccaaggcgct gatccatgtg gccgagcagt tccaccaggc ctcgcgcttt    5400
accgaacccct cgccgctggg catcagcgtg gcttcgccac gcctggacat cggccagagc    5460
gtggcctgga aagacggcat cgtcgatcgc ctgaccactg tgtcgccgc cctgctgaaa    5520
aagcacgggg tgaaggtggt gcacggctgg gccaaggtgc ttgatggcaa gcaggtcgag    5580
gtggatggcc agcgcatcca gtgcgagcac ctgttgctgg ccacgggctc cagcagtgtc    5640
gaactgccga tgctgccgtt gggtgggccg gtgatttcct cgaccgaggc cctggcaccg    5700
aaagccctgc cgcaacacct ggtggtggtg ggcggtggcc acatcggcct ggagctgggt    5760
atcgcctacc gcaagctcgg cgcgcaggtc agcgtggtgg aagcgcgcga gcgcatcctg    5820
ccgacttacg acagcgaact gaccgccccg gtggccgagt cgctgaaaaa gctgggtatc    5880
gccctgcacc ttggccacag cgtcgaaggt tacgaaaatg gctgcctgct ggccaacgat    5940
ggcaagggcg gacaactgcg cctggaagcc gaccgggtgc tggtggccgt gggccgccgc    6000
ccacgcacca agggcttcaa cctggaatgc ctggacctga agatgaatgg tgccgcgatt    6060
gccatcgacg agcgctgcca gaccagcatg cacaacgtct gggccatcgg cgacgtggcc    6120
ggcgaaccga tgctggcgca ccgggccatg gcccagggcg agatggtggc cgagatcatc    6180
gccggcaagg cacgccgctt cgaacccgct gcgatagccg ccgtgtgctt caccgacccg    6240
gaagtggtcg tggtcggcaa gacgccggaa caggccagtc agcaaggcct ggactgcatc    6300
gtcgcgcagt tcccgttcgc cgccaacggc cgggccatga gcctggagtc gaaaagcggt    6360
ttcgtgcgcg tggtcgcgcg gcgtgacaac cacctgatcc tgggctggca gcggttggc    6420
gtggcggttt ccgagctgtc cacggcgttt gcccagtcgc tggagatggg tgcctgcctg    6480
gaggatgtgg ccggtaccat ccatgcccac ccgaccctgg gtgaagcggt acaggaagcg    6540
gcactgcgtg ccctgggcca cgccctgcat atctgacact gaagcggccg aggccgattt    6600
ggcccgccgc gccgagaggc gctgcgggtc tttttttatac ctg                    6643
```

<210> SEQ ID NO 61
<211> LENGTH: 468
<212> TYPE: PRT
<213> ORGANISM: Clostridium beijerinckii

<400> SEQUENCE: 61

```
Met Asn Lys Asp Thr Leu Ile Pro Thr Thr Lys Asp Leu Lys Leu Lys
1               5                   10                  15
```

-continued

```
Thr Asn Val Glu Asn Ile Asn Leu Lys Asn Tyr Lys Asp Asn Ser Ser
             20                  25                  30
Cys Phe Gly Val Phe Glu Asn Val Glu Asn Ala Ile Asn Ser Ala Val
             35                  40                  45
His Ala Gln Lys Ile Leu Ser Leu His Tyr Thr Lys Glu Gln Arg Glu
 50                  55                  60
Lys Ile Ile Thr Glu Ile Arg Lys Ala Ala Leu Glu Asn Lys Glu Val
 65                  70                  75                  80
Leu Ala Thr Met Ile Leu Glu Glu Thr His Met Gly Arg Tyr Glu Asp
                 85                  90                  95
Lys Ile Leu Lys His Glu Leu Val Ala Lys Tyr Thr Pro Gly Thr Glu
                100                 105                 110
Asp Leu Thr Thr Thr Ala Trp Ser Gly Asp Asn Gly Leu Thr Val Val
            115                 120                 125
Glu Met Ser Pro Tyr Gly Val Ile Gly Ala Ile Thr Pro Ser Thr Asn
            130                 135                 140
Pro Thr Glu Thr Val Ile Cys Asn Ser Ile Gly Met Ile Ala Ala Gly
145                 150                 155                 160
Asn Ala Val Val Phe Asn Gly His Pro Gly Ala Lys Lys Cys Val Ala
                165                 170                 175
Phe Ala Ile Glu Met Ile Asn Lys Ala Ile Ile Ser Cys Gly Gly Pro
            180                 185                 190
Glu Asn Leu Val Thr Thr Ile Lys Asn Pro Thr Met Glu Ser Leu Asp
            195                 200                 205
Ala Ile Ile Lys His Pro Leu Ile Lys Leu Leu Cys Gly Thr Gly Gly
            210                 215                 220
Pro Gly Met Val Lys Thr Leu Leu Asn Ser Gly Lys Lys Ala Ile Gly
225                 230                 235                 240
Ala Gly Ala Gly Asn Pro Pro Val Ile Val Asp Asp Thr Ala Asp Ile
                245                 250                 255
Glu Lys Ala Gly Lys Ser Ile Ile Glu Gly Cys Ser Phe Asp Asn Asn
            260                 265                 270
Leu Pro Cys Ile Ala Glu Lys Glu Val Phe Val Phe Glu Asn Val Ala
            275                 280                 285
Asp Asp Leu Ile Ser Asn Met Leu Lys Asn Asn Ala Val Ile Ile Asn
            290                 295                 300
Glu Asp Gln Val Ser Lys Leu Ile Asp Leu Val Leu Gln Lys Asn Asn
305                 310                 315                 320
Glu Thr Gln Glu Tyr Phe Ile Asn Lys Lys Trp Val Gly Lys Asp Ala
                325                 330                 335
Lys Leu Phe Ser Asp Glu Ile Asp Val Glu Ser Pro Ser Asn Ile Lys
            340                 345                 350
Cys Ile Val Cys Glu Val Asn Ala Asn His Pro Phe Val Met Thr Glu
            355                 360                 365
Leu Met Met Pro Ile Leu Pro Ile Val Arg Val Lys Asp Ile Asp Glu
            370                 375                 380
Ala Val Lys Tyr Thr Lys Ile Ala Glu Gln Asn Arg Lys His Ser Ala
385                 390                 395                 400
Tyr Ile Tyr Ser Lys Asn Ile Asp Asn Leu Asn Arg Phe Glu Arg Glu
                405                 410                 415
Ile Asp Thr Thr Ile Phe Val Lys Asn Ala Lys Ser Phe Ala Gly Val
            420                 425                 430
```

```
Gly Tyr Glu Ala Glu Gly Phe Thr Thr Phe Thr Ile Ala Gly Ser Thr
        435                 440                 445

Gly Glu Gly Ile Thr Ser Ala Arg Asn Phe Thr Arg Gln Arg Arg Cys
    450                 455                 460

Val Leu Ala Gly
465

<210> SEQ ID NO 62
<211> LENGTH: 6558
<212> TYPE: DNA
<213> ORGANISM: Clostridium beijerinckii

<400> SEQUENCE: 62
aagcttaaaa tatccatagg ctattgttaa taagactata gcgcttaata ctctaagcgc      60
accatctaaa aaattataca taggaattgg ataaactcca atcttctcca taatactttt     120
cataggtgaa attgatatta taattaaggc tgcataaagc aaactcatat ctccaataaa     180
tgtcactatc ataggtaatt tccttttcat gttcacatac tcccccgtat tctataataa     240
tttacaataa acttccatca caaataaatt ataacatata ttgtaaatat agttttatta     300
ttcgcatatt tatagataaa caatatataa cttagactta tgcaataacc taccgaaagt     360
aaaaacattg ttatttcaca ggactatgaa aatttcgctg aaagtactaa attgcaggtt     420
gcaccactaa tgcttgctcc caatttcatt gtgacaagca ttagttgaac aacctacaat     480
taagagcctt taacagctca tttccaatgc ctgctacata aaaatgtttc tactttctaa     540
tatggtattt acttcaaagt gtaaatcaaa ttcttaagtt gtttatctat atagggttcc     600
atattgataa caatacatat ctactgtttc aatttcatga ataccagcga tattgaaatt     660
ttgtaagttt gaatatcatt gtgaaaccct atatatcaaa tacaatctca aaattataca     720
aaaagatccc aacttcacaa tatgaatttg agatcttcta tcttaacttc ttcaatattt     780
ttaagattat ttatactgcg tgcaaatctt ctataagtat caattatcag ctatgtacat     840
tgatagtgga cttgtaatct gaacagctta tatatttaca cttttaagtt ctcttccact     900
aacccctgct ttgaaacttc tcataaacaa atcgaaagta cctttaatta gctgtgcatt     960
ctcaaactca gaatttaact taagtacttc aattgccgct tcgatagtat agagctctcc    1020
ttctgaagca ccttttctta aagtatattc tgatttatta attggattta atgaaattct    1080
tggaagcttc tttaagtagt cgctctttct tagtatcttc tctgcttctt tccatgtgcc    1140
atctaagata ataaatgctg gaatttttc tgaatcttta catttagact ttctttctag     1200
aggttcatca tcatccatag gaaataatac acgtatttca taatcatcgc tattaatata    1260
ttcaattaat ttttcaggag tctttactct ctcccaaaga attaactcag ttgattctgg    1320
attcaccaat ttcaataatc tagcggtatt tgaaggccta ctaaattctc tttctgttga    1380
taatatcaat atctttgctt ttgtctctat tttaggcaca atatcgcaga tacaatttat    1440
tattggcaac ccacatttat tgcagctctc atataactta gtaatttgct taactttaaa    1500
ttcagactcc attttacctc cattattagt tggttagtgt gtcatatctt cttgctatta    1560
ctaactgatt ataacatatg tattcaatat atcactccta gttttcaaag cactggcaat    1620
acgaattaca aattaatttc tggatttatg tcagtatttc attaataaaa ggtcggactt    1680
ttaagatact tgttttagct attgatcata tttattaaag actatgcatt taatgtataa    1740
ttataatgaa tattatcaat aatatttatt ttatattaca atcttacagt ctttattcta    1800
aatttcactc aaataccaaa cgagctttat tcataaacaa tatataacaa taattccaaa    1860
```

```
ataatacgat attttatctg taacagccat ataaaaaaaa tatcatatag tcttgtcatt    1920
tgataacgtt ttgtcttcct tatatttact ttttcggttt aataggttga ttctgtaaat    1980
tttagtgata acatatattt gatgacatta aaaatttaat atttcatata aattttttaat   2040 gtctattaat ttttaaatca caaggaggaa tagttcatga ataaagacac actaatacct    2100
acaactaaag atttaaaatt aaaaacaaat gttgaaaaca ttaatttaaa gaactacaag    2160
gataattctt catgtttcgg agtattcgaa aatgttgaaa atgctataaa cagcgctgta    2220
cacgcgcaaa agatattatc ccttcattat acaaagaac aaagagaaaa atcataact     2280 gagataagaa aggccgcatt agaaaataaa gaggttttag ctaccatgat tctggaagaa    2340
acacatatgg gaaggtatga agataaaata ttaaagcatg aattagtagc taaatatact    2400
cctggtacag aagatttaac tactactgct tggtcaggtg ataatggtct tacagttgta    2460
gaaatgtctc catatggcgt tataggtgca ataactcctt ctacgaatcc aactgaaact    2520
gtaatatgta atagcatcgg catgatagct gctggaaatg ctgtagtatt taacggacac    2580
ccaggcgcta aaaatgtgt tgcttttgct attgaaatga taaataaagc aattatttca    2640
tgtggcggtc ctgagaattt agtaacaact ataaaaaatc caactatgga atccctagat    2700
gcaattatta agcatccttt aataaaactt ctttgcggaa ctggaggtcc aggaatggta    2760 aaaccctct taaattctgg caagaaagct ataggtgctg gtgctggaaa tccaccagtt    2820
attgtagatg ataccgctga tatagaaaag gctggtaaga gtatcattga aggctgttct    2880
tttgataata atttaccttg tattgcagaa aaagaagtat tgtttttga gaatgttgca    2940 gatgatttaa tatctaacat gctaaaaaat aatgctgtaa ttataaatga agatcaagta    3000
tcaaaattaa tagatttagt attacaaaaa aataatgaaa ctcaagaata ctttataaac    3060
aaaaaatggg taggaaaaga tgcaaaatta ttctcagatg aaatagatgt tgagtctcct    3120
tcaaatatta aatgcatagt ctgcgaagta aatgcaaatc atccatttgt catgacagaa    3180
ctcatgatgc caatattacc aattgtaaga gttaaagata tagatgaagc tgttaaatat    3240
acaaagatag cagaacaaaa tagaaaacat agtgcctata tttattctaa aaatatagac    3300
aacctaaata gatttgaaag agaaattgat actactattt ttgtaaagaa tgctaaatct    3360
tttgctggtg ttggttatga agctgaagga tttacaactt tcactattgc tggatctact    3420
ggtgaaggca taacctctgc aagaaatttt acaagacaaa gaagatgtgt acttgccggc    3480
taacttcttg ctaaatttat acatttattc acataacttt aatatgcaat gttcccacaa    3540
aatattaaaa actatttaga agggagatat taaatgaata aattagtaaa attaacagat    3600
ttaaagcgca ttttcaaaga tggtatgaca attatggttg ggggttttt agattgtgga    3660 actcctgaaa atattataga tatgctagtt gatttaaata taaaaatct gactattata    3720 agcaatgata cagcttttcc taataaagga ataggaaaac ttattgtaaa tggtcaagtt    3780
tctaaagtaa ttgcttcaca tattggaact aatcctgaaa ctgggaaaaa aatgagctct    3840
ggtgaactta agttgagct ttctccacaa ggaacactga tcgaaagaat tcgtgcagct    3900
ggatctggac tcggaggtgt attaactcca accggacttg gactatcgt tgaagaaggt    3960 aagaaaaaag ttactatcgg tggcaaagaa tatctattag aacttccttt atccgctgat    4020
gtttcattaa taaaaggtag cattgtagat gaatttggaa ataccttcta tagagctgct    4080
actaaaaatt tcaatccata tatggcaatg gctgcaaaaa cagttatagt tgaagcagaa    4140
aatttagtta aatgtgaaga tttaaaaaga gatgccataa tgactcctgg cgtattagta    4200
gattatatcg ttaaggaggc ggcttaattg attgtagata aagtttagc aaaagagata    4260
```

```
attgccaaaa gagttgcaaa agaactaaaa aaaggccaac tcgtaaacct tggaatagga    4320
cttccaactt tagtagctaa ttatgtgcca aagaaatga acattacttt cgaatcagaa    4380
aatggcatgg ttggcatggc acaaatggcc tcatcaggtg aaaatgaccc agatataata    4440
aatgctggtg gggaatatgt aacattatta cctcaaggtg catttttga tagttcaacg    4500 tcttttgcac taataagagg aggacatgtt gatgttgctg ttcttggtgc tctagaagtt    4560
gatgaagaag gtaatttagc taactggatt gttccaaata aaattgtccc aggtatggga    4620
ggcgccatgg atttggcaat aggcgcaaaa aaaataatag tggcaatgca acatacagga    4680
aaaggtaaac ctaaaatcgt aaaaaaatgt actctcccac ttactgctaa ggctcaggta    4740
gatttaattg ttacagaact ttgtgtaatt gatgtaacaa atgatggttt acttttcaga    4800
gaaattcata aagatacaac tattgatgaa ataaaatttt taacagatgc agatttaatt    4860
attcccgaca acttaaaaat tatggatatc taaatcattc tattttaaat ataaacttt    4920 aaaaatctta tgtattaaaa actaagaaaa gaggttgatt attttatgtt agaaagtgaa    4980
gtatctaaac aaattacaac tccacttgct gctccagcgt ttcctagagg accatataga    5040
tttcacaata gagaatatct aaacattatt tatcgaactg atttagatgc tcttcgaaaa    5100
atagtaccag agccacttga attagatgga gcatatgtta ggtttgagat gatggctatg    5160
cctgatacaa ccggactagg ctcatatact gagtgtggtc aagccattcc agtaaaaatat    5220 aatgaggtta aggtgactga cttgcatatg atgtacctag ataatgaacc tgctattgct    5280
gttggaagag aaagcagtgc ttatcccaaa aagttcggct atccaaagct atttgttgat    5340
tcagacgccc tagttggcgc ccttaagtat ggtgcattac cggtagttac tgcgacgatg    5400
ggatataagc atgagcccct agatcttaaa gaagcctata ctcaaattgc aagacccaat    5460
ttcatgctaa aaatcattca aggttatgat ggtaagccaa gaatttgtga actcatctgt    5520
gcagaaaata ctgatataac tatccacggt gcttggactg aagtgcacg cctacaatta    5580 tttagccatg cactagctcc tcttgctgat ttacctgtat tagagatcgt atcagcatct    5640
catatcctaa cagatttaac tcttggaaca cctaaggttg tacatgatta tctttcagta    5700
aaataaaagc aatatagaat aaccactaca aaagtagtgg ttattctata ttttaaatca    5760
aactgtaaaa cttaagtttt atagtaccta ataatatttt actaccagca ttagattagt    5820
taaaatacaa agtttgtggt aaaagtattt tagattgcat aatagccttc tatacttta    5880 acaatataac caattgctca ccatctgctt agaatatgct tctttaagct ctaaaataca    5940
tataaaaaag taggaattc ttattaaaat tcctacttat attatatata aatttaatcg    6000
ttaggtttta ttcgcattgt tcctctttaa tttatctctt ataacatttt attataattg    6060
ttcatataat taattcaata tactattata tattttcaag cattaataat tattcagcat    6120
ctgtcattac atatgcttcc atactttgac ttcttattaa atcatagcta atccatccat    6180
agccattgat tccccagtct ttaccccatg aatttattat ttttacagct tttttactat    6240
catcataacc aactacgcaa actgcatgac cacctctatt ttctccatca atctggtcat    6300
aaattggatt atcagaattt aaattatcaa aatctggata tactgatatt ccaataacta    6360
ctggatttcc agctgctatt tgtgccttta ttgcattata gtcaccatct ggaagttgac    6420
tccaactttt tgctttatat ttggctgcat tagccttttg ttcatctgta ggtgtaacct    6480
cccaactata ttcactacca tcataaggca tatcagataa tgtagtacaa ccttgttctt    6540
ctaataattt aaatgcat                                                 6558
```

<210> SEQ ID NO 63
<211> LENGTH: 862
<212> TYPE: PRT
<213> ORGANISM: Clostridium acetobutylicum

<400> SEQUENCE: 63

```
Met Lys Val Thr Thr Val Lys Glu Leu Asp Glu Lys Leu Lys Val Ile
1               5                   10                  15

Lys Glu Ala Gln Lys Lys Phe Ser Cys Tyr Ser Gln Glu Met Val Asp
            20                  25                  30

Glu Ile Phe Arg Asn Ala Ala Met Ala Ala Ile Asp Ala Arg Ile Glu
        35                  40                  45

Leu Ala Lys Ala Ala Val Leu Glu Thr Gly Met Gly Leu Val Glu Asp
50                  55                  60

Lys Val Ile Lys Asn His Phe Ala Gly Glu Tyr Ile Tyr Asn Lys Tyr
65                  70                  75                  80

Lys Asp Glu Lys Thr Cys Gly Ile Ile Glu Arg Asn Glu Pro Tyr Gly
                85                  90                  95

Ile Thr Lys Ile Ala Glu Pro Ile Gly Val Val Ala Ala Ile Ile Pro
            100                 105                 110

Val Thr Asn Pro Thr Ser Thr Thr Ile Phe Lys Ser Leu Ile Ser Leu
        115                 120                 125

Lys Thr Arg Asn Gly Ile Phe Phe Ser Pro His Pro Arg Ala Lys Lys
130                 135                 140

Ser Thr Ile Leu Ala Ala Lys Thr Ile Leu Asp Ala Ala Val Lys Ser
145                 150                 155                 160

Gly Ala Pro Glu Asn Ile Ile Gly Trp Ile Asp Glu Pro Ser Ile Glu
                165                 170                 175

Leu Thr Gln Tyr Leu Met Gln Lys Ala Asp Ile Thr Leu Ala Thr Gly
            180                 185                 190

Gly Pro Ser Leu Val Lys Ser Ala Tyr Ser Ser Gly Lys Pro Ala Ile
        195                 200                 205

Gly Val Gly Pro Gly Asn Thr Pro Val Ile Ile Asp Glu Ser Ala His
210                 215                 220

Ile Lys Met Ala Val Ser Ser Ile Ile Leu Ser Lys Thr Tyr Asp Asn
225                 230                 235                 240

Gly Val Ile Cys Ala Ser Glu Gln Ser Val Ile Val Leu Lys Ser Ile
                245                 250                 255

Tyr Asn Lys Val Lys Asp Glu Phe Gln Glu Arg Gly Ala Tyr Ile Ile
            260                 265                 270

Lys Lys Asn Glu Leu Asp Lys Val Arg Glu Val Ile Phe Lys Asp Gly
        275                 280                 285

Ser Val Asn Pro Lys Ile Val Gly Gln Ser Ala Tyr Thr Ile Ala Ala
290                 295                 300

Met Ala Gly Ile Lys Val Pro Lys Thr Thr Arg Ile Leu Ile Gly Glu
305                 310                 315                 320

Val Thr Ser Leu Gly Glu Glu Pro Phe Ala His Glu Lys Leu Ser
                325                 330                 335

Pro Val Leu Ala Met Tyr Glu Ala Asp Asn Phe Asp Asp Ala Leu Lys
            340                 345                 350

Lys Ala Val Thr Leu Ile Asn Leu Gly Gly Leu Gly His Thr Ser Gly
        355                 360                 365

Ile Tyr Ala Asp Glu Ile Lys Ala Arg Asp Lys Ile Asp Arg Phe Ser
370                 375                 380
```

```
Ser Ala Met Lys Thr Val Arg Thr Phe Val Asn Ile Pro Thr Ser Gln
385                 390                 395                 400

Gly Ala Ser Gly Asp Leu Tyr Asn Phe Arg Ile Pro Pro Ser Phe Thr
            405                 410                 415

Leu Gly Cys Gly Phe Trp Gly Gly Asn Ser Val Ser Glu Asn Val Gly
            420                 425                 430

Pro Lys His Leu Leu Asn Ile Lys Thr Val Ala Glu Arg Arg Glu Asn
            435                 440                 445

Met Leu Trp Phe Arg Val Pro His Lys Val Tyr Phe Lys Phe Gly Cys
    450                 455                 460

Leu Gln Phe Ala Leu Lys Asp Leu Lys Asp Leu Lys Lys Lys Arg Ala
465                 470                 475                 480

Phe Ile Val Thr Asp Ser Asp Pro Tyr Asn Leu Asn Tyr Val Asp Ser
            485                 490                 495

Ile Ile Lys Ile Leu Glu His Leu Asp Ile Asp Phe Lys Val Phe Asn
            500                 505                 510

Lys Val Gly Arg Glu Ala Asp Leu Lys Thr Ile Lys Lys Ala Thr Glu
            515                 520                 525

Glu Met Ser Ser Phe Met Pro Asp Thr Ile Ile Ala Leu Gly Gly Thr
    530                 535                 540

Pro Glu Met Ser Ser Ala Lys Leu Met Trp Val Leu Tyr Glu His Pro
545                 550                 555                 560

Glu Val Lys Phe Glu Asp Leu Ala Ile Lys Phe Met Asp Ile Arg Lys
            565                 570                 575

Arg Ile Tyr Thr Phe Pro Lys Leu Gly Lys Lys Ala Met Leu Val Ala
            580                 585                 590

Ile Thr Thr Ser Ala Gly Ser Gly Ser Glu Val Thr Pro Phe Ala Leu
            595                 600                 605

Val Thr Asp Asn Asn Thr Gly Asn Lys Tyr Met Leu Ala Asp Tyr Glu
    610                 615                 620

Met Thr Pro Asn Met Ala Ile Val Asp Ala Glu Leu Met Met Lys Met
625                 630                 635                 640

Pro Lys Gly Leu Thr Ala Tyr Ser Gly Ile Asp Ala Leu Val Asn Ser
            645                 650                 655

Ile Glu Ala Tyr Thr Ser Val Tyr Ala Ser Glu Tyr Thr Asn Gly Leu
            660                 665                 670

Ala Leu Glu Ala Ile Arg Leu Ile Phe Lys Tyr Leu Pro Glu Ala Tyr
            675                 680                 685

Lys Asn Gly Arg Thr Asn Glu Lys Ala Arg Glu Lys Met Ala His Ala
            690                 695                 700

Ser Thr Met Ala Gly Met Ala Ser Ala Asn Ala Phe Leu Gly Leu Cys
705                 710                 715                 720

His Ser Met Ala Ile Lys Leu Ser Ser Glu His Asn Ile Pro Ser Gly
            725                 730                 735

Ile Ala Asn Ala Leu Leu Ile Glu Glu Val Ile Lys Phe Asn Ala Val
            740                 745                 750

Asp Asn Pro Val Lys Gln Ala Pro Cys Pro Gln Tyr Lys Tyr Pro Asn
            755                 760                 765

Thr Ile Phe Arg Tyr Ala Arg Ile Ala Asp Tyr Ile Lys Leu Gly Gly
            770                 775                 780

Asn Thr Asp Glu Glu Lys Val Asp Leu Leu Ile Asn Lys Ile His Glu
785                 790                 795                 800
```

```
Leu Lys Lys Ala Leu Asn Ile Pro Thr Ser Ile Lys Asp Ala Gly Val
            805                 810                 815

Leu Glu Glu Asn Phe Tyr Ser Ser Leu Asp Arg Ile Ser Glu Leu Ala
        820                 825                 830

Leu Asp Asp Gln Cys Thr Gly Ala Asn Pro Arg Phe Pro Leu Thr Ser
    835                 840                 845

Glu Ile Lys Glu Met Tyr Ile Asn Cys Phe Lys Lys Gln Pro
850                 855                 860

<210> SEQ ID NO 64
<211> LENGTH: 1665
<212> TYPE: DNA
<213> ORGANISM: Clostridium acetobutylicum

<400> SEQUENCE: 64
ttgaagagtg aatacacaat tggaagatat tgttagacc gtttatcaga gttgggtatt       60
cggcatatct ttggtgtacc tggagattac aatctatcct ttttagacta tataatggag      120
tacaaaggga tagattgggt tggaaattgc aatgaattga atgctgggta tgctgctgat      180
ggatatgcaa gaataaatgg aattggagcc atacttacaa catttggtgt tggagaatta      240
agtgccatta acgcaattgc tggggcatac gctgagcaag ttccagttgt taaaattaca      300
ggtatcccca cagcaaaagt tagggacaat ggattatatg tacaccacac attaggtgac      360
ggaaggtttg atcactttt tgaaatgttt agagaagtaa cagttgctga ggcattacta      420
agcgaagaaa atgcagcaca agaaattgat cgtgttctta tttcatgctg agacaaaaa       480 cgtcctgttc ttataaattt accgattgat gtatatgata aaccaattaa caaaccatta      540
aagccattac tcgattatac tatttcaagt aacaagagg ctgcatgtga atttgttaca      600
gaaatagtac ctataataaa tagggcaaaa agcctgtta ttcttgcaga ttatggagta      660
tatcgttacc aagttcaaca tgtgcttaaa acttggccg aaaaaaccgg atttcctgtg      720
gctacactaa gtatgggaaa aggtgttttc aatgaagcac accctcaatt tattggtgtt      780
tataatggtg atgtaagttc tccttattta aggcagcgag ttgatgaagc agactgcatt      840
attagcgttg gtgtaaaatt gacggattca accacagggg gatttctca tggattttct      900 aaaaggaatg taattcacat tgatcctttt tcaataaagg caaaggtaa aaaatatgca      960 cctattacga tgaaagatgc tttaacagaa ttaacaagta aaattgagca tagaaacttt     1020
gaggatttag atataaagcc ttacaaatca gataatcaaa agtattttgc aaaagagaag     1080
ccaattacac aaaaacgttt ttttgagcgt attgctcact ttataaaaga aaagatgta      1140 ttattagcag aacagggtac atgctttttt ggtgcgtcaa ccatacaact acccaaagat     1200
gcaactttta ttggtcaacc tttatgggga tctattggat acacacttcc tgctttatta     1260
ggttcacaat tagctgatca aaaaaggcgt aatattcttt taattgggga tggtgcattt     1320
caaatgacag cacaagaaat ttcaacaatg cttcgtttac aaatcaaacc tattattttt     1380
ttaattaata cgatggtta tacaattgaa cgtgctattc atggtagaga caagtatat     1440 aacaatattc aaatgtggcg atatcataat gttccaaagg ttttaggtcc taaagaatgc     1500
agcttaacct ttaaagtaca aagtgaaact gaacttgaaa aggctctttt agtggcagat     1560
aaggattgtg aacatttgat ttttatagaa gttgttatgg atcgttatga taaacccgag     1620
cctttagaac gtctttcgaa acgttttgca aatcaaaata attag                      1665

<210> SEQ ID NO 65
<211> LENGTH: 858
```

<212> TYPE: PRT
<213> ORGANISM: Clostridium acetobutylicum

<400> SEQUENCE: 65

Met Lys Val Thr Asn Gln Lys Glu Leu Lys Gln Lys Leu Asn Glu Leu
1               5                   10                  15

Arg Glu Ala Gln Lys Lys Phe Ala Thr Tyr Thr Gln Glu Gln Val Asp
            20                  25                  30

Lys Ile Phe Lys Gln Cys Ala Ile Ala Ala Lys Glu Arg Ile Asn
        35                  40                  45

Leu Ala Lys Leu Ala Val Glu Glu Thr Gly Ile Gly Leu Val Glu Asp
    50                  55                  60

Lys Ile Ile Lys Asn His Phe Ala Ala Glu Tyr Ile Tyr Asn Lys Tyr
65                  70                  75                  80

Lys Asn Glu Lys Thr Cys Gly Ile Ile Asp His Asp Asp Ser Leu Gly
                85                  90                  95

Ile Thr Lys Val Ala Glu Pro Ile Gly Ile Val Ala Ala Ile Val Pro
            100                 105                 110

Thr Thr Asn Pro Thr Ser Thr Ala Ile Phe Lys Ser Leu Ile Ser Leu
        115                 120                 125

Lys Thr Arg Asn Ala Ile Phe Phe Ser Pro His Pro Arg Ala Lys Lys
130                 135                 140

Ser Thr Ile Ala Ala Ala Lys Leu Ile Leu Asp Ala Ala Val Lys Ala
145                 150                 155                 160

Gly Ala Pro Lys Asn Ile Ile Gly Trp Ile Asp Glu Pro Ser Ile Glu
                165                 170                 175

Leu Ser Gln Asp Leu Met Ser Glu Ala Asp Ile Ile Leu Ala Thr Gly
            180                 185                 190

Gly Pro Ser Met Val Lys Ala Ala Tyr Ser Ser Gly Lys Pro Ala Ile
        195                 200                 205

Gly Val Gly Ala Gly Asn Thr Pro Ala Ile Ile Asp Glu Ser Ala Asp
    210                 215                 220

Ile Asp Met Ala Val Ser Ser Ile Ile Leu Ser Lys Thr Tyr Asp Asn
225                 230                 235                 240

Gly Val Ile Cys Ala Ser Glu Gln Ser Ile Leu Val Met Asn Ser Ile
                245                 250                 255

Tyr Glu Lys Val Lys Glu Phe Val Lys Arg Gly Ser Tyr Ile Leu
            260                 265                 270

Asn Gln Asn Glu Ile Ala Lys Ile Lys Glu Thr Met Phe Lys Asn Gly
        275                 280                 285

Ala Ile Asn Ala Asp Ile Val Gly Lys Ser Ala Tyr Ile Ile Ala Lys
    290                 295                 300

Met Ala Gly Ile Glu Val Pro Gln Thr Thr Lys Ile Leu Ile Gly Glu
305                 310                 315                 320

Val Gln Ser Val Glu Lys Ser Glu Leu Phe Ser His Glu Lys Leu Ser
                325                 330                 335

Pro Val Leu Ala Met Tyr Lys Val Lys Asp Phe Asp Glu Ala Leu Lys
            340                 345                 350

Lys Ala Gln Arg Leu Ile Glu Leu Gly Gly Ser Gly His Thr Ser Ser
        355                 360                 365

Leu Tyr Ile Asp Ser Gln Asn Asn Lys Asp Lys Val Lys Glu Phe Gly
    370                 375                 380

Leu Ala Met Lys Thr Ser Arg Thr Phe Ile Asn Met Pro Ser Ser Gln
385                 390                 395                 400

```
Gly Ala Ser Gly Asp Leu Tyr Asn Phe Ala Ile Ala Pro Ser Phe Thr
                405             410             415

Leu Gly Cys Gly Thr Trp Gly Gly Asn Ser Val Ser Gln Asn Val Glu
                420             425             430

Pro Lys His Leu Leu Asn Ile Lys Ser Val Ala Glu Arg Arg Glu Asn
                435             440             445

Met Leu Trp Phe Lys Val Pro Gln Lys Ile Tyr Phe Lys Tyr Gly Cys
450             455             460

Leu Arg Phe Ala Leu Lys Glu Leu Lys Asp Met Asn Lys Lys Arg Ala
465             470             475             480

Phe Ile Val Thr Asp Lys Asp Leu Phe Lys Leu Gly Tyr Val Asn Lys
                485             490             495

Ile Thr Lys Val Leu Asp Glu Ile Asp Ile Lys Tyr Ser Ile Phe Thr
                500             505             510

Asp Ile Lys Ser Asp Pro Thr Ile Asp Ser Val Lys Lys Gly Ala Lys
                515             520             525

Glu Met Leu Asn Phe Glu Pro Asp Thr Ile Ile Ser Ile Gly Gly Gly
                530             535             540

Ser Pro Met Asp Ala Ala Lys Val Met His Leu Leu Tyr Glu Tyr Pro
545             550             555             560

Glu Ala Glu Ile Glu Asn Leu Ala Ile Asn Phe Met Asp Ile Arg Lys
                565             570             575

Arg Ile Cys Asn Phe Pro Lys Leu Gly Thr Lys Ala Ile Ser Val Ala
                580             585             590

Ile Pro Thr Thr Ala Gly Thr Gly Ser Glu Ala Thr Pro Phe Ala Val
                595             600             605

Ile Thr Asn Asp Glu Thr Gly Met Lys Tyr Pro Leu Thr Ser Tyr Glu
                610             615             620

Leu Thr Pro Asn Met Ala Ile Ile Asp Thr Glu Leu Met Leu Asn Met
625             630             635             640

Pro Arg Lys Leu Thr Ala Ala Thr Gly Ile Asp Ala Leu Val His Ala
                645             650             655

Ile Glu Ala Tyr Val Ser Val Met Ala Thr Asp Tyr Thr Asp Glu Leu
                660             665             670

Ala Leu Arg Ala Ile Lys Met Ile Phe Lys Tyr Leu Pro Arg Ala Tyr
                675             680             685

Lys Asn Gly Thr Asn Asp Ile Glu Ala Arg Glu Lys Met Ala His Ala
                690             695             700

Ser Asn Ile Ala Gly Met Ala Phe Ala Asn Ala Phe Leu Gly Val Cys
705             710             715             720

His Ser Met Ala His Lys Leu Gly Ala Met His His Val Pro His Gly
                725             730             735

Ile Ala Cys Ala Val Leu Ile Glu Glu Val Ile Lys Tyr Asn Ala Thr
                740             745             750

Asp Cys Pro Thr Lys Gln Thr Ala Phe Pro Gln Tyr Lys Ser Pro Asn
                755             760             765

Ala Lys Arg Lys Tyr Ala Glu Ile Ala Glu Tyr Leu Asn Leu Lys Gly
                770             775             780

Thr Ser Asp Thr Glu Lys Val Thr Ala Leu Ile Glu Ala Ile Ser Lys
785             790             795             800

Leu Lys Ile Asp Leu Ser Ile Pro Gln Asn Ile Ser Ala Ala Gly Ile
                805             810             815
```

| Asn | Lys | Lys | Asp | Phe | Tyr | Asn | Thr | Leu | Asp | Lys | Met | Ser | Glu | Leu | Ala |
|-----|-----|-----|-----|-----|-----|-----|-----|-----|-----|-----|-----|-----|-----|-----|-----|
|     |     |     | 820 |     |     |     |     | 825 |     |     |     |     | 830 |     |     |

| Phe | Asp | Asp | Gln | Cys | Thr | Thr | Ala | Asn | Pro | Arg | Tyr | Pro | Leu | Ile | Ser |
|-----|-----|-----|-----|-----|-----|-----|-----|-----|-----|-----|-----|-----|-----|-----|-----|
|     |     | 835 |     |     |     |     | 840 |     |     |     |     | 845 |     |     |     |

| Glu | Leu | Lys | Asp | Ile | Tyr | Ile | Lys | Ser | Phe |
|-----|-----|-----|-----|-----|-----|-----|-----|-----|-----|
|     | 850 |     |     |     |     | 855 |     |     |     |

<210> SEQ ID NO 66
<211> LENGTH: 2589
<212> TYPE: DNA
<213> ORGANISM: Clostridium acetobutylicum

<400> SEQUENCE: 66

```
atgaaagtca acacagtaaa ggaattagat gaaaaactca aggtaattaa agaagctcaa      60
aaaaaattct cttgttactc gcaagaaatg gttgatgaaa tctttagaaa tgcagcaatg     120
gcagcaatcg acgcaaggat agagctagca aaagcagctg ttttggaaac cggtatgggc     180
ttagttgaag acaaggttat aaaaaatcat tttgcaggcg aatacatcta taacaaatat     240
aaggatgaaa aaacctgcgg tataattgaa cgaaatgaac cctacggaat tacaaaaata     300
gcagaaccta taggagttgt agctgctata atccctgtaa caaaccccac atcaacaaca     360
atatttaaat ccttaatatc ccttaaaact agaaatggaa ttttcttttc gcctcaccca     420
agggcaaaaa aatccacaat actagcagct aaaacaatac ttgatgcagc cgttaagagt     480
ggtgccccgg aaaatataat aggttggata gatgaacctt caattgaact aactcaatat     540
ttaatgcaaa aagcagatat aacccttgca actggtggtc cctcactagt taaatctgct     600
tattcttccg gaaaaccagc aataggtgtt ggtccgggta cacccccagt aataattgat     660
gaatctgctc atataaaaat ggcagtaagt tcaattatat tatccaaaac ctatgataat     720
ggtgttatat gtgcttctga acaatctgta atagtcttaa aatccatata taacaaggta     780
aaagatgagt tccaagaaag aggagcttat ataataaaga aaacgaatt ggataaagtc     840
cgtgaagtga ttttaaaga tggatccgta aaccctaaaa tagtcggaca gtcagcttat     900
actatagcag ctatggctgg cataaaagta cctaaaacca caagaatatt aataggagaa     960
gttacctcct aggtgaaga gaaccttttt gcccacgaaa actatctcc tgttttggct    1020
atgtatgagg ctgacaattt tgatgatgct ttaaaaaaag cagtaactct aataaactta    1080
ggaggcctcg gccatacctc aggaatatat gcagatgaaa taaaagcacg agataaaata    1140
gatagattta gtagtgccat gaaaaccgta agaacctttg taaatatccc aacctcacaa    1200
ggtgcaagtg gagatctata aatttagaa ataccaccct ctttcacgct ggctgcgga    1260
ttttggggag gaaattctgt ttccgagaat gttggtccaa acatcttttt gaatattaaa    1320
accgtagctg aaaggagaga aaacatgctt tggtttagag ttccacataa agtatatttt    1380
aagttcggtt gtcttcaatt tgctttaaaa gatttaaaag atctaaagaa aaaaagagcc    1440
tttatagtta ctgatagtga cccctataat ttaaactatg ttgattcaat aataaaaata    1500
cttgagcacc tagatattga ttttaaagta tttaataagg ttggaagaga agctgatctt    1560
aaaaccataa aaaagcaac tgaagaaatg tcctcctta tgccagacac tataatagct    1620
ttaggtggta cccctgaaat gagctctgca agctaatgt gggtactata tgaacatcca    1680
gaagtaaaat ttgaagatct tgcaataaaa tttatggaca taagaaagag aatatatact    1740
ttcccaaaac tcggtaaaaa ggctatgtta gttgcaatta caacttctgc tggttccggt    1800
tctgaggtta ctccttttgc tttagtaact gacaataaca ctgaaataaa gtacatgtta    1860
```

-continued

```
gcagattatg aaatgacacc aaatatggca attgtagatg cagaacttat gatgaaaatg    1920
ccaaagggat taaccgctta ttcaggtata gatgcactag taaatagtat agaagcatac    1980
acatccgtat atgcttcaga atacacaaac ggactagcac tagaggcaat acgattaata    2040
tttaaatatt tgcctgaggc ttacaaaaac ggaagaacca atgaaaaagc aagagagaaa    2100
atggctcacg cttcaactat ggcaggtatg gcatccgcta atgcatttct aggtctatgt    2160
cattccatgg caataaaatt aagttcagaa cacaatattc ctagtggcat tgccaatgca    2220
ttactaatag aagaagtaat aaaatttaac gcagttgata atcctgtaaa acaagcccct    2280
tgcccacaat ataagtatcc aaacaccata tttagatatg ctcgaattgc agattatata    2340
aagcttggag gaaatactga tgaggaaaag gtagatctct taattaacaa aatacatgaa    2400
ctaaaaaaag ctttaaatat accaacttca ataaggatg caggtgtttt ggaggaaaac     2460
ttctattcct cccttgatag aatatctgaa cttgcactag atgatcaatg cacaggcgct    2520
aatcctagat ttcctcttac aagtgagata aagaaatgt atataaattg ttttaaaaaa     2580
caaccttaa                                                            2589
```

<210> SEQ ID NO 67
<211> LENGTH: 307
<212> TYPE: PRT
<213> ORGANISM: Pseudomonas putida

<400> SEQUENCE: 67

```
Met Ser Lys Lys Leu Lys Ala Ala Ile Ile Gly Pro Gly Asn Ile Gly
1               5                   10                  15

Thr Asp Leu Val Met Lys Met Leu Arg Ser Glu Trp Ile Glu Pro Val
            20                  25                  30

Trp Met Val Gly Ile Asp Pro Asn Ser Asp Gly Leu Lys Arg Ala Arg
        35                  40                  45

Asp Phe Gly Met Lys Thr Thr Ala Glu Gly Val Asp Gly Leu Leu Pro
    50                  55                  60

His Val Leu Asp Asp Asp Ile Arg Ile Ala Phe Asp Ala Thr Ser Ala
65                  70                  75                  80

Tyr Val His Ala Glu Asn Ser Arg Lys Leu Asn Ala Leu Gly Val Leu
                85                  90                  95

Met Val Asp Leu Thr Pro Ala Ala Ile Gly Pro Tyr Cys Val Pro Pro
            100                 105                 110

Val Asn Leu Lys Gln His Val Gly Arg Leu Glu Met Asn Val Asn Met
        115                 120                 125

Val Thr Cys Gly Gly Gln Ala Thr Ile Pro Met Val Ala Ala Val Ser
    130                 135                 140

Arg Val Gln Pro Val Ala Tyr Ala Glu Ile Val Ala Thr Val Ser Ser
145                 150                 155                 160

Arg Ser Val Gly Pro Gly Thr Arg Lys Asn Ile Asp Glu Phe Thr Arg
                165                 170                 175

Thr Thr Ala Gly Ala Ile Glu Gln Val Gly Gly Ala Arg Glu Gly Lys
            180                 185                 190

Ala Ile Ile Val Ile Asn Pro Ala Glu Pro Pro Leu Met Met Arg Asp
        195                 200                 205

Thr Ile His Cys Leu Thr Asp Ser Glu Pro Asp Gln Ala Ala Ile Thr
    210                 215                 220

Ala Ser Val His Ala Met Ile Ala Glu Val Gln Lys Tyr Val Pro Gly
225                 230                 235                 240
```

```
Tyr Arg Leu Lys Asn Gly Pro Val Phe Asp Gly Asn Arg Val Ser Ile
            245                 250                 255

Phe Met Glu Val Glu Gly Leu Gly Asp Tyr Leu Pro Lys Tyr Ala Gly
        260                 265                 270

Asn Leu Asp Ile Met Thr Ala Ala Leu Arg Thr Gly Glu Met Phe
            275                 280                 285

Ala Glu Glu Ile Ala Ala Gly Thr Ile Gln Leu Pro Arg Arg Asp Ile
        290                 295                 300

Ala Leu Ala
305

<210> SEQ ID NO 68
<211> LENGTH: 2180
<212> TYPE: DNA
<213> ORGANISM: Pseudomonas putida

<400> SEQUENCE: 68
```

| | | | | | |
|---|---|---|---|---|---|
| ggtaccctg | gagccggtca | aggccggcga | cttcatgcgc | gtcgagatcg | gcggcatcgg | 60 |
| cagcgcctcc | gtgcgcttca | cctgatcgaa | cagaggacaa | acccatgagc | aagaaactca | 120 |
| aggcggccat | cataggcccc | ggcaatatcg | gtaccgatct | ggtgatgaag | atgctccgtt | 180 |
| ccgagtggat | tgagccggtg | tggatggtcg | gcatcgaccc | caactccgac | ggcctcaaac | 240 |
| gcgcccgcga | tttcggcatg | aagaccacag | ccgaaggcgt | cgacggcctg | ctcccgcacg | 300 |
| tgctggacga | cgacatccgc | atcgccttcg | acgccacctc | ggcctatgtg | catgccgaga | 360 |
| atagccgcaa | gctcaacgcg | cttggcgtgc | tgatggtcga | cctgaccccg | gcggccatcg | 420 |
| gcccctactg | cgtgccgccg | gtcaacctca | agcagcatgt | cggccgcctg | gaaatgaacg | 480 |
| tcaacatggt | cacctgcggc | ggccaggcca | ccatccccat | ggtcgccgcg | gtgtcccgcg | 540 |
| tgcagccggt | ggcctacgcc | gagatcgtcg | ccaccgtctc | ctcgcgctcg | gtcggcccgg | 600 |
| gcacgcgcaa | gaacatcgac | gagttcaccc | gcaccaccgc | cggcgccatc | gagcaggtcg | 660 |
| gcggcgccag | ggaaggcaag | gcgatcatcg | tcatcaaccc | ggccgagccg | ccgctgatga | 720 |
| tgcgcgacac | catccactgc | ctgaccgaca | gcgagccgga | ccaggctgcg | atcaccgctt | 780 |
| cggttcacgc | gatgatcgcc | gaggtgcaga | aatacgtgcc | cggctaccgc | ctgaagaacg | 840 |
| gcccggtgtt | cgacggcaac | cgcgtgtcga | tcttcatgga | agtcgaaggc | ctgggcgact | 900 |
| acctgcccaa | gtacgccggc | aacctcgaca | tcatgaccgc | cgccgcgctg | cgtaccggcg | 960 |
| agatgttcgc | cgaggaaatc | gccgccggca | ccattcaact | gccgcgtcgc | gacatcgcgc | 1020 |
| tggcttgagg | agtagcacca | tgaatttgca | cggcaagagc | gtcatcctgc | acgacatgag | 1080 |
| cctgcgcgac | ggcatgcacg | ccaagcgcca | ccagatcagc | ctggagcaga | tggtcgcggt | 1140 |
| cgccaccggc | ctcgatcaag | ccggtatgcc | gctgatcgag | atcacccacg | cgacggcct | 1200 |
| cggcggtcgt | cgatcaact | acggcttccc | ggcccacagt | gacgaggagt | acctgcgcgc | 1260 |
| ggtgatcccg | cagctcaagc | aggccaaagt | ctcggcgctg | ctgctgcccg | gcatcggcac | 1320 |
| cgtcgaccac | ctgaagatgg | ccctggactg | cggcgtctcg | actattcgcg | tggccaccca | 1380 |
| ctgtaccgag | gcggatgtct | ccgagcagca | catcggcatg | gcgcgcaagc | tggggtcga | 1440 |
| caccgtcggc | ttcctgatga | tggcgcacat | gatcagcgcc | gagaaagtcc | tggagcaggc | 1500 |
| caagctgatg | gaaagctatg | gtgccaactg | catctactgc | accgactcgg | ccggctacat | 1560 |
| gctgcctgat | gaagtcagcg | agaaaatcgg | cctcctgcgc | gccgagctga | acccggccac | 1620 |
| cgaagtcggc | ttccacggcc | accacaacat | gggcatggct | atcgccaact | cgctggccgc | 1680 |

```
catcgaagcc ggtgccgcgc gcatcgacgg ctcggtcgcc ggcctcggcg ccggtgccgg    1740
caacaccccg ctggaagtgt tcgtcgcagt gtgcaaacgc atgggcgtgg agaccggcat    1800
cgacctgtac aagatcatgg acgtggccga ggacctggtg gtgccgatga tggatcagcc    1860
gatccgcgtc gaccgcgacg ccctgaccct gggctacgcc ggggtgtaca gctcgttcct    1920
gctgttcgcc cagcgcgccg agaagaaata tggcgtgtcg gcccgcgaca tcctggtcga    1980
actgggccgg cgcggcaccg tcggtggcca ggaagacatg atcgaagacc tcgccctgga    2040
catggcccgg gcccgtcagc agcagaaggt gagcgcatga accgtaccct gacccgcgaa    2100
caggtgctgg ccctggccga gcacatcgaa aacgccgagc tgaatgtcca cgacatcggc    2160
aaggtgacca acgattttcc                                                2180
```

<210> SEQ ID NO 69
<211> LENGTH: 307
<212> TYPE: PRT
<213> ORGANISM: Thermus thermophilus

<400> SEQUENCE: 69

```
Met Ser Glu Arg Val Lys Val Ala Ile Leu Gly Ser Gly Asn Ile Gly
1               5                   10                  15

Thr Asp Leu Met Tyr Lys Leu Leu Lys Asn Pro Gly His Met Glu Leu
            20                  25                  30

Val Ala Val Gly Ile Asp Pro Lys Ser Glu Gly Leu Ala Arg Ala
        35                  40                  45

Arg Ala Leu Gly Leu Glu Ala Ser His Glu Gly Ile Ala Tyr Ile Leu
    50                  55                  60

Glu Arg Pro Glu Ile Lys Ile Val Phe Asp Ala Thr Ser Ala Lys Ala
65                  70                  75                  80

His Val Arg His Ala Lys Leu Leu Arg Glu Ala Gly Lys Ile Ala Ile
                85                  90                  95

Asp Leu Thr Pro Ala Ala Arg Gly Pro Tyr Val Val Pro Val Asn
            100                 105                 110

Leu Lys Glu His Leu Asp Lys Asp Asn Val Asn Leu Ile Thr Cys Gly
        115                 120                 125

Gly Gln Ala Thr Ile Pro Leu Val Tyr Ala Val His Arg Val Ala Pro
    130                 135                 140

Val Leu Tyr Ala Glu Met Val Ser Thr Val Ala Ser Arg Ser Ala Gly
145                 150                 155                 160

Pro Gly Thr Arg Gln Asn Ile Asp Glu Phe Thr Phe Thr Thr Ala Arg
                165                 170                 175

Gly Leu Glu Ala Ile Gly Gly Ala Lys Lys Gly Lys Ala Ile Ile Ile
            180                 185                 190

Leu Asn Pro Ala Glu Pro Pro Ile Leu Met Thr Asn Thr Val Arg Cys
        195                 200                 205

Ile Pro Glu Asp Glu Gly Phe Asp Arg Glu Ala Val Val Ala Ser Val
    210                 215                 220

Arg Ala Met Glu Arg Glu Val Gln Ala Tyr Val Pro Gly Tyr Arg Leu
225                 230                 235                 240

Lys Ala Asp Pro Val Phe Glu Arg Leu Pro Thr Pro Trp Gly Glu Arg
                245                 250                 255

Thr Val Val Ser Met Leu Leu Glu Val Glu Gly Ala Gly Asp Tyr Leu
            260                 265                 270

Pro Lys Tyr Ala Gly Asn Leu Asp Ile Met Thr Ala Ser Ala Arg Arg
        275                 280                 285
```

Val Gly Glu Val Phe Ala Gln His Leu Leu Gly Lys Pro Val Glu Glu
    290                 295                 300

Val Val Ala
305

<210> SEQ ID NO 70
<211> LENGTH: 924
<212> TYPE: DNA
<213> ORGANISM: Thermus thermophilus

<400> SEQUENCE: 70

```
atgtccgaaa gggttaaggt agccatcctg ggctccggca acatcgggac ggacctgatg      60
tacaagctcc tgaagaaccc gggccacatg agcttgtgg cggtggtggg gatagacccc     120
aagtccgagg gcctggcccg ggcgcgggcc ttagggttag aggcgagcca cgaagggatc     180
gcctacatcc tggagaggcc ggagatcaag atcgtctttg acgccaccag cgccaaggcc     240
cacgtgcgcc acgccaagct cctgaggag gcggggaaga tcgccataga cctcacgccg     300
gcggcccggg cccttacgt ggtgcccccg gtgaacctga aggaacacct ggacaaggac     360
aacgtgaacc tcatcacctg cggggggcag gccaccatcc ccctggtcta cgcggtgcac     420
cgggtggccc ccgtgctcta cgcggagatg gtctccacgg tggcctcccg ctccgcgggc     480
cccggcaccc ggcagaacat cgacgagttc accttcacca ccgccggggg cctggaggcc     540
atcggggggg ccaagaaggg gaaggccatc atcatcctga accggcgga accccccatc     600
ctcatgacca acaccgtgcg ctgcatcccc gaggacgagg gctttgaccg ggaggccgtg     660
gtggcgagcg tccgggccat ggagcgggag gtccaggcct acgtgcccgg ctaccgcctg     720
aaggcggacc cggtgtttga gaggcttccc accccctggg gggagcgcac cgtggtctcc     780
atgctcctgg aggtggaggg ggcggggggac tatttgccca aatacgccgg caacctggac     840
atcatgacgg cttctgcccg gagggtgggg gaggtcttcg cccagcacct cctggggaag     900
cccgtggagg aggtggtggc gtga                                            924
```

<210> SEQ ID NO 71
<211> LENGTH: 417
<212> TYPE: PRT
<213> ORGANISM: Escherichia coli

<400> SEQUENCE: 71

Met Thr Phe Ser Leu Phe Gly Asp Lys Phe Thr Arg His Ser Gly Ile
1               5                   10                  15

Thr Leu Leu Met Glu Asp Leu Asn Asp Gly Leu Arg Thr Pro Gly Ala
            20                  25                  30

Ile Met Leu Gly Gly Gly Asn Pro Ala Gln Ile Pro Glu Met Gln Asp
        35                  40                  45

Tyr Phe Gln Thr Leu Leu Thr Asp Met Leu Glu Ser Gly Lys Ala Thr
    50                  55                  60

Asp Ala Leu Cys Asn Tyr Asp Gly Pro Gln Gly Lys Thr Glu Leu Leu
65                  70                  75                  80

Thr Leu Leu Ala Gly Met Leu Arg Glu Lys Leu Gly Trp Asp Ile Glu
                85                  90                  95

Pro Gln Asn Ile Ala Leu Thr Asn Gly Ser Gln Ser Ala Phe Phe Tyr
            100                 105                 110

Leu Phe Asn Leu Phe Ala Gly Arg Arg Ala Asp Gly Arg Val Lys Lys
        115                 120                 125

```
Val Leu Phe Pro Leu Ala Pro Glu Tyr Ile Gly Tyr Ala Asp Ala Gly
    130                 135                 140

Leu Glu Glu Asp Leu Phe Val Ser Ala Arg Pro Asn Ile Glu Leu Leu
145                 150                 155                 160

Pro Glu Gly Gln Phe Lys Tyr His Val Asp Phe Glu His Leu His Ile
                165                 170                 175

Gly Glu Glu Thr Gly Met Ile Cys Val Ser Arg Pro Thr Asn Pro Thr
            180                 185                 190

Gly Asn Val Ile Thr Asp Glu Leu Leu Lys Leu Asp Ala Leu Ala
        195                 200                 205

Asn Gln His Gly Ile Pro Leu Val Ile Asp Asn Ala Tyr Gly Val Pro
210                 215                 220

Phe Pro Gly Ile Ile Phe Ser Glu Ala Arg Pro Leu Trp Asn Pro Asn
225                 230                 235                 240

Ile Val Leu Cys Met Ser Leu Ser Lys Leu Gly Leu Pro Gly Ser Arg
                245                 250                 255

Cys Gly Ile Ile Ile Ala Asn Glu Lys Ile Ile Thr Ala Ile Thr Asn
            260                 265                 270

Met Asn Gly Ile Ile Ser Leu Ala Pro Gly Gly Ile Gly Pro Ala Met
        275                 280                 285

Met Cys Glu Met Ile Lys Arg Asn Asp Leu Leu Arg Leu Ser Glu Thr
290                 295                 300

Val Ile Lys Pro Phe Tyr Tyr Gln Arg Val Gln Glu Thr Ile Ala Ile
305                 310                 315                 320

Ile Arg Arg Tyr Leu Pro Glu Asn Arg Cys Leu Ile His Lys Pro Glu
                325                 330                 335

Gly Ala Ile Phe Leu Trp Leu Trp Phe Lys Asp Leu Pro Ile Thr Thr
            340                 345                 350

Lys Gln Leu Tyr Gln Arg Leu Lys Ala Arg Gly Val Leu Met Val Pro
        355                 360                 365

Gly His Asn Phe Phe Pro Gly Leu Asp Lys Pro Trp Pro His Thr His
370                 375                 380

Gln Cys Met Arg Met Asn Tyr Val Pro Glu Pro Glu Lys Ile Glu Ala
385                 390                 395                 400

Gly Val Lys Ile Leu Ala Glu Ile Glu Arg Ala Trp Ala Glu Ser
                405                 410                 415

His

<210> SEQ ID NO 72
<211> LENGTH: 417
<212> TYPE: PRT
<213> ORGANISM: Escherichia coli

<400> SEQUENCE: 72

Met Thr Phe Ser Leu Phe Gly Asp Lys Phe Thr Arg His Ser Gly Ile
1               5                   10                  15

Thr Leu Leu Met Glu Asp Leu Asn Asp Gly Leu Arg Thr Pro Gly Ala
            20                  25                  30

Ile Met Leu Gly Gly Gly Asn Pro Ala Gln Ile Pro Glu Met Gln Asp
        35                  40                  45

Tyr Phe Gln Thr Leu Leu Thr Asp Met Leu Glu Ser Gly Lys Ala Thr
    50                  55                  60

Asp Ala Leu Cys Asn Tyr Asp Gly Pro Gln Gly Lys Thr Glu Leu Leu
65                  70                  75                  80
```

Thr Leu Leu Ala Gly Met Leu Arg Glu Lys Leu Gly Trp Asp Ile Glu
            85                  90                  95

Pro Gln Asn Ile Ala Leu Thr Asn Gly Ser Gln Ser Ala Phe Phe Tyr
           100                 105                 110

Leu Phe Asn Leu Phe Ala Gly Arg Arg Ala Asp Gly Arg Val Lys Lys
           115                 120                 125

Val Leu Phe Pro Leu Ala Pro Glu Tyr Ile Gly Tyr Ala Asp Ala Gly
130                 135                 140

Leu Glu Glu Asp Leu Phe Val Ser Ala Arg Pro Asn Ile Glu Leu Leu
145                 150                 155                 160

Pro Glu Gly Gln Phe Lys Tyr His Val Asp Phe Glu His Leu His Ile
           165                 170                 175

Gly Glu Glu Thr Gly Met Ile Cys Val Ser Arg Pro Thr Asn Pro Thr
           180                 185                 190

Gly Asn Val Ile Thr Asp Glu Glu Leu Leu Lys Leu Asp Ala Leu Ala
           195                 200                 205

Asn Gln His Gly Ile Pro Leu Val Ile Asp Asn Ala Tyr Gly Val Pro
           210                 215                 220

Phe Pro Gly Ile Ile Phe Ser Glu Ala Arg Pro Leu Trp Asn Pro Asn
225                 230                 235                 240

Ile Val Leu Cys Met Ser Leu Ser Lys Leu Gly Leu Pro Gly Ser Arg
                245                 250                 255

Cys Gly Ile Ile Ile Ala Asn Glu Lys Ile Ile Thr Ala Ile Thr Asn
           260                 265                 270

Met Asn Gly Ile Ile Ser Leu Ala Pro Gly Gly Ile Gly Pro Ala Met
           275                 280                 285

Met Cys Glu Met Ile Lys Arg Asn Asp Leu Leu Arg Leu Ser Glu Thr
           290                 295                 300

Val Ile Lys Pro Phe Tyr Tyr Gln Arg Val Gln Glu Thr Ile Ala Ile
305                 310                 315                 320

Ile Arg Arg Tyr Leu Pro Glu Asn Arg Cys Leu Ile His Lys Pro Glu
                325                 330                 335

Gly Ala Ile Phe Leu Trp Leu Trp Phe Lys Asp Leu Pro Ile Thr Thr
           340                 345                 350

Lys Gln Leu Tyr Gln Arg Leu Lys Ala Arg Gly Val Leu Met Val Pro
           355                 360                 365

Gly His Asn Phe Phe Pro Gly Leu Asp Lys Pro Trp Pro His Thr His
           370                 375                 380

Gln Cys Met Arg Met Asn Tyr Val Pro Glu Pro Glu Lys Ile Glu Ala
385                 390                 395                 400

Gly Val Lys Ile Leu Ala Glu Glu Ile Glu Arg Ala Trp Ala Glu Ser
                405                 410                 415

His

<210> SEQ ID NO 73
<211> LENGTH: 425
<212> TYPE: PRT
<213> ORGANISM: Bacillus licheniformis

<400> SEQUENCE: 73

Met Lys Pro Pro Leu Ser Lys Ile Gly Glu Lys Met Ile Glu Lys Thr
1               5                   10                  15

Gly Val Arg Ala Val Met Ser Asp Ile Gln Glu Val Leu Ala Gly Gly
            20                  25                  30

Glu Arg Ser Tyr Ile Asn Leu Ser Ala Gly Asn Pro Met Ile Leu Pro
              35                  40                  45

Gly Val Ser Ala Met Trp Lys Ser Ala Leu Ala Asp Leu Leu Asp Asp
 50                  55                  60

Asp Arg Phe Ser Ser Val Ile Gly Gln Tyr Gly Ser Ser Tyr Gly Thr
 65                  70                  75                  80

Asp Glu Leu Ile Ala Ser Val Val Arg Phe Phe Ser Glu Arg Tyr Ser
                 85                  90                  95

Ala Gly Ile Arg Lys Glu Asn Val Leu Ile Thr Ala Gly Ser Gln Gln
             100                 105                 110

Leu Phe Phe Leu Ala Ile Asn Ser Phe Cys Gly Met Gly Ser Gly Ser
             115                 120                 125

Val Met Lys Lys Ala Leu Ile Pro Met Leu Pro Asp Tyr Ser Gly Tyr
130                 135                 140

Ser Gly Ala Ala Leu Glu Arg Glu Met Ile Glu Gly Ile Pro Pro Leu
145                 150                 155                 160

Ile Ser Lys Leu Asp Asp His Thr Phe Arg Tyr Glu Leu Asp Arg Lys
                 165                 170                 175

Gly Phe Leu Glu Arg Met Arg Ile Gly Ala Val Leu Leu Ser Arg Pro
             180                 185                 190

Asn Asn Pro Cys Gly Asn Ile Leu Pro Lys Glu Asp Val Ala Phe Ile
             195                 200                 205

Ser Asp Ala Cys Arg Glu Ala Asn Val Pro Leu Phe Ile Asp Ser Ala
210                 215                 220

Tyr Ala Pro Pro Phe Pro Ala Ile His Phe Ile Asp Met Glu Pro Ile
225                 230                 235                 240

Phe Asn Glu Gln Ile Ile His Cys Met Ser Leu Ser Lys Ala Gly Leu
                 245                 250                 255

Pro Gly Glu Arg Ile Gly Ile Ala Ile Gly Pro Ser Arg Tyr Ile Gln
             260                 265                 270

Ala Met Glu Ala Phe Gln Ser Asn Ala Ala Ile His Ser Ser Arg Leu
             275                 280                 285

Gly Gln Tyr Met Ala Ala Ser Val Leu Asn Asp Gly Arg Leu Ala Asp
290                 295                 300

Val Ser Leu Asn Glu Val Arg Pro Tyr Tyr Arg Asn Lys Phe Met Leu
305                 310                 315                 320

Leu Lys Glu Thr Leu Leu Cys Lys Met Pro Glu Asp Ile Lys Trp Tyr
                 325                 330                 335

Leu His Gln Gly Glu Gly Ser Leu Phe Gly Trp Leu Trp Phe Glu Asp
             340                 345                 350

Leu Pro Val Thr Asp Ala Ala Leu Tyr Glu Tyr Met Lys Ala Asp Gly
             355                 360                 365

Val Ile Ile Val Pro Gly Ser Ser Phe Phe His Arg Gln Ser Arg Arg
370                 375                 380

Leu Ala His Ser His Gln Cys Ile Arg Ile Ser Leu Thr Ala Ala Asp
385                 390                 395                 400

Glu Asp Ile Ile Arg Gly Ile Asp Val Leu Ala Lys Ile Ala Lys Gly
                 405                 410                 415

Val Tyr Glu Lys Gln Val Glu Tyr Leu
             420                 425

<210> SEQ ID NO 74
<211> LENGTH: 1278
<212> TYPE: DNA

<213> ORGANISM: Bacillus licheniformis

<400> SEQUENCE: 74

```
ttataagtat tcaacctgtt tctcatatac acccttcgca attttagcta aaacatcgat       60
tcccctata atatcttcat ccgccgcggt taggctgatt cgtatacact ggtgtgaatg      120
cgccaggcgc cgggattgac ggtgaaagaa agatgatccg ggaacgataa tgactccatc      180
cgctttcata tactcataca gcgctgcatc ggtcaccggc aggtcttcaa accacagcca      240
tccgaaaagc gatccttccc cttgatgcag ataccatttg atgtcttcag gcatcttgca      300
taaaagcgtt tccttgagca gcatgaattt attgcggtaa tatggcctga cttcattcag      360
cgacacgtcg gcgaggcgcc cgtcattcaa tactgatgca gccatatact gccccagcct      420
tgaagaatgg atcgccgcat tcgactgaaa agcttccatt gcctgaatat accgggacgg      480
cccgatggcg attccgatcc tttcgccagg caggccggct tttgaaaggc tcatacagtg      540
aatgatctgc tcgttgaaaa tcggttccat gtcgataaag tgaatcgccg gaaaaggcgg      600
agcatatgcg gaatcaatga acagcggaac attcgcttct cggcatgcgt ctgaaatgaa      660
tgctacatct tctttaggca agatgtttcc gcaaggattg ttcgggcgcg atagcaagac      720
agcaccgatg cgcatcctct ctaaaaaccc cttacggtcg agctcatatc gaaacgtatg      780
atcatccaat ttcgatatga gcggagggat ccctcaatc atctcccgct ccagtgccgc      840
cccgctgtat cccgaatagt caggcagcat cgggatcaag gcttttttca tcacagatcc      900
gcttcccatt ccgcaaaacg aattgatcgc cagaaaaaac agctgctggc ttccggctgt      960
aatcaacacg ttctctttc gaatgccggc gctataccgc tctgaaaaga agcggacaac     1020
acttgcaatc agttcatcgg ttccatagct cgatccgtat tggccgatca ccgaagaaaa     1080
cctgtcatcg tcaaggagat cggcaagagc cgacttccac atggctgaca cgccgggcaa     1140
aatcatcgga ttgcccgcac ttaaattaat gtatgaccgt tcaccgccgg ccaggacttc     1200
ctgaatatcg ctcatcacag ccctgacccc tgttttctca atcattttct ctccgatttt     1260
gcttaatggc ggcttcac                                                   1278
```

<210> SEQ ID NO 75
<211> LENGTH: 309
<212> TYPE: PRT
<213> ORGANISM: Escherichia coli

<400> SEQUENCE: 75

```
Met Thr Thr Lys Lys Ala Asp Tyr Ile Trp Phe Asn Gly Glu Met Val
1               5                   10                  15

Arg Trp Glu Asp Ala Lys Val His Val Met Ser His Ala Leu His Tyr
            20                  25                  30

Gly Thr Ser Val Phe Glu Gly Ile Arg Cys Tyr Asp Ser His Lys Gly
        35                  40                  45

Pro Val Val Phe Arg His Arg Glu His Met Gln Arg Leu His Asp Ser
    50                  55                  60

Ala Lys Ile Tyr Arg Phe Pro Val Ser Gln Ser Ile Asp Glu Leu Met
65                  70                  75                  80

Glu Ala Cys Arg Asp Val Ile Arg Lys Asn Asn Leu Thr Ser Ala Tyr
            85                  90                  95

Ile Arg Pro Leu Ile Phe Val Gly Asp Val Gly Met Gly Val Asn Pro
        100                 105                 110

Pro Ala Gly Tyr Ser Thr Asp Val Ile Ile Ala Ala Phe Pro Trp Gly
    115                 120                 125
```

Ala Tyr Leu Gly Ala Glu Ala Leu Glu Gln Gly Ile Asp Ala Met Val
    130                 135                 140

Ser Ser Trp Asn Arg Ala Ala Pro Asn Thr Ile Pro Thr Ala Ala Lys
145                 150                 155                 160

Ala Gly Gly Asn Tyr Leu Ser Ser Leu Leu Val Gly Ser Glu Ala Arg
                165                 170                 175

Arg His Gly Tyr Gln Glu Gly Ile Ala Leu Asp Val Asn Gly Tyr Ile
            180                 185                 190

Ser Glu Gly Ala Gly Glu Asn Leu Phe Glu Val Lys Asp Gly Val Leu
        195                 200                 205

Phe Thr Pro Pro Phe Thr Ser Ser Ala Leu Pro Gly Ile Thr Arg Asp
    210                 215                 220

Ala Ile Ile Lys Leu Ala Lys Glu Leu Gly Ile Glu Val Arg Glu Gln
225                 230                 235                 240

Val Leu Ser Arg Glu Ser Leu Tyr Leu Ala Asp Glu Val Phe Met Ser
                245                 250                 255

Gly Thr Ala Ala Glu Ile Thr Pro Val Arg Ser Val Asp Gly Ile Gln
            260                 265                 270

Val Gly Glu Gly Arg Cys Gly Pro Val Thr Lys Arg Ile Gln Gln Ala
        275                 280                 285

Phe Phe Gly Leu Phe Thr Gly Glu Thr Glu Asp Lys Trp Gly Trp Leu
    290                 295                 300

Asp Gln Val Asn Gln
305

<210> SEQ ID NO 76
<211> LENGTH: 1476
<212> TYPE: DNA
<213> ORGANISM: Escherichia coli

<400> SEQUENCE: 76
atggctaact acttcaatac actgaatctg cgccagcagc tggcacagct gggcaaatgt      60
cgctttatgg ccgcgatga attcgccgat ggcgcgagct accttcaggg taaaaaagta     120
gtcatcgtcg gctgtggcgc acagggtctg aaccagggcc tgaacatgcg tgattctggt     180
ctcgatatct cctacgctct gcgtaaagaa gcgattgccg agaagcgcgc gtcctggcgt     240
aaagcgaccg aaaatggttt taagtgggt acttacgaag aactgatccc acaggcggat     300
ctggtgatta acctgacgcc ggacaagcag cactctgatg tagtgcgcac cgtacagcca     360
ctgatgaaag acggcgcggc gctgggctac tcgcacggtt tcaacatcgt cgaagtgggc     420
gagcagatcc gtaaagatat caccgtagtg atggttgcgc gaaatgccc aggcaccgaa     480 gtgcgtgaag agtacaaacg tgggttcggc gtaccgacgc tgattgccgt tcacccggaa     540
aacgatccga aggcgaagg catggcgatt gccaaagcct gggcggctgc aaccggtggt     600
caccgtgcgg gtgtgctgga atcgtccttc gttgcggaag tgaaatctga cctgatgggc     660
gagcaaacca tcctgtgcgg tatgttgcag ctggctctc tgctgtgctt cgacaagctg     720
gtggaagaag gtaccgatcc agcatacgca gaaaaactga ttcagttcgg ttgggaaacc     780
atcaccgaag cactgaaaca gggcggcatc accctgatga tggaccgtct ctctaacccg     840
gcgaaactgc gtgcttatgc gctttctgaa cagctgaaag agatcatggc accctgttc     900 cagaaacata tggacgacat catctccggc gaattctctt ccggtatgat ggcggactgg     960
gccaacgatg ataagaaact gctgacctgg cgtgaagaga ccggcaaaac cgcgtttgaa    1020

```
accgcgccgc agtatgaagg caaaatcggc gagcaggagt acttcgataa aggcgtactg    1080
atgattgcga tggtgaaagc gggcgttgaa ctggcgttcg aaaccatggt cgattccggc    1140
atcattgaag agtctgcata ttatgaatca ctgcacgagc tgccgctgat tgccaacacc    1200
atcgcccgta agcgtctgta cgaaatgaac gtggttatct ctgataccgc tgagtacggt    1260
aactatctgt tctcttacgc ttgtgtgccg ttgctgaaac cgtttatggc agagctgcaa    1320
ccgggcgacc tgggtaaagc tattccggaa ggcgcggtag ataacgggca actgcgtgat    1380
gtgaacgaag cgattcgcag ccatgcgatt gagcaggtag gtaagaaact gcgcggctat    1440
atgacagata tgaaacgtat tgctgttgcg ggttaa                              1476
```

<210> SEQ ID NO 77
<211> LENGTH: 376
<212> TYPE: PRT
<213> ORGANISM: Saccharomyces cerevisiae

<400> SEQUENCE: 77

```
Met Thr Leu Ala Pro Leu Asp Ala Ser Lys Val Lys Ile Thr Thr Thr
1               5                   10                  15

Gln His Ala Ser Lys Pro Lys Pro Asn Ser Glu Leu Val Phe Gly Lys
            20                  25                  30

Ser Phe Thr Asp His Met Leu Thr Ala Glu Trp Thr Ala Glu Lys Gly
        35                  40                  45

Trp Gly Thr Pro Glu Ile Lys Pro Tyr Gln Asn Leu Ser Leu Asp Pro
    50                  55                  60

Ser Ala Val Val Phe His Tyr Ala Phe Glu Leu Phe Glu Gly Met Lys
65                  70                  75                  80

Ala Tyr Arg Thr Val Asp Asn Lys Ile Thr Met Phe Arg Pro Asp Met
                85                  90                  95

Asn Met Lys Arg Met Asn Lys Ser Ala Gln Arg Ile Cys Leu Pro Thr
            100                 105                 110

Phe Asp Pro Glu Glu Leu Ile Thr Leu Ile Gly Lys Leu Ile Gln Gln
        115                 120                 125

Asp Lys Cys Leu Val Pro Glu Gly Lys Gly Tyr Ser Leu Tyr Ile Arg
    130                 135                 140

Pro Thr Leu Ile Gly Thr Thr Ala Gly Leu Gly Val Ser Thr Pro Asp
145                 150                 155                 160

Arg Ala Leu Leu Tyr Val Ile Cys Cys Pro Val Gly Pro Tyr Tyr Lys
                165                 170                 175

Thr Gly Phe Lys Ala Val Arg Leu Glu Ala Thr Asp Tyr Ala Thr Arg
            180                 185                 190

Ala Trp Pro Gly Gly Cys Gly Asp Lys Lys Leu Gly Ala Asn Tyr Ala
        195                 200                 205

Pro Cys Val Leu Pro Gln Leu Gln Ala Ala Ser Arg Gly Tyr Gln Gln
    210                 215                 220

Asn Leu Trp Leu Phe Gly Pro Asn Asn Ile Thr Glu Val Gly Thr
225                 230                 235                 240

Met Asn Ala Phe Phe Val Phe Lys Asp Ser Lys Thr Gly Lys Lys Glu
                245                 250                 255

Leu Val Thr Ala Pro Leu Asp Gly Thr Ile Leu Glu Gly Val Thr Arg
            260                 265                 270

Asp Ser Ile Leu Asn Leu Ala Lys Glu Arg Leu Glu Pro Ser Glu Trp
        275                 280                 285

Thr Ile Ser Glu Arg Tyr Phe Thr Ile Gly Glu Val Thr Glu Arg Ser
```

```
            290                 295                 300
Lys Asn Gly Glu Leu Leu Glu Ala Phe Gly Ser Gly Thr Ala Ala Ile
305                 310                 315                 320

Val Ser Pro Ile Lys Glu Ile Gly Trp Lys Gly Glu Gln Ile Asn Ile
                325                 330                 335

Pro Leu Leu Pro Gly Glu Gln Thr Gly Pro Leu Ala Lys Glu Val Ala
                340                 345                 350

Gln Trp Ile Asn Gly Ile Gln Tyr Gly Glu Thr Glu His Gly Asn Trp
                355                 360                 365

Ser Arg Val Val Thr Asp Leu Asn
            370                 375

<210> SEQ ID NO 78
<211> LENGTH: 376
<212> TYPE: PRT
<213> ORGANISM: Saccharomyces cerevisiae

<400> SEQUENCE: 78

Met Thr Leu Ala Pro Leu Asp Ala Ser Lys Val Lys Ile Thr Thr Thr
1               5                   10                  15

Gln His Ala Ser Lys Pro Lys Pro Asn Ser Glu Leu Val Phe Gly Lys
            20                  25                  30

Ser Phe Thr Asp His Met Leu Thr Ala Glu Trp Thr Ala Glu Lys Gly
        35                  40                  45

Trp Gly Thr Pro Glu Ile Lys Pro Tyr Gln Asn Leu Ser Leu Asp Pro
    50                  55                  60

Ser Ala Val Val Phe His Tyr Ala Phe Glu Leu Phe Glu Gly Met Lys
65                  70                  75                  80

Ala Tyr Arg Thr Val Asp Asn Lys Ile Thr Met Phe Arg Pro Asp Met
                85                  90                  95

Asn Met Lys Arg Met Asn Lys Ser Ala Gln Arg Ile Cys Leu Pro Thr
            100                 105                 110

Phe Asp Pro Glu Glu Leu Ile Thr Leu Ile Gly Lys Leu Ile Gln Gln
        115                 120                 125

Asp Lys Cys Leu Val Pro Glu Gly Lys Gly Tyr Ser Leu Tyr Ile Arg
    130                 135                 140

Pro Thr Leu Ile Gly Thr Thr Ala Gly Leu Gly Val Ser Thr Pro Asp
145                 150                 155                 160

Arg Ala Leu Leu Tyr Val Ile Cys Cys Pro Val Gly Pro Tyr Tyr Lys
                165                 170                 175

Thr Gly Phe Lys Ala Val Arg Leu Glu Ala Thr Asp Tyr Ala Thr Arg
            180                 185                 190

Ala Trp Pro Gly Gly Cys Gly Asp Lys Lys Leu Gly Ala Asn Tyr Ala
        195                 200                 205

Pro Cys Val Leu Pro Gln Leu Gln Ala Ala Ser Arg Gly Tyr Gln Gln
    210                 215                 220

Asn Leu Trp Leu Phe Gly Pro Asn Asn Asn Ile Thr Glu Val Gly Thr
225                 230                 235                 240

Met Asn Ala Phe Phe Val Phe Lys Asp Ser Lys Thr Gly Lys Lys Glu
                245                 250                 255

Leu Val Thr Ala Pro Leu Asp Gly Thr Ile Leu Glu Gly Val Thr Arg
            260                 265                 270

Asp Ser Ile Leu Asn Leu Ala Lys Glu Arg Leu Glu Pro Ser Glu Trp
        275                 280                 285
```

```
Thr Ile Ser Glu Arg Tyr Phe Thr Ile Gly Glu Val Thr Glu Arg Ser
        290                 295                 300

Lys Asn Gly Glu Leu Leu Glu Ala Phe Gly Ser Gly Thr Ala Ala Ile
305                 310                 315                 320

Val Ser Pro Ile Lys Glu Ile Gly Trp Lys Gly Glu Gln Ile Asn Ile
                325                 330                 335

Pro Leu Leu Pro Gly Glu Gln Thr Gly Pro Leu Ala Lys Glu Val Ala
                340                 345                 350

Gln Trp Ile Asn Gly Ile Gln Tyr Gly Glu Thr Glu His Gly Asn Trp
                355                 360                 365

Ser Arg Val Val Thr Asp Leu Asn
370                 375

<210> SEQ ID NO 79
<211> LENGTH: 330
<212> TYPE: PRT
<213> ORGANISM: Methanobacterium thermoautotrophicum

<400> SEQUENCE: 79

Met Arg Leu Trp Arg Ala Leu Tyr Arg Pro Thr Ile Thr Tyr Pro
1               5                   10                  15

Ser Lys Ser Pro Glu Val Ile Ile Met Ser Cys Glu Ala Ser Gly Lys
                20                  25                  30

Ile Trp Leu Asn Gly Glu Met Val Glu Trp Glu Ala Thr Val His
                35                  40                  45

Val Leu Ser His Val Val His Tyr Gly Ser Ser Val Phe Glu Gly Ile
    50                  55                  60

Arg Cys Tyr Arg Asn Ser Lys Gly Ser Ala Ile Phe Arg Leu Arg Glu
65                  70                  75                  80

His Val Lys Arg Leu Phe Asp Ser Ala Lys Ile Tyr Arg Met Asp Ile
                85                  90                  95

Pro Tyr Thr Gln Glu Gln Ile Cys Asp Ala Ile Val Glu Thr Val Arg
                100                 105                 110

Glu Asn Gly Leu Glu Glu Cys Tyr Ile Arg Pro Val Val Phe Arg Gly
                115                 120                 125

Tyr Gly Glu Met Gly Val His Pro Val Asn Cys Pro Val Asp Val Ala
                130                 135                 140

Val Ala Ala Trp Glu Trp Gly Ala Tyr Leu Gly Ala Glu Ala Leu Glu
145                 150                 155                 160

Val Gly Val Asp Ala Gly Val Ser Thr Trp Arg Arg Met Ala Pro Asn
                165                 170                 175

Thr Met Pro Asn Met Ala Lys Ala Gly Gly Asn Tyr Leu Asn Ser Gln
                180                 185                 190

Leu Ala Lys Met Glu Ala Val Arg His Gly Tyr Asp Glu Ala Ile Met
                195                 200                 205

Leu Asp Tyr His Gly Tyr Ile Ser Glu Gly Ser Gly Glu Asn Ile Phe
                210                 215                 220

Leu Val Ser Glu Gly Glu Ile Tyr Thr Pro Pro Val Ser Ser Ser Leu
225                 230                 235                 240

Leu Arg Gly Ile Thr Arg Asp Ser Val Ile Lys Ile Ala Arg Thr Glu
                245                 250                 255

Gly Val Thr Val His Glu Glu Pro Ile Thr Arg Glu Met Leu Tyr Ile
                260                 265                 270

Ala Asp Glu Ala Phe Phe Thr Gly Thr Ala Ala Glu Ile Thr Pro Ile
                275                 280                 285
```

Arg Ser Val Asp Gly Ile Glu Ile Gly Ala Gly Arg Arg Gly Pro Val
          290                 295                 300

Thr Lys Leu Leu Gln Asp Glu Phe Phe Arg Ile Ile Arg Ala Glu Thr
305                 310                 315                 320

Glu Asp Ser Phe Gly Trp Leu Thr Tyr Ile
                325                 330

<210> SEQ ID NO 80
<211> LENGTH: 993
<212> TYPE: DNA
<213> ORGANISM: Methanobacterium thermoautotrophicum

<400> SEQUENCE: 80

```
tcagatgtag gtgagccatc cgaagctgtc ctctgtctct gccctgatta tcctgaagaa      60
ctcatcctgc agcagctttg taacgggacc ccttcgcccg gcacctatct ctataccatc     120
aactgatctg atgggtgtta tctctgcggc tgtacctgtg aagaaggcct catctgcgat     180
gtagagcatc tccctggtta tgggttcctc atgcacggta acaccctcgg tcctggctat     240
ctttattacg gagtcccttg ttatccccct cagaagggat gatgaaacag ggggggtgta     300
aatttcaccc tcactgacga ggaatatgtt ctccccgcta ccctcactta tgtagccatg     360
gtagtccagc attatggcct catcatagcc gtgtctcaca gcctccatct tggcaagctg     420
tgagttgagg tagttaccgc cggcctttgc catgttgggc attgtgtttg gtgccatcct     480
ccgccaggtt gaaacaccag catcgacacc aacctcaagg gcctctgcac ccagataggc     540
cccccattcc caggcagcca cagcgacgtc cactgggcag ttcaccgggt gaacacccat     600
ctcaccgtat ccctgaata ccacgggtct tatatagcac tcctcaagtc cgttctccct     660
gacggtctca actatggcat cacatatctg ctcctgggtg tagggtatgt ccatccggta     720
tatctttgca gaatcaaaaa ggcgtttaac atgctcccgc aaacggaaga tggctgaccc     780
cttactgttc ctgtagcacc ttattccctc aaagacagat gatccataat gcacaacatg     840
tgagagtacg tggacggtgg cttcttccca ttcaaccatt tcaccgttta accatatctt     900
tccactggct tcgcatgaca tgataataac ctcaggtgat ttactaggat aggttatggt     960
tggaggccta taatgctc tccataaccg caa                                    993
```

<210> SEQ ID NO 81
<211> LENGTH: 364
<212> TYPE: PRT
<213> ORGANISM: Streptomyces coelicolor

<400> SEQUENCE: 81

Met Thr Asp Val Asn Gly Ala Pro Ala Asp Val Leu His Thr Leu Phe
1               5                   10                  15

His Ser Asp Gln Gly Gly His Glu Gln Val Val Leu Cys Gln Asp Arg
                20                  25                  30

Ala Ser Gly Leu Lys Ala Val Ile Ala Leu His Ser Thr Ala Leu Gly
            35                  40                  45

Pro Ala Leu Gly Gly Thr Arg Phe Tyr Pro Tyr Ala Ser Glu Ala Glu
        50                  55                  60

Ala Val Ala Asp Ala Leu Asn Leu Ala Arg Gly Met Ser Tyr Lys Asn
65                  70                  75                  80

Ala Met Ala Gly Leu Asp His Gly Gly Gly Lys Ala Val Ile Ile Gly
                85                  90                  95

Asp Pro Glu Gln Ile Lys Ser Glu Glu Leu Leu Leu Ala Tyr Gly Arg

```
            100                 105                 110
Phe Val Ala Ser Leu Gly Gly Arg Tyr Val Thr Ala Cys Asp Val Gly
        115                 120                 125
Thr Tyr Val Ala Asp Met Asp Val Val Ala Arg Glu Cys Arg Trp Thr
    130                 135                 140
Thr Gly Arg Ser Pro Glu Asn Gly Gly Ala Gly Asp Ser Ser Val Leu
145                 150                 155                 160
Thr Ser Phe Gly Val Tyr Gln Gly Met Arg Ala Ala Gln His Leu
                165                 170                 175
Trp Gly Asp Pro Thr Leu Arg Asp Arg Thr Val Gly Ile Ala Gly Val
            180                 185                 190
Gly Lys Val Gly His His Leu Val Glu His Leu Ala Glu Gly Ala
        195                 200                 205
His Val Val Val Thr Asp Val Arg Lys Asp Val Val Arg Gly Ile Thr
    210                 215                 220
Glu Arg His Pro Ser Val Val Ala Val Ala Asp Thr Asp Ala Leu Ile
225                 230                 235                 240
Arg Val Glu Asn Leu Asp Ile Tyr Ala Pro Cys Ala Leu Gly Ala
                245                 250                 255
Leu Asn Asp Asp Thr Val Pro Val Leu Thr Ala Lys Val Val Cys Gly
            260                 265                 270
Ala Ala Asn Asn Gln Leu Ala His Pro Gly Val Glu Lys Asp Leu Ala
        275                 280                 285
Asp Arg Gly Ile Leu Tyr Ala Pro Asp Tyr Val Asn Ala Gly Gly
    290                 295                 300
Val Ile Gln Val Ala Asp Glu Leu His Gly Phe Asp Phe Asp Arg Cys
305                 310                 315                 320
Lys Ala Lys Ala Ser Lys Ile Tyr Asp Thr Thr Leu Ala Ile Phe Ala
                325                 330                 335
Arg Ala Lys Glu Asp Gly Ile Pro Pro Ala Ala Ala Asp Arg Ile
            340                 345                 350
Ala Glu Gln Arg Met Ala Glu Ala Arg Pro Arg Pro
        355                 360

<210> SEQ ID NO 82
<211> LENGTH: 1095
<212> TYPE: DNA
<213> ORGANISM: Streptomyces coelicolor

<400> SEQUENCE: 82
tcacggccgg ggacgggcct ccgccatccg ctgctcggcg atccggtcgg ccgccgcggc     60
cggcggaata ccgtcctcct tcgcacgtgc gaatatggcc agcgtggtgt cgtagatctt    120
cgaggccttc gccttgcacc ggtcgaagtc gaacccgtgc agctcgtcgg cgacctggat    180
gacaccgccg gcgttcacca catagtccgg cgcgtagagg atcccgcggt cggcgaggtc    240
cttctcgacg cccgggtggg cgagctggtt gttggccgcg ccgcacacca ccttggcggt    300
cagcaccggc acggtgtcgt cgttcagcgc gccgccgagc gcgcagggcg cgtagatgtc    360
caggttctcc accggatca gcgcgtcggt gtcggcgacg cgaccaccg acgggtgccg    420 ctccgtgatc ccgcgcacca cgtccttgcg cacgtccgtg acgacgacgt gggcgccctc    480
ggcgagcagg tgctcgacca ggtggtggcc gaccttgccg acgcccgcga tgccgacggt    540
gcggtcgcgc agcgtcgggt cgccccacag gtgctgggcg gcggcccgca tgccctggta    600
gacgccgaag gaggtgagca cggaggagtc gcccgcgccg ccgttctccg gggaacgccc    660
```

```
ggtcgtccag cggcactcgc gggccacgac gtccatgtcg gcgacgtagg tgccgacgtc    720
gcacgcggtg acgtagcggc cgcccagcga ggcgacgaac cggccgtagg cgaggagcag    780
ctcctcgctc ttgatctgct ccggatcgcc gatgatcacg gccttgccgc caccgtggtc    840
cagaccggcc atggcgttct tgtacgacat cccgcgggcg aggttcagcg cgtcggcgac    900
ggcctccgcc tcgctcgcgt acgggtagaa gcgggtaccg ccgagcgccg ggcccagggc    960
ggtggagtgg agggcgatca cggccttgag gccgctggca cggtcctggc agagcacgac   1020
ttgctcatgt cccccctgat ccgagtggaa cagggtgtgc agtacatcag caggtgcgcc   1080
gtttacgtcg gtcac                                                   1095
```

<210> SEQ ID NO 83
<211> LENGTH: 364
<212> TYPE: PRT
<213> ORGANISM: Bacillus subtilis

<400> SEQUENCE: 83

```
Met Glu Leu Phe Lys Tyr Met Glu Lys Tyr Asp Tyr Glu Gln Leu Val
1               5                   10                  15

Phe Cys Gln Asp Glu Gln Ser Gly Leu Lys Ala Ile Ile Ala Ile His
                20                  25                  30

Asp Thr Thr Leu Gly Pro Ala Leu Gly Gly Thr Arg Met Trp Thr Tyr
            35                  40                  45

Glu Asn Glu Glu Ala Ala Ile Glu Asp Ala Leu Arg Leu Ala Arg Gly
    50                  55                  60

Met Thr Tyr Lys Asn Ala Ala Gly Leu Asn Leu Gly Gly Gly Lys
65                  70                  75                  80

Thr Val Ile Ile Gly Asp Pro Arg Lys Asp Lys Asn Glu Glu Met Phe
                85                  90                  95

Arg Ala Phe Gly Arg Tyr Ile Gln Gly Leu Asn Gly Arg Tyr Ile Thr
            100                 105                 110

Ala Glu Asp Val Gly Thr Thr Val Glu Asp Met Asp Ile Ile His Asp
    115                 120                 125

Glu Thr Asp Tyr Val Thr Gly Ile Ser Pro Ala Phe Gly Ser Ser Gly
130                 135                 140

Asn Pro Ser Pro Val Thr Ala Tyr Gly Val Tyr Arg Gly Met Lys Ala
145                 150                 155                 160

Ala Ala Lys Ala Ala Phe Gly Thr Asp Ser Leu Glu Gly Lys Thr Ile
                165                 170                 175

Ala Val Gln Gly Val Gly Asn Val Ala Tyr Asn Leu Cys Arg His Leu
            180                 185                 190

His Glu Glu Gly Ala Asn Leu Ile Val Thr Asp Ile Asn Lys Gln Ser
    195                 200                 205

Val Gln Arg Ala Val Glu Asp Phe Gly Ala Arg Ala Val Asp Pro Asp
210                 215                 220

Asp Ile Tyr Ser Gln Asp Cys Asp Ile Tyr Ala Pro Cys Ala Leu Gly
225                 230                 235                 240

Ala Thr Ile Asn Asp Asp Thr Ile Lys Gln Leu Lys Ala Lys Val Ile
                245                 250                 255

Ala Gly Ala Ala Asn Asn Gln Leu Lys Glu Thr Arg His Gly Asp Gln
            260                 265                 270

Ile His Glu Met Gly Ile Val Tyr Ala Pro Asp Tyr Val Ile Asn Ala
    275                 280                 285
```

```
Gly Gly Val Ile Asn Val Ala Asp Glu Leu Tyr Gly Tyr Asn Ala Glu
    290                 295                 300

Arg Ala Leu Lys Lys Val Glu Gly Ile Tyr Gly Asn Ile Glu Arg Val
305                 310                 315                 320

Leu Glu Ile Ser Gln Arg Asp Gly Ile Pro Ala Tyr Leu Ala Ala Asp
                325                 330                 335

Arg Leu Ala Glu Glu Arg Ile Glu Arg Met Arg Arg Ser Arg Ser Gln
                340                 345                 350

Phe Leu Gln Asn Gly His Ser Val Leu Ser Arg Arg
                355                 360

<210> SEQ ID NO 84
<211> LENGTH: 364
<212> TYPE: PRT
<213> ORGANISM: Bacillus subtilis

<400> SEQUENCE: 84

Met Glu Leu Phe Lys Tyr Met Glu Lys Tyr Asp Tyr Glu Gln Leu Val
1               5                   10                  15

Phe Cys Gln Asp Glu Gln Ser Gly Leu Lys Ala Ile Ile Ala Ile His
                20                  25                  30

Asp Thr Thr Leu Gly Pro Ala Leu Gly Gly Thr Arg Met Trp Thr Tyr
            35                  40                  45

Glu Asn Glu Glu Ala Ala Ile Glu Asp Ala Leu Arg Leu Ala Arg Gly
50                  55                  60

Met Thr Tyr Lys Asn Ala Ala Gly Leu Asn Leu Gly Gly Gly Lys
65                  70                  75                  80

Thr Val Ile Ile Gly Asp Pro Arg Lys Asp Lys Asn Glu Glu Met Phe
                85                  90                  95

Arg Ala Phe Gly Arg Tyr Ile Gln Gly Leu Asn Gly Arg Tyr Ile Thr
                100                 105                 110

Ala Glu Asp Val Gly Thr Thr Val Glu Asp Met Asp Ile Ile His Asp
            115                 120                 125

Glu Thr Asp Tyr Val Thr Gly Ile Ser Pro Ala Phe Gly Ser Ser Gly
130                 135                 140

Asn Pro Ser Pro Val Thr Ala Tyr Gly Val Tyr Arg Gly Met Lys Ala
145                 150                 155                 160

Ala Ala Lys Ala Ala Phe Gly Thr Asp Ser Leu Glu Gly Lys Thr Ile
                165                 170                 175

Ala Val Gln Gly Val Gly Asn Val Ala Tyr Asn Leu Cys Arg His Leu
            180                 185                 190

His Glu Glu Gly Ala Asn Leu Ile Val Thr Asp Ile Asn Lys Gln Ser
        195                 200                 205

Val Gln Arg Ala Val Glu Asp Phe Gly Ala Arg Ala Val Asp Pro Asp
210                 215                 220

Asp Ile Tyr Ser Gln Asp Cys Asp Ile Tyr Ala Pro Cys Ala Leu Gly
225                 230                 235                 240

Ala Thr Ile Asn Asp Asp Thr Ile Lys Gln Leu Lys Ala Lys Val Ile
                245                 250                 255

Ala Gly Ala Ala Asn Asn Gln Leu Lys Glu Thr Arg His Gly Asp Gln
            260                 265                 270

Ile His Glu Met Gly Ile Val Tyr Ala Pro Asp Tyr Val Ile Asn Ala
        275                 280                 285

Gly Gly Val Ile Asn Val Ala Asp Glu Leu Tyr Gly Tyr Asn Ala Glu
290                 295                 300
```

```
Arg Ala Leu Lys Lys Val Glu Gly Ile Tyr Gly Asn Ile Glu Arg Val
305                 310                 315                 320

Leu Glu Ile Ser Gln Arg Asp Gly Ile Pro Ala Tyr Leu Ala Ala Asp
                325                 330                 335

Arg Leu Ala Glu Glu Arg Ile Glu Arg Met Arg Arg Ser Arg Ser Gln
            340                 345                 350

Phe Leu Gln Asn Gly His Ser Val Leu Ser Arg Arg
        355                 360
```

<210> SEQ ID NO 85
<211> LENGTH: 594
<212> TYPE: PRT
<213> ORGANISM: Streptomyces viridifaciens

<400> SEQUENCE: 85

```
Met Ser Thr Ser Ser Ala Ser Ser Gly Pro Asp Leu Pro Phe Gly Pro
1               5                   10                  15

Glu Asp Thr Pro Trp Gln Lys Ala Phe Ser Arg Leu Arg Ala Val Asp
                20                  25                  30

Gly Val Pro Arg Val Thr Ala Pro Ser Ser Asp Pro Arg Glu Val Tyr
            35                  40                  45

Met Asp Ile Pro Glu Ile Pro Phe Ser Lys Val Gln Ile Pro Pro Asp
50                  55                  60

Gly Met Asp Glu Gln Gln Tyr Ala Glu Ala Glu Ser Leu Phe Arg Arg
65                  70                  75                  80

Tyr Val Asp Ala Gln Thr Arg Asn Phe Ala Gly Tyr Gln Val Thr Ser
                85                  90                  95

Asp Leu Asp Tyr Gln His Leu Ser His Tyr Leu Asn Arg His Leu Asn
                100                 105                 110

Asn Val Gly Asp Pro Tyr Glu Ser Ser Ser Tyr Thr Leu Asn Ser Lys
            115                 120                 125

Val Leu Glu Arg Ala Val Leu Asp Tyr Phe Ala Ser Leu Trp Asn Ala
    130                 135                 140

Lys Trp Pro His Asp Ala Ser Asp Pro Glu Thr Tyr Trp Gly Tyr Val
145                 150                 155                 160

Leu Thr Met Gly Ser Ser Glu Gly Asn Leu Tyr Gly Leu Trp Asn Ala
                165                 170                 175

Arg Asp Tyr Leu Ser Gly Lys Leu Leu Arg Arg Gln His Arg Glu Ala
                180                 185                 190

Gly Gly Asp Lys Ala Ser Val Val Tyr Thr Gln Ala Leu Arg His Glu
            195                 200                 205

Gly Gln Ser Pro His Ala Tyr Glu Pro Val Ala Phe Phe Ser Gln Asp
    210                 215                 220

Thr His Tyr Ser Leu Thr Lys Ala Val Arg Val Leu Gly Ile Asp Thr
225                 230                 235                 240

Phe His Ser Ile Gly Ser Ser Arg Tyr Pro Asp Glu Asn Pro Leu Gly
                245                 250                 255

Pro Gly Thr Pro Trp Pro Thr Glu Val Pro Ser Val Asp Gly Ala Ile
                260                 265                 270

Asp Val Asp Lys Leu Ala Ser Leu Val Arg Phe Phe Ala Ser Lys Gly
            275                 280                 285

Tyr Pro Ile Leu Val Ser Leu Asn Tyr Gly Ser Thr Phe Lys Gly Ala
    290                 295                 300

Tyr Asp Asp Val Pro Ala Val Ala Gln Ala Val Arg Asp Ile Cys Thr
```

```
              305                 310                 315                 320
Glu Tyr Gly Leu Asp Arg Arg Val Tyr His Asp Arg Ser Lys Asp
                325                 330                 335
Ser Asp Phe Asp Glu Arg Ser Gly Phe Trp Ile His Ile Asp Ala Ala
                340                 345                 350
Leu Gly Ala Gly Tyr Ala Pro Tyr Leu Gln Met Ala Arg Asp Ala Gly
                355                 360                 365
Met Val Glu Glu Ala Pro Pro Val Phe Asp Phe Arg Leu Pro Glu Val
        370                 375                 380
His Ser Leu Thr Met Ser Gly His Lys Trp Met Gly Thr Pro Trp Ala
385                 390                 395                 400
Cys Gly Val Tyr Met Thr Arg Thr Gly Leu Gln Met Thr Pro Pro Lys
                405                 410                 415
Ser Ser Glu Tyr Ile Gly Ala Ala Asp Thr Thr Phe Ala Gly Ser Arg
                420                 425                 430
Asn Gly Phe Ser Ser Leu Leu Leu Trp Asp Tyr Leu Ser Arg His Ser
                435                 440                 445
Tyr Asp Asp Leu Val Arg Leu Ala Ala Asp Cys Asp Arg Leu Ala Gly
        450                 455                 460
Tyr Ala His Asp Arg Leu Leu Thr Leu Gln Asp Lys Leu Gly Met Asp
465                 470                 475                 480
Leu Trp Val Ala Arg Ser Pro Gln Ser Leu Thr Val Arg Phe Arg Gln
                485                 490                 495
Pro Cys Ala Asp Ile Val Arg Lys Tyr Ser Leu Ser Cys Glu Thr Val
                500                 505                 510
Tyr Glu Asp Asn Glu Gln Arg Thr Tyr Val His Leu Tyr Ala Val Pro
        515                 520                 525
His Leu Thr Arg Glu Leu Val Asp Glu Leu Val Arg Asp Leu Arg Gln
                530                 535                 540
Pro Gly Ala Phe Thr Asn Ala Gly Ala Leu Glu Gly Glu Ala Trp Ala
545                 550                 555                 560
Gly Val Ile Asp Ala Leu Gly Arg Pro Asp Pro Asp Gly Thr Tyr Ala
                565                 570                 575
Gly Ala Leu Ser Ala Pro Ala Ser Gly Pro Arg Ser Glu Asp Gly Gly
                580                 585                 590
Gly Ser

<210> SEQ ID NO 86
<211> LENGTH: 1785
<212> TYPE: DNA
<213> ORGANISM: Streptomyces viridifaciens

<400> SEQUENCE: 86
gtgtcaactt cctccgcttc ttccgggccg gacctcccct cgggcccga ggacacgcca      60
tggcagaagg ccttcagcag gctgcgggcg gtgatggcg tgccgcgcgt caccgcgccg     120
tccagtgatc cgcgtgaggt ctacatggac atcccggaga tcccttctc caaggtccag     180
atcccccggg acggaatgga cgagcagcag tacgcagagg ccgagagcct cttccgccgc     240
tacgtagacg cccagacccg caacttcgcg ggataccagg tcaccagcga cctcgactac     300
cagcacctca gtcactatct caaccggcat ctgaacaacg tcggcgatcc ctatgagtcc     360
agctcctaca cgctgaactc caaggtcctt gagcgagccg ttctcgacta cttcgcctcc     420
ctgtggaacg ccaagtggcc ccatgacgca agcgatccgg aaacgtactg ggttacgtg     480
```

```
ctgaccatgg gctccagcga aggcaacctg tacgggttgt ggaacgcacg ggactatctg    540
tcgggcaagc tgctgcggcg ccagcaccgg gaggccggcg cgacaaggc ctcggtcgtc     600 tacacgcaag cgctgcgaca cgaagggcag agtccgcatg cctacgagcc ggtggcgttc    660
ttctcgcagg acacgcacta ctcgctcacg aaggccgtgc gggttctggg catcgacacc    720
ttccacagca tcggcagcag tcggtatccg gacgagaacc cgctgggccc cggcactccg    780
tggccgaccg aagtgccctc ggttgacggt gccatcgatg tcgacaaact cgcctcgttg    840
gtccgcttct tcgccagcaa gggctacccg atactggtca gcctcaacta cgggtcaacg    900
ttcaagggcg cctacgacga cgtcccggcc gtggcacagg ccgtgcggga catctgcacg    960
gaatacggtc tggatcggcg gcgggtatac cacgaccgca gtaaggacag tgacttcgac   1020
gagcgcagcg gcttctggat ccacatcgat gccgccctgg gggcgggcta cgctcccctac  1080 ctgcagatgg cccgggatgc cggcatggtc gaggaggcgc cgcccgtttt cgacttccgg   1140
ctcccggagg tgcactcgct gaccatgagc ggccacaagt ggatgggaac accgtgggca   1200
tgcggtgtct acatgacacg gaccgggctg cagatgaccc cgccgaagtc gtccgagtac   1260
atcggggcgg ccgacaccac cttcgcgggc tcccgcaacg gcttctcgtc actgctgctg   1320
tgggactacc tgtcccggca ttcgtatgac gatctggtgc cctggccgc cgactgcgac    1380 cggctggccg gctacgccca cgaccggttg ctgaccttgc aggacaaact cggcatggat   1440
ctgtgggtcg cccgcagccc gcagtccctc acggtgcgct tccgtcagcc atgtgcagac   1500
atcgtccgca gtactcgct gtcgtgtgag acggtctacg aagacaacga gcaacggacc    1560
tacgtacatc tctacgccgt tccccacctc actcgggaac tcgtggatga gctcgtgcgc   1620
gatctgcgcc agcccggagc cttcaccaac gctggtgcac tggaggggga ggcctgggcc   1680
ggggtgatcg atgccctcgg ccgccccgac ccgacggaa cctatgccgg cgccttgagc    1740
gctccggctt ccggcccccg ctccgaggac ggcggcggga gctga                   1785
```

<210> SEQ ID NO 87
<211> LENGTH: 440
<212> TYPE: PRT
<213> ORGANISM: Alcaligenes denitrificans

<400> SEQUENCE: 87

```
Met Ser Ala Ala Lys Leu Pro Asp Leu Ser His Leu Trp Met Pro Phe
1               5                   10                  15

Thr Ala Asn Arg Gln Phe Lys Ala Asn Pro Arg Leu Leu Ala Ser Ala
            20                  25                  30

Lys Gly Met Tyr Tyr Thr Ser Phe Asp Gly Arg Gln Ile Leu Asp Gly
        35                  40                  45

Thr Ala Gly Leu Trp Cys Val Asn Ala Gly His Cys Arg Glu Glu Ile
    50                  55                  60

Val Ser Ala Ile Ala Ser Gln Ala Gly Val Met Asp Tyr Ala Pro Gly
65                  70                  75                  80

Phe Gln Leu Gly His Pro Leu Ala Phe Glu Ala Thr Ala Val Ala
                85                  90                  95

Gly Leu Met Pro Gln Gly Leu Asp Arg Val Phe Phe Thr Asn Ser Gly
            100                 105                 110

Ser Glu Ser Val Asp Thr Ala Leu Lys Ile Ala Leu Ala Tyr His Arg
        115                 120                 125

Ala Arg Gly Glu Ala Gln Arg Thr Arg Leu Ile Gly Arg Glu Arg Gly
    130                 135                 140
```

```
Tyr His Gly Val Gly Phe Gly Gly Ile Ser Val Gly Gly Ile Ser Pro
145                 150                 155                 160

Asn Arg Lys Thr Phe Ser Gly Ala Leu Leu Pro Ala Val Asp His Leu
                165                 170                 175

Pro His Thr His Ser Leu Glu His Asn Ala Phe Thr Arg Gly Gln Pro
            180                 185                 190

Glu Trp Gly Ala His Leu Ala Asp Glu Leu Glu Arg Ile Ile Ala Leu
        195                 200                 205

His Asp Ala Ser Thr Ile Ala Ala Val Ile Val Glu Pro Met Ala Gly
210                 215                 220

Ser Thr Gly Val Leu Val Pro Pro Lys Gly Tyr Leu Glu Lys Leu Arg
225                 230                 235                 240

Glu Ile Thr Ala Arg His Gly Ile Leu Leu Ile Phe Asp Glu Val Ile
                245                 250                 255

Thr Ala Tyr Gly Arg Leu Gly Glu Ala Thr Ala Ala Ala Tyr Phe Gly
            260                 265                 270

Val Thr Pro Asp Leu Ile Thr Met Ala Lys Gly Val Ser Asn Ala Ala
        275                 280                 285

Val Pro Ala Gly Ala Val Ala Val Arg Arg Glu Val His Asp Ala Ile
290                 295                 300

Val Asn Gly Pro Gln Gly Ile Glu Phe Phe His Gly Tyr Thr Tyr
305                 310                 315                 320

Ser Ala His Pro Leu Ala Ala Ala Val Leu Ala Thr Leu Asp Ile
                325                 330                 335

Tyr Arg Arg Glu Asp Leu Phe Ala Arg Ala Lys Leu Ser Ala Ala
            340                 345                 350

Phe Glu Glu Ala Ala His Ser Leu Lys Gly Ala Pro His Val Ile Asp
        355                 360                 365

Val Arg Asn Ile Gly Leu Val Ala Gly Ile Glu Leu Ser Pro Arg Glu
370                 375                 380

Gly Ala Pro Gly Ala Arg Ala Ala Glu Ala Phe Gln Lys Cys Phe Asp
385                 390                 395                 400

Thr Gly Leu Met Val Arg Tyr Thr Gly Asp Ile Leu Ala Val Ser Pro
                405                 410                 415

Pro Leu Ile Val Asp Glu Asn Gln Ile Gly Gln Ile Phe Glu Gly Ile
            420                 425                 430

Gly Lys Val Leu Lys Glu Val Ala
            435                 440

<210> SEQ ID NO 88
<211> LENGTH: 1947
<212> TYPE: DNA
<213> ORGANISM: Alcaligenes denitrificans

<400> SEQUENCE: 88
ttcgatggcg cgctgcacgg cggccaccag ctgctccacc aggggtgggc gcctgcccgc      60
gcgcgcggtc gggctggaaa tcgatcatgg atgaatctat acagttgtca tgattgcaac     120
tatacagtta gcccgttttg cggcaattgt atatttcat cgctcgtgg acgtccgaga       180 atcggtttga tcgcgccgcc cgcccctttc cgcgcagcgg cgtttctttt cctcggagt     240 ctccccatga gcgctgccaa actgcccgac ctgtcccacc tctggatgcc ctttaccgcc    300
aaccggcagt tcaaggcgaa ccccccgcctg ctggcctcgg ccaagggcat gtactacacg   360
tctttcgacg gcgccagat cctggacggc acggccggcc tgtggtgcgt gaacgccggc     420
```

```
cactgccgcg aagaaatcgt ctccgccatc gccagccagg ccggcgtcat ggactacgcg      480
ccggggttcc agctcggcca cccgctggcc ttcgaggccg ccaccgccgt ggccggcctg      540
atgccgcagg gcctggaccg cgtgttcttc accaattcgg gctccgaatc ggtggacacc      600
gcgctgaaga tcgccctggc ctaccaccgc gcgcgcggcg aggcgcagcg cacccgcctc      660
atcgggcgcg agcgcggcta ccacggcgtg ggcttcggcg catttccgt gggcggcatc       720
tcgcccaacc gcaagacctt ctccggcgcg ctgctgccgg ccgtggacca cctgccgcac      780
acccacagcc tggaacacaa cgccttcacg cgcggccagc ccgagtgggg cgcgcacctg      840
gccgacgagt tggaacgcat catcgccctg cacgacgcct ccaccatcgc ggccgtgatc      900
gtcgagccca tggccggctc caccggcgtg ctcgtcccgc caagggcta tctcgaaaaa        960
ctgcgcgaaa tcaccgcccg ccacggcatt ctgctgatct tcgacgaagt catcaccgcg     1020
tacgccgcc tgggcgaggc caccgccgcg gcctatttcg gcgtaacgcc cgacctcatc      1080
accatggcca agggcgtgag caacgccgcc gttccggccg gcgccgtcgc ggtgcgccgc     1140
gaagtgcatg acgccatcgt caacggaccg caaggcggca tcgagttctt ccacggctac     1200
acctactcgg cccacccgct ggccgccgcc gccgtgctcg ccacgctgga catctaccgc     1260
cgcgaagacc tgttcgcccg cgcccgcaag ctgtcggccg cgttcgagga agccgcccac     1320
agcctcaagg gcgcgccgca cgtcatcgac gtgcgcaaca tcggcctggt ggccggcatc     1380
gagctgtcgc cgcgcgaagg cgccccgggc gcgcgcgccg ccgaagcctt ccagaaatgc     1440
ttcgacaccg gcctcatggt cgcgctacacg ggcgacatcc tcgcggtgtc gcctccgctc     1500
atcgtcgacg aaaaccagat cggccagatc ttcgagggca tcggcaaggt gctcaaggaa     1560
gtggcttagg gtgaacacgc cctgagccgg ccccggcagg aaacgcgccg ccgcgcggcg     1620
gcgcgtccat cgaactcccg catcgagctt ttgcattcat gaagaaaatc acgcatttca     1680
tcaacggcca gccccacgaa ggccgcagca accgctacac cgagggcttc aacccggcca     1740
cgggcgagtc gtctcctcga tctgcctggg cggggccgaa gaagtggacc tggccgtggc     1800
ggccgcccgc gcggccttt ccgcctggtc cgaaacgccg gcgctcaagc gcgcgcgcgt     1860
gctgttcaac ttcaaggcgc tgctggacaa gcaccaggac gagctggccg cgctcatcac     1920
gcgcgagcac ggcaaggtgt tttccga                                         1947
```

<210> SEQ ID NO 89
<211> LENGTH: 443
<212> TYPE: PRT
<213> ORGANISM: Ralstonia eutropha

<400> SEQUENCE: 89

```
Met Asp Ala Ala Lys Thr Val Ile Pro Asp Leu Asp Ala Leu Trp Met
1               5                   10                  15

Pro Phe Thr Ala Asn Arg Gln Tyr Lys Ala Ala Pro Arg Leu Leu Ala
                20                  25                  30

Ser Ala Ser Gly Met Tyr Tyr Thr Thr His Asp Gly Arg Gln Ile Leu
            35                  40                  45

Asp Gly Cys Ala Gly Leu Trp Cys Val Ala Ala Gly His Cys Arg Lys
        50                  55                  60

Glu Ile Ala Glu Ala Val Ala Arg Gln Ala Ala Thr Leu Asp Tyr Ala
65                  70                  75                  80

Pro Pro Phe Gln Met Gly His Pro Leu Ser Phe Glu Ala Ala Thr Lys
                85                  90                  95

Val Ala Ala Ile Met Pro Gln Gly Leu Asp Arg Ile Phe Phe Thr Asn
```

```
            100                 105                 110
Ser Gly Ser Glu Ser Val Asp Thr Ala Leu Lys Ile Ala Leu Ala Tyr
        115                 120                 125

His Arg Ala Arg Gly Glu Gly Gln Arg Thr Arg Phe Ile Gly Arg Glu
    130                 135                 140

Arg Gly Tyr His Gly Val Gly Phe Gly Gly Met Ala Val Gly Gly Ile
145                 150                 155                 160

Gly Pro Asn Arg Lys Ala Phe Ser Ala Asn Leu Met Pro Gly Thr Asp
                165                 170                 175

His Leu Pro Ala Thr Leu Asn Ile Ala Glu Ala Ala Phe Ser Lys Gly
            180                 185                 190

Gln Pro Thr Trp Gly Ala His Leu Ala Asp Glu Leu Glu Arg Ile Val
        195                 200                 205

Ala Leu His Asp Pro Ser Thr Ile Ala Ala Val Ile Val Glu Pro Leu
    210                 215                 220

Ala Gly Ser Ala Gly Val Leu Val Pro Pro Val Gly Tyr Leu Asp Lys
225                 230                 235                 240

Leu Arg Glu Ile Thr Thr Lys His Gly Ile Leu Leu Ile Phe Asp Glu
                245                 250                 255

Val Ile Thr Ala Phe Gly Arg Leu Gly Thr Ala Thr Ala Ala Glu Arg
            260                 265                 270

Phe Lys Val Thr Pro Asp Leu Ile Thr Met Ala Lys Ala Ile Asn Asn
        275                 280                 285

Ala Ala Val Pro Met Gly Ala Val Ala Val Arg Arg Glu Val His Asp
    290                 295                 300

Thr Val Val Asn Ser Ala Ala Pro Gly Ala Ile Glu Leu Ala His Gly
305                 310                 315                 320

Tyr Thr Tyr Ser Gly His Pro Leu Ala Ala Ala Ala Ile Ala Thr
                325                 330                 335

Leu Asp Leu Tyr Gln Arg Glu Asn Leu Phe Gly Arg Ala Ala Glu Leu
            340                 345                 350

Ser Pro Val Phe Glu Ala Ala Val His Ser Val Arg Ser Ala Pro His
        355                 360                 365

Val Lys Asp Ile Arg Asn Leu Gly Met Val Ala Gly Ile Glu Leu Glu
    370                 375                 380

Pro Arg Pro Gly Gln Pro Gly Ala Arg Ala Tyr Glu Ala Phe Leu Lys
385                 390                 395                 400

Cys Leu Glu Arg Gly Val Leu Val Arg Tyr Thr Gly Asp Ile Leu Ala
                405                 410                 415

Phe Ser Pro Pro Leu Ile Ile Ser Glu Ala Gln Ile Ala Glu Leu Phe
            420                 425                 430

Asp Thr Val Lys Gln Ala Leu Gln Glu Val Gln
        435                 440

<210> SEQ ID NO 90
<211> LENGTH: 1341
<212> TYPE: DNA
<213> ORGANISM: Ralstonia eutropha

<400> SEQUENCE: 90
atggccgact cacccaacaa cctcgctcac gaacatcctt cacttgaaca ctattggatg    60
ccttttaccg ccaatcgcca attcaaagcg agccctcgtt tactcgccca agctgaaggt   120
atgtattaca cagatatcaa tggcaacaag gtattagact ctacagcggg cttatggtgt   180
```

-continued

```
tgtaatgctg gccatggtcg ccgtgagatc agtgaagccg tcagcaaaca aattcggcag    240
atggattacg ctccctcctt ccaaatgggc catcccatcg cttttgaact ggccgaacgt    300
ttaaccgaac tcagcccaga aggactcaac aaagtattct ttaccaactc aggctctgag    360
tcggttgata ccgcgctaaa aatggctctt tgctaccata gagccaatgg ccaagcgtca    420
cgcacccgct ttattggccg tgaaatgggt taccatggcg taggatttgg tgggatctcg    480
gtgggtggtt taagcaataa ccgtaaagcc ttcagcggcc agctattgca aggcgtggat    540
cacctgcccc acaccttaga cattcaacat gccgccttta gtcgtggctt accgagcctc    600
ggtgctgaaa aagctgaggt attagaacaa ttagtcacac tccatggcgc cgaaaatatt    660
gccgccgtta ttgttgaacc catgtcaggt tctgcagggg taattttacc acctcaaggc    720
tacttaaaac gcttacgtga aatcactaaa aaacacggca tcttattgat tttcgatgaa    780
gtcattaccg catttggccg tgtaggtgca gcattcgcca gccaacgttg gggcgttatt    840
ccagacataa tcaccacggc taaagccatt aataatggcg ccatccccat gggcgcagtg    900
tttgtacagg attatatcca cgatacttgc atgcaagggc caaccgaact gattgaattt    960
ttccacggtt ataccctattc gggccaccca gtcgccgcag cagcagcact cgccacgctc   1020
tccatctacc aaaacgagca actgtttgag cgcagttttg agcttgagcg gtatttcgaa   1080
gaagccgttc atagcctcaa agggttaccg aatgtgattg atattcgcaa caccggatta   1140
gtcgcgggtt ccagctagc accgaatagc caaggtgttg gtaaacgcgg atacagcgtg    1200
ttcgagcatt gtttccatca aggcacactc gtgcgggcaa cgggcgatat tatcgccatg   1260
tccccaccac tcattgttga aaacatcag attgaccaaa tggtaaatag ccttagcgat   1320
gcaattcacg ccgttggatg a                                              1341
```

<210> SEQ ID NO 91
<211> LENGTH: 446
<212> TYPE: PRT
<213> ORGANISM: Shewanella oneidensis

<400> SEQUENCE: 91

Met Ala Asp Ser Pro Asn Asn Leu Ala His Glu His Pro Ser Leu Glu
1               5                   10                  15

His Tyr Trp Met Pro Phe Thr Ala Asn Arg Gln Phe Lys Ala Ser Pro
            20                  25                  30

Arg Leu Leu Ala Gln Ala Glu Gly Met Tyr Tyr Thr Asp Ile Asn Gly
        35                  40                  45

Asn Lys Val Leu Asp Ser Thr Ala Gly Leu Trp Cys Cys Asn Ala Gly
    50                  55                  60

His Gly Arg Arg Glu Ile Ser Glu Ala Val Ser Lys Gln Ile Arg Gln
65                  70                  75                  80

Met Asp Tyr Ala Pro Ser Phe Gln Met Gly His Pro Ile Ala Phe Glu
                85                  90                  95

Leu Ala Glu Arg Leu Thr Glu Leu Ser Pro Gly Leu Asn Lys Val
            100                 105                 110

Phe Phe Thr Asn Ser Gly Ser Glu Ser Val Asp Thr Ala Leu Lys Met
        115                 120                 125

Ala Leu Cys Tyr His Arg Ala Asn Gly Gln Ala Ser Arg Thr Arg Phe
    130                 135                 140

Ile Gly Arg Glu Met Gly Tyr His Gly Val Gly Phe Gly Gly Ile Ser
145                 150                 155                 160

Val Gly Gly Leu Ser Asn Asn Arg Lys Ala Phe Ser Gly Gln Leu Leu

|  |  |  |  | 165 |  |  |  | 170 |  |  |  | 175 |  |
|--|--|--|--|--|--|--|--|--|--|--|--|--|--|

Gln Gly Val Asp His Leu Pro His Thr Leu Asp Ile Gln His Ala Ala
              180                 185                 190

Phe Ser Arg Gly Leu Pro Ser Leu Gly Ala Glu Lys Ala Glu Val Leu
          195                 200                 205

Glu Gln Leu Val Thr Leu His Gly Ala Glu Asn Ile Ala Ala Val Ile
      210                 215                 220

Val Glu Pro Met Ser Gly Ser Ala Gly Val Ile Leu Pro Pro Gln Gly
225                 230                 235                 240

Tyr Leu Lys Arg Leu Arg Glu Ile Thr Lys Lys His Gly Ile Leu Leu
                245                 250                 255

Ile Phe Asp Glu Val Ile Thr Ala Phe Gly Arg Val Gly Ala Ala Phe
            260                 265                 270

Ala Ser Gln Arg Trp Gly Val Ile Pro Asp Ile Ile Thr Thr Ala Lys
        275                 280                 285

Ala Ile Asn Asn Gly Ala Ile Pro Met Gly Ala Val Phe Val Gln Asp
    290                 295                 300

Tyr Ile His Asp Thr Cys Met Gln Gly Pro Thr Glu Leu Ile Glu Phe
305                 310                 315                 320

Phe His Gly Tyr Thr Tyr Ser Gly His Pro Val Ala Ala Ala Ala Ala
                325                 330                 335

Leu Ala Thr Leu Ser Ile Tyr Gln Asn Glu Gln Leu Phe Glu Arg Ser
            340                 345                 350

Phe Glu Leu Glu Arg Tyr Phe Glu Glu Ala Val His Ser Leu Lys Gly
        355                 360                 365

Leu Pro Asn Val Ile Asp Ile Arg Asn Thr Gly Leu Val Ala Gly Phe
    370                 375                 380

Gln Leu Ala Pro Asn Ser Gln Gly Val Gly Lys Arg Gly Tyr Ser Val
385                 390                 395                 400

Phe Glu His Cys Phe His Gln Gly Thr Leu Val Arg Ala Thr Gly Asp
                405                 410                 415

Ile Ile Ala Met Ser Pro Pro Leu Ile Val Glu Lys His Gln Ile Asp
            420                 425                 430

Gln Met Val Asn Ser Leu Ser Asp Ala Ile His Ala Val Gly
        435                 440                 445

<210> SEQ ID NO 92
<211> LENGTH: 1341
<212> TYPE: DNA
<213> ORGANISM: Shewanella oneidensis

<400> SEQUENCE: 92
atggccgact cacccaacaa cctcgctcac gaacatcctt cacttgaaca ctattggatg      60
ccttttaccg ccaatcgcca attcaaagcg agccctcgtt tactcgccca agctgaaggt     120
atgtattaca cagatatcaa tgcaacaagg tattagact ctacagcggg cttatggtgt      180
tgtaatgctg gccatggtcg ccgtgagatc agtgaagccg tcagcaaaca aattcggcag     240
atggattacg ctccctcctt ccaaatgggc catcccatcg cttttgaact ggccgaacgt     300
ttaaccgaac tcagcccaga aggactcaac aaagtattct ttaccaactc aggctctgag     360
tcggttgata ccgcgctaaa aatggctctt tgctaccata gagccaatgg ccaagcgtca     420
cgcacccgct ttattggccg tgaaatgggt accatggcg taggatttgg tgggatctcg      480
gtgggtggtt taagcaataa ccgtaaagcc ttcagcggcc agctattgca aggcgtggat     540

```
cacctgcccc acaccttaga cattcaacat gccgccttta gtcgtggctt accgagcctc   600
ggtgctgaaa aagctgaggt attagaacaa ttagtcacac tccatggcgc cgaaaatatt   660
gccgccgtta ttgttgaacc catgtcaggt tctgcagggg taattttacc acctcaaggc   720
tacttaaaac gcttacgtga atcactaaa aaacacggca tcttattgat tttcgatgaa    780
gtcattaccg catttggccg tgtaggtgca gcattcgcca gccaacgttg gggcgttatt   840
ccagacataa tcaccacggc taaagccatt aataatggcg ccatccccat gggcgcagtg   900
tttgtacagg attatatcca cgatacttgc atgcaagggc caaccgaact gattgaattt   960
ttccacggtt ataccctatc gggccaccca gtcgccgcag cagcagcact cgccacgctc   1020
tccatctacc aaaacgagca actgtttgag cgcagttttg agcttgagcg gtatttcgaa   1080
gaagccgttc atagcctcaa agggttaccg aatgtgattg atattcgcaa caccggatta   1140
gtcgcgggtt tccagctagc accgaatagc caaggtgttg gtaaacgcgg atacagcgtg   1200
ttcgagcatt gtttccatca aggcacactc gtgcgggcaa cgggcgatat tatcgccatg   1260
tccccaccac tcattgttga gaaacatcag attgaccaaa tggtaaatag ccttagcgat   1320
gcaattcacg ccgttggatg a                                              1341
```

<210> SEQ ID NO 93
<211> LENGTH: 448
<212> TYPE: PRT
<213> ORGANISM: Pseudomonas putida

<400> SEQUENCE: 93

```
Met Asn Met Pro Glu Thr Gly Pro Ala Gly Ile Ala Ser Gln Leu Lys
1               5                   10                  15

Leu Asp Ala His Trp Met Pro Tyr Thr Ala Asn Arg Asn Phe Gln Arg
            20                  25                  30

Asp Pro Arg Leu Ile Val Ala Ala Glu Gly Asn Tyr Leu Val Asp Asp
        35                  40                  45

His Gly Arg Lys Ile Phe Asp Ala Leu Ser Gly Leu Trp Thr Cys Gly
    50                  55                  60

Ala Gly His Thr Arg Lys Glu Ile Ala Asp Ala Val Thr Arg Gln Leu
65                  70                  75                  80

Ser Thr Leu Asp Tyr Ser Pro Ala Phe Gln Phe Gly His Pro Leu Ser
                85                  90                  95

Phe Gln Leu Ala Glu Lys Ile Ala Glu Leu Val Pro Gly Asn Leu Asn
            100                 105                 110

His Val Phe Tyr Thr Asn Ser Gly Ser Glu Cys Ala Asp Thr Ala Leu
        115                 120                 125

Lys Met Val Arg Ala Tyr Trp Arg Leu Lys Gly Gln Ala Thr Lys Thr
    130                 135                 140

Lys Ile Ile Gly Arg Ala Arg Gly Tyr His Gly Val Asn Ile Ala Gly
145                 150                 155                 160

Thr Ser Leu Gly Gly Val Asn Gly Asn Arg Lys Met Phe Gly Gln Leu
                165                 170                 175

Leu Asp Val Asp His Leu Pro His Thr Val Leu Pro Val Asn Ala Phe
            180                 185                 190

Ser Lys Gly Leu Pro Glu Glu Gly Gly Ile Ala Leu Ala Asp Glu Met
        195                 200                 205

Leu Lys Leu Ile Glu Leu His Asp Ala Ser Asn Ile Ala Ala Val Ile
    210                 215                 220

Val Glu Pro Leu Ala Gly Ser Ala Gly Val Leu Pro Pro Pro Lys Gly
```

```
                225                 230                 235                 240
        Tyr Leu Lys Arg Leu Arg Glu Ile Cys Thr Gln His Asn Ile Leu Leu
                            245                 250                 255

Ile Phe Asp Glu Val Ile Thr Gly Phe Gly Arg Met Gly Ala Met Thr
                            260                 265                 270

Gly Ser Glu Ala Phe Gly Val Thr Pro Asp Leu Met Cys Ile Ala Lys
                            275                 280                 285

Gln Val Thr Asn Gly Ala Ile Pro Met Gly Ala Val Ile Ala Ser Ser
                290                 295                 300

Glu Ile Tyr Gln Thr Phe Met Asn Gln Pro Thr Pro Glu Tyr Ala Val
        305                 310                 315                 320

Glu Phe Pro His Gly Tyr Thr Tyr Ser Ala His Pro Val Ala Cys Ala
                            325                 330                 335

Ala Gly Leu Ala Ala Leu Asp Leu Leu Gln Lys Glu Asn Leu Val Gln
                            340                 345                 350

Ser Ala Ala Glu Leu Ala Pro His Phe Glu Lys Leu Leu His Gly Val
                            355                 360                 365

Lys Gly Thr Lys Asn Ile Val Asp Ile Arg Asn Tyr Gly Leu Ala Gly
                    370                 375                 380

Ala Ile Gln Ile Ala Ala Arg Asp Gly Asp Ala Ile Val Arg Pro Tyr
        385                 390                 395                 400

Glu Ala Ala Met Lys Leu Trp Lys Ala Gly Phe Tyr Val Arg Phe Gly
                            405                 410                 415

Gly Asp Thr Leu Gln Phe Gly Pro Thr Phe Asn Thr Lys Pro Gln Glu
                            420                 425                 430

Leu Asp Arg Leu Phe Asp Ala Val Gly Glu Thr Leu Asn Leu Ile Asp
                            435                 440                 445

<210> SEQ ID NO 94
<211> LENGTH: 930
<212> TYPE: DNA
<213> ORGANISM: Pseudomonas putida

<400> SEQUENCE: 94
atgaccacga agaaagctga ttacatttgg ttcaatgggg agatggttcg ctgggaagac    60
gcgaaggtgc atgtgatgtc gcacgcgctg cactatggca cttcggtttt tgaaggcatc   120
cgttgctacg actcgcacaa aggaccggtt gtattccgcc atcgtgagca tatgcagcgt   180
ctgcatgact ccgccaaaat ctatcgcttc ccggtttcgc agagcattga tgagctgatg   240
gaagcttgtc gtgacgtgat ccgcaaaaac aatctcacca cgcctatat ccgtccgctg    300 atcttcgtcg gtgatgttgg catgggagta accegccag cgggatactc aaccgacgtg    360
attatcgctg ctttcccgtg gggagcgtat ctgggcgcag aagcgctgga gcaggggatc   420
gatgcgatgg tttcctcctg aaccgcgca gcaccaaaca ccatcccgac ggcggcaaaa    480
gccggtggta actacctctc ttccctgctg gtgggtagcg aagcgcgccg ccacggttat   540
caggaaggta tcgcgctgga tgtgaacggt tatatctctg aaggcgcagg cgaaaacctg    600
tttgaagtga agatggtgt gctgttcacc ccaccgttca cctcctccgc gctgccgggt    660
attacccgtg atgccatcat caaactggcg aaagagctgg gaattgaagt acgtgagcag    720
gtgctgtcgc gcgaatccct gtacctggcg gatgaagtgt ttatgtccgg tacggcggca   780
gaaatcacgc cagtgcgcag cgtagacggt attcaggttg gcgaaggccg ttgtggcccg   840
gttaccaaac gcattcagca agccttcttc ggcctcttca ctggcgaaac cgaagataaa   900
```
tggggctggt tagatcaagt taatcaataa							930

<210> SEQ ID NO 95
<211> LENGTH: 566
<212> TYPE: PRT
<213> ORGANISM: Streptomyces cinnamonensis

<400> SEQUENCE: 95

Met Asp Ala Asp Ala Ile Glu Glu Gly Arg Arg Trp Gln Ala Arg
1               5                   10                  15

Tyr Asp Lys Ala Arg Lys Arg Asp Ala Asp Phe Thr Thr Leu Ser Gly
                20                  25                  30

Asp Pro Val Asp Pro Val Tyr Gly Pro Arg Pro Gly Thr Tyr Asp
            35                  40                  45

Gly Phe Glu Arg Ile Gly Trp Pro Gly Glu Tyr Pro Phe Thr Arg Gly
    50                  55                  60

Leu Tyr Ala Thr Gly Tyr Arg Gly Arg Thr Trp Thr Ile Arg Gln Phe
65                  70                  75                  80

Ala Gly Phe Gly Asn Ala Glu Gln Thr Asn Glu Arg Tyr Lys Met Ile
                85                  90                  95

Leu Ala Asn Gly Gly Gly Leu Ser Val Ala Phe Met Pro Thr
                100                 105                 110

Leu Met Gly Arg Asp Ser Asp Pro Arg Ser Leu Gly Glu Val Gly
            115                 120                 125

His Cys Gly Val Ala Ile Asp Ser Ala Ala Asp Met Glu Val Leu Phe
    130                 135                 140

Lys Asp Ile Pro Leu Gly Asp Val Thr Thr Ser Met Thr Ile Ser Gly
145                 150                 155                 160

Pro Ala Val Pro Val Phe Cys Met Tyr Leu Val Ala Ala Glu Arg Gln
                165                 170                 175

Gly Val Asp Pro Ala Val Leu Asn Gly Thr Leu Gln Thr Asp Ile Phe
            180                 185                 190

Lys Glu Tyr Ile Ala Gln Lys Glu Trp Leu Phe Gln Pro Glu Pro His
        195                 200                 205

Leu Arg Leu Ile Gly Asp Leu Met Glu His Cys Ala Arg Asp Ile Pro
    210                 215                 220

Ala Tyr Lys Pro Leu Ser Val Ser Gly Tyr His Ile Arg Glu Ala Gly
225                 230                 235                 240

Ala Thr Ala Ala Gln Glu Leu Ala Tyr Thr Leu Ala Asp Gly Phe Gly
                245                 250                 255

Tyr Val Glu Leu Gly Leu Ser Arg Gly Leu Asp Val Asp Val Phe Ala
            260                 265                 270

Pro Gly Leu Ser Phe Phe Phe Asp Ala His Val Asp Phe Glu Glu
        275                 280                 285

Ile Ala Lys Phe Arg Ala Ala Arg Ile Trp Ala Arg Trp Leu Arg
    290                 295                 300

Asp Glu Tyr Gly Ala Lys Thr Glu Lys Ala Gln Trp Leu Arg Phe His
305                 310                 315                 320

Thr Gln Thr Ala Gly Val Ser Leu Thr Ala Gln Gln Pro Tyr Asn Asn
                325                 330                 335

Val Val Arg Thr Ala Val Glu Ala Leu Ala Ala Val Leu Gly Gly Thr
            340                 345                 350

Asn Ser Leu His Thr Asn Ala Leu Asp Glu Thr Leu Ala Leu Pro Ser
        355                 360                 365

Glu Gln Ala Ala Glu Ile Ala Leu Arg Thr Gln Gln Val Leu Met Glu
370                 375                 380

Glu Thr Gly Val Ala Asn Val Ala Asp Pro Leu Gly Gly Ser Trp Tyr
385                 390                 395                 400

Ile Glu Gln Leu Thr Asp Arg Ile Glu Ala Asp Ala Glu Lys Ile Phe
                405                 410                 415

Glu Gln Ile Arg Glu Arg Gly Arg Arg Ala Cys Pro Asp Gly Gln His
                420                 425                 430

Pro Ile Gly Pro Ile Thr Ser Gly Ile Leu Arg Gly Ile Glu Asp Gly
                435                 440                 445

Trp Phe Thr Gly Glu Ile Ala Glu Ser Ala Phe Gln Tyr Gln Arg Ser
450                 455                 460

Leu Glu Lys Gly Asp Lys Arg Val Val Gly Val Asn Cys Leu Glu Gly
465                 470                 475                 480

Ser Val Thr Gly Asp Leu Glu Ile Leu Arg Val Ser His Glu Val Glu
                485                 490                 495

Arg Glu Gln Val Arg Glu Leu Ala Gly Arg Lys Gly Arg Arg Asp Asp
                500                 505                 510

Ala Arg Val Arg Ala Ser Leu Asp Ala Met Leu Ala Ala Ala Arg Asp
                515                 520                 525

Gly Ser Asn Met Ile Ala Pro Met Leu Glu Val Arg Ala Glu Ala
530                 535                 540

Thr Leu Gly Glu Ile Cys Gly Val Leu Arg Asp Glu Trp Gly Val Tyr
545                 550                 555                 560

Val Glu Pro Pro Gly Phe
                565

<210> SEQ ID NO 96
<211> LENGTH: 4362
<212> TYPE: DNA
<213> ORGANISM: Streptomyces cinnamonensis

<400> SEQUENCE: 96

```
tgaggcgctg gatcgcctcg agagcagct  ggtaacggtc cgcgtggtac tcggccgggg     60
tgcagccgtc cacgatgtgc gggatcgcgt cgggctcgag gatcaccagg gcggggggcgt    120 cgccgatcgc gtcggcgaac gtgtccaccc agctccggta ggcctccgca ctggccgcgc    180
cgcccgcgga gtgctgaccg cagtcgcggt gcgggatgtt gtacgcgacg agtacgcggg    240
tgcggtcctc cttgaccgcg ccccgcgtcg ccttcgcgac gtcgggcgcc ggatcgtccc    300
cggccggcca cacggccatg gcccgttcgg agatgcgcct gagcgtctcg gcgtcctcgg    360
cgcggccctg ttcctcccac tgcctgacct ggcgcgcggc ggggctgtcg gggtcgaccc    420
agaaggtgcc ggcgggggc cggcgctcg cggtggcggg cttgcgcacg gccgcctcct    480
ccttcgtgcc gtcggacccc gggtctgagg aggagcagcc tgccgggagc ccgagggcgg    540
cgagggccgc gagtgccgtg aacgtgcgga gcagccggtg catccagccc ccttgggcga    600
tggtgacagt gacggtcagt cagcccggca atcgttacat aaaggactat tcaagctctt    660
gtgccacacc gcctccggtg ccgagcgcga accggcggg caccagagcc cgccgcggc    720 cgcggagccg tacgtacgac cgaattgcga cggggctg accaccatat gaccggcggg    780
taaggtcgat gccgtgccga agccgctcag cctccccttc gatcccatcg cccgcgccga    840
cgagctctgg aagcagcgct ggggatcggt ccggccatg ggcgcgatca cctcgatcat    900
gcgggcgcac cagatcctgc tcgccgaggt cgacgcggtc gtcaagccgt acggactgac    960
```

-continued

```
cttcgcgcgc tacgaggcgc tggtgctcct caccttctcg caggccggcg agttgccgat    1020
gtcgaagatc ggcgagcggc tcatggtgca cccgacctcg gtcacgaaca ccgtggaccg    1080
cctggtgaag tccggcctgg tcgacaagcg cccgaacccc aacgacggcc gcggcacgct    1140
cgcctccatc acgagaaagg gccgcgaggc cgtcgaggcg ccacccgcg agctgatggc     1200
gatggacttc gggctcgggg tgtacgacgc ggaggagtgc ggggagatct tcgcgatgct    1260
gcggcccctg cgggtggcgg cgcgcgattt cgaggagcag tagggcccgc cggtgagaa     1320
gtgggatcgg gtcgtcccgg tacgggcggg ggcggcgaag atcgcgtgaa aagggcggtt    1380
acgctcgtag ccatgaaacg cagcgtgctg acccgctacc gggtgatggc ctacgtcacc    1440
gccgtcatgc tcctcatcct gtgcgcctgc atggtggcca agtacggctt cgacaagggc    1500
gagggtctga ccctcgtcgt gtcgcaggtg cacggcgtgc tctacatcat ctacctgatc    1560
ttcgccttcg acctgggctc caaggcgaag tggccgttcg gcaagctgct ctgggtgctg    1620
gtctcgggca cgatcccgac cgccgccttc ttcgtcgagc gcaaggtcgc ccgtgacgtc    1680
gagccgctga tcgccgacgg ctccccggtc accgcgaagg cgtaacccgc accgccacgg    1740
acaggtccgt ggcggttggc catcgacttt tactaggacg tcctagtaaa ttcgatggta    1800
tggacgctga cgcgatcgag gaaggccgcc gacgctggca ggcccgttac gacaaggccc    1860
gcaagcgcga cgcggacttc accacgctct ccggggaccc cgtcgacccc gtctacggcc    1920
cccgccccgg ggacacgtac gacgggttcg agccggatcgg ctggccgggg gagtaccct    1980
tcacccgcgg gctctacgcc accgggtacc gcggccgcac ctggaccatc cgccagttcg    2040
ccggcttcgg caacgccgag cagacgaacg agcgctacaa gatgatcctg gccaacggcg    2100
gcggcggcct ctccgtcgcc ttcgacatgc cgaccctcat gggccgcgac tccgacgacc    2160
cgcgctcgct cggcgaggtc ggccactgcg gtgtcgccat cgactccgcc gccgacatgg    2220
aggtcctctt caaggacatc ccgctcggcg acgtcacgac gtccatgacc atcagcgggc    2280
ccgccgtgcc cgtcttctgc atgtacctcg tcgcggccga cgccagggc gtcgacccgg     2340
ccgtcctcaa cggcacgctg cagaccgaca tcttcaagga gtacatcgcc cagaaggagt    2400
ggctcttcca gcccgagccg cacctgcgcc tcatcggcga cctgatggag cactgcgcgc    2460
gcgacatccc cgcgtacaag ccgctctcgg tctccggcta ccacatccgc gaggccgggg    2520
cgacggccgc gcaggagctc gcgtacaccc tcgcggacgg cttcgggtac gtggaactgg    2580
gcctctcgcg cggcctggac gtggacgtct tcgcgcccgg cctctccttc ttcttcgacg    2640
cgcacgtcga cttcttcgag gagatcgcga agttccgcgc cgcacgccgc atctgggcgc    2700
gctggctccg ggacgagtac ggagcgaaga ccgagaaggc acagtggctg cgcttccaca    2760
cgcagaccgc gggggtctcg ctcacggccc agcagccgta caacaacgtg gtgcggacgg    2820
cggtggaggc cctcgccgcg gtgctcggcg gcacgaactc cctgcacacc aacgctctcg    2880
acgagaccct tgccctcccc agcgagcagg ccgcggagat cgcgctgcgc acccagcagg    2940
tgctgatgga ggagaccggc gtcgccaacg tcgcggaccc gctgggcggc tcctggtaca    3000
tcgagcagct caccgaccgc atcgaggccg acgccgagaa gatcttcgag cagatcaggg    3060
agcggggccg gcgggcctgc cccgacgggc agcaccgat cgggccgatc acctccggca    3120
tcctgcgcgg catcgaggac ggctggttca ccggcgagat cgccgagtcc gccttccagt    3180
accagcggtc cctggagaag ggcgacaagc gggtcgtcgg cgtcaactgc ctcgaaggct    3240
ccgtcaccgg cgacctggag atcctgcgcg tcagccacga ggtcgagcgc gagcaggtgc    3300
gggagcttgc ggggcgcaag gggcggcgtg acgatgcgcg ggtgcgggcc tcgctcgacg    3360
```

```
cgatgctcgc cgctgcgcgg gacgggtcga acatgattgc ccccatgctg gaggcggtgc   3420
gggccgaggc gaccctcggg gagatctgcg gggtgcttcg cgatgagtgg ggggtctacg   3480
tggagccgcc cgggttctga gggcgcgctc cctttgcctg cgggtctgct gtggctggtc   3540
gcgcagttcc ccgcacccct gaaagacccc ggcgctttcc cttcctggct cgcctcgtcg   3600
ctgtctgcgg ggccgtgggg gctggtcgcg cagttccccg cgccctgcc cgcacctgcg    3660 ccccgccgcc tgcatgccgc ccccaccctg acggggcgt tcggggccca ccctgacggg    3720
tgcggtcggg gcgtgccggg gtcttttagg ggcgcgggga actgcgcgag caaccccac   3780 ccacccgcag gtgcacgcgg agcggcggac gccccgcaga cggggcaaa acgggcggag   3840 tgccccgcc cgccgggcgg cgcgaattcg taggtttaag gggcaggggt cagggcaggc     3900
gccgagccgc tcaaccgccc ccgtcccagg agacccgtg acctcgaccg gccacgcccg     3960
caccgccgcc atcgccatcg gagccgccac cgccaccgtc ctcggcgcgc tgctggtcgg    4020
cggctccggc gaggtgagtg cgagcccgcc gcccgagccc aaggtccagg acgacttcga    4080
ctccctcggc cccgaggtgc gcgccgcgaa gctctccgac gggcggacgg cccactactc    4140
ggacacgggc gacaaggacg gcaagccggc cctgttcatc ggcggcaccg gcacgagcgc    4200
ccgcgcctcc cacatgaccg acttcttccg ctcgacgcgc gaggacctgg gcctgcgcct    4260
catctccgtg gagcgcaacg gcttcggcga caccgcgttc gacgagaagc tgggcaccgc    4320
cgacttcgcg aaggacgccc tcgaagtcct cgaccggctc gg                      4362
```

<210> SEQ ID NO 97
<211> LENGTH: 136
<212> TYPE: PRT
<213> ORGANISM: Streptomyces cinnamonensis

<400> SEQUENCE: 97

```
Met Gly Val Ala Ala Gly Pro Ile Arg Val Val Ala Lys Pro Gly
1               5                   10                  15

Leu Asp Gly His Asp Arg Gly Ala Lys Val Ile Ala Arg Ala Leu Arg
            20                  25                  30

Asp Ala Gly Met Glu Val Ile Tyr Thr Gly Leu His Gln Thr Pro Glu
        35                  40                  45

Gln Val Val Asp Thr Ala Ile Gln Glu Asp Ala Asp Ala Ile Gly Leu
    50                  55                  60

Ser Ile Leu Ser Gly Ala His Asn Thr Leu Phe Ala Arg Val Leu Glu
65                  70                  75                  80

Leu Leu Lys Glu Arg Asp Ala Glu Asp Ile Lys Val Phe Gly Gly Gly
                85                  90                  95

Ile Ile Pro Glu Ala Asp Ile Ala Pro Leu Lys Glu Lys Gly Val Ala
            100                 105                 110

Glu Ile Phe Thr Pro Gly Ala Thr Thr Thr Ser Ile Val Glu Trp Val
        115                 120                 125

Arg Gly Asn Val Arg Gln Ala Val
    130                 135
```

<210> SEQ ID NO 98
<211> LENGTH: 1643
<212> TYPE: DNA
<213> ORGANISM: Streptomyces cinnamonensis

<400> SEQUENCE: 98

```
gtcgacctcc cgtttggcgc acggaaggga ggctctgtcc cccgtgtgcc ctaggggag    60
```

```
tcgtggtcga ggagtcggct gtgcgatggc gatcccggcc accgccctgc ggtgactccg    120
tgccccgtt  gcatcgccga tgcgcggtgt caccacgccg tgcggctgcc ggcgcggtgg    180
cccggcgtct cgttgcggct ccctcgcgc  ctggtccgga tgcggagcgt gaaccctgg    240
gttacggacg ggcgcgcagc gaacgtgtcc cacgtgtgat ttccccctcg ctctccaccg    300
cgaaactgcc gcttgcgcga tgctggggat aacgttcgtt cacttccccg gccggtgcgg    360
tgcggggtat ctgtgccggg acagactttg tcggtacgga tatcggtaca tggaggcagt    420
gatgggtgtg gcagccgggc cgatccgcgt ggtggtcgcc aagccggggc tcgacgggca    480
cgatcgcggg gccaaggtga tcgcgcggc  gttgcgtgac gcgggtatgg aggtcatcta    540
caccgggctg caccagacgc ccgagcaggt ggtggacacc gcgatccagg aggacgccga    600
cgcgatcggc ctctccatcc tctccggagc gcacaacacg ctgttcgcgc gcgtgttgga    660
gctcttgaag gagcgggacg cggaggacat caaggtgttt ggtggcggca tcatcccgga    720
ggcggacatc gcgccgctga aggagaaggg cgtcgcggag atcttcacgc ccggggccac    780
caccacgtcg atcgtggagt gggttcgggg gaacgtgcga caggccgtct gaggcattcc    840
ccgtcgcccg tctgccgtgg tcggcgtcat atcggcggac atcgtctcgg tggacgtcat    900
ggcggcgggg ggagttcgtc gcgtatcgcc gcgcggaggc gcagggtggt gaccaggcgc    960
tggaacgctt ccgaccagta gctgcccgcg ccgggtgacg cgtcctccgc ttcgtcgggg   1020
accgcggtga gcgcttccag gcggaccgcc tcggccgggt ccagacagcg ttccgccagg   1080
cccatcactc cgctgaagct ccatgggtaa ctgcccgcgt cgcgcgcgat gttcagggcg   1140
tccaccacgg cccggccgag agggccggcc cagggcaccg cgcagacgcc gagcagttgg   1200
aacgcctccg acaggccgtg tgccgctatg aaccccgcca cccagtccgc gcgctcggcg   1260
gcaggcatgg aggcgagcag tttggcccgc tcggcgaggg acacgcgcc  aggccccgcc   1320
gcgtcgggtg aggcggggc  gccgagcagc gctctggacc aggcgacgtc acgctggcgt   1380
acggccgcgc ggcaccatgc ggcgtgcagt tcgccccgcc agtcgtcggc caccgggagc   1440
gccacgatct ccgccggggt gcggttgccg agccggggcg gccaggtggc gagcggggcc   1500
gattccacga gctggccgag ccaccaggag cgctcgcccc ggccggtggg gggcttcggg   1560
acgacgccgt cccgctccat gcccgcgtcg cactcgtgcg gcgcctcgac ggtgagggtc   1620
ggcgtgctcg atgtgtggtc gac                                           1643
```

<210> SEQ ID NO 99
<211> LENGTH: 566
<212> TYPE: PRT
<213> ORGANISM: Streptomyces coelicolor

<400> SEQUENCE: 99

Met Asp Ala His Ala Ile Glu Glu Gly Arg Leu Arg Trp Gln Ala Arg
1               5                   10                  15

Tyr Asp Ala Ala Arg Lys Arg Asp Ala Asp Phe Thr Thr Leu Ser Gly
            20                  25                  30

Asp Pro Val Glu Pro Val Tyr Gly Pro Arg Pro Gly Asp Glu Tyr Glu
        35                  40                  45

Gly Phe Glu Arg Ile Gly Trp Pro Gly Glu Tyr Pro Phe Thr Arg Gly
    50                  55                  60

Leu Tyr Pro Thr Gly Tyr Arg Gly Arg Thr Trp Thr Ile Arg Gln Phe
65                  70                  75                  80

Ala Gly Phe Gly Asn Ala Glu Gln Thr Asn Glu Arg Tyr Lys Met Ile

```
                     85                  90                  95
Leu Arg Asn Gly Gly Gly Leu Ser Val Ala Phe Asp Met Pro Thr
                100                 105                 110
Leu Met Gly Arg Asp Ser Asp Pro Arg Ser Leu Gly Glu Val Gly
                115                 120                 125
His Cys Gly Val Ala Ile Asp Ser Ala Ala Asp Met Glu Val Leu Phe
                130                 135                 140
Lys Asp Ile Pro Leu Gly Asp Val Thr Thr Ser Met Thr Ile Ser Gly
145                 150                 155                 160
Pro Ala Val Pro Val Phe Cys Met Tyr Leu Val Ala Ala Glu Arg Gln
                165                 170                 175
Gly Val Asp Ala Ser Val Leu Asn Gly Thr Leu Gln Thr Asp Ile Phe
                180                 185                 190
Lys Glu Tyr Ile Ala Gln Lys Glu Trp Leu Phe Gln Pro Glu Pro His
                195                 200                 205
Leu Arg Leu Ile Gly Asp Leu Met Glu Tyr Cys Ala Ala Gly Ile Pro
                210                 215                 220
Ala Tyr Lys Pro Leu Ser Val Ser Gly Tyr His Ile Arg Glu Ala Gly
225                 230                 235                 240
Ala Thr Ala Ala Gln Glu Leu Ala Tyr Thr Leu Ala Asp Gly Phe Gly
                245                 250                 255
Tyr Val Glu Leu Gly Leu Ser Arg Gly Leu Asp Val Asp Val Phe Ala
                260                 265                 270
Pro Gly Leu Ser Phe Phe Phe Asp Ala His Leu Asp Phe Phe Glu Glu
                275                 280                 285
Ile Ala Lys Phe Arg Ala Ala Arg Ile Trp Ala Arg Trp Met Arg
290                 295                 300
Asp Val Tyr Gly Ala Arg Thr Asp Lys Ala Gln Trp Leu Arg Phe His
305                 310                 315                 320
Thr Gln Thr Ala Gly Val Ser Leu Thr Ala Gln Gln Pro Tyr Asn Asn
                325                 330                 335
Val Val Arg Thr Ala Val Glu Ala Leu Ala Ala Val Leu Gly Gly Thr
                340                 345                 350
Asn Ser Leu His Thr Asn Ala Leu Asp Glu Thr Leu Ala Leu Pro Ser
                355                 360                 365
Glu Gln Ala Ala Glu Ile Ala Leu Arg Thr Gln Gln Val Leu Met Glu
                370                 375                 380
Glu Thr Gly Val Ala Asn Val Ala Asp Pro Leu Gly Gly Ser Trp Phe
385                 390                 395                 400
Ile Glu Gln Leu Thr Asp Arg Ile Glu Ala Asp Ala Glu Lys Ile Phe
                405                 410                 415
Glu Gln Ile Lys Glu Arg Gly Leu Arg Ala His Pro Asp Gly Gln His
                420                 425                 430
Pro Val Gly Pro Ile Thr Ser Gly Leu Leu Arg Gly Ile Glu Asp Gly
                435                 440                 445
Trp Phe Thr Gly Glu Ile Ala Glu Ser Ala Phe Arg Tyr Gln Gln Ser
                450                 455                 460
Leu Glu Lys Asp Asp Lys Lys Val Val Gly Val Asn Val His Thr Gly
465                 470                 475                 480
Ser Val Thr Gly Asp Leu Glu Ile Leu Arg Val Ser His Glu Val Glu
                485                 490                 495
Arg Glu Gln Val Arg Val Leu Gly Glu Arg Lys Asp Ala Arg Asp Asp
                500                 505                 510
```

```
Ala Ala Val Arg Gly Ala Leu Asp Ala Met Leu Ala Ala Ala Arg Ser
        515                 520                 525

Gly Gly Asn Met Ile Gly Pro Met Leu Asp Ala Val Arg Ala Glu Ala
        530                 535                 540

Thr Leu Gly Glu Ile Cys Gly Val Leu Arg Asp Glu Trp Gly Val Tyr
545                 550                 555                 560

Thr Glu Pro Ala Gly Phe
                565

<210> SEQ ID NO 100
<211> LENGTH: 1701
<212> TYPE: DNA
<213> ORGANISM: Streptomyces coelicolor

<400> SEQUENCE: 100
```

| | | | | | |
|---|---|---|---|---|---|
| atggacgctc | atgccataga | ggagggccgc | cttcgctggc | aggcccggta | cgacgcggcg | 60 |
| cgcaagcgcg | acgcggactt | caccacgctc | tccggagacc | ccgtggagcc | ggtgtacggg | 120 |
| ccccgccccg | gggacgagta | cgagggcttc | gagcggatcg | gctggccggg | cgagtacccc | 180 |
| ttcacccgcg | gcctgtatcc | gaccgggtac | cggggggcgta | cgtggaccat | ccggcagttc | 240 |
| gccgggttcg | gcaacgccga | gcagaccaac | gagcgctaca | agatgatcct | ccgcaacggc | 300 |
| ggcggcgggc | tctcggtcgc | cttcgacatg | ccgaccctga | tgggccgcga | ctccgacgac | 360 |
| ccgcgctcgc | tgggcgaggt | cgggcactgc | ggggtggcca | tcgactcggc | cgccgacatg | 420 |
| gaagtgctgt | tcaaggacat | cccgctcggg | gacgtgacga | cctccatgac | gatcagcggg | 480 |
| cccgccgtgc | ccgtgttctg | catgtacctc | gtcgccgccg | agcgccaggg | cgtcgacgca | 540 |
| tccgtgctca | acggcacgct | gcagaccgac | atcttcaagg | agtacatcgc | ccagaaggag | 600 |
| tggctcttcc | agcccgagcc | ccacctccgg | ctcatcggcg | acctcatgga | gtactgcgcg | 660 |
| gccggcatcc | ccgcctacaa | gccgctctcc | gtctccggct | accacatccg | cgaggcgggc | 720 |
| gcgacggccg | cgcaggagct | ggcgtacacg | ctcgccgacg | gcttcggata | cgtggagctg | 780 |
| ggcctcagcc | gcgggctcga | cgtggacgtc | ttcgcgcccg | gcctctcctt | cttcttcgac | 840 |
| gcgcacctcg | acttcttcga | ggagatcgcc | aagttccgcg | cggcccgcag | gatctgggcc | 900 |
| cgctggatgc | gcgacgtgta | cggcgcgcgg | accgacaagg | cccagtggct | gcggttccac | 960 |
| acccagaccg | ccggagtctc | gctcaccgcg | cagcagccgt | acaacaacgt | cgtacgcacc | 1020 |
| gcggtggagg | cgctggcggc | cgtgctcggc | ggcaccaact | ccctgcacac | caacgcgctc | 1080 |
| gacgagaccc | tcgccctgcc | cagcgagcag | gccgccgaga | tcgccctgcg | cacccagcag | 1140 |
| gtgctgatgg | aggagaccgg | cgtcgccaac | gtcgccgacc | cgctgggcgg | ttcctggttc | 1200 |
| atcgagcagc | tgaccgaccg | catcgaggcc | gacgccgaga | agatcttcga | gcagatcaag | 1260 |
| gagcgggggc | tgcgcgccca | ccccgacggg | cagcacccccg | tcggaccgat | cacctccggc | 1320 |
| ctgctgcgcg | gcatcgagga | cggctggttc | accggcgaga | tcgccgagtc | cgccttccgc | 1380 |
| taccagcagt | ccttggagaa | ggacgacaag | aaggtggtcg | gcgtcaacgt | ccacaccggc | 1440 |
| tccgtcaccg | gcgacctgga | gatcctgcgg | gtcagccacg | aggtcgagcg | cgagcaggtg | 1500 |
| cgggtcctgg | gcgagcgcaa | ggacgcccgg | gacgacgccg | ccgtgcgcgg | cgccctggac | 1560 |
| gccatgctgg | ccgcggcccg | ctccggcggc | aacatgatcg | ggccgatgct | ggacgcggtg | 1620 |
| cgcgcggagg | cgacgctggg | cgagatctgc | ggtgtgctgc | gcgacgagtg | gggggtgtac | 1680 |
| acggaaccgg | cggggttctg | a | | | | 1701 |

<210> SEQ ID NO 101
<211> LENGTH: 138
<212> TYPE: PRT
<213> ORGANISM: Streptomyces coelicolor

<400> SEQUENCE: 101

Met Gly Val Ala Ala Gly Pro Ile Arg Val Val Ala Lys Pro Gly
1               5                   10                  15

Leu Asp Gly His Asp Arg Gly Ala Lys Val Ile Ala Arg Ala Leu Arg
            20                  25                  30

Asp Ala Gly Met Glu Val Ile Tyr Thr Gly Leu His Gln Thr Pro Glu
        35                  40                  45

Gln Ile Val Asp Thr Ala Ile Gln Glu Asp Ala Asp Ala Ile Gly Leu
    50                  55                  60

Ser Ile Leu Ser Gly Ala His Asn Thr Leu Phe Ala Ala Val Ile Glu
65                  70                  75                  80

Leu Leu Arg Glu Arg Asp Ala Ala Asp Ile Leu Val Phe Gly Gly Gly
                85                  90                  95

Ile Ile Pro Glu Ala Asp Ile Ala Pro Leu Lys Glu Lys Gly Val Ala
            100                 105                 110

Glu Ile Phe Thr Pro Gly Ala Thr Thr Ala Ser Ile Val Asp Trp Val
        115                 120                 125

Arg Ala Asn Val Arg Glu Pro Ala Gly Ala
    130                 135

<210> SEQ ID NO 102
<211> LENGTH: 417
<212> TYPE: DNA
<213> ORGANISM: Streptomyces coelicolor

<400> SEQUENCE: 102
atgggtgtgg cagccggtcc gatccgcgtg gtggtggcca agccggggct cgacggccac    60
gatcgcgggg ccaaggtgat cgcgagggcc ctgcgtgacg ccggtatgga ggtgatctac   120
accgggctcc accagacgcc cgagcagatc gtcgacaccg cgatccagga ggacgccgac   180
gcgatcgggc tgtccatcct ctccggtgcg cacaacacgc tcttcgccgc cgtgatcgag   240
ctgctccggg agcgggacgc cgcggacatc ctggtcttcg gcggcgggat catccccgag   300
gcggacatcg ccccgctgaa ggagaagggc gtcgcggaga tcttcacgcc cggcgccacc   360
acggcgtcca tcgtggactg ggtccgggcg aacgtgcggg agcccgcggg agcatag     417

<210> SEQ ID NO 103
<211> LENGTH: 566
<212> TYPE: PRT
<213> ORGANISM: Streptomyces avermitilis

<400> SEQUENCE: 103

Met Asp Ala Asp Ala Ile Glu Glu Gly Arg Arg Arg Trp Gln Ala Arg
1               5                   10                  15

Tyr Asp Ala Ser Arg Lys Arg Glu Ala Asp Phe Thr Thr Leu Ser Gly
            20                  25                  30

Asp Pro Val Glu Pro Ala Tyr Gly Pro Arg Pro Gly Ala Tyr Glu
        35                  40                  45

Gly Phe Glu Arg Ile Gly Trp Pro Gly Glu Tyr Pro Phe Thr Arg Gly
    50                  55                  60

Leu Tyr Pro Thr Gly Tyr Arg Gly Arg Thr Trp Thr Ile Arg Gln Phe
65                  70                  75                  80

Ala Gly Phe Gly Asn Ala Glu Gln Thr Asn Glu Arg Tyr Lys Lys Ile
                85                  90                  95

Leu Ala Asn Gly Gly Gly Leu Ser Val Ala Phe Asp Met Pro Thr
            100                 105                 110

Leu Met Gly Arg Asp Ser Asp Arg Arg Ala Leu Gly Glu Val Gly
        115                 120                 125

His Cys Gly Val Ala Ile Asp Ser Ala Ala Asp Met Glu Val Leu Phe
    130                 135                 140

Lys Asp Ile Pro Leu Gly Asp Val Thr Thr Ser Met Thr Ile Ser Gly
145                 150                 155                 160

Pro Ala Val Pro Val Phe Cys Met Tyr Leu Val Ala Ala Glu Arg Gln
                165                 170                 175

Gly Val Asp Pro Ser Val Leu Asn Gly Thr Leu Gln Thr Asp Ile Phe
            180                 185                 190

Lys Glu Tyr Ile Ala Gln Lys Glu Trp Leu Phe Gln Pro Glu Pro His
        195                 200                 205

Leu Arg Leu Ile Gly Asp Leu Met Glu His Cys Ala Ser Lys Ile Pro
    210                 215                 220

Ala Tyr Lys Pro Leu Ser Val Ser Gly Tyr His Ile Arg Glu Ala Gly
225                 230                 235                 240

Ala Thr Ala Ala Gln Glu Leu Ala Tyr Thr Leu Ala Asp Gly Phe Gly
                245                 250                 255

Tyr Val Glu Leu Gly Leu Ser Arg Gly Leu Asp Val Asp Val Phe Ala
            260                 265                 270

Pro Gly Leu Ser Phe Phe Asp Ala His Val Asp Phe Phe Glu Glu
        275                 280                 285

Ile Ala Lys Phe Arg Ala Ala Arg Arg Ile Trp Ala Arg Trp Leu Arg
290                 295                 300

Asp Val Tyr Gly Ala Lys Ser Glu Lys Ala Gln Trp Leu Arg Phe His
305                 310                 315                 320

Thr Gln Thr Ala Gly Val Ser Leu Thr Ala Gln Gln Pro Tyr Asn Asn
                325                 330                 335

Val Val Arg Thr Ala Val Glu Ala Leu Ala Ala Val Leu Gly Gly Thr
            340                 345                 350

Asn Ser Leu His Thr Asn Ala Leu Asp Glu Thr Leu Ala Leu Pro Ser
        355                 360                 365

Glu Gln Ala Ala Glu Ile Ala Leu Arg Thr Gln Gln Val Leu Met Glu
    370                 375                 380

Glu Thr Gly Val Ala Asn Val Ala Asp Pro Leu Gly Gly Ser Trp Tyr
385                 390                 395                 400

Val Glu Gln Leu Thr Asp Arg Ile Glu Ala Asp Ala Glu Lys Ile Phe
                405                 410                 415

Glu Gln Ile Arg Glu Arg Gly Leu Arg Ala His Pro Asp Gly Arg His
            420                 425                 430

Pro Ile Gly Pro Ile Thr Ser Gly Ile Leu Arg Gly Ile Glu Asp Gly
        435                 440                 445

Trp Phe Thr Gly Glu Ile Ala Glu Ser Ala Phe Gln Tyr Gln Gln Ala
    450                 455                 460

Leu Glu Lys Gly Asp Lys Arg Val Val Gly Val Asn Val His His Gly
465                 470                 475                 480

Ser Val Thr Gly Asp Leu Glu Ile Leu Arg Val Ser His Glu Val Glu
                485                 490                 495

```
Arg Glu Gln Val Arg Val Leu Gly Glu Arg Lys Ser Gly Arg Asp Asp
            500                 505                 510

Thr Ala Val Thr Ala Ala Leu Asp Ala Met Leu Ala Ala Ala Arg Asp
        515                 520                 525

Gly Ser Asn Met Ile Ala Pro Met Leu Asp Ala Val Arg Ala Glu Ala
        530                 535                 540

Thr Leu Gly Glu Ile Cys Asp Val Leu Arg Glu Glu Trp Gly Val Tyr
545                 550                 555                 560

Thr Glu Pro Ala Gly Phe
                565

<210> SEQ ID NO 104
<211> LENGTH: 1701
<212> TYPE: DNA
<213> ORGANISM: Streptomyces avermitilis

<400> SEQUENCE: 104
tcagaaaccg gcgggctccg tgtagacccc ccactcctcc cggaggacat cgcagatctc        60
gcccagcgtg gcctccgcgc ggaccgcgtc cagcatcggg gcgatcatgt tcgaccgtc        120
gcgcgcggcg gcgagcatcg cgtccagggc gcggttacg gccgtgtcgt cgcgccccga        180
cttccgctcg cccagcaccc gcacctgctc gcgctccacc tcgtggctga cgcgcaggat       240
ctccaggtcg cccgtcacgg accgtggtg gacgttgacg ccgacgaccc gcttgtcgcc         300
cttctccagc gcctgctggt actggaaggc cgactcggcg atctccccgg tgaaccagcc       360
gtcctcgatg ccgcgcagga tgccggaggt gatgggcccg atcgggtgcc gcccgtccgg       420
gtgggcccgc agcccgcgct ccctgatctg ttcgaagatc ttctcggcgt cggcctcgat      480
ccggtcggtc agctgctcca cgtaccagga accgcccagc ggatcggcca cgttggcgac       540
gcccgtctcc tccatcagca cctgctgggt gcgcagggcg atctcggccg cctgctcgga      600
cggcagggcg agggtctcgt cgagggcgtt ggtgtgcagc gagttcgtcc cgccgagcac      660
cgcggcgagg gcctccacgg ccgtccgtac gacgttgttg tacggctgct gcgcggtgag     720
cgagacgccc gcggtctggg tgtggaagcg cagccactgc gccttctccg acttcgcccc       780
gtacacgtcc cgcagccagc gcgcccagat gcgccgcgcc gcacggaact tggcgatctc       840
ctcgaagaag tcgacgtgcg cgtcgaagaa gaaggagagc ccgggcgcga acacgtccac       900
gtccaggccg cggctcagcc ccagctccac gtatccgaaa ccgtcggcga gggtgtacgc       960
cagctcctgg gcggccgtgg caccggcctc ccggatgtgg tacccggaga cggacagcgg      1020
cttgtacgcg gggatcttcg aggcgcagtg ctccatcagg tcgccgatga ccgcagatg       1080
gggctcgggc tggaagagcc actccttctg cgcgatgtac tccttgaaga tgtcggtctg     1140
gagggtgccg ttgaggacgg aggggtcgac gccctgccgc tcggccgcga ccaggtacat     1200
gcagaagacg ggcacggcgg gcccgctgat cgtcatcgac gtcgtcacgt cacccagcgg    1260
gatgtccttg aacaggacct ccatgtcggc cgccgagtcg atcgcgaccc cgcagtgccc     1320
gacctcgccg agcgcgcggc ggtcgtcgga gtcgcgcccc atgagcgtcg gcatgtcgaa      1380
ggccacggac agcccaccgc cgccgttggc gaggatcttc ttgtagcgct cgttggtctg     1440
ctcggcgttg ccgaacccgg cgaactgccg gatggtccag gtccgccccc ggtagccggt     1500
cggatacaga ccgcgcgtga agggtactc acccggccag ccgatccgct cgaaaccctc    1560
gtacgcgtcc ccgggccggg gcccgtacgc cggctccacg ggatcgccgg agagcgtggt      1620
gaaatcggcc tcgcgcttgc gtgaggcgtc gtagcggggc tgccagcgtc ggcggccttc     1680
```
ctcgatggcg tcagcgtcca t					1701

<210> SEQ ID NO 105
<211> LENGTH: 138
<212> TYPE: PRT
<213> ORGANISM: Streptomyces avermitilis

<400> SEQUENCE: 105

```
Met Gly Val Ala Ala Gly Pro Ile Arg Val Val Ala Lys Pro Gly
1               5                   10                  15

Leu Asp Gly His Asp Arg Gly Ala Lys Val Ile Ala Arg Ala Leu Arg
            20                  25                  30

Asp Ala Gly Met Glu Val Ile Tyr Thr Gly Leu His Gln Thr Pro Glu
            35                  40                  45

Gln Ile Val Gly Thr Ala Ile Gln Glu Asp Ala Asp Ala Ile Gly Leu
        50                  55                  60

Ser Ile Leu Ser Gly Ala His Asn Thr Leu Phe Ala Ala Val Ile Asp
65              70                  75                  80

Leu Leu Lys Glu Arg Asp Ala Glu Asp Ile Lys Val Phe Gly Gly
            85                  90                  95

Ile Ile Pro Glu Ala Asp Ile Ala Pro Leu Lys Glu Lys Gly Val Ala
            100                 105                 110

Glu Ile Phe Thr Pro Gly Ala Thr Thr Ala Ser Ile Val Glu Trp Val
            115                 120                 125

Arg Ala Asn Val Arg Gln Pro Ala Gly Ala
            130                 135
```

<210> SEQ ID NO 106
<211> LENGTH: 1701
<212> TYPE: DNA
<213> ORGANISM: Streptomyces avermitilis

<400> SEQUENCE: 106
tcagaaaccg gcgggctccg tgtagacccc ccactcctcc cggaggacat cgcagatctc    60
gcccagcgtg gcctccgcgc ggaccgcgtc cagcatcggg gcgatcatgt tcgacccgtc    120
gcgcgcggcg gcgagcatcg cgtccagggc cgcggttacg gccgtgtcgt cgcgccccga    180
cttccgctcg cccagcaccc gcacctgctc gcgctccacc tcgtggctga cgcgcaggat    240
ctccaggtcg cccgtcacgg acccgtggtg gacgttgacg ccgacgaccc gcttgtcgcc    300
cttctccagc gcctgctggt actggaaggc cgactcggcg atctccccgg tgaaccagcc    360
gtcctcgatg ccgcgcagga tgccggaggt gatgggcccg atcgggtgcc gcccgtccgg    420
gtgggcccgc agcccgcgct ccctgatctg ttcgaagatc ttctcggcgt cggcctcgat    480
ccggtcggtc agctgctcca cgtaccagga accgcccagc ggatcggcca cgttggcgac    540
gcccgtctcc tccatcagca cctgctgggt gcgcagggcg atctcggccg cctgctcgga    600
cggcagggcg agggtctcgt cgagggcgtt ggtgtgcagc gagttcgtcc cgccgagcac    660
cgcggcgagg gcctccacgg ccgtccgtac gacgttgttg tacggctgct gcgcggtgag    720
cgagacgccc gcggtctggg tgtggaagcg cagccactgc gccttctccg acttcgcccc    780
gtacacgtcc cgcagccagc gcgcccagat gcgccgcgcc gcacggaact tggcgatctc    840
ctcgaagaag tcgacgtgcg cgtcgaagaa gaaggagagc ccgggcgcga acacgtccac    900
gtccaggccg cggctcagcc ccagctccac gtatccgaaa ccgtcggcga gggtgtacgc    960
cagctcctgg gcggccgtgg caccggcctc ccggatgtgg tacccggaga cggacagcgg    1020

```
cttgtacgcg gggatcttcg aggcgcagtg ctccatcagg tcgccgatga gccgcagatg      1080
gggctcgggc tggaagagcc actccttctg cgcgatgtac tccttgaaga tgtcggtctg      1140
gagggtgccg ttgaggacgg aggggtcgac gccctgccgc tcggccgcga ccaggtacat      1200
gcagaagacg ggcacggcgg gcccgctgat cgtcatcgac gtcgtcacgt cacccagcgg      1260
gatgtccttg aacaggacct ccatgtcggc cgccgagtcg atcgcgaccc cgcagtgccc      1320
gacctcgccg agcgcgcggc ggtcgtcgga gtcgcgcccc atgagcgtcg gcatgtcgaa      1380
ggccacggac agcccaccgc cgccgttggc gaggatcttc ttgtagcgct cgttggtctg      1440
ctcggcgttg ccgaacccgg cgaactgccg gatggtccag gtccggcccc ggtagccggt      1500
cggatacaga ccgcgcgtga aggggtactc acccggccag ccgatccgct cgaaaccctc      1560
gtacgcgtcc ccgggccggg gcccgtacgc cggctccacg ggatcgccgg agagcgtggt      1620
gaaatcggcc tcgcgcttgc gtgaggcgtc gtagcgggcc tgccagcgtc ggcggccttc      1680
ctcgatggcg tcagcgtcca t                                                1701

<210> SEQ ID NO 107
<211> LENGTH: 139
<212> TYPE: PRT
<213> ORGANISM: Saccharomyces cerevisiae

<400> SEQUENCE: 107

Met Ser Glu Ile Thr Leu Gly Lys Tyr Leu Phe Glu Arg Leu Lys Gln
1               5                   10                  15

Val Asn Val Asn Thr Val Phe Gly Leu Pro Gly Asp Phe Asn Leu Ser
            20                  25                  30

Leu Leu Asp Lys Ile Tyr Glu Val Glu Gly Met Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ala Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Ile
    130                 135

<210> SEQ ID NO 108
<211> LENGTH: 1689
<212> TYPE: DNA
<213> ORGANISM: Saccharomyces cerevisiae

<400> SEQUENCE: 108
atgtctgaaa ttactttggg taaatatttg ttcgaaagat aaagcaagt caacgttaac       60 accgttttcg gtttgccagg tgacttcaac ttgtccttgt tggacaagat ctacgaagtt      120
gaaggtatga gatgggctgg taacgccaac gaattgaacg ctgcttacgc cgctgatggt      180
tacgctcgta tcaagggtat gtcttgtatc atcaccacct tcggtgtcgg tgaattgtct      240
gctttgaacg gtattgccgg ttcttacgct gaacacgtcg gtgttttgca cgttgttggt      300
gtcccatcca tctctgctca agctaagcaa ttgttgttgc accacacctt gggtaacggt      360
```

```
gacttcactg ttttccacag aatgtctgcc aacatttctg aaaccactgc tatgatcact    420
gacattgcta ccgccccagc tgaaattgac agatgtatca gaaccactta cgtcacccaa    480
agaccagtct acttaggttt gccagctaac ttggtcgact tgaacgtccc agctaagttg    540
ttgcaaactc caattgacat gtctttgaag ccaaacgatg ctgaatccga aaaggaagtc    600
attgacacca tcttggcttt ggtcaaggat gctaagaacc cagttatctt ggctgatgct    660
tgttgttcca gacacgacgt caaggctgaa actaagaagt tgattgactt gactcaattc    720
ccagctttcg tcaccccaat gggtaagggt tccattgacg aacaacaccc aagatacggt    780
ggtgtttacg tcggtacctt gtccaagcca gaagttaagg aagccgttga atctgctgac    840
ttgattttgt ctgtcggtgc tttgttgtct gatttcaaca ccggttcttt ctcttactct    900
tacaagacca agaacattgt cgaattccac tccgaccaca tgaagatcag aaacgccact    960
ttcccaggtg tccaaatgaa attcgttttg caaaagttgt tgaccactat tgctgacgcc   1020
gctaagggtt acaagccagt tgctgtccca gctagaactc cagctaacgc tgctgtccca   1080
gcttctaccc cattgaagca agaatggatg tggaaccaat tgggtaactt cttgcaagaa   1140
ggtgatgttg tcattgctga accggtacc tccgctttcg gtatcaacca aaccactttc   1200
ccaaacaaca cctacggtat ctctcaagtc ttatggggtt ccattggttt caccactggt   1260
gctaccttgg gtgctgcttt cgctgctgaa gaaattgatc aaagaagag agttatctta   1320 ttcattggtg acggttcttt gcaattgact gttcaagaaa tctccaccat gatcagatgg   1380
ggcttgaagc atacttgtt cgtcttgaac aacgatggtt acaccattga aaagttgatt   1440
cacggtccaa aggctcaata caacgaaatt caaggttggg accacctatc cttgttgcca   1500
actttcggtg ctaaggacta tgaaacccac agagtcgcta ccaccggtga atgggacaag   1560
ttgacccaag acaagtcttt caacgacaac tctaagatca gaatgattga aatcatgttg   1620
ccagtcttcg atgctccaca aaacttggtt gaacaagcta agttgactgc tgctaccaac   1680
gctaagcaa                                                           1689
```

<210> SEQ ID NO 109  
<211> LENGTH: 563  
<212> TYPE: PRT  
<213> ORGANISM: Saccharomyces cerevisiae

<400> SEQUENCE: 109

```
Met Ser Glu Ile Thr Leu Gly Lys Tyr Leu Phe Glu Arg Leu Ser Gln
  1               5                  10                  15

Val Asn Cys Asn Thr Val Phe Gly Leu Pro Gly Asp Phe Asn Leu Ser
             20                  25                  30

Leu Leu Asp Lys Leu Tyr Glu Val Lys Gly Met Arg Trp Ala Gly Asn
         35                  40                  45

Ala Asn Glu Leu Asn Ala Ala Tyr Ala Ala Asp Gly Tyr Ala Arg Ile
     50                  55                  60

Lys Gly Met Ser Cys Ile Ile Thr Thr Phe Gly Val Gly Glu Leu Ser
 65                  70                  75                  80

Ala Leu Asn Gly Ile Ala Gly Ser Tyr Ala Glu His Val Gly Val Leu
                 85                  90                  95

His Val Val Gly Val Pro Ser Ile Ser Ser Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Ile Thr Asp Ile Ala Asn
```

```
            130                 135                 140
Ala Pro Ala Glu Ile Asp Arg Cys Ile Arg Thr Thr Tyr Thr Thr Gln
145                 150                 155                 160

Arg Pro Val Tyr Leu Gly Leu Pro Ala Asn Leu Val Asp Leu Asn Val
                165                 170                 175

Pro Ala Lys Leu Leu Glu Thr Pro Ile Asp Leu Ser Leu Lys Pro Asn
                180                 185                 190

Asp Ala Glu Ala Glu Ala Val Val Arg Thr Val Val Glu Leu Ile
                195                 200                 205

Lys Asp Ala Lys Asn Pro Val Ile Leu Ala Asp Ala Cys Ala Ser Arg
                210                 215                 220

His Asp Val Lys Ala Glu Thr Lys Lys Leu Met Asp Leu Thr Gln Phe
225                 230                 235                 240

Pro Val Tyr Val Thr Pro Met Gly Lys Gly Ala Ile Asp Glu Gln His
                245                 250                 255

Pro Arg Tyr Gly Gly Val Tyr Val Gly Thr Leu Ser Arg Pro Glu Val
                260                 265                 270

Lys Lys Ala Val Glu Ser Ala Asp Leu Ile Leu Ser Ile Gly Ala Leu
                275                 280                 285

Leu Ser Asp Phe Asn Thr Gly Ser Phe Ser Tyr Ser Tyr Lys Thr Lys
                290                 295                 300

Asn Ile Val Glu Phe His Ser Asp His Ile Lys Ile Arg Asn Ala Thr
305                 310                 315                 320

Phe Pro Gly Val Gln Met Lys Phe Ala Leu Gln Lys Leu Leu Asp Ala
                325                 330                 335

Ile Pro Glu Val Val Lys Asp Tyr Lys Pro Val Ala Val Pro Ala Arg
                340                 345                 350

Val Pro Ile Thr Lys Ser Thr Pro Ala Asn Thr Pro Met Lys Gln Glu
                355                 360                 365

Trp Met Trp Asn His Leu Gly Asn Phe Leu Arg Glu Gly Asp Ile Val
                370                 375                 380

Ile Ala Glu Thr Gly Thr Ser Ala Phe Gly Ile Asn Gln Thr Thr Phe
385                 390                 395                 400

Pro Thr Asp Val Tyr Ala Ile Val Gln Val Leu Trp Gly Ser Ile Gly
                405                 410                 415

Phe Thr Val Gly Ala Leu Leu Gly Ala Thr Met Ala Ala Glu Glu Leu
                420                 425                 430

Asp Pro Lys Lys Arg Val Ile Leu Phe Ile Gly Asp Gly Ser Leu Gln
                435                 440                 445

Leu Thr Val Gln Glu Ile Ser Thr Met Ile Arg Trp Gly Leu Lys Pro
                450                 455                 460

Tyr Ile Phe Val Leu Asn Asn Gly Tyr Thr Ile Glu Lys Leu Ile
465                 470                 475                 480

His Gly Pro His Ala Glu Tyr Asn Glu Ile Gln Gly Trp Asp His Leu
                485                 490                 495

Ala Leu Leu Pro Thr Phe Gly Ala Arg Asn Tyr Glu Thr His Arg Val
                500                 505                 510

Ala Thr Thr Gly Glu Trp Glu Lys Leu Thr Gln Asp Lys Asp Phe Gln
                515                 520                 525

Asp Asn Ser Lys Ile Arg Met Ile Glu Val Met Leu Pro Val Phe Asp
                530                 535                 540

Ala Pro Gln Asn Leu Val Lys Gln Ala Gln Leu Thr Ala Ala Thr Asn
545                 550                 555                 560
```

<210> SEQ ID NO 110
<211> LENGTH: 1689
<212> TYPE: DNA
<213> ORGANISM: Saccharomyces cerevisiae

<400> SEQUENCE: 110

```
atgtctgaaa taaccttagg taaatatttta tttgaaagat tgagccaagt caactgtaac    60
accgtcttcg gtttgccagg tgactttaac ttgtctcttt tggataagct ttatgaagtc   120
aaaggtatga gatgggctgg taacgctaac gaattgaacg ctgcctatgc tgctgatggt   180
tacgctcgta tcaagggtat gtcctgtatt attaccacct tcggtgttgg tgaattgtct   240
gctttgaatg gtattgccgg ttcttacgct gaacatgtcg gtgttttgca cgttgttggt   300
gttccatcca tctcttctca agctaagcaa ttgttgttgc atcatacctt gggtaacggt   360
gacttcactg ttttccacag aatgtctgcc aacatttctg aaaccactgc catgatcact   420
gatattgcta acgctccagc tgaaattgac agatgtatca gaaccaccta cactacccaa   480
agaccagtct acttgggttt gccagctaac ttggttgact gaacgtccc agccaagtta   540
ttggaaactc caattgactt gtctttgaag ccaaacgacg ctgaagctga agctgaagtt   600
gttagaactg ttgttgaatt gatcaaggat gctaagaacc cagttatctt ggctgatgct   660
tgtgcttcta gacatgatgt caaggctgaa actaagaagt tgatggactt gactcaattc   720
ccagtttacg tcaccccaat gggtaagggt gctattgacg aacaacaccc aagatacggt   780
ggtgtttacg ttggtaccct tgtctagacca gaagttaaga aggctgtaga atctgctgat   840
ttgatattgt ctatcggtgc tttgttgtct gatttcaata ccggttcttt ctcttactcc   900
tacaagacca aaaatatcgt tgaattccac tctgaccaca tcaagatcag aaacgccacc   960
ttcccaggtg ttcaaatgaa atttgccttg caaaaattgt tggatgctat tccagaagtc  1020
gtcaaggact acaaacctgt tgctgtccca gctagagttc caattaccaa gtctactcca  1080
gctaacactc caatgaagca agaatggatg tggaaccatt tgggtaactt cttgagagaa  1140
ggtgatattg ttattgctga aaccggtact tccgccttcg gtattaacca aactactttc  1200
ccaacagatg tatacgctat cgtccaagtc ttgtggggtt ccattggtt cacagtcggc  1260
gctctattgg gtgctactat ggccgctgaa gaacttgatc aaagaagag agttattta  1320
ttcattggtg acggttctct acaattgact gttcaagaaa tctctaccat gattagatgg  1380
ggtttgaagc catacatttt tgtcttgaat aacaacggtt acaccattga aaaattgatt  1440
cacggtcctc atgccgaata taatgaaatt caaggttggg accacttggc cttattgcca  1500
actttggtg ctagaaacta cgaaacccac agagttgcta ccactggtga atgggaaaag  1560
ttgactcaag acaaggactt ccaagacaac tctaagatta gaatgattga gttatgttg  1620
ccagtctttg atgctccaca aaacttggtt aaacaagctc aattgactgc cgctactaac  1680
gctaaacaa                                                          1689
```

<210> SEQ ID NO 111
<211> LENGTH: 533
<212> TYPE: PRT
<213> ORGANISM: Saccharomyces cerevisiae

<400> SEQUENCE: 111

```
Met Ser Glu Ile Thr Leu Gly Lys Tyr Leu Phe Glu Arg Leu Lys Gln
1               5                   10                  15
```

```
Val Asn Val Asn Thr Ile Phe Gly Leu Pro Gly Asp Phe Asn Leu Ser
                20                  25                  30

Leu Leu Asp Lys Ile Tyr Glu Val Asp Gly Leu Arg Trp Ala Gly Asn
            35                  40                  45

Ala Asn Glu Leu Asn Ala Ala Tyr Ala Ala Asp Gly Tyr Ala Arg Ile
50                          55                  60

Lys Gly Leu Ser Val Leu Val Thr Thr Phe Gly Val Gly Glu Leu Ser
65                      70                  75                  80

Ala Leu Asn Gly Ile Ala Gly Ser Tyr Ala Glu His Val Gly Val Leu
                    85                  90                  95

His Val Val Gly Val Pro Ser Ile Ser Ala Gln Ala Lys Gln Leu Leu
                100                 105                 110

Leu His His Thr Leu Gly Asn Gly Asp Phe Thr Val Phe His Arg Met
            115                 120                 125

Ser Ala Asn Ile Ser Glu Thr Thr Ser Met Ile Thr Asp Ile Ala Thr
130                         135                 140

Ala Pro Ser Glu Ile Asp Arg Leu Ile Arg Thr Thr Phe Ile Thr Gln
145                     150                 155                 160

Arg Pro Ser Tyr Leu Gly Leu Pro Ala Asn Leu Val Asp Leu Lys Val
                    165                 170                 175

Pro Gly Ser Leu Leu Glu Lys Pro Ile Asp Leu Ser Leu Lys Pro Asn
                180                 185                 190

Asp Pro Glu Ala Glu Lys Glu Val Ile Asp Thr Val Leu Glu Leu Ile
            195                 200                 205

Gln Asn Ser Lys Asn Pro Val Ile Leu Ser Asp Ala Cys Ala Ser Arg
210                         215                 220

His Asn Val Lys Lys Glu Thr Gln Lys Leu Ile Asp Leu Thr Gln Phe
225                     230                 235                 240

Pro Ala Phe Val Thr Pro Leu Gly Lys Gly Ser Ile Asp Glu Gln His
                245                 250                 255

Pro Arg Tyr Gly Gly Val Tyr Val Gly Thr Leu Ser Lys Gln Asp Val
                260                 265                 270

Lys Gln Ala Val Glu Ser Ala Asp Leu Ile Leu Ser Val Gly Ala Leu
            275                 280                 285

Leu Ser Asp Phe Asn Thr Gly Ser Phe Ser Tyr Ser Tyr Lys Thr Lys
290                         295                 300

Asn Val Val Glu Phe His Ser Asp Tyr Val Lys Val Lys Asn Ala Thr
305                     310                 315                 320

Phe Leu Gly Val Gln Met Lys Phe Ala Leu Gln Asn Leu Leu Lys Val
                    325                 330                 335

Ile Pro Asp Val Val Lys Gly Tyr Lys Ser Val Pro Val Pro Thr Lys
                340                 345                 350

Thr Pro Ala Asn Lys Gly Val Pro Ala Ser Thr Pro Leu Lys Gln Glu
            355                 360                 365

Trp Leu Trp Asn Glu Leu Ser Lys Phe Leu Gln Glu Gly Asp Val Ile
370                         375                 380

Ile Ser Glu Thr Gly Thr Ser Ala Phe Gly Ile Asn Gln Thr Ile Phe
385                     390                 395                 400

Pro Lys Asp Ala Tyr Gly Ile Ser Gln Val Leu Trp Gly Ser Ile Gly
                    405                 410                 415

Phe Thr Thr Gly Ala Thr Leu Gly Ala Ala Phe Ala Ala Glu Glu Ile
                420                 425                 430
```

```
Asp Pro Asn Lys Arg Val Ile Leu Phe Ile Gly Asp Gly Ser Leu Gln
            435                 440                 445

Leu Thr Val Gln Glu Ile Ser Thr Met Ile Arg Trp Gly Leu Lys Pro
        450                 455                 460

Tyr Leu Phe Val Leu Asn Asn Asp Gly Tyr Thr Ile Glu Lys Leu Ile
465                 470                 475                 480

His Gly Pro His Ala Glu Tyr Asn Glu Ile Gln Thr Trp Asp His Leu
                485                 490                 495

Ala Leu Leu Pro Ala Phe Gly Ala Lys Lys Tyr Glu Asn His Lys Ile
                500                 505                 510

Ala Thr Thr Gly Glu Trp Asp Ala Leu Thr Thr Asp Ser Glu Phe Gln
            515                 520                 525

Lys Asn Ser Val Ile
            530

<210> SEQ ID NO 112
<211> LENGTH: 1599
<212> TYPE: DNA
<213> ORGANISM: Saccharomyces cerevisiae

<400> SEQUENCE: 112
atgtctgaaa ttactcttgg aaaatactta tttgaaagat tgaagcaagt taatgttaac      60 accattttg ggctaccagg cgacttcaac ttgtccctat tggacaagat ttacgaggta      120
gatggattga gatgggctgg taatgcaaat gagctgaacg ccgcctatgc cgccgatggt      180
tacgcacgca tcaagggttt atctgtgctg gtaactactt ttggcgtagg tgaattatcc      240
gccttgaatg gtattgcagg atcgtatgca gaacacgtcg gtgtactgca tgttgttggt      300 gtccccctcta tctccgctca ggctaagcaa ttgttgttgc atcataccct tggtaacggt      360
gattttaccg tttttcacag aatgtccgcc aatatctcag aaactacatc aatgattaca      420
gacattgcta cagcccttc agaaatcgat aggttgatca ggacaacatt tataacacaa      480
aggcctagct acttggggtt gccagcgaat ttggtagatc taaggttcc tggttctctt      540 ttggaaaaac cgattgatct atcattaaaa cctaacgatc ccgaagctga aaaggaagtt      600
attgataccg tactagaatt gatccagaat tcgaaaaacc ctgttatact atcggatgcc      660
tgtgcttcta ggcacaacgt taaaaagaa acccagaagt taattgattt gacgcaattc      720
ccagcttttg tgacacctct aggtaaaggg tcaatagatg aacagcatcc cagatatggc      780
ggtgtttatg tgggaacgct gtccaaacaa gacgtgaaac aggccgttga gtcggctgat      840
ttgatccttt cggtcggtgc tttgctctct gattttaaca caggttcgtt ttcctactcc      900
tacaagacta aaaatgtagt ggagtttcat tccgattacg taaaggtgaa gaacgctacg      960
ttcctcggtg tacaaatgaa atttgcacta caaaacttac tgaaggttat tcccgatgtt      1020
gttaagggct acaagagcgt tcccgtacca accaaaactc ccgcaaacaa aggtgtacct      1080
gctagcacgc ccttgaaaca agagtggttg tggaacgaat gtccaaatt cttgcaagaa      1140 ggtgatgtta tcatttccga accggcacg tctgccttcg gtatcaatca aactatcttt      1200
cctaaggacg cctacggtat ctcgcaggtg ttgtgggggt ccatcggttt tacaacagga      1260
gcaactttag gtgctgcctt tgccgctgag gagattgacc ccaacaagag agtcatctta      1320
ttcataggtg acgggtcttt gcagttaacc gtccaagaaa tctccaccat gatcagatgg      1380
gggttaaagc cgtatctttt tgtccttaac aacgacggct acactatcga aaagctgatt      1440
catgggcctc acgcagagta caacgaaatc cagacctggg atcacctcgc cctgttgccc      1500
```

```
gcatttggtg cgaaaaagta cgaaaatcac aagatcgcca ctacgggtga gtgggatgcc      1560
ttaaccactg attcagagtt ccagaaaaac tcggtgatc                             1599
```

<210> SEQ ID NO 113
<211> LENGTH: 564
<212> TYPE: PRT
<213> ORGANISM: Candida glabrata

<400> SEQUENCE: 113

```
Met Ser Glu Ile Thr Leu Gly Arg Tyr Leu Phe Glu Arg Leu Asn Gln
1               5                   10                  15

Val Asp Val Lys Thr Ile Phe Gly Leu Pro Gly Asp Phe Asn Leu Ser
            20                  25                  30

Leu Leu Asp Lys Ile Tyr Glu Val Glu Gly Met Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ser Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Val Thr Asp Ile Ala Thr
    130                 135                 140

Ala Pro Ala Glu Ile Asp Arg Cys Ile Arg Thr Thr Tyr Ile Thr Gln
145                 150                 155                 160

Arg Pro Val Tyr Leu Gly Leu Pro Ala Asn Leu Val Asp Leu Lys Val
                165                 170                 175

Pro Ala Lys Leu Leu Glu Thr Pro Ile Asp Leu Ser Leu Lys Pro Asn
            180                 185                 190

Asp Pro Glu Ala Glu Thr Glu Val Val Asp Thr Val Leu Glu Leu Ile
        195                 200                 205

Lys Ala Ala Lys Asn Pro Val Ile Leu Ala Asp Ala Cys Ala Ser Arg
    210                 215                 220

His Asp Val Lys Ala Glu Thr Lys Lys Leu Ile Asp Ala Thr Gln Phe
225                 230                 235                 240

Pro Ser Phe Val Thr Pro Met Gly Lys Gly Ser Ile Asp Glu Gln His
                245                 250                 255

Pro Arg Phe Gly Gly Val Tyr Val Gly Thr Leu Ser Arg Pro Glu Val
            260                 265                 270

Lys Glu Ala Val Glu Ser Ala Asp Leu Ile Leu Ser Val Gly Ala Leu
        275                 280                 285

Leu Ser Asp Phe Asn Thr Gly Ser Phe Ser Tyr Ser Tyr Lys Thr Lys
    290                 295                 300

Asn Ile Val Glu Phe His Ser Asp Tyr Ile Lys Ile Arg Asn Ala Thr
305                 310                 315                 320

Phe Pro Gly Val Gln Met Lys Phe Ala Leu Gln Lys Leu Leu Asn Ala
                325                 330                 335

Val Pro Glu Ala Ile Lys Gly Tyr Lys Pro Val Pro Val Pro Ala Arg
            340                 345                 350

Val Pro Glu Asn Lys Ser Cys Asp Pro Ala Thr Pro Leu Lys Gln Glu
```

```
                355                 360                 365
Trp Met Trp Asn Gln Val Ser Lys Phe Leu Gln Glu Gly Asp Val Val
370                 375                 380

Ile Thr Glu Thr Gly Thr Ser Ala Phe Gly Ile Asn Gln Thr Pro Phe
385                 390                 395                 400

Pro Asn Asn Ala Tyr Gly Ile Ser Gln Val Leu Trp Gly Ser Ile Gly
                405                 410                 415

Phe Thr Thr Gly Ala Cys Leu Gly Ala Ala Phe Ala Ala Glu Glu Ile
                420                 425                 430

Asp Pro Lys Lys Arg Val Ile Leu Phe Ile Gly Asp Gly Ser Leu Gln
                435                 440                 445

Leu Thr Val Gln Glu Ile Ser Thr Met Ile Arg Trp Gly Leu Lys Pro
450                 455                 460

Tyr Leu Phe Val Leu Asn Asn Asp Gly Tyr Thr Ile Glu Arg Leu Ile
465                 470                 475                 480

His Gly Glu Lys Ala Gly Tyr Asn Asp Ile Gln Asn Trp Asp His Leu
                485                 490                 495

Ala Leu Leu Pro Thr Phe Gly Ala Lys Asp Tyr Glu Asn His Arg Val
                500                 505                 510

Ala Thr Thr Gly Glu Trp Asp Lys Leu Thr Gln Asp Lys Glu Phe Asn
                515                 520                 525

Lys Asn Ser Lys Ile Arg Met Ile Glu Val Met Leu Pro Val Met Asp
530                 535                 540

Ala Pro Thr Ser Leu Ile Glu Gln Ala Lys Leu Thr Ala Ser Ile Asn
545                 550                 555                 560

Ala Lys Gln Glu

<210> SEQ ID NO 114
<211> LENGTH: 1692
<212> TYPE: DNA
<213> ORGANISM: Candida glabrata

<400> SEQUENCE: 114
atgtctgaga ttactttggg tagatacttg ttcgagagat gaaccaagt cgacgttaag      60 accatcttcg gtttgccagg tgacttcaac ttgtccctat ggacaagat ctacgaagtt     120 gaaggtatga gatgggctgg taacgctaac gaattgaacg ctgcttacgc tgctgacggt     180
tacgctagaa tcaagggtat gtcctgtatc atcaccacct tcggtgtcgg tgaattgtct     240
gccttgaacg gtattgccgg ttcttacgct gaacacgtcg gtgtcttgca cgtcgtcggt     300
gtcccatcca tctcctctca agctaagcaa ttgttgttgc accacacctt gggtaacggt     360
gacttcactg tcttccacag aatgtccgct aacatctctg agaccaccgc tatggtcact     420
gacatcgcta ccgctccagc tgagatcgac agatgtatca gaaccaccta catcacccaa     480
agaccagtct acttgggtct accagctaac ttggtcgacc taaggtccc agccaagctt     540 ttggaaaccc caattgactt gtccttgaag ccaaacgacc agaagccga actgaagtc     600 gttgacaccg tcttggaatt gatcaaggct gctaagaacc cagttatctt ggctgatgct     660
tgtgcttcca gacacgacgt caaggctgaa accaagaagt tgattgacgc cactcaattc     720
ccatccttcg ttaccccaat gggtaagggt tccatcgacg aacaacaccc aagattcggt     780
ggtgtctacg tcggtacctt gtccagacca gaagttaagg aagctgttga atccgctgac     840
ttgatcttgt ctgtcggtgc tttgttgtcc gatttcaaca ctggttcttt ctcttactct     900
tacaagacca agaacatcgt cgaattccac tctgactaca tcaagatcag aaacgctacc     960
```

```
ttcccaggtg tccaaatgaa gttcgctttg caaaagttgt tgaacgccgt cccagaagct    1020
atcaagggtt acaagccagt ccctgtccca gctagagtcc cagaaaacaa gtcctgtgac    1080
ccagctaccc cattgaagca agaatggatg tggaaccaag tttccaagtt cttgcaagaa    1140
ggtgatgttg ttatcactga aaccggtacc tccgcttttg gtatcaacca aaccccattc    1200
ccaaacaacg cttacggtat ctcccaagtt ctatggggtt ccatcggttt caccaccggt    1260
gcttgtttgg gtgccgcttt cgctgctgaa gaaatcgacc aaagaagag agttatcttg    1320 ttcattggtg acggttcttt gcaattgact gtccaagaaa tctccaccat gatcagatgg    1380
ggcttgaagc atacttgtt cgtcttgaac aacgacggtt acaccatcga agattgatt     1440 cacggtgaaa aggctggtta acgacatc caaaactggg accacttggc tctattgcca     1500
accttcggtg ctaaggacta cgaaaaccac agagtcgcca ccaccggtga atgggacaag    1560
ttgacccaag acaaggaatt caacaagaac tccaagatca gaatgatcga agttatgttg    1620
ccagttatgg acgctccaac ttccttgatt gaacaagcta agttgaccgc ttccatcaac    1680
gctaagcaag aa                                                       1692

<210> SEQ ID NO 115
<211> LENGTH: 596
<212> TYPE: PRT
<213> ORGANISM: Pichia stipitis

<400> SEQUENCE: 115

Met Ala Glu Val Ser Leu Gly Arg Tyr Leu Phe Glu Arg Leu Tyr Gln
1               5                   10                  15

Leu Gln Val Gln Thr Ile Phe Gly Val Pro Gly Asp Phe Asn Leu Ser
            20                  25                  30

Leu Leu Asp Lys Ile Tyr Glu Val Glu Asp Ala His Gly Lys Asn Ser
        35                  40                  45

Phe Arg Trp Ala Gly Asn Ala Asn Glu Leu Asn Ala Ser Tyr Ala Ala
    50                  55                  60

Asp Gly Tyr Ser Arg Val Lys Arg Leu Gly Cys Leu Val Thr Thr Phe
65                  70                  75                  80

Gly Val Gly Glu Leu Ser Ala Leu Asn Gly Ile Ala Gly Ser Tyr Ala
                85                  90                  95

Glu His Val Gly Leu Leu His Val Gly Val Pro Ser Ile Ser Ser
            100                 105                 110

Gln Ala Lys Gln Leu Leu Leu His His Thr Leu Gly Asn Gly Asp Phe
        115                 120                 125

Thr Val Phe His Arg Met Ser Asn Asn Ile Ser Gln Thr Thr Ala Phe
    130                 135                 140

Ile Ser Asp Ile Asn Ser Ala Pro Ala Glu Ile Asp Arg Cys Ile Arg
145                 150                 155                 160

Glu Ala Tyr Val Lys Gln Arg Pro Val Tyr Ile Gly Leu Pro Ala Asn
                165                 170                 175

Leu Val Asp Leu Asn Val Pro Ala Ser Leu Leu Glu Ser Pro Ile Asn
            180                 185                 190

Leu Ser Leu Glu Lys Asn Asp Pro Glu Ala Gln Asp Glu Val Ile Asp
        195                 200                 205

Ser Val Leu Asp Leu Ile Lys Lys Ser Ser Asn Pro Ile Ile Leu Val
    210                 215                 220

Asp Ala Cys Ala Ser Arg His Asp Cys Lys Ala Glu Val Thr Gln Leu
225                 230                 235                 240
```

Ile Glu Gln Thr Gln Phe Pro Val Phe Val Thr Pro Met Gly Lys Gly
                245                 250                 255

Thr Val Asp Glu Gly Val Asp Gly Glu Leu Leu Glu Asp Asp Pro
            260                 265                 270

His Leu Ile Ala Lys Val Ala Arg Leu Ser Ala Gly Lys Asn Ala
        275                 280                 285

Ala Ser Arg Phe Gly Val Tyr Val Gly Thr Leu Ser Lys Pro Glu
    290                 295                 300

Val Lys Asp Ala Val Glu Ser Ala Asp Leu Ile Leu Ser Val Gly Ala
305                 310                 315                 320

Leu Leu Ser Asp Phe Asn Thr Gly Ser Phe Ser Tyr Ser Tyr Arg Thr
                325                 330                 335

Lys Asn Ile Val Glu Phe His Ser Asp Tyr Thr Lys Ile Arg Gln Ala
            340                 345                 350

Thr Phe Pro Gly Val Gln Met Lys Glu Ala Leu Gln Glu Leu Asn Lys
        355                 360                 365

Lys Val Ser Ser Ala Ala Ser His Tyr Glu Val Lys Pro Val Pro Lys
    370                 375                 380

Ile Lys Leu Ala Asn Thr Pro Ala Thr Arg Glu Val Lys Leu Thr Gln
385                 390                 395                 400

Glu Trp Leu Trp Thr Arg Val Ser Ser Trp Phe Arg Glu Gly Asp Ile
                405                 410                 415

Ile Ile Thr Glu Thr Gly Thr Ser Ser Phe Gly Ile Val Gln Ser Arg
            420                 425                 430

Phe Pro Asn Asn Thr Ile Gly Ile Ser Gln Val Leu Trp Gly Ser Ile
        435                 440                 445

Gly Phe Ser Val Gly Ala Thr Leu Gly Ala Ala Met Ala Ala Gln Glu
    450                 455                 460

Leu Asp Pro Asn Lys Arg Thr Ile Leu Phe Val Gly Asp Gly Ser Leu
465                 470                 475                 480

Gln Leu Thr Val Gln Glu Ile Ser Thr Ile Ile Arg Trp Gly Thr Thr
                485                 490                 495

Pro Tyr Leu Phe Val Leu Asn Asn Asp Gly Tyr Thr Ile Glu Arg Leu
            500                 505                 510

Ile His Gly Val Asn Ala Ser Tyr Asn Asp Ile Gln Pro Trp Gln Asn
        515                 520                 525

Leu Glu Ile Leu Pro Thr Phe Ser Ala Lys Asn Tyr Asp Ala Val Arg
    530                 535                 540

Ile Ser Asn Ile Gly Glu Ala Glu Asp Ile Leu Lys Asp Lys Glu Phe
545                 550                 555                 560

Gly Lys Asn Ser Lys Ile Arg Leu Ile Glu Val Met Leu Pro Arg Leu
                565                 570                 575

Asp Ala Pro Ser Asn Leu Ala Lys Gln Ala Ala Ile Thr Ala Ala Thr
            580                 585                 590

Asn Ala Glu Ala
        595

<210> SEQ ID NO 116
<211> LENGTH: 1788
<212> TYPE: DNA
<213> ORGANISM: Pichia stipitis

<400> SEQUENCE: 116
atggctgaag tctcattagg aagatatctc ttcgagagat tgtaccaatt gcaagtgcag     60

```
accatcttcg gtgtccctgg tgatttcaac ttgtcgcttt tggacaagat ctacgaagtg    120
gaagatgccc atggcaagaa ttcgtttaga tgggctggta atgccaacga attgaatgca    180
tcgtacgctg ctgacggtta ctcgagagtc aagcgtttag ggtgtttggt cactaccttt    240
ggtgtcggtg aattgtctgc tttgaatggt attgccggtt cttatgccga acatgttggt    300
ttgcttcatg tcgtaggtgt tccatcgatt tcctcgcaag ctaagcaatt gttacttcac    360
cacactttgg gtaatggtga tttcactgtt ttccatagaa tgtccaacaa catttctcag    420
accacagcct ttatctccga tatcaactcg gctccagctg aaattgatag atgtatcaga    480
gaggcctacg tcaaacaaag accagtttat atcgggttac cagctaactt agttgatttg    540
aatgttccgg cctctttgct tgagtctcca atcaacttgt cgttggaaaa gaacgaccca    600
gaggctcaag atgaagtcat tgactctgtc ttagacttga tcaaaaagtc gctgaaccca    660
atcatcttgg tcgatgcctg tgcctcgaga catgactgta aggctgaagt tactcagttg    720
attgaacaaa cccaattccc agtatttgtc actccaatgg gtaaaggtac cgttgatgag    780
ggtggtgtag acggagaatt gttagaagat gatcctcatt tgattgccaa ggtcgctgct    840
aggttgtctg ctggcaagaa cgctgcctct agattcggag gtgtttatgt cggaaccttg    900
tcgaagcccg aagtcaagga cgctgtagag agtgcagatt tgattttgtc tgtcggtgcc    960
cttttgtctg atttcaacac tggttcattt tcctactcct acagaaccaa gaacatcgtc   1020
gaattccatt ctgattacac taagattaga caagccactt tcccaggtgt gcagatgaag   1080
gaagccttgc aagaattgaa caagaaagtt tcatctgctg ctagtcacta tgaagtcaag   1140
cctgtgccca agatcaagtt ggccaataca ccagccacca gagaagtcaa gttaactcag   1200
gaatggttgt ggaccagagt gtcttcgtgg ttcagagaag gtgatattat tatcaccgaa   1260
accggtacat cctccttcgg tatagttcaa tccagattcc caaacaacac catcggtatc   1320
tcccaagtat tgtggggttc tattggtttc tctgttggtg ccacttttggg tgctgccatg   1380 gctgcccaag aactcgaccc taacaagaga accatcttgt tgttggaga tggttctttg   1440 caattgaccg ttcaggaaat ctccaccata atcagatggg gtaccacacc ttaccttttc   1500
gtgttgaaca atgacggtta caccatcgag cgtttgatcc acggtgtaaa tgcctcatat   1560
aatgacatcc aaccatggca aaacttggaa atcttgccta ctttctcggc caagaactac   1620
gacgctgtga gaatctccaa catcggagaa gcagaagata tcttgaaaga caggaattc    1680 ggaaagaact ccaagattag attgatagaa gtcatgttac caagattgga tgcaccatct   1740
aaccttgcca acaagctgc cattacagct gccaccaacg ccgaagct               1788
```

<210> SEQ ID NO 117
<211> LENGTH: 569
<212> TYPE: PRT
<213> ORGANISM: Pichia stipitis

<400> SEQUENCE: 117

```
Met Val Ser Thr Tyr Pro Glu Ser Glu Val Thr Leu Gly Arg Tyr Leu
1               5                   10                  15

Phe Glu Arg Leu His Gln Leu Lys Val Asp Thr Ile Phe Gly Leu Pro
            20                  25                  30

Gly Asp Phe Asn Leu Ser Leu Leu Asp Lys Val Tyr Glu Val Pro Asp
        35                  40                  45

Met Arg Trp Ala Gly Asn Ala Asn Glu Leu Asn Ala Ala Tyr Ala Ala
    50                  55                  60
```

-continued

```
Asp Gly Tyr Ser Arg Ile Lys Gly Leu Ser Cys Leu Val Thr Thr Phe
 65                  70                  75                  80

Gly Val Gly Glu Leu Ser Ala Leu Asn Gly Val Gly Ala Tyr Ala
                 85                  90                  95

Glu His Val Gly Leu Leu His Val Val Gly Val Pro Ser Ile Ser Ser
                100                 105                 110

Gln Ala Lys Gln Leu Leu Leu His His Thr Leu Gly Asn Gly Asp Phe
                115                 120                 125

Thr Val Phe His Arg Met Ser Asn Ser Ile Ser Gln Thr Thr Ala Phe
130                 135                 140

Leu Ser Asp Ile Ser Ile Ala Pro Gly Gln Ile Asp Arg Cys Ile Arg
145                 150                 155                 160

Glu Ala Tyr Val His Gln Arg Pro Val Tyr Val Gly Leu Pro Ala Asn
                165                 170                 175

Met Val Asp Leu Lys Val Pro Ser Ser Leu Leu Glu Thr Pro Ile Asp
                180                 185                 190

Leu Lys Leu Lys Gln Asn Asp Pro Glu Ala Gln Glu Val Val Glu Thr
                195                 200                 205

Val Leu Lys Leu Val Ser Gln Ala Thr Asn Pro Ile Ile Leu Val Asp
210                 215                 220

Ala Cys Ala Leu Arg His Asn Cys Lys Glu Glu Val Lys Gln Leu Val
225                 230                 235                 240

Asp Ala Thr Asn Phe Gln Val Phe Thr Thr Pro Met Gly Lys Ser Gly
                245                 250                 255

Ile Ser Glu Ser His Pro Arg Leu Gly Gly Val Tyr Val Gly Thr Met
                260                 265                 270

Ser Ser Pro Gln Val Lys Lys Ala Val Glu Asn Ala Asp Leu Ile Leu
                275                 280                 285

Ser Val Gly Ser Leu Leu Ser Asp Phe Asn Thr Gly Ser Phe Ser Tyr
                290                 295                 300

Ser Tyr Lys Thr Lys Asn Val Val Glu Phe His Ser Asp Tyr Met Lys
305                 310                 315                 320

Ile Arg Gln Ala Thr Phe Pro Gly Val Gln Met Lys Glu Ala Leu Gln
                325                 330                 335

Gln Leu Ile Lys Arg Val Ser Ser Tyr Ile Asn Pro Ser Tyr Ile Pro
                340                 345                 350

Thr Arg Val Pro Lys Arg Lys Gln Pro Leu Lys Ala Pro Ser Glu Ala
                355                 360                 365

Pro Leu Thr Gln Glu Tyr Leu Trp Ser Lys Val Ser Gly Trp Phe Arg
370                 375                 380

Glu Gly Asp Ile Ile Val Thr Glu Thr Gly Thr Ser Ala Phe Gly Ile
385                 390                 395                 400

Ile Gln Ser His Phe Pro Ser Asn Thr Ile Gly Ile Ser Gln Val Leu
                405                 410                 415

Trp Gly Ser Ile Gly Phe Thr Val Gly Ala Thr Val Gly Ala Ala Met
                420                 425                 430

Ala Ala Gln Glu Ile Asp Pro Ser Arg Arg Val Ile Leu Phe Val Gly
                435                 440                 445

Asp Gly Ser Leu Gln Leu Thr Val Gln Glu Ile Ser Thr Leu Cys Lys
                450                 455                 460

Trp Asp Cys Asn Asn Thr Tyr Leu Tyr Val Leu Asn Asn Asp Gly Tyr
465                 470                 475                 480

Thr Ile Glu Arg Leu Ile His Gly Lys Ser Ala Ser Tyr Asn Asp Ile
```

|     |     | 485 |     |     |     | 490 |     |     |     | 495 |     |     |
| --- | --- | --- | --- | --- | --- | --- | --- | --- | --- | --- | --- | --- |

Gln Pro Trp Asn His Leu Ser Leu Leu Arg Leu Phe Asn Ala Lys Lys
          500                       505                   510

Tyr Gln Asn Val Arg Val Ser Thr Ala Gly Glu Leu Asp Ser Leu Phe
      515                   520                 525

Ser Asp Lys Lys Phe Ala Ser Pro Asp Arg Ile Arg Met Ile Glu Val
    530                 535                 540

Met Leu Ser Arg Leu Asp Ala Pro Ala Asn Leu Val Ala Gln Ala Lys
545               550                 555                560

Leu Ser Glu Arg Val Asn Leu Glu Asn
             565

<210> SEQ ID NO 118
<211> LENGTH: 1707
<212> TYPE: DNA
<213> ORGANISM: Pichia stipitis

<400> SEQUENCE: 118

```
atggtatcaa cctacccaga atcagaggtt actctaggaa ggtacctctt tgagcgactc    60
caccaattga agtggacac  catttttcggc ttgccgggtg acttcaacct ttccttattg   120
gacaaagtgt atgaagttcc ggatatgagg tgggctggaa atgccaacga attgaatgct   180
gcctatgctg ccgatggtta ctccagaata aagggattgt cttgcttggt cacaactttt   240
ggtgttggtg aattgtctgc tttaaacgga gttggtggtg cctatgctga cacgtagga    300
cttctacatg tcgttggagt tccatccata tcgtcacagg ctaaacagtt gttgctccac   360
cataccttgg gtaatggtga cttcactgtt tttcacagaa tgtccaatag catttctcaa   420
actacagcat ttctctcaga tatctctatt gcaccaggtc aaatagatag atgcatcaga   480
gaagcatatg ttcatcagag accagtttat gttggtttac cggcaaatat ggttgatctc   540
aaggttcctt ctagtctctt agaaactcca attgatttga attgaaaaca aaatgatcct   600
gaagctcaag aagttgttga acagtcctg  aagttggtgt cccaagctac aaacccccatt  660
atcttggtag acgcttgtgc cctcagacac aattgcaaag aggaagtcaa acaattggtt   720
gatgccacta atttttcaagt cttttacaact ccaatgggta aatctggtat ctccgaatct   780
catccaagat gggcggtgt  ctatgtcggg acaatgtcga gtcctcaagt caaaaaagcc   840
gttgaaaatg ccgatcttat actatctgtt ggttcgttgt atcggactt  caatacaggt   900
tcattttcat actcctacaa gacgaagaat gttgttgaat ccactctga  ctatatgaaa   960
atcagacagg ccaccttccc aggagttcaa atgaaagaag ccttgcaaca gttgataaaa  1020
agggtctctt cttacatcaa tccaagctac attcctactc gagttcctaa aggaaacag   1080
ccattgaaag ctccatcaga agctcctttg acccaagaat atttgtggtc taaagtatcc  1140
ggctggttta gagagggtga tattatcgta accgaaactg gtacatctgc tttcggaatt  1200
attcaatccc attttcccag caacactatc ggtatatccc aagtcttgtg gggctcaatt  1260
ggtttcacag taggtgcaac agttggtgct gccatggcag cccaggaaat cgaccctagc  1320
aggagagtaa ttttgttcgt cggtgatggt tcattgcagt tgacggttca ggaaatctct  1380
acgttgtgta atgggattg  taacaatact tatctttacg tgttgaacaa tgatggttac  1440
actatagaaa ggttgatcca cggcaaaagt gccagctaca acgatataca gccttggaac  1500
catttatcct tgcttcgctt attcaatgct aagaaatacc aaaatgtcag agtatcgact  1560
gctggagaat tggactcttt tgttctctctgat aagaaatttg cttctccaga taggataaga  1620
```

```
atgattgagg tgatgttatc gagattggat gcaccagcaa atcttgttgc tcaagcaaag      1680
ttgtctgaac gggtaaacct tgaaaat                                          1707
```

<210> SEQ ID NO 119
<211> LENGTH: 563
<212> TYPE: PRT
<213> ORGANISM: Kluyveromyces lactis

<400> SEQUENCE: 119

| Met | Ser | Glu | Ile | Thr | Leu | Gly | Arg | Tyr | Leu | Phe | Glu | Arg | Leu | Lys | Gln |
|---|---|---|---|---|---|---|---|---|---|---|---|---|---|---|---|
| 1 | | | | 5 | | | | | 10 | | | | | 15 | |

| Val | Glu | Val | Gln | Thr | Ile | Phe | Gly | Leu | Pro | Gly | Asp | Phe | Asn | Leu | Ser |
|---|---|---|---|---|---|---|---|---|---|---|---|---|---|---|---|
| | | | 20 | | | | | 25 | | | | | 30 | | |

| Leu | Leu | Asp | Asn | Ile | Tyr | Glu | Val | Pro | Gly | Met | Arg | Trp | Ala | Gly | Asn |
|---|---|---|---|---|---|---|---|---|---|---|---|---|---|---|---|
| | | | 35 | | | | | 40 | | | | | 45 | | |

| Ala | Asn | Glu | Leu | Asn | Ala | Ala | Tyr | Ala | Ala | Asp | Gly | Tyr | Ala | Arg | Leu |
|---|---|---|---|---|---|---|---|---|---|---|---|---|---|---|---|
| | 50 | | | | | 55 | | | | | 60 | | | | |

| Lys | Gly | Met | Ser | Cys | Ile | Ile | Thr | Thr | Phe | Gly | Val | Gly | Glu | Leu | Ser |
|---|---|---|---|---|---|---|---|---|---|---|---|---|---|---|---|
| 65 | | | | | 70 | | | | | 75 | | | | | 80 |

| Ala | Leu | Asn | Gly | Ile | Ala | Gly | Ser | Tyr | Ala | Glu | His | Val | Gly | Val | Leu |
|---|---|---|---|---|---|---|---|---|---|---|---|---|---|---|---|
| | | | | 85 | | | | | 90 | | | | | 95 | |

| His | Val | Val | Gly | Val | Pro | Ser | Val | Ser | Ser | Gln | Ala | Lys | Gln | Leu | Leu |
|---|---|---|---|---|---|---|---|---|---|---|---|---|---|---|---|
| | | | 100 | | | | | 105 | | | | | 110 | | |

| Leu | His | His | Thr | Leu | Gly | Asn | Gly | Asp | Phe | Thr | Val | Phe | His | Arg | Met |
|---|---|---|---|---|---|---|---|---|---|---|---|---|---|---|---|
| | | 115 | | | | | 120 | | | | | 125 | | | |

| Ser | Ser | Asn | Ile | Ser | Glu | Thr | Thr | Ala | Met | Ile | Thr | Asp | Ile | Asn | Thr |
|---|---|---|---|---|---|---|---|---|---|---|---|---|---|---|---|
| | 130 | | | | | 135 | | | | | 140 | | | | |

| Ala | Pro | Ala | Glu | Ile | Asp | Arg | Cys | Ile | Arg | Thr | Thr | Tyr | Val | Ser | Gln |
|---|---|---|---|---|---|---|---|---|---|---|---|---|---|---|---|
| 145 | | | | | 150 | | | | | 155 | | | | | 160 |

| Arg | Pro | Val | Tyr | Leu | Gly | Leu | Pro | Ala | Asn | Leu | Val | Asp | Leu | Thr | Val |
|---|---|---|---|---|---|---|---|---|---|---|---|---|---|---|---|
| | | | | 165 | | | | | 170 | | | | | 175 | |

| Pro | Ala | Ser | Leu | Leu | Asp | Thr | Pro | Ile | Asp | Leu | Ser | Leu | Lys | Pro | Asn |
|---|---|---|---|---|---|---|---|---|---|---|---|---|---|---|---|
| | | | | 180 | | | | | 185 | | | | | 190 | |

| Asp | Pro | Glu | Ala | Glu | Glu | Val | Ile | Glu | Asn | Val | Leu | Gln | Leu | Ile |
|---|---|---|---|---|---|---|---|---|---|---|---|---|---|---|
| | | 195 | | | | | 200 | | | | | 205 | | |

| Lys | Glu | Ala | Lys | Asn | Pro | Val | Ile | Leu | Ala | Asp | Ala | Cys | Cys | Ser | Arg |
|---|---|---|---|---|---|---|---|---|---|---|---|---|---|---|---|
| | 210 | | | | | 215 | | | | | 220 | | | | |

| His | Asp | Ala | Lys | Ala | Glu | Thr | Lys | Lys | Leu | Ile | Asp | Leu | Thr | Gln | Phe |
|---|---|---|---|---|---|---|---|---|---|---|---|---|---|---|---|
| 225 | | | | | 230 | | | | | 235 | | | | | 240 |

| Pro | Ala | Phe | Val | Thr | Pro | Met | Gly | Lys | Gly | Ser | Ile | Asp | Glu | Lys | His |
|---|---|---|---|---|---|---|---|---|---|---|---|---|---|---|---|
| | | | | 245 | | | | | 250 | | | | | 255 | |

| Pro | Arg | Phe | Gly | Gly | Val | Tyr | Val | Gly | Thr | Leu | Ser | Ser | Pro | Ala | Val |
|---|---|---|---|---|---|---|---|---|---|---|---|---|---|---|---|
| | | | | 260 | | | | | 265 | | | | | 270 | |

| Lys | Glu | Ala | Val | Glu | Ser | Ala | Asp | Leu | Val | Leu | Ser | Val | Gly | Ala | Leu |
|---|---|---|---|---|---|---|---|---|---|---|---|---|---|---|---|
| | | 275 | | | | | 280 | | | | | 285 | | | |

| Leu | Ser | Asp | Phe | Asn | Thr | Gly | Ser | Phe | Ser | Tyr | Ser | Tyr | Lys | Thr | Lys |
|---|---|---|---|---|---|---|---|---|---|---|---|---|---|---|---|
| | 290 | | | | | 295 | | | | | 300 | | | | |

| Asn | Ile | Val | Glu | Phe | His | Ser | Asp | Tyr | Thr | Lys | Ile | Arg | Ser | Ala | Thr |
|---|---|---|---|---|---|---|---|---|---|---|---|---|---|---|---|
| 305 | | | | | 310 | | | | | 315 | | | | | 320 |

| Phe | Pro | Gly | Val | Gln | Met | Lys | Phe | Ala | Leu | Gln | Lys | Leu | Leu | Thr | Lys |
|---|---|---|---|---|---|---|---|---|---|---|---|---|---|---|---|
| | | | | 325 | | | | | 330 | | | | | 335 | |

| Val | Ala | Asp | Ala | Ala | Lys | Gly | Tyr | Lys | Pro | Val | Pro | Val | Pro | Ser | Glu |
|---|---|---|---|---|---|---|---|---|---|---|---|---|---|---|---|
| | | | 340 | | | | | 345 | | | | | 350 | | |

| Pro | Glu | His | Asn | Glu | Ala | Val | Ala | Asp | Ser | Thr | Pro | Leu | Lys | Gln | Glu |
|---|---|---|---|---|---|---|---|---|---|---|---|---|---|---|---|

```
                 355                 360                 365
Trp Val Trp Thr Gln Val Gly Glu Phe Leu Arg Glu Gly Asp Val Val
    370                 375                 380

Ile Thr Glu Thr Gly Thr Ser Ala Phe Gly Ile Asn Gln Thr His Phe
385                 390                 395                 400

Pro Asn Asn Thr Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
                420                 425                 430

Asp Pro Lys Lys Arg Val Ile Leu Phe Ile Gly Asp Gly Ser Leu Gln
                435                 440                 445

Leu Thr Val Gln Glu Ile Ser Thr Met Ile Arg Trp Gly Leu Lys Pro
    450                 455                 460

Tyr Leu Phe Val Leu Asn Asn Asp Gly Tyr Thr Ile Glu Arg Leu Ile
465                 470                 475                 480

His Gly Glu Thr Ala Gln Tyr Asn Cys Ile Gln Asn Trp Gln His Leu
                485                 490                 495

Glu Leu Leu Pro Thr Phe Gly Ala Lys Asp Tyr Glu Ala Val Arg Val
                500                 505                 510

Ser Thr Thr Gly Glu Trp Asn Lys Leu Thr Thr Asp Glu Lys Phe Gln
    515                 520                 525

Asp Asn Thr Arg Ile Arg Leu Ile Glu Val Met Leu Pro Thr Met Asp
530                 535                 540

Ala Pro Ser Asn Leu Val Lys Gln Ala Gln Leu Thr Ala Ala Thr Asn
545                 550                 555                 560

Ala Lys Asn

<210> SEQ ID NO 120
<211> LENGTH: 1689
<212> TYPE: DNA
<213> ORGANISM: Kluyveromyces lactis

<400> SEQUENCE: 120
atgtctgaaa ttacattagg tcgttacttg ttcgaaagat taaagcaagt cgaagttcaa      60
accatctttg gtctaccagg tgatttcaac ttgtccctat ggacaatat ctacgaagtc      120 ccaggtatga gatgggctgg taatgccaac gaattgaacg ctgcttacgc tgctgatggt     180
tacgccagat taaagggtat gtcctgtatc atcaccacct tcggtgtcgg tgaattgtct     240
gctttgaacg gtattgccgg ttcttacgct gaacacgttg gtgtcttgca cgttgtcggt     300
gttccatccg tctcttctca agctaagcaa ttgttgttgc accacacctt gggtaacggt     360
gacttcactg ttttccacag aatgtcctcc aacatttctg aaaccactgc tatgatcacc     420
gatatcaaca ctgccccagc tgaaatcgac agatgtatca gaaccactta cgtttcccaa     480
agaccagtct acttgggttt gccagctaac ttggtcgact tgactgtccc agcttctttg     540
ttggacactc caattgattt gagcttgaag ccaaatgacc agaagccga gaagaagtc      600 atcgaaaacg tcttgcaact gatcaaggaa gctaagaacc cagttatctt ggctgatgct     660
tgttgttcca gacacgatgc caaggctgag accaagaagt tgatcgactt gactcaattc     720
ccagccttcg ttaccccaat gggtaagggt tccattgacg aaaagcaccc aagattcggt     780
ggtgtctacg tcggtaccct atcttctcca gctgtcaagg aagccgttga atctgctgac     840
ttggttctat cggtcggtgc tctattgtcc gatttcaaca ctggttcttt ctcttactct     900
tacaagacca agaacattgt cgaattccac tctgactaca ccaagatcag aagcgctacc     960
```

```
ttcccaggtg tccaaatgaa gttcgcttta caaaaattgt tgactaaggt tgccgatgct    1020
gctaagggtt acaagccagt tccagttcca tctgaaccag aacacaacga agctgtcgct    1080
gactccactc cattgaagca agaatgggtc tggactcaag tcggtgaatt cttgagagaa    1140
ggtgatgttg ttatcactga aaccggtacc tctgccttcg gtatcaacca aactcatttc    1200
ccaaacaaca catacggtat ctctcaagtt ttatggggtt ccattggttt caccactggt    1260
gctaccttgg gtgctgcctt cgctgccgaa gaaattgatc aaagaagag agttatctta    1320 ttcattggtg acggttcttt gcaattgact gttcaagaaa tctccaccat gatcagatgg    1380
ggcttgaagc catacttgtt cgtattgaac aacgacggtt acaccattga agattgatt    1440 cacggtgaaa ccgctcaata aactgtatc caaaactggc aacacttgga attattgcca    1500
actttcggtg ccaaggacta cgaagctgtc agagtttcca ccactggtga atggaacaag    1560
ttgaccactg acgaaaagtt ccaagacaac accagaatca gattgatcga agttatgttg    1620
ccaactatgg atgctccatc taacttggtt aagcaagctc aattgactgc tgctaccaac    1680
gctaagaac                                                           1689
```

<210> SEQ ID NO 121
<211> LENGTH: 571
<212> TYPE: PRT
<213> ORGANISM: Yarrowia lipolytica

<400> SEQUENCE: 121

```
Met Ser Asp Ser Glu Pro Gln Met Val Asp Leu Gly Asp Tyr Leu Phe
1               5                   10                  15

Ala Arg Phe Lys Gln Leu Gly Val Asp Ser Val Phe Gly Val Pro Gly
            20                  25                  30

Asp Phe Asn Leu Thr Leu Leu Asp His Val Tyr Asn Val Asp Met Arg
        35                  40                  45

Trp Val Gly Asn Thr Asn Glu Leu Asn Ala Gly Tyr Ser Ala Asp Gly
    50                  55                  60

Tyr Ser Arg Val Lys Arg Leu Ala Cys Leu Val Thr Thr Phe Gly Val
65                  70                  75                  80

Gly Glu Leu Ser Ala Val Ala Val Ala Gly Ser Tyr Ala Glu His
            85                  90                  95

Val Gly Val Val His Val Gly Val Pro Ser Thr Ser Ala Glu Asn
            100                 105                 110

Lys His Leu Leu Leu His His Thr Leu Gly Asn Gly Asp Phe Arg Val
        115                 120                 125

Phe Ala Gln Met Ser Lys Leu Ile Ser Glu Tyr Thr His His Ile Glu
    130                 135                 140

Asp Pro Ser Glu Ala Ala Asp Val Ile Asp Thr Ala Ile Arg Ile Ala
145                 150                 155                 160

Tyr Thr His Gln Arg Pro Val Tyr Ile Ala Val Pro Ser Asn Phe Ser
                165                 170                 175

Glu Val Asp Ile Ala Asp Gln Ala Arg Leu Asp Thr Pro Leu Asp Leu
            180                 185                 190

Ser Leu Gln Pro Asn Asp Pro Glu Ser Gln Tyr Glu Val Ile Glu Glu
        195                 200                 205

Ile Cys Ser Arg Ile Lys Ala Ala Lys Lys Pro Val Ile Leu Val Asp
    210                 215                 220

Ala Cys Ala Ser Arg Tyr Arg Cys Val Asp Glu Thr Lys Glu Leu Ala
225                 230                 235                 240
```

Lys Ile Thr Asn Phe Ala Tyr Phe Val Thr Pro Met Gly Lys Gly Ser
                245                 250                 255

Val Asp Glu Asp Thr Asp Arg Tyr Gly Gly Thr Tyr Val Gly Ser Leu
            260                 265                 270

Thr Ala Pro Ala Thr Ala Glu Val Val Glu Thr Ala Asp Leu Ile Ile
            275                 280                 285

Ser Val Gly Ala Leu Leu Ser Asp Phe Asn Thr Gly Ser Phe Ser Tyr
        290                 295                 300

Ser Tyr Ser Thr Lys Asn Val Val Glu Leu His Ser Asp His Val Lys
305                 310                 315                 320

Ile Lys Ser Ala Thr Tyr Asn Asn Val Gly Met Lys Met Leu Phe Pro
                325                 330                 335

Pro Leu Leu Glu Ala Val Lys Lys Leu Val Ala Glu Thr Pro Asp Phe
            340                 345                 350

Ala Ser Lys Ala Leu Ala Val Pro Asp Thr Thr Pro Lys Ile Pro Glu
        355                 360                 365

Val Pro Asp Asp His Ile Thr Thr Gln Ala Trp Leu Trp Gln Arg Leu
    370                 375                 380

Ser Tyr Phe Leu Arg Pro Thr Asp Ile Val Val Thr Glu Thr Gly Thr
385                 390                 395                 400

Ser Ser Phe Gly Ile Ile Gln Thr Lys Phe Pro His Asn Val Arg Gly
                405                 410                 415

Ile Ser Gln Val Leu Trp Gly Ser Ile Gly Tyr Ser Val Gly Ala Ala
            420                 425                 430

Cys Gly Ala Ser Ile Ala Ala Gln Glu Ile Asp Pro Gln Gln Arg Val
        435                 440                 445

Ile Leu Phe Val Gly Asp Gly Ser Leu Gln Leu Thr Val Thr Glu Ile
    450                 455                 460

Ser Cys Met Ile Arg Asn Asn Val Lys Pro Tyr Ile Phe Val Leu Asn
465                 470                 475                 480

Asn Asp Gly Tyr Thr Ile Glu Arg Leu Ile His Gly Glu Asn Ala Ser
                485                 490                 495

Tyr Asn Asp Val His Met Trp Lys Tyr Ser Lys Ile Leu Asp Thr Phe
            500                 505                 510

Asn Ala Lys Ala His Glu Ser Ile Val Val Asn Thr Lys Gly Glu Met
        515                 520                 525

Asp Ala Leu Phe Asp Asn Glu Glu Phe Ala Lys Pro Asp Lys Ile Arg
    530                 535                 540

Leu Ile Glu Val Met Cys Asp Lys Met Asp Ala Pro Ala Ser Leu Ile
545                 550                 555                 560

Lys Gln Ala Glu Leu Ser Ala Lys Thr Asn Val
                565                 570

<210> SEQ ID NO 122
<211> LENGTH: 1713
<212> TYPE: DNA
<213> ORGANISM: Yarrowia lipolytica

<400> SEQUENCE: 122
atgagcgact ccgaacccca aatggtcgac ctgggcgact atctctttgc ccgattcaag     60
cagctaggcg tggactccgt ctttggagtg cccggcgact tcaacctcac cctgttggac    120
cacgtgtaca atgtcgacat gcggtgggtt gggaacacaa acgagctgaa tgccggctac    180
tcggccgacg gctactcccg ggtcaagcgg ctggcatgtc ttgtcaccac ctttggcgtg    240

```
ggagagctgt ctgccgtggc tgctgtggca ggctcgtacg ccgagcatgt gggcgtggtg      300
catgttgtgg gcgttcccag cacctctgct gagaacaagc atctgctgct gcaccacaca      360
ctcggtaacg gcgacttccg ggtctttgcc cagatgtcca aactcatctc cgagtacacc      420
caccatattg aggaccccag cgaggctgcc gacgtaatcg acaccgccat ccgaatcgcc      480
tacacccacc agcggcccgt ttacattgct gtgccctcca acttctccga ggtcgatatt      540
gccgaccagg ctagactgga taccccctg gacctttcgc tgcagcccaa cgaccccgag       600
agccagtacg aggtgattga ggagatttgc tcgcgtatca aggccgccaa gaagcccgtg      660
attctcgtcg acgcctgcgc ttcgcgatac agatgtgtgg acgagaccaa ggagctggcc      720
aagatcacca actttgccta ctttgtcact cccatgggta agggttctgt ggacgaggat      780
actgaccggt acgaggaaac atacgtcgga tcgctgactg ctcctgctac tgccgaggtg      840
gttgagacag ctgatctcat catctccgta ggagctcttc tgtcggactt caacaccggt      900
tccttctcgt actcctactc caccaaaaac gtggtggaat tgcattcgga ccacgtcaaa      960
atcaagtccg ccacctacaa caacgtcggc atgaaaatgc tgttcccgcc cctgctcgaa     1020
gccgtcaaga aactggttgc cgagacccct gactttgcat ccaaggctct ggctgttccc     1080
gacaccactc ccaagatccc cgaggtaccc gatgatcaca ttacgaccca ggcatggctg     1140
tggcagcgtc tcagttactt tctgaggccc accgacatcg tggtcaccga gaccggaacc     1200
tcgtcctttg gaatcatcca gaccaagttc ccccacaacg tccgaggtat ctcgcaggtg     1260
ctgtggggct ctattggata tcggtggga gcagcctgtg agcctccat tgctgcacag       1320
gagattgacc cccagcagcg agtgattctg tttgtgggcg acggctctct tcagctgacg     1380
gtgaccgaga tctcgtgcat gatccgcaac aacgtcaagc cgtacatttt tgtgctcaac     1440
aacgacggct acaccatcga gaggctcatt cacggcgaaa acgcctcgta caacgatgtg     1500
cacatgtgga agtactccaa gattctcgac acgttcaacg ccaaggccca cgagtcgatt     1560
gtggtcaaca ccaagggcga gatggacgct ctgttcgaca cgaagagtt tgccaagccc      1620
gacaagatcc ggctcattga ggtcatgtgc gacaagatgg acgcgcctgc ctcgttgatc     1680
aagcaggctg agctctctgc caagaccaac gtt                                  1713
```

<210> SEQ ID NO 123
<211> LENGTH: 571
<212> TYPE: PRT
<213> ORGANISM: Schizosaccharomyces pombe

<400> SEQUENCE: 123

```
Met Ser Gly Asp Ile Leu Val Gly Glu Tyr Leu Phe Lys Arg Leu Glu
1               5                   10                  15

Gln Leu Gly Val Lys Ser Ile Leu Gly Val Pro Gly Asp Phe Asn Leu
            20                  25                  30

Ala Leu Leu Asp Leu Ile Glu Lys Val Gly Asp Glu Lys Phe Arg Trp
        35                  40                  45

Val Gly Asn Thr Asn Glu Leu Asn Gly Ala Tyr Ala Ala Asp Gly Tyr
    50                  55                  60

Ala Arg Val Asn Gly Leu Ser Ala Ile Val Thr Thr Phe Gly Val Gly
65                  70                  75                  80

Glu Leu Ser Ala Ile Asn Gly Val Ala Gly Ser Tyr Ala Glu His Val
                85                  90                  95

Pro Val Val His Ile Val Gly Met Pro Ser Thr Lys Val Gln Asp Thr
            100                 105                 110
```

```
Gly Ala Leu Leu His His Thr Leu Gly Asp Gly Asp Phe Arg Thr Phe
            115                 120                 125

Met Asp Met Phe Lys Lys Val Ser Ala Tyr Ser Ile Met Ile Asp Asn
            130                 135                 140

Gly Asn Asp Ala Ala Glu Lys Ile Asp Glu Ala Leu Ser Ile Cys Tyr
145                 150                 155                 160

Lys Lys Ala Arg Pro Val Tyr Ile Gly Ile Pro Ser Asp Ala Gly Tyr
            165                 170                 175

Phe Lys Ala Ser Ser Ser Asn Leu Gly Lys Arg Leu Lys Leu Glu Glu
            180                 185                 190

Asp Thr Asn Asp Pro Ala Val Glu Gln Glu Val Ile Asn His Ile Ser
            195                 200                 205

Glu Met Val Val Asn Ala Lys Lys Pro Val Ile Leu Ile Asp Ala Cys
            210                 215                 220

Ala Val Arg His Arg Val Val Pro Glu Val His Glu Leu Ile Lys Leu
225                 230                 235                 240

Thr His Phe Pro Thr Tyr Val Thr Pro Met Gly Lys Ser Ala Ile Asp
            245                 250                 255

Glu Thr Ser Gln Phe Phe Asp Gly Val Tyr Val Gly Ser Ile Ser Asp
            260                 265                 270

Pro Glu Val Lys Asp Arg Ile Glu Ser Thr Asp Leu Leu Leu Ser Ile
            275                 280                 285

Gly Ala Leu Lys Ser Asp Phe Asn Thr Gly Ser Phe Ser Tyr His Leu
            290                 295                 300

Ser Gln Lys Asn Ala Val Glu Phe His Ser Asp His Met Arg Ile Arg
305                 310                 315                 320

Tyr Ala Leu Tyr Pro Asn Val Ala Met Lys Tyr Ile Leu Arg Lys Leu
            325                 330                 335

Leu Lys Val Leu Asp Ala Ser Met Cys His Ser Lys Ala Ala Pro Thr
            340                 345                 350

Ile Gly Tyr Asn Ile Lys Pro Lys His Ala Glu Gly Tyr Ser Ser Asn
            355                 360                 365

Glu Ile Thr His Cys Trp Phe Trp Pro Lys Phe Ser Glu Phe Leu Lys
            370                 375                 380

Pro Arg Asp Val Leu Ile Thr Glu Thr Gly Thr Ala Asn Phe Gly Val
385                 390                 395                 400

Leu Asp Cys Arg Phe Pro Lys Asp Val Thr Ala Ile Ser Gln Val Leu
            405                 410                 415

Trp Gly Ser Ile Gly Tyr Ser Val Gly Ala Met Phe Gly Ala Val Leu
            420                 425                 430

Ala Val His Asp Ser Lys Glu Pro Asp Arg Arg Thr Ile Leu Val Val
            435                 440                 445

Gly Asp Gly Ser Leu Gln Leu Thr Ile Thr Glu Ile Ser Thr Cys Ile
450                 455                 460

Arg His Asn Leu Lys Pro Ile Ile Phe Ile Ile Asn Asn Asp Gly Tyr
465                 470                 475                 480

Thr Ile Glu Arg Leu Ile His Gly Leu His Ala Ser Tyr Asn Glu Ile
            485                 490                 495

Asn Thr Lys Trp Gly Tyr Gln Gln Ile Pro Lys Phe Gly Ala Ala
            500                 505                 510

Glu Asn His Phe Arg Thr Tyr Cys Val Lys Thr Pro Asp Val Glu
            515                 520                 525
```

Lys Leu Phe Ser Asp Lys Glu Phe Ala Asn Ala Asp Val Ile Gln Val
            530                 535                 540

Val Glu Leu Val Met Pro Met Leu Asp Ala Pro Arg Val Leu Val Glu
545                 550                 555                 560

Gln Ala Lys Leu Thr Ser Lys Ile Asn Lys Gln
            565                 570

<210> SEQ ID NO 124
<211> LENGTH: 1713
<212> TYPE: DNA
<213> ORGANISM: Schizosaccharomyces pombe

<400> SEQUENCE: 124

| | | | | | |
|---|---|---|---|---|---|
| atgagtgggg | atattttagt | cggtgaatat | ctattcaaaa | ggcttgaaca | attaggggtc | 60 |
| aagtccattc | ttggtgttcc | aggagatttc | aatttagctc | tacttgactt | aattgagaaa | 120 |
| gttggagatg | agaaatttcg | ttgggttggc | aataccaatg | agttgaatgg | tgcttatgcc | 180 |
| gctgatggtt | atgctcgtgt | taatggtctt | tcagccattg | ttacaacgtt | cggcgtggga | 240 |
| gagctttccg | ctattaatgg | agtggcaggt | tcttatgcgg | agcatgtccc | agtagttcat | 300 |
| attgttggaa | tgccttccac | aaaggtgcaa | gatactggag | ctttgcttca | tcatacttta | 360 |
| ggagatggag | actttcgcac | tttcatggat | atgtttaaga | agtttctgc | ctacagtata | 420 |
| atgatcgata | acgaaacga | tgcagctgaa | aagatcgatg | aagccttgtc | gatttgttat | 480 |
| aaaaaggcta | ggcctgttta | cattggtatt | ccttctgatg | ctggctactt | caaagcatct | 540 |
| tcatcaaatc | ttgggaaaag | actaaagctc | gaggaggata | ctaacgatcc | agcagttgag | 600 |
| caagaagtca | tcaatcatat | ctcggaaatg | gttgtcaatg | caaagaaacc | agtgattta | 660 |
| attgacgctt | gtgctgtaag | acatcgtgtc | gttccagaag | tacatgagct | gattaaattg | 720 |
| acccatttcc | ctacatatgt | aactcccatg | ggtaaatctg | caattgacga | aacttcgcaa | 780 |
| ttttttgacg | gcgtttatgt | tggttcaatt | tcagatcctg | aagttaaaga | cagaattgaa | 840 |
| tccactgatc | tgttgctatc | catcggtgct | ctcaaatcag | actttaacac | gggttccttc | 900 |
| tcttaccacc | tcagccaaaa | gaatgccgtt | gagtttcatt | cagaccacat | gcgcattcga | 960 |
| tatgctcttt | atccaaatgt | agccatgaag | tatattcttc | gcaaactgtt | gaaagtactt | 1020 |
| gatgcttcta | tgtgtcattc | caaggctgct | cctaccattg | gctacaacat | caagcctaag | 1080 |
| catgcggaag | gatattcttc | caacgagatt | actcattgct | ggttttggcc | taaatttagt | 1140 |
| gaattttga | agccccgaga | tgttttgatc | accgagactg | gaactgcaaa | ctttggtgtc | 1200 |
| cttgattgca | ggtttccaaa | ggatgtaaca | gccattccc | aggtattatg | gggatctatt | 1260 |
| ggatactccg | ttggtgcaat | gtttggtgct | gttttggccg | tccacgattc | taaagagccc | 1320 |
| gatcgtcgta | ccattcttgt | agtaggtgat | ggatccttac | aactgacgat | tacagagatt | 1380 |
| tcaacctgca | ttcgccataa | cctcaaacca | attattttca | taattaacaa | cgacggttac | 1440 |
| accattgagc | gttaattca | tggtttgcat | gctagctata | acgaaattaa | cactaaatgg | 1500 |
| ggctaccaac | agattcccaa | gttttcgga | gctgctgaaa | accacttccg | cacttactgt | 1560 |
| gttaaaactc | ctactgacgt | tgaaaagttg | tttagcgaca | aggagtttgc | aaatgcagat | 1620 |
| gtcattcaag | tagttgagct | tgtaatgcct | atgttggatg | cacctcgtgt | cctagttgag | 1680 |
| caagccaagt | tgacgtctaa | gatcaataag | caa | | | 1713 |

<210> SEQ ID NO 125
<211> LENGTH: 563
<212> TYPE: PRT

<213> ORGANISM: Zygosaccharomyces rouxii

<400> SEQUENCE: 125

Met Ser Glu Ile Thr Leu Gly Arg Tyr Leu Phe Glu Arg Leu Lys Gln
1               5                   10                  15

Val Asp Thr Asn Thr Ile Phe Gly Val Pro Gly Asp Phe Asn Leu Ser
            20                  25                  30

Leu Leu Asp Lys Val Tyr Glu Val Gln Gly Leu Arg Trp Ala Gly Asn
        35                  40                  45

Ala Asn Glu Leu Asn Ala Ala Tyr Ala Ala Asp Gly Tyr Ala Arg Val
    50                  55                  60

Lys Gly Leu Ala Ala Leu Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Ile Val Gly Val Pro Ser Val Ser Ser Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Leu Thr Asp Ile Thr Ala
    130                 135                 140

Ala Pro Ala Glu Ile Asp Arg Cys Ile Arg Val Ala Tyr Val Asn Gln
145                 150                 155                 160

Arg Pro Val Tyr Leu Gly Leu Pro Ala Asn Leu Val Asp Gln Lys Val
                165                 170                 175

Pro Ala Ser Leu Leu Asn Thr Pro Ile Asp Leu Ser Leu Lys Glu Asn
            180                 185                 190

Asp Pro Glu Ala Glu Thr Glu Val Val Asp Thr Val Leu Glu Leu Ile
        195                 200                 205

Lys Glu Ala Lys Asn Pro Val Ile Leu Ala Asp Ala Cys Cys Ser Arg
    210                 215                 220

His Asp Val Lys Ala Glu Thr Lys Lys Leu Ile Asp Leu Thr Gln Phe
225                 230                 235                 240

Pro Ser Phe Val Thr Pro Met Gly Lys Gly Ser Ile Asp Glu Gln Asn
                245                 250                 255

Pro Arg Phe Gly Gly Val Tyr Val Gly Thr Leu Ser Ser Pro Glu Val
            260                 265                 270

Lys Glu Ala Val Glu Ser Ala Asp Leu Val Leu Ser Val Gly Ala Leu
        275                 280                 285

Leu Ser Asp Phe Asn Thr Gly Ser Phe Ser Tyr Ser Tyr Lys Thr Lys
    290                 295                 300

Asn Val Val Glu Phe His Ser Asp His Ile Lys Ile Arg Asn Ala Thr
305                 310                 315                 320

Phe Pro Gly Val Gln Met Lys Phe Val Leu Lys Lys Leu Leu Gln Ala
                325                 330                 335

Val Pro Glu Ala Val Lys Asn Tyr Lys Pro Gly Pro Val Pro Ala Pro
            340                 345                 350

Pro Ser Pro Asn Ala Glu Val Ala Asp Ser Thr Thr Leu Lys Gln Glu
        355                 360                 365

Trp Leu Trp Arg Gln Val Gly Ser Phe Leu Arg Glu Gly Asp Val Val
    370                 375                 380

Ile Thr Glu Thr Gly Thr Ser Ala Phe Gly Ile Asn Gln Thr His Phe
385                 390                 395                 400

```
Pro Asn Gln Thr Tyr Gly Ile Ser Gln Val Leu Trp Gly Ser Ile Gly
                405                 410                 415
Tyr Thr Thr Gly Ser Thr Leu Gly Ala Ala Phe Ala Ala Glu Glu Ile
            420                 425                 430
Asp Pro Lys Lys Arg Val Ile Leu Phe Ile Gly Asp Gly Ser Leu Gln
            435                 440                 445
Leu Thr Val Gln Glu Ile Ser Thr Met Ile Arg Trp Gly Leu Lys Pro
450                 455                 460
Tyr Leu Phe Val Leu Asn Asn Asp Gly Tyr Thr Ile Glu Arg Leu Ile
465                 470                 475                 480
His Gly Glu Thr Ala Glu Tyr Asn Cys Ile Gln Pro Trp Lys His Leu
                485                 490                 495
Glu Leu Leu Asn Thr Phe Gly Ala Lys Asp Tyr Glu Asn His Arg Val
            500                 505                 510
Ser Thr Val Gly Glu Trp Asn Lys Leu Thr Gln Asp Pro Lys Phe Asn
            515                 520                 525
Glu Asn Ser Arg Ile Arg Met Ile Glu Val Met Leu Glu Val Met Asp
530                 535                 540
Ala Pro Ser Ser Leu Val Ala Gln Ala Gln Leu Thr Ala Ala Thr Asn
545                 550                 555                 560
Ala Lys Gln

<210> SEQ ID NO 126
<211> LENGTH: 1689
<212> TYPE: DNA
<213> ORGANISM: Zygosaccharomyces rouxii

<400> SEQUENCE: 126
atgtctgaaa ttactctagg tcgttacttg ttcgaaagat taaagcaagt tgacactaac    60
accatcttcg gtgttccagg tgacttcaac ttgtccttgt tggacaaggt ctacgaagtg   120
caaggtctaa gatgggctgg taacgctaac gaattgaacg ctgcctacgc tgctgacggt   180
tacgccagag ttaagggttt ggctgctttg atcaccacct tcggtgtcgg tgaattgtct   240
gctttgaacg gtattgcagg ttcttacgct gaacacgttg gtgttttgca cattgttggt   300
gttccatctg tctcttctca agctaagcaa ttgttgttgc accacacctt gggtaacggt   360
gacttcactg ttttccacag aatgtccgcc aacatctctg aaaccaccgc tatgttgacc   420
gacatcactg ctgctccagc tgaaattgac cgttgcatca gagttgctta cgtcaaccaa   480
agaccagtct acttgggtct accagctaac ttggttgacc aaaaggtccc agcttctttg   540
ttgaacactc caattgatct atctctaaag gagaacgacc cagaagctga accgaagtt    600
gttgacaccg ttttggaatt gatcaaggaa gctaagaacc cagttatctt ggctgatgct   660
tgctgctcca gacacgacgt caaggctgaa accaagaagt tgatcgactt gactcaattc   720
ccatctttcg ttactcctat gggtaagggt tccatcgacg aacaaaaccc aagattcggt   780
ggtgtctacg tcggtactct atccagccca gaagttaagg aagctgttga atctgctgac   840
ttggttctat ctgtcggtgc tctattgtcc gatttcaaca ctggttcttt ctcttactct   900
tacaagacca gaacgttgt tgaattccac tctgaccaca tcaagatcag aaacgctacc   960
ttcccaggtg ttcaaatgaa attcgttttg aagaaactat gcaagctgt cccagaagct  1020
gtcaagaact acaagccagg tccagtccca gctccgccat ctccaaacgc tgaagttgct  1080
gactctacca ccttgaagca agaatggtta tggagacaag tcggtagctt cttgagagaa  1140
ggtgatgttg ttattaccga aactggtacc tctgctttcg gtatcaacca aactcacttc  1200
```

```
cctaaccaaa cttacggtat ctctcaagtc ttgtggggtt ctattggtta caccactggt    1260
tccactttgg gtgctgcctt cgctgctgaa gaaattgacc ctaagaagag agttatcttg    1320
ttcattggtg acggttctct acaattgacc gttcaagaaa tctccaccat gatcagatgg    1380
ggtctaaagc catacttgtt cgttttgaac aacgatggtt acaccattga agattgatt    1440 cacggtgaaa ccgctgaata caactgtatc caaccatgga agcacttgga attgttgaac    1500
accttcggtg ccaaggacta cgaaaaccac agagtctcca ctgtcggtga atggaacaag    1560
ttgactcaag atccaaaatt caacgaaaac tctagaatta gaatgatcga agttatgctt    1620
gaagtcatgg acgctccatc ttctttggtc gctcaagctc aattgaccgc tgctactaac    1680
gctaagcaa                                                            1689
```

<210> SEQ ID NO 127
<211> LENGTH: 267
<212> TYPE: PRT
<213> ORGANISM: Saccharomyces cerevisiae

<400> SEQUENCE: 127

```
Met Ser Gln Gly Arg Lys Ala Ala Glu Arg Leu Ala Lys Lys Thr Val
1               5                   10                  15

Leu Ile Thr Gly Ala Ser Ala Gly Ile Gly Lys Ala Thr Ala Leu Glu
            20                  25                  30

Tyr Leu Glu Ala Ser Asn Gly Asp Met Lys Leu Ile Leu Ala Ala Arg
        35                  40                  45

Arg Leu Glu Lys Leu Glu Glu Leu Lys Lys Thr Ile Asp Gln Glu Phe
    50                  55                  60

Pro Asn Ala Lys Val His Val Ala Gln Leu Asp Ile Thr Gln Ala Glu
65                  70                  75                  80

Lys Ile Lys Pro Phe Ile Glu Asn Leu Pro Gln Glu Phe Lys Asp Ile
                85                  90                  95

Asp Ile Leu Val Asn Asn Ala Gly Lys Ala Leu Gly Ser Asp Arg Val
            100                 105                 110

Gly Gln Ile Ala Thr Glu Asp Ile Gln Asp Val Phe Asp Thr Asn Val
        115                 120                 125

Thr Ala Leu Ile Asn Ile Thr Gln Ala Val Leu Pro Ile Phe Gln Ala
    130                 135                 140

Lys Asn Ser Gly Asp Ile Val Asn Leu Gly Ser Ile Ala Gly Arg Asp
145                 150                 155                 160

Ala Tyr Pro Thr Gly Ser Ile Tyr Cys Ala Ser Lys Phe Ala Val Gly
                165                 170                 175

Ala Phe Thr Asp Ser Leu Arg Lys Glu Leu Ile Asn Thr Lys Ile Arg
            180                 185                 190

Val Ile Leu Ile Ala Pro Gly Leu Val Glu Thr Glu Phe Ser Leu Val
        195                 200                 205

Arg Tyr Arg Gly Asn Glu Glu Gln Ala Lys Asn Val Tyr Lys Asp Thr
    210                 215                 220

Thr Pro Leu Met Ala Asp Asp Val Ala Asp Leu Ile Val Tyr Ala Thr
225                 230                 235                 240

Ser Arg Lys Gln Asn Thr Val Ile Ala Asp Thr Leu Ile Phe Pro Thr
                245                 250                 255

Asn Gln Ala Ser Pro His His Ile Phe Arg Gly
            260                 265
```

<210> SEQ ID NO 128
<211> LENGTH: 804
<212> TYPE: DNA
<213> ORGANISM: Saccharomyces cerevisiae

<400> SEQUENCE: 128

| | |
|---|---|
| atgtcccaag gtagaaaagc tgcagaaaga ttggctaaga agactgtcct cattacaggt | 60 |
| gcatctgctg gtattggtaa ggcgaccgca ttagagtact tggaggcatc caatggtgat | 120 |
| atgaaactga tcttggctgc tagaagatta gaaaagctcg aggaattgaa gaagaccatt | 180 |
| gatcaagagt ttccaaacgc aaaagttcat gtggcccagc tggatatcac tcaagcagaa | 240 |
| aaaatcaagc ccttcattga aacttgcca aagagttca aggatattga cattctggtg | 300 |
| aacaatgccg aaaggctct tggcagtgac cgtgtgggcc agatcgcaac ggaggatatc | 360 |
| caggacgtgt ttgacaccaa cgtcacggct ttaatcaata tcacacaagc tgtactgccc | 420 |
| atattccaag ccaagaattc aggagatatt gtaaatttgg ttcaatcgc tggcagagac | 480 |
| gcatacccaa caggttctat ctattgtgcc tctaagtttg ccgtgggggc gttcactgat | 540 |
| agtttgagaa aggagctcat caacactaaa attagagtca ttctaattgc accagggcta | 600 |
| gtcgagactg aattttcact agttagatac agaggtaacg aggaacaagc caagaatgtt | 660 |
| tacaaggata ctaccccatt gatggctgat gacgtggctg atctgatcgt ctatgcaact | 720 |
| tccagaaaac aaaatactgt aattgcagac actttaatct ttccaacaaa ccaagcgtca | 780 |
| cctcatcata tcttccgtgg ataa | 804 |

<210> SEQ ID NO 129
<211> LENGTH: 12298
<212> TYPE: DNA
<213> ORGANISM: Artificial Sequence
<220> FEATURE:
<223> OTHER INFORMATION: Plasmid pLH804::L2V4

<400> SEQUENCE: 129

| | |
|---|---|
| tcccattacc gacatttggg cgctatacgt gcatatgttc atgtatgtat ctgtatttaa | 60 |
| aacactttg tattatttt cctcatatat gtgtataggt ttatacggat gatttaatta | 120 |
| ttacttcacc acccttatt tcaggctgat atcttagcct tgttactaga ttaatcatgt | 180 |
| aattagttat gtcacgctta cattcacgcc ctcccccac atccgctcta accgaaaagg | 240 |
| aaggagttag acaacctgaa gtctaggtcc ctatttatt ttttatagtt atgttagtat | 300 |
| taagaacgtt atttatattt caaattttc ttttttttct gtacagacgc gtgtacgcat | 360 |
| gtaacattat actgaaaacc ttgcttgaga aggttttggg acgctcgaag gctttaattt | 420 |
| gcgggcggcc gcacctggta aaacctctag tggagtagta gatgtaatca atgaagcgga | 480 |
| agccaaaaga ccagagtaga ggcctataga agaaactgcg ataccttttg tgatggctaa | 540 |
| acaaacagac atcttttat atgtttttac ttctgtatat cgtgaagtag taagtgataa | 600 |
| gcgaatttgg ctaagaacgt tgtaagtgaa caagggacct cttttgcctt tcaaaaaagg | 660 |
| attaaatgga gttaatcatt gagatttagt tttcgttaga ttctgtatcc ctaaataact | 720 |
| cccttacccg acgggaaggc acaaaagact tgaataatag caaacggcca gtagccaaga | 780 |
| ccaaataata ctagagttaa ctgatggtct taaacaggca ttacgtggtg aactccaaga | 840 |
| ccaatataca aaatatcgat aagttattct tgcccaccaa tttaaggagc ctacatcagg | 900 |
| acagtagtac cattcctcag agaagaggta tacataacaa gaaaatcgcg tgaacacctt | 960 |
| atataactta gcccgttatt gagctaaaaa accttgcaaa atttcctatg aataagaata | 1020 |

```
cttcagacgt gataaaaatt tactttctaa ctcttctcac gctgccccta tctgttcttc    1080
cgctctaccg tgagaaataa agcatcgagt acggcagttc gctgtcactg aactaaaaca    1140
ataaggctag ttcgaatgat gaacttgctt gctgtcaaac ttctgagttg ccgctgatgt    1200
gacactgtga caataaattc aaaccggtta tagcggtctc ctccggtacc ggttctgcca    1260
cctccaatag agctcagtag gagtcagaac ctctgcggtg gctgtcagtg actcatccgc    1320
gtttcgtaag ttgtgcgcgt gcacatttcg cccgttcccg ctcatcttgc agcaggcgga    1380
aattttcatc acgctgtagg acgcaaaaaa aaaataatta atcgtacaag aatcttggaa    1440
aaaaaattga aaattttgt ataaaaggga tgacctaact tgactcaatg gcttttacac    1500
ccagtatttt ccctttcctt gtttgttaca attatagaag caagacaaaa acatatagac    1560
aacctattcc taggagttat attttttac cctaccagca atataagtaa aaaactgttt    1620
aaacagtatg gaagaatgta agatggctaa gatttactac caagaagact gtaacttgtc    1680
cttgttggat ggtaagacta tcgccgttat cggttacggt tctcaaggtc acgctcatgc    1740
cctgaatgct aaggaatccg gttgtaacgt tatcattggt ttatacgaag gtgcggagga    1800
gtggaaaaga gctgaagaac aaggtttcga agtctcacac gctgctgaag ctgctaagaa    1860
ggctgacatc attatgatct tgatcccaga tgaaaagcag gctaccatgt acaaaaacga    1920
catcgaacca aacttggaag ccggtaacat gttgatgttc gctcacggtt tcaacatcca    1980
tttcggttgt attgttccac caaggacgt tgatgtcact atgatcgctc caaagggtcc    2040
aggtcacacc gttagatccg aatacgaaga aggtaaaggt gtcccatgct tggttgctgt    2100
cgaacaagac gctactggca aggctttgga tatggctttg gcctacgctt tagccatcgg    2160
tggtgctaga gccggtgtct tggaaactac cttcagaacc gaaactgaaa ccgacttgtt    2220
cggtgaacaa gctgttttat gtggtggtgt ctgcgctttg atgcaggccg ttttgaaac    2280 cttggttgaa gccggttacg acccaagaaa cgcttacttc gaatgtatcc acgaaatgaa    2340
gttgatcgtt gacttgatct accaatctgg tttctccggt atgcgttact ctatctccaa    2400
cactgctgaa tacggtgact acattaccgg tccaaagatc attactgaag ataccaagaa    2460
ggctatgaag aagattttgt ctgacattca agatggtacc tttgccaagg acttcttggt    2520
tgacatgtct gatgctggtt cccaggtcca cttcaaggct atgagaaagt ggcctccga    2580 acacccagct gaagttgtcg gtgaagaaat tagatccttg tactcctggt ccgacgaaga    2640
caagttgatt aacaactgag gccctgcagg ccagaggaaa ataatatcaa gtgctggaaa    2700 cttttctct tggaattttt gcaacatcaa gtcatagtca attgaattga cccaatttca    2760
catttaagat tttttttttt tcatccgaca tacatctgta cactaggaag ccctgttttt    2820
ctgaagcagc ttcaaatata tatttttt acatatttat tatgattcaa tgaacaatct    2880
aattaaatcg aaaacaagaa ccgaaacgcg aataaataat ttatttagat ggtgacaagt    2940
gtataagtcc tcatcgggac agctacgatt tctctttcgg ttttggctga gctactggtt    3000
gctgtgacgc agcggcatta gcgcggcgtt atgagctacc ctcgtggcct gaaagatggc    3060
gggaataaag cggaactaaa aattactgac tgagccatat tgaggtcaat tgtcaactc    3120 gtcaagtcac gttggtgga cggcccctt ccaacgaatc gtatatacta acatgcgcgc    3180
gcttcctata tacacatata catatatata tatatatata tgtgtgcgtg tatgtgtaca    3240
cctgtattta atttccttac tcgcgggttt ttcttttttc tcaattcttg gcttcctctt    3300
tctcgagcgg accggatcct cgcgaactcc aaaatgagct atcaaaaacg atagatcgat    3360
taggatgact ttgaaatgac tccgcagtgg actggccgtt aatttcaagc gtgagtaaaa    3420
```

```
tagtgcatga caaaagatga gctaggcttt tgtaaaaata tcttacgttg taaaatttta    3480
gaaatcatta tttccttcat atcattttgt cattgacctt cagaagaaaa gagccgacca    3540
ataatataaa taaataaata aaaataatat tccattattt ctaaacagat tcaatactca    3600
ttaaaaaact atatcaatta atttgaatta acttaattaa ttatttttg ccagtttctt     3660
caggcttcca aaagtctgtt acggctcccc tagaagcaga cgaaacgatg tgagcatatt    3720
taccaaggat accgcgtgaa tagagcggtg gcaattcaat ggtctcttga cgatgtttta    3780
actcttcatc ggagatatca aagtgtaatt ccttagtgtc ttggtcaata gtgactatgt    3840
ctcctgtttg caggtaggcg attggaccgc catcttgtgc ttcaggagcg atatgaccca    3900
cgacaagacc ataagtacca cctgagaagc ggccatctgt cagaagggca acttttttcac   3960
cttgcccttt accaacaatc attgatgaaa gggaaagcat ttcaggcata ccaggaccgc    4020
cctttggtcc tacaaaacgt acgacaacaa catcaccatc aacaatatca tcattcaaga    4080
cagcttcaat ggcttcttct tcagaattaa agaccttagc aggaccgaca tgacgacgca    4140
cttttacacc agaaactttg gcaacggcac cgtctggagc caagttacca tggagaataa    4200
tgaccggacc atcttcacgt ttaggatttt caagcggcat aataaccttt tgaccaggtg    4260
ttaaatcatc aaaagccttc aaattttcag cgactgtttt gccagtacaa gtgatacggt    4320
caccatgaag gaagccattt ttaaggagat atttcataac tgctggtacc cctccgacct    4380
tgtaaaggtc ttggaataca tattgaccag aaggtttcaa atcagccaaa tgaggaactt    4440
tttcttggaa agtattgaaa tcatcaagtg tcaattccac attagcagca tgggcaatag    4500
ctaagaggtg aagggttgag ttggttgaac ctcccagagc catagttaca gtaatagcat    4560
cttcaaaagc ttcacgcgtt aaaatgtcag aaggttttaa gcccatttcg agcattttga    4620
caacagcgcg accagcttct tcaatatctg cttttctttc tgcggattca gccgggtgag    4680
aagatgaacc cggaaggcta agtcccaaaa cttcaatagc tgtcgccatt gtgttagcag    4740
tatacatacc accgcagcct ccaggaccgg gacaagcatt acattccaaa gctttaactt    4800
cttctttggt catatcgccg tggttccaat ggccgacacc ttcaaagaca gagactaaat    4860
cgatatcttt gccgtctaaa ttaccaggtg caattgttcc gccgtaagca aaaatggctg    4920
ggatatccat gttagccata gcgataacag aaccgggcat gttttttatca caaccgccaa   4980
tggctacaaa agcatccgca ttatgacctc ccatggctgc ttcaatagaa tctgcaataa    5040
tatcacgaga tgtcaaggag aaacgcattc cttgggttcc catggcgatt ccatcagaaa    5100
ccgtgattgt tccgaactga actggccaag caccagcttc cttaacaccg actttggcta    5160
gtttaccaaa gtcatgtaag tggatattac aaggtgtgtt ttcagcccaa gttgaaatga    5220
caccgacgat aggtttttca aagtcttcat cttgcatacc agttgcacgc aacatagcac    5280
gattaggtga tttaaccatt gaatcgtaaa cagaactacg atttcttaag tctttaagag    5340
ttttttttgtc agtcatactc acgtgaaact tagattagat tgctatgctt tctttccaat    5400
gagcaagaag taaaaaaagt tgtaatagaa caggaaaaat gaagctgaaa cttgagaaat    5460
tgaagaccgt ttgttaactc aaatatcaat gggaggtcgt cgaaagaaa caaaatcgaa     5520
aaaaagttt tcaagagaaa gaaacgtgat aaaaatttt attgccttct ccgacgaaga     5580
aaaagggacg aggcggtctc ttttccttt tccaaacctt tagtacgggt aattaacggc     5640
acccctagagag aaggaggagg gggaatttag tatgctgtgc ttgggtgttt tgaagtggta  5700
cggcggtgcg cggagtccga gaaaatctgg aagagtaaaa aaggagtaga gacatttga    5760
```

```
agctatgccg gcagatctat ttaaatggcg cgccgacgtc aggtggcact tttcggggaa    5820
atgtgcgcgg aacccctatt tgtttatttt tctaaataca ttcaaatatg tatccgctca    5880
tgagacaata accctgataa atgcttcaat aatattgaaa aaggaagagt atgagtattc    5940
aacatttccg tgtcgccctt attccctttt tgcggcatt tgccttcct gtttttgctc     6000 acccagaaac gctggtgaaa gtaaaagatg ctgaagatca gttgggtgca cgagtgggtt    6060
acatcgaact ggatctcaac agcggtaaga tccttgagag ttttcgcccc gaagaacgtt    6120
ttccaatgat gagcactttt aaagttctgc tatgtggcgc ggtattatcc cgtattgacg    6180
ccgggcaaga gcaactcggt cgccgcatac actattctca gaatgacttg gttgagtact    6240
caccagtcac agaaaagcat cttacggatg gcatgacagt aagagaatta tgcagtgctg    6300
ccataaccat gagtgataac actgcggcca acttacttct gacaacgatc ggaggaccga    6360
aggagctaac cgcttttttg cacaacatgg gggatcatgt aactcgcctt gatcgttggg    6420
aaccggagct gaatgaagcc ataccaaacg acgagcgtga caccacgatg cctgtagcaa    6480
tggcaacaac gttgcgcaaa ctattaactg gcgaactact tactctagct tcccggcaac    6540
aattaataga ctggatggag gcggataaag ttgcaggacc acttctgcgc tcggcccttc    6600
cggctggctg gtttattgct gataaatctg gagccggtga gcgtgggtct cgcggtatca    6660
ttgcagcact ggggccagat ggtaagccct cccgtatcgt agttatctac acgacgggga    6720
gtcaggcaac tatggatgaa cgaaatagac agatcgctga gataggtgcc tcactgatta    6780
agcattggta actgtcagac caagtttact catatatact ttagattgat ttaaaacttc    6840
atttttaatt taaaaggatc taggtgaaga tccttttga taatctcatg accaaaatcc    6900
cttaacgtga gttttcgttc cactgagcgt cagaccccgt agaaaagatc aaaggatctt    6960
cttgagatcc tttttttctg cgcgtaatct gctgcttgca acaaaaaaa ccaccgctac    7020 cagcggtggt ttgtttgccg gatcaagagc taccaactct ttttccgaag gtaactggct    7080
tcagcagagc gcagatacca atactgttc ttctagtgta gccgtagtta ggccaccact    7140
tcaagaactc tgtagcaccg cctacatacc tcgctctgct aatcctgtta ccagtggctg    7200
ctgccagtgg cgataagtcg tgtcttaccg ggttggactc aagacgatag ttaccggata    7260
aggcgcagcg gtcgggctga acggggggtt cgtgcacaca gcccagcttg gagcgaacga    7320
cctacaccga actgagatac ctacagcgtg agctatgaga aagcgccacg cttcccgaag    7380
ggagaaaggc ggacaggtat ccggtaagcg gcagggtcgg aacaggagag cgcacgaggg    7440
agcttccagg gggaaacgcc tggtatcttt atagtcctgt cgggtttcgc cacctctgac    7500
ttgagcgtcg atttttgtga tgctcgtcag ggggggcggag cctatggaaa aacgccagca    7560
acgcggcctt tttacggttc ctggcctttt gctggccttt tgctcacatg ttctttcctg    7620
cgttatcccc tgattctgtg gataaccgta ttaccgcctt tgagtgagct gataccgctc    7680
gccgcagccg aacgaccgag cgcagcgagt cagtgagcga ggaagcggaa gagcgcccaa    7740
tacgcaaacc gcctctcccc gcgcgttggc cgattcatta atgcagctgg cacgacaggt    7800
ttcccgactg gaaagcgggc agtgagcgca acgcaattaa tgtgagttag ctcactcatt    7860 aggcaccca ggctttacac tttatgcttc cggctcgtat gttgtgtgga attgtgagcg    7920
gataacaatt tcacacagga aacagctatg accatgatta cgccaagctt ttctttccca    7980 atttttttt tttcgtcatt ataaaaatca ttacgaccga gattcccggg taataactga    8040
tataattaaa ttgaagctct aatttgtgag tttagtatac atgcatttac ttataataca    8100
gttttttagt tttgctggcc gcatcttctc aaatatgctt cccagcctgc ttttctgtaa    8160
```

```
cgttcaccct ctaccttagc atcccttccc tttgcaaata gtcctcttcc aacaataata   8220
atgtcagatc ctgtagagac cacatcatcc acggttctat actgttgacc caatgcgtct   8280
cccttgtcat ctaaacccac accgggtgtc ataatcaacc aatcgtaacc ttcatctctt   8340
ccacccatgt ctctttgagc aataaagccg ataacaaaat ctttgtcgct cttcgcaatg   8400
tcaacagtac ccttagtata ttctccagta gatagggagc ccttgcatga caattctgct   8460
aacatcaaaa ggcctctagg ttcctttgtt acttcttctg ccgcctgctt caaaccgcta   8520
acaatacctg ggcccaccac accgtgtgca ttcgtaatgt ctgcccattc tgctattctg   8580
tatacacccg cagagtactg caatttgact gtattaccaa tgtcagcaaa ttttctgtct   8640
tcgaagagta aaaaattgta cttggcggat aatgccttta gcggcttaac tgtgccctcc   8700
atggaaaaat cagtcaagat atccacatgt gttttagta aacaaatttt gggacctaat    8760
gcttcaacta actccagtaa ttccttggtg gtacgaacat ccaatgaagc acacaagttt   8820
gtttgctttt cgtgcatgat attaaatagc ttggcagcaa caggactagg atgagtagca   8880
gcacgttcct tatatgtagc tttcgacatg atttatcttc gtttcctgca ggttttgtt    8940 ctgtgcagtt gggttaagaa tactgggcaa tttcatgttt cttcaacact acatatgcgt   9000
atatatacca atctaagtct gtgctccttc cttcgttctt ccttctgttc ggagattacc   9060
gaatcaaaaa aatttcaagg aaaccgaaat caaaaaaaag aataaaaaaa aaatgatgaa   9120
ttgaaaagct tgcatgcctg caggtcgact ctagtatact ccgtctactg tacgatacac   9180
ttccgctcag gtccttgtcc tttaacgagg ccttaccact cttttgttac tctattgatc   9240
cagctcagca aaggcagtgt gatctaagat tctatcttcg cgatgtagta aaactagcta   9300
gaccgagaaa gagactagaa atgcaaaagg cacttctaca atggctgcca tcattattat   9360
ccgatgtgac gctgcatttt tttttttttt tttttttttt tttttttttt tttttttttt   9420 tttttttttgt acaaatatca taaaaaaaga gaatctttttt aagcaaggat tttcttaact   9480
tcttcggcga cagcatcacc gacttcggtg gtactgttgg aaccacctaa atcaccagtt   9540
ctgatacctg catccaaaac cttttttaact gcatcttcaa tggctttacc ttcttcaggc   9600
aagttcaatg acaatttcaa catcattgca gcagacaaga tagtggcgat agggttgacc   9660
ttattctttg gcaaatctgg agcggaacca tggcatggtt cgtacaaacc aaatgcggtg   9720
ttcttgtctg gcaaagaggc caaggacgca gatggcaaca acccaagga gcctgggata   9780 acggaggctt catcggagat gatatcacca aacatgttgc tggtgattat aataccattt   9840
aggtgggttg ggttcttaac taggatcatg gcggcagaat caatcaattg atgttgaact   9900
ttcaatgtag ggaattcgtt cttgatggtt tcctccacag ttttctcca taatcttgaa    9960 gaggccaaaa cattagcttt atccaaggac caaataggca atggtggctc atgttgtagg  10020
gccatgaaag cggccattct tgtgattctt tgcacttctg gaacggtgta ttgttcacta  10080
tcccaagcga caccatcacc atcgtcttcc tttctcttac caaagtaaat acctcccact  10140
aattctctaa caacaacgaa gtcagtacct ttagcaaatt gtggcttgat tggagataag  10200
tctaaaagag agtcggatgc aaagttacat ggtcttaagt tggcgtacaa ttgaagttct  10260
ttacggattt ttagtaaacc ttgttcaggt ctaacactac cggtacccca tttaggacca  10320
cccacagcac ctaacaaaac ggcatcagcc ttcttggagg cttccagcgc ctcatctgga  10380
agtggaacac ctgtagcatc gatagcagca ccaccaatta aatgattttc gaatcgaac   10440 ttgacattgg aacgaacatc agaaatagct ttaagaacct taatggcttc ggctgtgatt  10500
```

| | | | | | |
|---|---|---|---|---|---|
| tcttgaccaa | cgtggtcacc | tggcaaaacg | acgatcttct | taggggcaga | cattacaatg | 10560 |
| gtatatcctt | gaatatata | taaaaaaaaa | aaaaaaaaaa | aaaaaaaaaa | atgcagcttc | 10620 |
| tcaatgatat | tcgaatacgc | tttgaggaga | tacagcctaa | tatccgacaa | actgttttac | 10680 |
| agatttacga | tcgtacttgt | tacccatcat | tgaattttga | acatccgaac | ctgggagttt | 10740 |
| tccctgaaac | agatagtata | tttgaacctg | tataataata | tatagtctag | cgctttacgg | 10800 |
| aagacaatgt | atgtatttcg | gttcctggag | aaactattgc | atctattgca | taggtaatct | 10860 |
| tgcacgtcgc | atccccggtt | catttttctgc | gtttccatct | tgcacttcaa | tagcatatct | 10920 |
| ttgttaacga | agcatctgtg | cttcattttg | tagaacaaaa | atgcaacgcg | agagcgctaa | 10980 |
| ttttttcaaac | aaagaatctg | agctgcattt | ttacagaaca | gaaatgcaac | gcgaaagcgc | 11040 |
| tattttacca | acgaagaatc | tgtgcttcat | ttttgtaaaa | caaaaatgca | acgcgagagc | 11100 |
| gctaattttt | caaacaaaga | atctgagctg | cattttttaca | gaacagaaat | gcaacgcgag | 11160 |
| agcgctattt | taccaacaaa | gaatctatac | ttcttttttg | ttctacaaaa | atgcatcccg | 11220 |
| agagcgctat | ttttctaaca | aagcatctta | gattactttt | tttctccttt | gtgcgctcta | 11280 |
| taatgcagtc | tcttgataac | ttttgcact | gtaggtccgt | taaggttaga | agaaggctac | 11340 |
| tttggtgtct | atttttctctt | ccataaaaaa | agcctgactc | cacttcccgc | gtttactgat | 11400 |
| tactagcgaa | gctgcgggtg | cattttttca | agataaaggc | atccccgatt | atattctata | 11460 |
| ccgatgtgga | ttgcgcatac | tttgtgaaca | gaaagtgata | gcgttgatga | ttcttcattg | 11520 |
| gtcagaaaat | tatgaacggt | ttcttctatt | ttgtctctat | atactacgta | taggaaatgt | 11580 |
| ttacattttc | gtattgtttt | cgattcactc | tatgaatagt | tcttactaca | attttttttgt | 11640 |
| ctaaagagta | atactagaga | taaacataaa | aaatgtagag | gtcgagttta | gatgcaagtt | 11700 |
| caaggagcga | aaggtggatg | ggtaggttat | atagggatat | agcacagaga | tatatagcaa | 11760 |
| agagatactt | ttgagcaatg | tttgtggaag | cggtattcgc | aatattttag | tagctcgtta | 11820 |
| cagtccggtg | cgtttttggt | tttttgaaag | tgcgtcttca | gagcgctttt | ggttttcaaa | 11880 |
| agcgctctga | agttcctata | cttttctagag | aataggaact | tcggaatagg | aacttcaaag | 11940 |
| cgtttccgaa | aacgagcgct | tccgaaaatg | caacgcgagc | tgcgcacata | cagctcactg | 12000 |
| ttcacgtcgc | acctatatct | gcgtgttgcc | tgtatatata | tacatgag | aagaacggca | 12060 |
| tagtgcgtgt | ttatgcttaa | atgcgtactt | atatgcgtct | atttatgtag | gatgaaaggt | 12120 |
| agtctagtac | ctcctgtgat | attatcccat | tccatgcggg | gtatcgtatg | cttccttcag | 12180 |
| cactacccttt | tagctgttct | atatgctgcc | actcctcaat | tggattagtc | tcatccttca | 12240 |
| atgctatcat | ttcctttgat | attggatcat | atgcatagta | ccgagaaact | agaggatc | 12298 |

<210> SEQ ID NO 130
<211> LENGTH: 11013
<212> TYPE: DNA
<213> ORGANISM: Artificial Sequence
<220> FEATURE:
<223> OTHER INFORMATION: Plasmid pRS413::BiADH-kivD

<400> SEQUENCE: 130

| | | | | | |
|---|---|---|---|---|---|
| tcgcgcgttt | cggtgatgac | ggtgaaaacc | tctgacacat | gcagctcccg | gagacggtca | 60 |
| cagcttgtct | gtaagcggat | gccggagca | gacaagcccg | tcagggcgcg | tcagcgcgtg | 120 |
| ttggcgggtg | tcgggctgg | cttaactatg | cggcatcaga | gcagattgta | ctgagagtgc | 180 |
| accataaaatt | cccgttttaa | gagcttggtg | agcgctagga | gtcactgcca | ggtatcgttt | 240 |
| gaacacggca | ttagtcaggg | aagtcataac | acagtccttt | cccgcaattt | tctttttcta | 300 |

```
ttactcttgg cctcctctag tacactctat attttttat gcctcggtaa tgattttcat     360
ttttttttt cccctagcgg atgactcttt ttttttctta gcgattggca ttatcacata     420
atgaattata cattatataa agtaatgtga tttcttcgaa gaatatacta aaaaatgagc    480
aggcaagata aacgaaggca aagatgacag agcagaaagc cctagtaaag cgtattacaa    540
atgaaaccaa gattcagatt gcgatctctt taaagggtgg tcccctagcg atagagcact    600
cgatcttccc agaaaaagag gcagaagcag tagcagaaca ggccacacaa tcgcaagtga    660
ttaacgtcca cacaggtata gggtttctgg accatatgat acatgctctg ccaagcatt    720
ccggctggtc gctaatcgtt gagtgcattg gtgacttaca catagacgac catcacacca    780
ctgaagactg cgggattgct ctcggtcaag cttttaaaga ggccctactg gcgcgtggag    840
taaaaaggtt tggatcagga tttgcgcctt tggatgaggc actttccaga gcggtggtag    900
atctttcgaa caggccgtac gcagttgtcg aacttggttt gcaaagggag aaagtaggag    960
atctctcttg cgagatgatc ccgcattttc ttgaaagctt tgcagaggct agcagaatta   1020
ccctccacgt tgattgtctg cgaggcaaga atgatcatca ccgtagtgag agtgcgttca   1080
aggctcttgc ggttgccata agagaagcca cctcgcccaa tggtaccaac gatgttccct   1140
ccaccaaagg tgttcttatg tagtgacacc gattatttaa agctgcagca tacgatatat   1200
atacatgtgt atatatgtat acctatgaat gtcagtaagt atgtatacga acagtatgat   1260
actgaagatg acaaggtaat gcatcattct atacgtgtca ttctgaacga ggcgcgcttt   1320
ccttttttct ttttgctttt tcttttttt tctcttgaac tcgacggatc tatgcggtgt   1380
gaaataccgc acagatgcgt aaggagaaaa taccgcatca ggaaattgta aacgttaata   1440
ttttgttaaa attcgcgtta aattttgtt aaatcagctc attttttaac caataggccg   1500
aaatcggcaa aatcccttat aaatcaaaag aatagaccga gatagggttg agtgttgttc   1560
cagtttggaa caagagtcca ctattaaaga acgtggactc caacgtcaaa gggcgaaaaa   1620
ccgtctatca gggcgatggc ccactacgtg aaccatcacc ctaatcaagt ttttgggt    1680
cgaggtgccg taaagcacta aatcggaacc ctaaagggag cccccgattt agagcttgac   1740
ggggaaagcc ggcgaacgtg gcgagaaagg aaggaagaa agcgaaagga gcgggcgcta   1800
gggcgctggc aagtgtagcg gtcacgctgc gcgtaaccac cacacccgcc gcgcttaatg   1860
cgccgctaca gggcgcgtcg cgccattcgc cattcaggct gcgcaactgt tgggaagggc   1920
gatcggtgcg ggcctcttcg ctattacgcc agctggcgaa aggggatgt gctgcaaggc   1980
gattaagttg ggtaacgcca gggttttccc agtcacgacg ttgtaaaacg acggccagtg   2040
agcgcgcgta atacgactca ctatagggcg aattgggtac cgggccccc ctgtacgcat   2100
gtaacattat actgaaaacc ttgcttgaga aggttttggg acgctcgaag ctttaatttt   2160
cctgcaggaa ttaccgtcgc tcgtgatttg tttgcaaaaa gaacaaaact gaaaaaaccc   2220
agacacgctc gacttcctgt cttcctattg attgcagctt ccaatttcgt cacacaacaa   2280
ggtcctgtcg acgcctactt ggcttcacat acgttgcata cgtcgatata gataataatg   2340
ataatgacag caggattatc gtaatacgta atagttgaaa atctcaaaaa tgtgtgggtc   2400
attacgtaaa taatgatagg aatgggattc ttctattttt cctttttcca ttctagcagc   2460
cgtcgggaaa acgtggcatc ctctctttcg ggctcaattg gagtcacgct gccgtgagca   2520
tcctctcttt ccatatctaa caactgagca cgtaaccaat ggaaaagcat gagcttagcg   2580
ttgctccaaa aaagtattgg atggttaata ccatttgtct gttctcttct gactttgact   2640
```

```
cctcaaaaaa aaaaaatcta caatcaacag atcgcttcaa ttacgccctc acaaaaactt    2700
ttttccttct tcttcgccca cgttaaattt tatccctcat gttgtctaac ggatttctgc    2760
acttgattta ttataaaaag acaaagacat aatacttctc tatcaatttc agttattgtt    2820
cttccttgcg ttattcttct gttcttcttt ttcttttgtc atatataacc ataaccaagt    2880
aatacatatt caagtttaaa catgtatacc gtaggacagt acttggtaga tagactagaa    2940
gagattggta tcgataaggt tttcggtgtg ccagggatt acaatttgac ttttctagat     3000
tacattcaaa atcacgaagg actttcctgg caagggaata ctaatgaact aaacgcagca    3060
tatgcagcag atggctacgc ccgtgaaaga ggcgtatcag ctcttgttac tacattcgga    3120
gtgggtgaac tgtcagccat taacggaaca gctggtagtt ttgcagaaca agtccctgtc    3180
atccacatcg tgggttctcc aactatgaat gtgcaatcca acaaaaagct ggttcatcat    3240
tccttaggaa tgggtaactt tcataacttt agtgaaatgg ctaaggaagt cactgccgct    3300
acaaccatgc ttactgaaga gaatgcagct tcagagatcg acagagtatt agaaacagcc    3360
ttgttggaaa agaggccagt atacatcaat cttccaattg atatagctca taaagcaata    3420
gttaaacctg caaaagcact acaaacagag aaatcatctg gtgagagaga ggcacaactt    3480
gcagaaatca tactatcaca cttagaaaag gccgctcaac ctatcgtaat cgccggtcat    3540
gagatcgccc gtttccagat aagagaaaga tttgaaaact ggataaacca aacaaagttg    3600
ccagtaacca atttggcata tggcaaaggc tctttcaatg aagagaacga acatttcatt    3660
ggtacctatt acccagcttt ttctgacaaa aacgttctgg attacgttga caatagtgac    3720
ttcgttttac attttggtgg gaaaatcatt gacaattcta cctcctcatt ttctcaaggc    3780
tttaagactg aaaacacttt aaccgctgca aatgacatca ttatgctgcc agatgggtct    3840
acttactctg ggatttctct taacggtctt ttggcagagc tggaaaaact aaactttact    3900
tttgctgata ctgctgctaa acaagctgaa ttagctgttt tcgaaccaca ggccgaaaca    3960
ccactaaagc aagacagatt tcaccaagct gttatgaact ttttgcaagc tgatgatgtg    4020
ttggtcactg agcaggggac atcatctttc ggtttgatgt tggcacctct gaaaaagggt    4080
atgaatttga tcagtcaaac attatggggc tccataggat acacattacc tgctatgatt    4140
ggttcacaaa ttgctgcccc agaaaggaga cacattctat ccatcggtga tggatctttt    4200
caactgacag cacaggaaat gtccaccatc ttcagagaga aattgacacc agtgatattc    4260
attatcaata cgatggcta cagtcgaa agagccatcc atggagagga tgagagttac      4320
aatgatatac caacttggaa cttgcaatta gttgctgaaa catttggtgg tgatgccgaa    4380
actgtcgaca ctcacaacgt tttcacagaa acagacttcg ctaatacttt agctgctatc    4440
gatgctactc ctcaaaaagc acatgtcgtt gaagttcata tggaacaaat ggatatgcca    4500
gaatcattga gacagattgg cttagcctta tctaagcaaa actcttaacc tgcagggccg    4560
tgaatttact ttaaatcttg catttaaata aattttcttt ttatagcttt atgacttagt    4620
ttcaatttat atactatttt aatgacattt tcgattcatt gattgaaagc tttgtgtttt    4680
ttcttgatgc gctattgcat tgttcttgtc ttttcgcca catgtaatat ctgtagtaga    4740
tacctgatac attgtggatg ctgagtgaaa ttttagttaa taatgagc gctcttaata    4800
attttgggga tattggcttt ttttttaaa gtttacaaat gaatttttc cgccaggata     4860
acgattctga agttactctt agcgttccta tcggtacagc catcaaatca tgcctataaa    4920
tcatgcctat atttgcgtgc agtcagtatc atctacatga aaaaaactcc cgcaatttct    4980
tatagaatac gttgaaaatt aaatgtacgc gccaagataa gataacatat atctagatgc    5040
```

```
agtaatatac acagattccc gcggacgtgg gaaggaaaaa attagataac aaaatctgag   5100
tgatatggaa attccgctgt atagctcata tcttccccta cctggtaaaa cctctagtgg   5160
agtagtagat gtaatcaatg aagcggaagc caaaagacca gagtagaggc ctatagaaga   5220
aactgcgata ccttttgtga tggctaaaca aacagacatc tttttatatg tttttacttc   5280
tgtatatcgt gaagtagtaa gtgataagcg aatttggcta agaacgttgt aagtgaacaa   5340
gggacctctt ttgcctttca aaaaggatt aaatggagtt aatcattgag atttagtttt     5400
cgttagattc tgtatcccta ataactccc ttacccgacg ggaaggcaca aaagacttga     5460
ataatagcaa acgccagta gccaagacca aataatacta gagttaactg atggtcttaa    5520
acaggcatta cgtggtgaac tccaagacca atatacaaaa tatcgataag ttattcttgc   5580
ccaccaattt aaggagccta catcaggaca gtagtaccat tcctcagaga agaggtatac   5640
ataacaagaa atcgcgtga acaccttata taacttagcc cgttattgag ctaaaaaacc    5700
ttgcaaaatt tcctatgaat aagaatactt cagacgtgat aaaaatttac tttctaactc   5760
ttctcacgct gccctatct gttcttccgc tctaccgtga gaaataaagc atcgagtacg     5820
gcagttcgct gtcactgaac taaaacaata aggctagttc gaatgatgaa cttgcttgct   5880
gtcaaacttc tgagttgccg ctgatgtgac actgtgacaa taaattcaaa ccggttatag   5940
cggtctcctc cggtaccggt tctgccacct ccaatagagc tcccgcacgc cgaaatgcat   6000
gcaagtaacc tattcaaagt aatatctcat acatgtttca tgagggtaac aacatgcgac   6060
tgggtgagca tatgttccgc tgatgtgatg tgcaagataa acaagcaagg cagaaactaa   6120
cttcttcttc atgtaataaa cacaccccgc gtttatttac ctatctctaa acttcaacac   6180
cttatatcat aactaatatt tcttgagata agcacactgc acccataccc tccttaaaaa   6240
cgtagcttcc agtttttggt ggttccggct tccttcccga ttccgcccgc taaacgcata   6300
tttttgttgc ctggtggcat ttgcaaaatg cataacctat gcatttaaaa gattatgtat   6360
gctcttctga cttttcgtgt gatgaggctc gtggaaaaaa tgaataattt atgaatttga   6420
gaacaatttt gtgttgttac ggtatttac tatggaataa tcaatcaatt gaggatttta    6480
tgcaaatatc gtttgaatat ttttccgacc ctttgagtac ttttcttcat aattgcataa   6540
tattgtccgc tgccccttt tctgttagac ggtgtcttga tctacttgct atcgttcaac    6600 accacttat tttctaacta ttttttttt agctcatttg aatcagctta tggtgatggc      6660 acattttgc ataaacctag ctgtcctcgt tgaacatagg aaaaaaat atataaacaa      6720 ggctctttca ctctccttgc aatcagattt gggtttgttc cctttatttt catatttctt    6780
gtcatattcc tttctcaatt attattttct actcataacc tcacgcaaaa taacacagtc   6840
aaatcaatca aaatgaaagc attagtgtat aggggcccag gccagaagtt ggtggaagag   6900
agacagaagc cagagcttaa ggaacctggt gacgctatag tgaaggtaac aaagactaca   6960
atttgcggaa ccgatctaca cattcttaaa ggtgacgttg cgacttgtaa acccggtcgt   7020
gtattagggc atgaaggagt gggggttatt gaatcagtcg gatctggggt tactgctttc   7080
caaccaggcg atagagtttt gatatcatgt atatcgagtt gcggaaagtg ctcatttgt    7140 agaagaggaa tgttcagtca ctgtacgacc ggggttgga ttctgggcaa cgaaattgat    7200
ggtacccaag cagagtacgt aagagtacca catgctgaca catcccttta tcgtattccg   7260
gcaggtgcgg atgaagaggc cttagtcatg ttatcagata ttctaccaac gggttttgag   7320
tgcggagtcc taaacggcaa agtcgcacct ggttcttcgg tggctatagt aggtgctggt   7380
```

```
cccgttggtt tggccgcctt actgacagca caattctact ccccagctga atcataatg    7440
atcgatcttg atgataacag gctgggatta gccaaacaat ttggtgccac cagaacagta    7500
aactccacgg gtggtaacgc cgcagccgaa gtgaaagctc ttactgaagg cttaggtgtt    7560
gatactgcga ttgaagcagt tgggatacct gctacatttg aattgtgtca gaatatcgta    7620
gctcccggtg aactatcgc  taatgtcggc gttcacggta gcaaagttga tttgcatctt    7680
gaaagtttat ggtcccataa tgtcacgatt actacaaggt tggttgacac ggctaccacc    7740
ccgatgttac tgaaaactgt tcaaagtcac aagctagatc catctagatt gataacacat    7800
agattcagcc tggaccagat cttggacgca tatgaaactt ttggccaagc tgcgtctact    7860
caagcactaa aagtcatcat ttcgatggag gcttgattaa ttaagagtaa gcgaatttct    7920
tatgatttat gattttatt  attaaataag ttataaaaaa aataagtgta tacaaatttt    7980
aaagtgactc ttaggtttta aaacgaaaat tcttattctt gagtaactct ttcctgtagg    8040
tcaggttgct ttctcaggta tagcatgagg tcgctcttat tgaccacacc tctaccggca    8100
tgccgagcaa atgcctgcaa atcgctcccc atttcaccca attgtagata tgctaactcc    8160
agcaatgagt tgatgaatct cggtgtgtat tttatgtcct cagaggacaa cacctgtggt    8220
gagctccagc ttttgttccc tttagtgagg gttaattgcg cgcttggcgt aatcatggtc    8280
atagctgttt cctgtgtgaa attgttatcc gctcacaatt ccacacaaca taggagccgg    8340
aagcataaag tgtaaagcct ggggtgccta atgagtgagg taactcacat taattgcgtt    8400
gcgctcactg cccgctttcc agtcgggaaa cctgtcgtgc cagctgcatt aatgaatcgg    8460
ccaacgcgcg gggagaggcg gtttgcgtat tgggcgctct tccgcttcct cgctcactga    8520
ctcgctgcgc tcggtcgttc ggctgcggcg agcggtatca gctcactcaa aggcggtaat    8580
acggttatcc acagaatcag gggataacgc aggaaagaac atgtgagcaa aaggccagca    8640
aaaggccagg aaccgtaaaa aggccgcgtt gctggcgttt ttccataggc tccgcccccc    8700
tgacgagcat cacaaaaatc gacgctcaag tcagaggtgg cgaaacccga caggactata    8760
aagataccag gcgtttcccc ctggaagctc cctcgtgcgc tctcctgttc cgaccctgcc    8820
gcttaccgga tacctgtccg cctttctccc ttcgggaagc gtggcgcttt ctcatagctc    8880
acgctgtagg tatctcagtt cggtgtaggt cgttcgctcc aagctgggct gtgtgcacga    8940
accccccgtt cagcccgacc gctgcgcctt atccggtaac tatcgtcttg agtccaaccc    9000
ggtaagacac gacttatcgc cactggcagc agccactggt aacaggatta gcagagcgag    9060
gtatgtaggc ggtgctacag agttcttgaa gtggtggcct aactacggct acactagaag    9120
gacagtattt ggtatctgcg ctctgctgaa gccagttacc ttcggaaaaa gagttggtag    9180
ctcttgatcc ggcaaacaaa ccaccgctgg tagcggtggt ttttttgttt gcaagcagca    9240
gattacgcgc agaaaaaaag gatctcaaga agatcctttg atcttttcta cggggtctga    9300
cgctcagtgg aacgaaaact cacgttaagg gattttggtc atgagattat caaaaaggat    9360
cttcacctag atccttttaa attaaaaatg aagttttaaa tcaatctaaa gtatatatga    9420
gtaaacttgg tctgacagtt accaatgctt aatcagtgag gcacctatct cagcgatctg    9480
tctatttcgt tcatccatag ttgcctgact ccccgtcgtg tagataacta cgatacggga    9540
gggcttacca tctggcccca gtgctgcaat gataccgcga cccacgct caccggctcc    9600
agatttatca gcaataaacc agccagccgg aagggccgag cgcagaagtg gtcctgcaac    9660
tttatccgcc tccatccagt ctattaattg ttgccgggaa gctagagtaa gtagttcgcc    9720
agttaatagt ttgcgcaacg ttgttgccat tgctacaggc atcgtggtgt cacgctcgtc    9780
```

```
gtttggtatg gcttcattca gctccggttc ccaacgatca aggcgagtta catgatcccc   9840
catgttgtgc aaaaaagcgg ttagctcctt cggtcctccg atcgttgtca gaagtaagtt   9900
ggccgcagtg ttatcactca tggttatggc agcactgcat aattctctta ctgtcatgcc   9960
atccgtaaga tgcttttctg tgactggtga gtactcaacc aagtcattct gagaatagtg  10020
tatgcggcga ccgagttgct cttgcccggc gtcaatacgg gataataccg cgccacatag  10080
cagaacttta aaagtgctca tcattggaaa acgttcttcg gggcgaaaac tctcaaggat  10140
cttaccgctg ttgagatcca gttcgatgta acccactcgt gcacccaact gatcttcagc  10200
atcttttact tcaccagcg tttctgggtg agcaaaaaca ggaaggcaaa atgccgcaaa  10260
aaagggaata agggcgacac ggaaatgttg aatactcata ctcttccttt ttcaatatta  10320
ttgaagcatt tatcagggtt attgtctcat gagcggatac atatttgaat gtatttagaa  10380
aaataaacaa ataggggttc cgcgcacatt tccccgaaaa gtgccacctg gtccttttc   10440 atcacgtgct ataaaaataa ttataattta aattttttaa tataaatata taaattaaaa  10500
atagaaagta aaaaagaaa ttaaagaaaa aatagttttt gttttccgaa gatgtaaaag  10560
actctagggg gatcgccaac aaatactacc tttatcttg ctcttcctgc tctcaggtat  10620
taatgccgaa ttgtttcatc ttgtctgtgt agaagaccac acacgaaaat cctgtgattt  10680
tacattttac ttatcgttaa tcgaatgtat atctatttaa tctgcttttc ttgtctaata  10740
aatatatatg taaagtacgc ttttgttga aatttttaa accttgttt atttttttt     10800 cttcattccg taactcttct accttcttta tttactttct aaaatccaaa tacaaaacat  10860
aaaaataaat aaacacagag taaattccca aattattcca tcattaaaag atacgaggcg  10920
cgtgtaagtt acaggcaagc gatccgtcct aagaaaccat tattatcatg acattaacct  10980
ataaaaatag gcgtatcacg aggccctttc gtc                              11013
```

<210> SEQ ID NO 131
<211> LENGTH: 12319
<212> TYPE: DNA
<213> ORGANISM: Artificial Sequence
<220> FEATURE:
<223> OTHER INFORMATION: Plasmid pHR81::ILV5p-K9JB4P

<400> SEQUENCE: 131

```
tcccattacc gacatttggg cgctatacgt gcatatgttc atgtatgtat ctgtatttaa     60 aacactttg tattatttt cctcatatat gtgtataggt ttatacggat gatttaatta    120
ttacttcacc acccttttatt tcaggctgat atcttagcct tgttactaga ttaatcatgt    180
aattagttat gtcacgctta cattcacgcc ctccccccac atccgctcta accgaaaagg    240
aaggagttag acaacctgaa gtctaggtcc ctatttattt tttatagtt atgttagtat    300 taagaacgtt atttatattt caaattttc tttttttct gtacagacgc gtgtacgcat    360
gtaacattat actgaaaacc ttgcttgaga aggttttggg acgctcgaag gctttaattt    420
gcgggcggcc gcacctggta aaacctctag tggagtagta gatgtaatca atgaagcgga    480
agccaaaaga ccagagtaga ggcctataga agaaactgcg ataccttttg tgatggctaa    540
acaaacagac atctttttat atgttttac ttctgtatat cgtgaagtag taagtgataa    600
gcgaatttgg ctaagaacgt tgtaagtgaa caagggacct cttttgcctt tcaaaaagg    660 attaaatgga gttaatcatt gagatttagt tttcgttaga ttctgtatcc ctaaataact    720
cccttacccg acgggaaggc acaaaagact tgaataataag caaacggcca gtagccaaga    780
```

```
ccaaataata ctagagttaa ctgatggtct taaacaggca ttacgtggtg aactccaaga    840
ccaatataca aaatatcgat aagttattct tgcccaccaa tttaaggagc ctacatcagg    900
acagtagtac cattcctcag agaagaggta tacataacaa gaaaatcgcg tgaacacctt    960
atataactta gcccgttatt gagctaaaaa accttgcaaa atttcctatg aataagaata   1020
cttcagacgt gataaaaatt tactttctaa ctcttctcac gctgcccta tctgttcttc    1080 cgctctaccg tgagaaataa agcatcgagt acggcagttc gctgtcactg aactaaaaca   1140
ataaggctag ttcgaatgat gaacttgctt gctgtcaaac ttctgagttg ccgctgatgt   1200
gacactgtga caataaattc aaaccggtta tagcggtctc ctccggtacc ggttctgcca   1260
cctccaatag agctcagtag gagtcagaac ctctgcggtg gctgtcagtg actcatccgc   1320
gtttcgtaag ttgtgcgcgt gcacatttcg cccgttccg ctcatcttgc agcaggcgga    1380
aattttcatc acgctgtagg acgcaaaaaa aaaataatta atcgtacaag aatcttggaa   1440
aaaaaattga aaattttgt ataaagggga tgacctaact tgactcaatg gcttttacac    1500
ccagtatttt cccttccctt gtttgttaca attatagaag caagacaaaa acatatagac   1560
aacctattcc taggagttat atttttttac cctaccagca ataaagtaa aaaactgttt    1620 aaacagtatg gaagaatgta agatggctaa gatttactac caagaagact gtaacttgtc   1680
cttgttggat ggtaagacta tcgccgttat cggttacggt tctcaaggtc acgctcatgc   1740
cctgaatgct aaggaatccg gttgtaacgt tatcattggt ttatacgaag gtgcggagga   1800
gtggaaaaga gctgaagaac aaggtttcga agtctacacc gctgctgaag ctgctaagaa   1860
ggctgacatc attatgatct tgatcccaga tgaaaagcag gctaccatgt acaaaaacga   1920
catcgaacca aacttggaag ccggtaacat gttgatgttc gctcacggtt tcaacatcca   1980
tttcggttgt attgttccac caaaggacgt tgatgtcact atgatcgctc caagggtcc    2040 aggtcacacc gttagatccg aatacgaaga aggtaaaggt gtcccatgct tggttgctgt   2100
cgaacaagac gctactggca aggctttgga tatggctttg cctacgctt agccatcgg    2160 tggtgctaga gccggtgtct tggaaactac cttcagaacc gaaactgaaa ccgacttgtt   2220
cggtgaacaa gctgttttat gtggtggtgt ctgcgctttg atgcaggccg ttttgaaac    2280 cttggttgaa gccggttacg acccaagaaa cgcttacttc gaatgtatcc acgaaatgaa   2340
gttgatcgtt gacttgatct accaatctgg tttctccggt atgcgttact ctatctccaa   2400
cactgctgaa tacggtgact acattaccgg tccaaagatc attactgaag ataccaagaa   2460
ggctatgaag aagattttgt ctgacattca agatggtacc tttgccaagg acttcttggt   2520
tgacatgtct gatgctggtt cccaggtcca cttcaaggct atgagaaagt ggcctccga    2580 acacccagct gaagttgtcg gtgaagaaat tagatccttg tactcctggt ccgacgaaga   2640
caagttgatt aacaactgag gccctgcagg ccagaggaaa ataatatcaa gtgctggaaa   2700 cttttttctct tggaattttt gcaacatcaa gtcatagtca attgaattga cccaatttca   2760
catttaagat ttttttttt tcatccgaca tacatctgta cactaggaag ccctgttttt   2820
ctgaagcagc ttcaaatata tattttttt acatatttat tatgattcaa tgaacaatct   2880
aattaaatcg aaaacaagaa ccgaaacgcg aataaataat ttatttagat ggtgacaagt   2940
gtataagtcc tcatcgggac agctacgatt tctctttcgg ttttggctga ctactggtt   3000 gctgtgacgc agcggcatta gcgcggcgtt atgagctacc ctcgtggcct gaaagatggc   3060
gggaataaag cggaactaaa aattactgac tgagccatat tgaggtcaat ttgtcaactc   3120
gtcaagtcac gtttggtgga cggccccttt ccaacgaatc gtatatacta acatgcgcgc   3180
```

```
gcttcctata tacacatata catatatata tatatatata tgtgtgcgtg tatgtgtaca    3240
cctgtattta atttccttac tcgcgggttt ttcttttttc tcaattcttg gcttcctctt    3300
tctcgagcgg accggatcct cgcgaactcc aaaatgagct atcaaaaacg atagatcgat    3360
taggatgact ttgaaatgac tccgcagtgg actggccgtt aatttcaagc gtgagtaaaa    3420
tagtgcatga caaagatga gctaggcttt tgtaaaaata tcttacgttg taaaatttta    3480
gaaatcatta tttccttcat atcatttgt cattgacctt cagaagaaaa gagccgacca    3540
ataatataaa taaataaata aaaataatat tccattattt ctaaacagat tcaatactca    3600
ttaaaaaact atatcaatta atttgaatta acgcggccgc ttaaccacag caaccaggac    3660 aacattttt gccagtttct tcaggcttcc aaaagtctgt tacggctccc ctagaagcag    3720
acgaaacgat gtgagcatat ttaccaagga taccgcgtga atagagcggt ggcaattcaa    3780
tggtctcttg acgatgtttt aactcttcat cggagatatc aaagtgtaat tccttagtgt    3840
cttggtcaat agtgactatg tctcctgttt gcaggtaggc gattggaccg ccatcttgtg    3900
cttcaggagc gatatgaccc acgacaagac cataagtacc acctgagaag cggccatctg    3960
tcagaagggc aacttttttca ccttgcccctt taccaacaat cattgatgaa agggaaagca    4020
tttcaggcat accaggaccg ccctttggtc ctacaaaacg tacgacaaca acatcaccat    4080
caacaatatc atcattcaag acagcttcaa tggcttcttc ttcagaatta aagaccttag    4140
caggaccgac atgacgacgc acttttacac cagaaacttt ggcaacggca ccgtctggag    4200
ccaagttacc atggagaata atgagcggac catcttcacg tttaggattt tcaagcggca    4260
taataacctt ttgaccaggt gttaaatcat caaaagcctt caaattttca gcgactgttt    4320
tgccagtaca agtgatacgg tcaccatgaa ggaagccatt tttaaggaga tatttcataa    4380
ctgctggtac ccctccgacc ttgtaaaggt cttggaatac atattgacca gaaggtttca    4440
aatcagccaa atgaggaact ttttcttgga aagtattgaa atcatcaagt gtcaattcca    4500 cattgcagc atgggcaata gctaagaggt gaagggttga gttggttgaa cctcccagag    4560
ccatagttac agtaatagca tcttcaaaag cttcacgcgt taaatgtca gaaggtttta    4620 agcccatttc gagcattttg acaacagcgc gaccagcttc ttcaatatct gctttctttt    4680
ctgcggattc agccgggtga gaagatgaac ccggaaggct aagtcccaaa acttcaatag    4740
ctgtcgccat tgtgttagca gtatacatac caccgcagcc tccaggaccg ggacaagcat    4800
tacattccaa gctttaaact tcttctttgg tcatatcgcc gtggttccaa tggccgacac    4860
cttcaaagac agagactaaa tcgatatctt tgccgtctaa attaccaggt gcaattgttc    4920
cgccgtaagc aaaaatggct gggatatcca tgttagccat agcgataaca gaaccgggca    4980 tgttttttatc acaaccgcca atggctacaa aagcatccgc attatgacct cccatggctg    5040
cttcaataga atctgcaata atatcacgag atgtcaagga gaaacgcatt ccttgggttc    5100
ccatggcgat tccatcagaa accgtgattg ttccgaactg aactggccaa gcaccagctt    5160
ccttaacacc gactttggct agtttaccaa agtcatgtaa gtggatatta caaggtgtgt    5220
tttcagccca agttgaaatg acaccgacga taggttttc aaagtcttca tcttgcatac    5280
cagttgcacg caacatagca cgattaggtg atttaaccat tgaatcgtaa acagaactac    5340
gatttcttaa gtctttaaga gttttttttgt cagtcatact cacgtgaaac ttagattaga    5400
ttgctatgct ttctttccaa tgagcaagaa gtaaaaaaag ttgtaataga acaggaaaaa    5460
tgaagctgaa acttgagaaa ttgaagaccg tttgttaact caaatatcaa tgggaggtcg    5520
```

```
tcgaaagaga acaaaatcga aaaaaaagtt ttcaagagaa agaaacgtga taaaaatttt     5580
tattgccttc tccgacgaag aaaaagggac gaggcggtct cttttttcctt ttccaaacct     5640 ttagtacggg taattaacgg caccctagag gaaggaggag ggggaattta gtatgctgtg     5700
cttgggtgtt ttgaagtggt acggcggtgc gcggagtccg agaaaatctg aagagtaaa      5760 aaaggagtag agacattttg aagctatgcc ggcagatcta tttaaatggc gcgccgacgt     5820
caggtggcac ttttcgggga aatgtgcgcg gaaccCctat ttgtttattt ttctaaatac     5880
attcaaatat gtatccgctc atgagacaat aaccctgata aatgcttcaa taatattgaa     5940
aaaggaagag tatgagtatt caacattccc gtgtcgccct tattcccttt tttgcggcat     6000
tttgccttcc tgtttttgct cacccagaaa cgctggtgaa agtaaaagat gctgaagatc     6060
agttgggtgc acgagtgggt tacatcgaac tggatctcaa cagcggtaag atccttgaga     6120
gttttcgccc cgaagaacgt tttccaatga tgagcacttt taaagttctg ctatgtggcg     6180
cggtattatc ccgtattgac gccgggcaag agcaactcgg tcgccgcata cactattctc     6240
agaatgactt ggttgagtac tcaccagtca cagaaaagca tcttacggat ggcatgacag     6300
taagagaatt atgcagtgct gccataacca tgagtgataa cactgcggcc aacttacttc     6360
tgacaacgat cggaggaccg aaggagctaa ccgcttttt gcacaacatg ggggatcatg      6420
taactcgcct tgatcgttgg gaaccggagc tgaatgaagc cataccaaac gacgagcgtg     6480
acaccacgat gcctgtagca atggcaacaa cgttgcgcaa actattaact ggcgaactac     6540
ttactctagc ttcccggcaa caattaatag actggatgga ggcggataaa gttgcaggac     6600
cacttctgcg ctcggccctt ccggctggct ggtttattgc tgataaatct ggagccggtg     6660
agcgtgggtc tcgcggtatc attgcagcac tggggccaga tggtaagccc tcccgtatcg     6720
tagttatcta cacgacgggg agtcaggcaa ctatggatga acgaaataga cagatcgctg     6780
agataggtgc ctcactgatt aagcattggt aactgtcaga ccaagtttac tcatatatac     6840
tttagattga tttaaaactt cattttaat ttaaaaggat ctaggtgaag atccttttg       6900 ataatctcat gaccaaaatc ccttaacgtg agttttcgtt ccactgagcg tcagaccccg     6960
tagaaaagat caaaggatct tcttgagatc cttttttct gcgcgtaatc tgctgcttgc      7020
aaacaaaaaa accaccgcta ccagcggtgg tttgtttgcc ggatcaagag ctaccaactc     7080 ttttttccgaa ggtaactggc ttcagcagag cgcagatacc aaatactgtt cttctagtgt    7140
agccgtagtt aggccaccac ttcaagaact ctgtagcacc gcctacatac ctcgctctgc     7200
taatcctgtt accagtggct gctgccagtg gcgataagtc gtgtcttacc gggttggact     7260
caagacgata gttaccggat aaggcgcagc ggtcgggctg aacggggggt tcgtgcacac     7320
agcccagctt ggagcgaacg acctacaccg aactgagata cctacagcgt gagctatgag     7380
aaagcgccac gcttcccgaa gggagaaagg cggacaggta tccggtaagc ggcagggtcg     7440
gaacaggaga gcgcacgagg gagcttccag ggggaaacgc ctggtatctt tatagtcctg     7500
tcgggtttcg ccacctctga cttgagcgtc gatttttgtg atgctcgtca ggggggcgga     7560
gcctatggaa aaacgccagc aacgcggcct ttttacggtt cctggccttt tgctggcctt     7620
ttgctcacat gttctttcct gcgttatccc ctgattctgt ggataaccgt attaccgcct     7680
ttgagtgagc tgataccgct cgccgcagcc gaacgaccga gcgcagcgag tcagtgagcg     7740
aggaagcgga gagagcccca atacgcaaac cgcctctccc cgcgcgttgg ccgattcatt     7800
aatgcagctg gcacgacagg tttcccgact ggaaagcggg cagtgagcgc aacgcaatta     7860
atgtgagtta gctcactcat taggcacccc aggctttaca ctttatgctt ccggctcgta     7920
```

-continued

```
tgttgtgtgg aattgtgagc ggataacaat ttcacacagg aaacagctat gaccatgatt    7980
acgccaagct ttttctttcc aattttttt tttcgtcat tataaaaatc attacgaccg      8040
agattcccgg gtaataactg atataattaa attgaagctc taatttgtga gtttagtata    8100
catgcattta cttataatac agttttttag ttttgctggc cgcatcttct caaatatgct    8160
tcccagcctg cttttctgta acgttcaccc tctaccttag catcccttcc ctttgcaaat    8220
agtcctcttc caacaataat aatgtcagat cctgtagaga ccacatcatc cacgttcta     8280 tactgttgac ccaatgcgtc tcccttgtca tctaaaccca caccgggtgt cataatcaac    8340
caatcgtaac cttcatctct tccacccatg tctctttgag caataaagcc gataacaaaa    8400
tctttgtcgc tcttcgcaat gtcaacagta cccttagtat attctccagt agatagggag    8460
cccttgcatg acaattctgc taacatcaaa aggcctctag gttcctttgt tacttcttct    8520
gccgcctgct tcaaaccgct aacaatacct gggcccacca caccgtgtgc attcgtaatg    8580
tctgcccatt ctgctattct gtatacaccc gcagagtact gcaatttgac tgtattacca    8640
atgtcagcaa attttctgtc ttcgaagagt aaaaaattgt acttggcgga taatgccttt    8700
agcggcttaa ctgtgccctc catggaaaaa tcagtcaaga tatccacatg tgttttagt     8760 aaacaaattt tgggacctaa tgcttcaact aactccagta attccttggt ggtacgaaca    8820
tccaatgaag cacacaagtt tgtttgcttt tcgtgcatga tattaaatag cttggcagca    8880
acaggactag gatgagtagc agcacgttcc ttatatgtag ctttcgacat gatttatctt    8940
cgtttcctgc aggttttgt tctgtgcagt tgggttaaga atactgggca atttcatgtt     9000
tcttcaacac tacatatgcg tatatatacc aatctaagtc tgtgctcctt ccttcgttct    9060
tccttctgtt cggagattac cgaatcaaaa aaatttcaag gaaaccgaaa tcaaaaaaaa    9120
gaataaaaaa aaaatgatga attgaaaagc ttgcatgcct gcaggtcgac tctagtatac    9180
tccgtctact gtacgataca cttccgctca ggtccttgtc ctttaacgag gccttaccac    9240 tctttgtta ctctattgat ccagctcagc aaaggcagtg tgatctaaga ttctatcttc      9300
gcgatgtagt aaaactagct agaccgagaa agagactaga aatgcaaaag gcacttctac    9360
aatggctgcc atcattatta tccgatgtga cgctgcattt ttttttttt ttttttttt      9420 tttttttt ttttttttt ttttttttg tacaaatatc ataaaaaag agaatctttt          9480 taagcaagga ttttcttaac ttcttcggcg acagcatcac cgacttcggt ggtactgttg    9540
gaaccaccta aatcaccagt tctgatacct gcatccaaaa ccttttaac tgcatcttca     9600 atggctttac cttcttcagg caagttcaat gacaatttca acatcattgc agcagacaag    9660
atagtggcga tagggttgac cttattcttt ggcaaatctg gagcggaacc atggcatggt    9720
tcgtacaaac caaatgcggt gttcttgtct ggcaaagagg ccaaggacgc agatggcaac    9780
aaacccaagg agcctgggat aacggaggct tcatcggaga tgatatcacc aaacatgttg    9840
ctggtgatta taataccatt taggtgggtt gggttcttaa ctaggatcat ggcggcagaa    9900
tcaatcaatt gatgttgaac tttcaatgta gggaattcgt tcttgatggt ttcctccaca    9960
gtttttctcc ataatcttga agaggccaaa acattagctt tatccaagga ccaaataggc    10020
aatggtggct catgttgtag ggccatgaaa gcggccattc ttgtgattct ttgcacttct    10080
ggaacggtgt attgttcact atcccaagcg acaccatcac catcgtcttc ctttctctta    10140
ccaaagtaaa tacctcccac taattctcta acaacaacga agtcagtacc tttagcaaat    10200
tgtggcttga ttggagataa gtctaaaaga gagtcggatg caaagttaca tggtcttaag    10260
```

| | | | | |
|---|---|---|---|---|
| ttggcgtaca | attgaagttc | tttacggatt | tttagtaaac | cttgttcagg tctaacacta 10320 |
| ccggtacccc | atttaggacc | acccacagca | cctaacaaaa | cggcatcagc cttcttggag 10380 |
| gcttccagcg | cctcatctgg | aagtggaaca | cctgtagcat | cgatagcagc accaccaatt 10440 |
| aaatgatttt | cgaaatcgaa | cttgacattg | gaacgaacat | cagaaatagc tttaagaacc 10500 |
| ttaatggctt | cggctgtgat | tcttgacca | acgtggtcac | ctggcaaaac gacgatcttc 10560 |
| ttaggggcag | acattacaat | ggtatatcct | tgaaatatat | ataaaaaaaa aaaaaaaaaa 10620 |
| aaaaaaaaaa | aatgcagctt | ctcaatgata | ttcgaatacg | ctttgaggag atacagccta 10680 |
| atatccgaca | aactgtttta | cagatttacg | atcgtacttg | ttacccatca ttgaattttg 10740 |
| aacatccgaa | cctgggagtt | ttccctgaaa | cagatagtat | atttgaacct gtataataat 10800 |
| atatagtcta | gcgctttacg | gaagacaatg | tatgtatttc | ggttcctgga gaaactattg 10860 |
| catctattgc | ataggtaatc | ttgcacgtcg | catccccggt | tcattttctg cgtttccatc 10920 |
| ttgcacttca | atagcatatc | tttgttaacg | aagcatctgt | gcttcatttt gtagaacaaa 10980 |
| aatgcaacgc | gagagcgcta | atttttcaaa | caaagaatct | gagctgcatt tttacagaac 11040 |
| agaaatgcaa | cgcgaaagcg | ctattttacc | aacgaagaat | ctgtgcttca tttttgtaaa 11100 |
| acaaaaatgc | aacgcgagag | cgctaatttt | tcaaacaaag | aatctgagct gcattttac 11160 |
| agaacagaaa | tgcaacgcga | gagcgctatt | ttaccaacaa | agaatctata cttctttttt 11220 |
| gttctacaaa | aatgcatccc | gagagcgcta | ttttctaac | aaagcatctt agattacttt 11280 |
| ttttctcctt | tgtgcgctct | ataatgcagt | ctcttgataa | cttttgcac tgtaggtccg 11340 |
| ttaaggttag | aagaaggcta | ctttggtgtc | tattttctct | tccataaaaa aagcctgact 11400 |
| ccacttcccg | cgtttactga | ttactagcga | agctgcgggt | gcatttttc aagataaagg 11460 |
| catccccgat | tatattctat | accgatgtgg | attgcgcata | ctttgtgaac agaaagtgat 11520 |
| agcgttgatg | attcttcatt | ggtcagaaaa | ttatgaacgg | tttcttctat tttgtctcta 11580 |
| tatactacgt | ataggaaatg | tttacatttt | cgtattgttt | tcgattcact ctatgaatag 11640 |
| ttcttactac | aattttttg | tctaaagagt | aatactagag | ataaacataa aaaatgtaga 11700 |
| ggtcgagttt | agatgcaagt | tcaaggagcg | aaaggtggat | gggtaggtta tagggata 11760 |
| tagcacagag | atatatagca | aagagatact | tttgagcaat | gtttgtggaa gcggtattcg 11820 |
| caatatttta | gtagctcgtt | acagtccggt | gcgtttttgg | tttttgaaa gtgcgtcttc 11880 |
| agagcgcttt | tggttttcaa | aagcgctctg | aagttcctat | actttctaga gaataggaac 11940 |
| ttcggaatag | gaacttcaaa | gcgtttccga | aaacgagcgc | ttccgaaaat gcaacgcgag 12000 |
| ctgcgcacat | acagctcact | gttcacgtcg | cacctatatc | tgcgtgttgc ctgtatatat 12060 |
| atatacatga | gaagaacggc | atagtgcgtg | tttatgctta | aatgcgtact tatatgcgtc 12120 |
| tatttatgta | ggatgaaagg | tagtctagta | cctcctgtga | tattatccca ttccatgcgg 12180 |
| ggtatcgtat | gcttccttca | gcactaccct | ttagctgttc | tatatgctgc cactcctcaa 12240 |
| ttggattagt | ctcatccttc | aatgctatca | tttcctttga | tattggatca tatgcatagt 12300 |
| accgagaaac | tagaggatc | | | 12319 |

<210> SEQ ID NO 132
<211> LENGTH: 13022
<212> TYPE: DNA
<213> ORGANISM: Artificial Sequence
<220> FEATURE:
<223> OTHER INFORMATION: Plasmid pLA84

<400> SEQUENCE: 132

-continued

| | |
|---|---|
| ccagcttttg ttcccttag tgagggttaa ttgcgcgctt ggcgtaatca tggtcatagc | 60 |
| tgtttcctgt gtgaaattgt tatccgctca caattccaca caacatacga gccggaagca | 120 |
| taaagtgtaa agcctggggt gcctaatgag tgagctaact cacattaatt gcgttgcgct | 180 |
| cactgcccgc tttccagtcg ggaaacctgt cgtgccagct gcattaatga atcggccaac | 240 |
| gcgcggggag aggcggtttg cgtattgggc gctcttccgc ttcctcgctc actgactcgc | 300 |
| tgcgctcggt cgttcggctg cggcgagcgg tatcagctca ctcaaaggcg gtaatacggt | 360 |
| tatccacaga atcaggggat aacgcaggaa agaacatgtg agcaaaaggc cagcaaaagg | 420 |
| ccaggaaccg taaaaaggcc gcgttgctgg cgttttttcca taggctccgc cccctgacg | 480 |
| agcatcacaa aaatcgacgc tcaagtcaga ggtggcgaaa cccgacagga ctataaagat | 540 |
| accaggcgtt tcccctgga agctccctcg tgcgctctcc tgttccgacc ctgccgctta | 600 |
| ccggatacct gtccgccttt ctcccttcgg gaagcgtggc gctttctcat agctcacgct | 660 |
| gtaggtatct cagttcggtg taggtcgttc gctccaagct gggctgtgtg cacgaacccc | 720 |
| ccgttcagcc cgaccgctgc gccttatccg gtaactatcg tcttgagtcc aacccggtaa | 780 |
| gacacgactt atcgccactg gcagcagcca ctggtaacag gattagcaga gcgaggtatg | 840 |
| taggcggtgc tacagagttc ttgaagtggt ggcctaacta cggctacact agaagaacag | 900 |
| tatttggtat ctgcgctctg ctgaagccag ttaccttcgg aaaaagagtt ggtagctctt | 960 |
| gatccggcaa acaaaccacc gctggtagcg gtggtttttt tgtttgcaag cagcagatta | 1020 |
| cgcgcagaaa aaaaggatct caagaagatc ctttgatctt ttctacgggg tctgacgctc | 1080 |
| agtggaacga aaactcacgt taagggattt tggtcatgag attatcaaaa aggatcttca | 1140 |
| cctagatcct tttaaattaa aaatgaagtt ttaaatcaat ctaaagtata tatgagtaaa | 1200 |
| cttggtctga cagttaccaa tgcttaatca gtgaggcacc tatctcagcg atctgtctat | 1260 |
| ttcgttcatc catagttgcc tgactccccg tcgtgtagat aactacgata cgggagggct | 1320 |
| taccatctgg ccccagtgct gcaatgatac cgcgagaccc acgctcaccg gctccagatt | 1380 |
| tatcagcaat aaaccagcca gccggaaggg ccgagcgcag aagtggtcct gcaactttat | 1440 |
| ccgcctccat ccagtctatt aattgttgcc gggaagctag agtaagtagt tcgccagtta | 1500 |
| atagtttgcg caacgttgtt gccattgcta caggcatcgt ggtgtcacgc tcgtcgtttg | 1560 |
| gtatggcttc attcagctcc ggttcccaac gatcaaggcg agttacatga tcccccatgt | 1620 |
| tgtgcaaaaa agcggttagc tccttcggtc ctccgatcgt tgtcagaagt aagttggccg | 1680 |
| cagtgttatc actcatggtt atggcagcac tgcataattc tcttactgtc atgccatccg | 1740 |
| taagatgctt ttctgtgact ggtgagtact caaccaagtc attctgagaa tagtgtatgc | 1800 |
| ggcgaccgag ttgctcttgc ccggcgtcaa tacgggataa taccgcgcca catagcagaa | 1860 |
| ctttaaaagt gctcatcatt ggaaaacgtt cttcggggcg aaaactctca aggatcttac | 1920 |
| cgctgttgag atccagttcg atgtaaccca ctcgtgcacc caactgatct tcagcatctt | 1980 |
| ttactttcac cagcgtttct gggtgagcaa aaacaggaag gcaaaatgcc gcaaaaaagg | 2040 |
| gaataagggc gacacggaaa tgttgaatac tcatactctt cctttttcaa tattattgaa | 2100 |
| gcatttatca gggttattgt ctcatgagcg gatacatatt tgaatgtatt tagaaaaata | 2160 |
| aacaaatagg ggttccgcgc acatttcccc gaaaagtgcc acctgaacga agcatctgtg | 2220 |
| cttcattttg tagaacaaaa atgcaacgcg agagcgctaa ttttttcaaac aaagaatctg | 2280 |
| agctgcattt ttacagaaca gaaatgcaac gcgaaagcgc tattttacca acgaagaatc | 2340 |

-continued

```
tgtgcttcat ttttgtaaaa caaaaatgca acgcgagagc gctaattttt caaacaaaga    2400
atctgagctg cattttaca gaacagaaat gcaacgcgag agcgctattt taccaacaaa     2460
gaatctatac ttcttttttg ttctacaaaa atgcatcccg agagcgctat ttttctaaca    2520
aagcatctta gattactttt tttctccttt gtgcgctcta taatgcagtc tcttgataac    2580
ttttgcact gtaggtccgt taaggttaga agaaggctac tttggtgtct attttctctt     2640
ccataaaaaa agcctgactc cacttcccgc gtttactgat tactagcgaa gctgcgggtg    2700
catttttca agataaaggc atccccgatt atattctata ccgatgtgga ttgcgcatac     2760
tttgtgaaca gaaagtgata gcgttgatga ttcttcattg gtcagaaaat tatgaacggt    2820
ttcttctatt ttgtctctat atactacgta taggaaatgt ttacattttc gtattgtttt    2880
cgattcactc tatgaatagt tcttactaca attttttgt ctaaagagta atactagaga     2940
taaacataaa aaatgtagag gtcgagttta gatgcaagtt caaggagcga aggtggatg     3000
ggtaggttat atagggatat agcacagaga tatatagcaa agagatactt ttgagcaatg    3060
tttgtggaag cggtattcgc aatattttag tagctcgtta cagtccggtg cgttttggt     3120
tttttgaaag tgcgtcttca gagcgctttt ggttttcaaa agcgctctga agttcctata    3180
cttttctagag aataggaact tcggaatagg aacttcaaag cgtttccgaa aacgagcgct    3240
tccgaaaatg caacgcgagc tgcgcacata cagctcactg ttcacgtcgc acctatatct    3300
gcgtgttgcc tgtatatata tatacatgag aagaacggca tagtgcgtgt ttatgcttaa    3360
atgcgtactt atatgcgtct atttatgtag gatgaaaggt agtctagtac ctcctgtgat    3420
attatcccat tccatgcggg gtatcgtatg cttccttcag cactacccott tagctgttct    3480
atatgctgcc actcctcaat tggattagtc tcatccttca atgctatcat ttccttgat     3540
attggatcat actaagaaac cattattatc atgacattaa cctataaaaa taggcgtatc    3600
acgaggccct ttcgtctcgc gcgtttcggt gatgacggtg aaaacctctg acacatgcag    3660
ctcccggaga cggtcacagc ttgtctgtaa gcggatgccg ggagcagaca gcccgtcag    3720
ggcgcgtcag cgggtgttgg cgggtgtcgg ggctggctta actatgcggc atcagagcag    3780
attgtactga gagtgcacca taaattcccg ttttaagagc ttggtgagcg ctaggagtca    3840
ctgccaggta tcgtttgaac acggcattag tcagggaagt cataacacag tccttttccg    3900
caattttctt tttctattac tcttggcctc ctctagtaca ctctatattt ttttatgcct    3960
cggtaatgat tttcattttt tttttccac ctagcggatg actcttttttt tttcttagcg    4020
attggcatta tcacataatg aattatacat tatataaagt aatgtgattt cttcgaagaa    4080
tatactaaaa aatgagcagg caagataaac gaaggcaaag atgacagagc agaaagccct    4140
agtaaagcgt attacaaatg aaaccaagat tcagattgcg atctctttaa agggtggtcc    4200
cctagcgata gagcactcga tcttcccaga aaaagaggca gaagcagtag cagaacaggc    4260
cacacaatcg caagtgatta acgtccacac aggtataggg tttctggacc atatgataca    4320
tgctctggcc aagcattccg gctggtcgct aatcgttgag tgcattggtg acttacacat    4380
agacgaccat cacaccactg aagactgcgg gattgctctc ggtcaagctt ttaaagaggc    4440
cctaggggcc gtgcgtggag taaaaaggtt tggatcagga tttgcgcctt tggatgaggc    4500
actttccaga gcggtggtag atctttcgaa caggccgtac gcagttgtcg aacttggttt    4560
gcaaagggag aaagtaggag atctctcttg cgagatgatc ccgcatttc ttgaaagctt    4620
tgcagaggct agcagaatta ccctccacgt tgattgtctg cgaggcaaga atgatcatca    4680
ccgtagtgag agtgcgttca aggctcttgc ggttgccata agagaagcca cctcgcccaa    4740
```

```
tggtaccaac gatgttccct ccaccaaagg tgttcttatg tagtgacacc gattatttaa    4800
agctgcagca tacgatatat atacatgtgt atatatgtat acctatgaat gtcagtaagt    4860
atgtatacga acagtatgat actgaagatg acaaggtaat gcatcattct atacgtgtca    4920
ttctgaacga ggcgcgcttt cctttttttct ttttgctttt tctttttttt tctcttgaac    4980
tcgacggatc tatgcggtgt gaaataccgc acagatgcgt aaggagaaaa taccgcatca    5040
ggaaattgta agcgttaata ttttgttaaa attcgcgtta aattttttgtt aaatcagctc    5100 atttttttaac caataggccg aaatcggcaa aatcccttat aaatcaaaag aatagaccga    5160
gatagggttg agtgttgttc cagtttggaa caagagtcca ctattaaaga acgtggactc    5220
caacgtcaaa gggcgaaaaa ccgtctatca gggcgatggc ccactacgtg gccggcttca    5280
catacgttgc atacgtcgat atagataata atgataatga cagcaggatt atcgtaatac    5340
gtaatagctg aaaatctcaa aaatgtgtgg gtcattacgt aaataatgat aggaatggga    5400
ttcttctatt tttccttttt ccattctagc agccgtcggg aaaacgtggc atcctctctt    5460
tcgggctcaa ttggagtcac gctgccgtga gcatcctctc tttccatatc taacaactga    5520
gcacgtaacc aatggaaaag catgagctta gcgttgctcc aaaaaagtat tggatggtta    5580
ataccatttg tctgttctct tctgactttg actcctcaaa aaaaaaatc tacaatcaac    5640 agatcgcttc aattacgccc tcacaaaaac tttttttcctt cttcttcgcc cacgttaaat    5700
tttatccctc atgttgtcta acggatttct gcacttgatt tattataaaa agacaaagac    5760
ataatacttc tctatcaatt tcagttattg ttcttccttg cgttattctt ctgttcttct    5820
ttttcttttg tcatatataa ccataaccaa gtaatacata ttcaaacacg tgagtatgac    5880
tgacaaaaaa actcttaaag acttaagaaa tcgtagttct gtttacgatt caatggttaa    5940
atcacctaat cgtgctatgt tgcgtgcaac tggtatgcaa gatgaagact ttgaaaaacc    6000
tatcgtcggt gtcatttcaa cttgggctga aacacacct tgtaatatcc acttacatga    6060
ctttggtaaa ctagccaaag tcggtgttaa ggaagctggt gcttggccag ttcagttcgg    6120
aacaatcacg gttctgatg gaatcgccat gggaacccaa ggaatgcgtt ctccttgac    6180 atctcgtgat attattgcag attctattga agcagccatg ggaggtcata atgcggatgc    6240
ttttgtagcc attggcggtt gtgataaaaa catgcccggt tctgttatcg ctatggctaa    6300 catgatatc ccagccattt ttgcttacgg cggaacaatt gcacctggta atttagacgg    6360
caaagatatc gatttagtct ctgtctttga aggtgtcggc cattggaacc acggcgatat    6420
gaccaaagaa gaagttaaag ctttggaatg taatgcttgt cccggtcctg gaggctgcgg    6480
tggtatgtat actgctaaca caatggcgac agctattgaa gttttgggac ttagccttcc    6540
gggttcatct tctcacccgg ctgaatccgc agaaagaaa gcagatattg aagaagctgg    6600
tcgcgctgtt gtcaaaatgc tcgaaatggg cttaaaacct tctgacattt taacgcgtga    6660
agcttttgaa gatgctatta ctgtaactat ggctctggga ggttcaacca actcaaccct    6720
tcacctctta gctattgccc atgctgctaa tgtggaattg acacttgatg atttcaatac    6780
tttccaagaa aaagttcctc atttggctga tttgaaccct tctggtcaat atgtattcca    6840 agaccttttac aaggtcggag gggtaccagc agttatgaaa tatctcctta aaaatggctt    6900
ccttcatggt gaccgtatca cttgtactgg caaaacagtc gctgaaaatt tgaaggcttt    6960
tgatgattta acacctggtc aaaaggttat tatgccgctt gaaaatccta acgtgaaga    7020 tggtccgctc attattctcc atggtaactt ggctccagac ggtgccgttg ccaaagtttc    7080
```

-continued

```
tggtgtaaaa gtgcgtcgtc atgtcggtcc tgctaaggtc tttaattctg aagaagaagc    7140
cattgaagct gtcttgaatg atgatattgt tgatggtgat gttgttgtcg tacgttttgt    7200
aggaccaaag ggcggtcctg gtatgcctga aatgctttcc ctttcatcaa tgattgttgg    7260
taaagggcaa ggtgaaaaag ttgcccttct gacagatggc cgcttctcag gtggtactta    7320
tggtcttgtc gtgggtcata tcgctcctga agcacaagat ggcggtccaa tcgcctacct    7380
gcaaacagga gacatagtca ctattgacca agacactaag gaattacact ttgatatctc    7440
cgatgaagag ttaaaacatc gtcaagagac cattgaattg ccaccgctct attcacgcgg    7500
tatccttggt aaatatgctc acatcgtttc gtctgcttct aggggagccg taacagactt    7560
ttggaagcct gaagaaactg gcaaaaaatg ttgtcctggt tgctgtggtt aagcggccgc    7620
gttaattcaa attaattgat atagtttttt aatgagtatt gaatctgttt agaataatg     7680
gaatattatt tttatttatt tatttatatt attggtcggc tcttttcttc tgaaggtcaa    7740
tgacaaaatg atatgaagga ataatgatt tctaaaattt tacaacgtaa gatatttta     7800
caaaagccta gctcatcttt tgtcatgcac tattttactc acgcttgaaa ttaacggcca    7860
gtccactgcg gagtcatttc aaagtcatcc taatcgatct atcgttttg atagctcatt     7920
ttggagttcg cgaggatcca ctagttctag agcggccgct ctagaactag taccacaggt    7980
gttgtcctct gaggacataa aatacacacc gagattcatc aactcattgc tggagttagc    8040
atatctacaa ttgggtgaaa tggggagcga tttgcaggca tttgctcggc atgccggtag    8100
aggtgtggtc aataagagcg acctcatgct atacctgaga agcaacctg acctacagga     8160
aagagttact caagaataag aattttcgtt ttaaaaccta agagtcactt taaaatttgt    8220
atacacttat tttttttata acttatttaa taataaaaat cataaatcat aagaaattcg    8280
cttactctta attaatcaag cctccatcga aatgatgact tttagtgctt gagtagacgc    8340
agcttggcca aaagtttcat atgcgtccaa gatctggtcc aggctgaatc tatgtgttat    8400
caatctagat ggatctagct tgtgactttg aacagttttc agtaacatcg gggtggtagc    8460
cgtgtcaacc aaccttgtag taatcgtgac attatgggac cataaacttt caagatgcaa    8520
atcaactttg ctaccgtgaa cgccgacatt agcgatagtt ccaccgggag ctacgatatt    8580
ctgacacaat tcaaatgtag caggtatccc aactgcttca atcgcagtat caacacctaa    8640
gccttcagta agagctttca cttcggctgc ggcgttacca cccgtggagt ttactgttct    8700
ggtggcacca aattgtttgg ctaatcccag cctgttatca tcaagatcga tcattatgat    8760
ttcagctggg gagtagaatt gtgctgtcag taaggcggcc aaaccaacgg gaccagcacc    8820
tactatagcc accgaagaac caggtgcgac tttgccgttt aggactccgc actcaaaacc    8880
cgttggtaga atatctgata acatgactaa ggcctcttca tccgcacctg ccggaatacg    8940
ataaagggat gtgtcagcat gtggtactct tacgtactct gcttgggtac catcaatttc    9000
gttgcccaga atccaacccc cggtcgtaca gtgactgaac attcctcttc tacaaaatga    9060
gcactttccg caactcgata tacatgatat caaaactcta tcgcctggtt ggaaagcagt    9120
aaccccagat ccgactgatt caataacccc cactccttca tgccctaata cacgaccggg    9180
tttacaagtc gcaacgtcac ctttaagaat gtgtagatcg gttccgcaaa ttgtagtctt    9240
tgttaccttc actatagcgt caccaggttc cttaagctct ggcttctgtc tctcttccac    9300
caacttctgg cctgggcccc tatacactaa tgctttcatc ctcagctagc tattgtaata    9360
tgtgtgtttg tttggattat taagaagaat aattacaaaa aaaattacaa aggaaggtaa    9420
ttacaacaga attaagaaag gacaagaagg aggaagagaa tcagttcatt atttcttctt    9480
```

```
tgttatataa caaacccaag tagcgatttg gccatacatt aaaagttgag aaccaccctc    9540
cctggcaaca gccacaactc gttaccattg ttcatcacga tcatgaaact cgctgtcagc    9600
tgaaatttca cctcagtgga tctctctttt tattcttcat cgttccacta acctttttcc    9660
atcagctggc agggaacgga aagtggaatc ccatttagcg agcttcctct tttcttcaag    9720
aaaagacgaa gcttgtgtgt gggtgcgcgc gctagtatct ttccacatta agaaatatac    9780
cataaaggtt acttagacat cactatggct atatatatat atatatatat atgtaactta    9840
gcaccatcgc gcgtgcatca ctgcatgtgt taaccgaaaa gtttggcgaa cacttcaccg    9900
acacggtcat ttagatctgt cgtctgcatt gcacgtccct tagccttaaa tcctaggcgg    9960
gagcattctc gtgtaattgt gcagcctgcg tagcaactca acatagcgta gtctacccag   10020
tttttcaagg gttatcgtt agaagattct ccctttctt cctgctcaca aatcttaaag    10080
tcatacattg cacgactaaa tgcaagcgac gtcagggaaa gatatgagct atacagcgga   10140
atttccatat cactcagatt ttgttatcta attttttcct tcccacgtcc gcgggaatct   10200
gtgtatatta ctgcatctag atatatgtta tcttatcttg gcgcgtacat ttaattttca   10260
acgtattcta taagaaattg cgggagtttt tttcatgtag atgatactga ctgcacgcaa   10320
atataggcat gatttatagg catgatttga tggctgtacc gataggaacg ctaagagtaa   10380
cttcagaatc gttatcctgg cggaaaaaat tcatttgtaa actttaaaaa aaaaagccaa   10440
tatccccaaa attattaaga gcgcctccat tattaactaa aatttcactc agcatccaca   10500
atgtatcagg tatctactac agatattaca tgtggcgaaa aagacaagaa caatgcaata   10560
gcgcatcaag aaaaaacaca aagctttcaa tcaatgaatc gaaaatgtca ttaaaatagt   10620
atataaattg aaactaagtc ataaagctat aaaagaaaa tttatttaaa tgcaagattt   10680
aaagtaaatt cacggccctg caggccttaa gagttttgct tagataaggc taagccaatc   10740
tgtctcaatg attctggcat atccatttgt tccatatgaa cttcaacgac atgtgctttt   10800
tgaggagtag catcgatagc agctaaagta ttagcgaagt ctgtttctgt gaaaacgttg   10860
tgagtgtcga cagtttcggc atcaccacca aatgtttcag caactaattg caagttccaa   10920
gttggtatat cattgtaact ctcatcctct ccatggatgg ctctttcgac tgtatagcca   10980
tcgttattga taatgaatat cactggtgtc aatttctctc tgaagatggt ggacatttcc   11040
tgtgctgtca gttgaaaaga tccatcaccg atggatagaa tgtgtctcct ttctgggca   11100 gcaatttgtg aaccaatcat agcaggtaat gtgtatccta tggagcccca taatgtttga   11160
ctgatcaaat tcatacccctt tttcagaggt gccaacatca aaccgaaaga tgatgtcccc   11220
tgctcagtga ccaacacatc atcagcttgc aaaaagttca taacagcttg gtgaaatctg   11280
tcttgcttta gtggtgtttc ggcctgtggt tcgaaaacag ctaattcagc ttgtttagca   11340
gcagtatcag caaaagtaaa gtttagtttt tccagctctg ccaaaagacc gttaagagaa   11400
atcccagagt aagtagaccc atctggcagc ataatgatgt catttgcagc ggttaaagtg   11460
ttttcagtct taaagccttg agaaaatgag gaggtagaat tgtcaatgat tttcccacca   11520
aaatgtaaaa cgaagtcact attgtcaacg taatccagaa cgttttttgtc agaaaaagct   11580 gggtaatagg taccaatgaa atgttcgttc tcttcattga aagagccttt gccatatgcc   11640
aaattggtta ctggcaactt tgtttggttt atccagtttt caaatctttc tcttatctgg   11700
aaacgggcga tctcatgacc ggcgattacg ataggttgag cggcctttttc taagtgtgat   11760 agtatgattt ctgcaagttg tgcctctctc tcaccagatg atttctctgt ttgtagtgct   11820
```

-continued

```
tttgcaggtt taactattgc tttatgagct atatcaattg gaagattgat gtatactggc   11880
ctcttttcca acaaggctgt ttctaatact ctgtcgatct ctgaagctgc attctcttca   11940
gtaagcatgg ttgtagcggc agtgacttcc ttagccattt cactaaagtt atgaaagtta   12000
cccattccta aggaatgatg aaccagcttt tgttggatt gcacattcat agttggagaa    12060
cccacgatgt ggatgacagg gacttgttct gcaaaactac cagctgttcc gttaatggct   12120
gacagttcac ccactccgaa tgtagtaaca agagctgata cgcctctttc acgggcgtag   12180
ccatctgctg catatgctgc gtttagttca ttagtattcc cttgccagga aagtccttcg   12240
tgattttgaa tgtaatctag aaaagtcaaa ttgtaatccc ctggcacacc gaaaacctta   12300
tcgataccaa tctcttctag tctatctacc aagtactgtc ctacggtata cattttgttt   12360
actagtttat gtgtgtttat tcgaaactaa gttcttggtg ttttaaaact aaaaaaaaga   12420
ctaactataa aagtagaatt taagaagttt aagaaataga tttacagaat tacaatcaat   12480
acctaccgtc tttatatact tattagtcaa gtaggggaat aatttcaggg aactggtttc   12540
aacctttttt ttcagctttt tccaaatcag agagagcaga aggtaataga aggtgtaaga   12600
aaatgagata gatacatgcg tgggtcaatt gccttgtgtc atcatttact ccaggcaggt   12660
tgcatcactc cattgaggtt gtgcccgttt tttgcctgtt tgtgcccctg ttctctgtag   12720
ttgcgctaag agaatggacc tatgaactga tggttggtga agaaaacaat attttggtgc   12780
tgggattctt ttttttttctg gatgccagct taaaagcgg gctccattat atttagtgga    12840
tgccaggaat aaactgttca cccagacacc tacgatgtta tatattctgt gtaacccgcc   12900
ccctatttg ggcatgtacg ggttacagca gaattaaaag gctaattttt tgactaaata    12960
aagttaggaa aatcactact attaattatt tacgtattct ttgaaatggc agtattggag   13020
ct                                                                  13022
```

<210> SEQ ID NO 133
<211> LENGTH: 495
<212> TYPE: PRT
<213> ORGANISM: Saccharomyces cerevisiae
<400> SEQUENCE: 133

```
Met Thr Thr Asp Asn Ala Lys Ala Gln Leu Thr Ser Ser Ser Gly Gly
1               5                   10                  15

Asn Ile Ile Val Val Ser Asn Arg Leu Pro Val Thr Ile Thr Lys Asn
            20                  25                  30

Ser Ser Thr Gly Gln Tyr Glu Tyr Ala Met Ser Ser Gly Gly Leu Val
        35                  40                  45

Thr Ala Leu Glu Gly Leu Lys Lys Thr Tyr Thr Phe Lys Trp Phe Gly
    50                  55                  60

Trp Pro Gly Leu Glu Ile Pro Asp Asp Glu Lys Asp Gln Val Arg Lys
65                  70                  75                  80

Asp Leu Leu Glu Lys Phe Asn Ala Val Pro Ile Phe Leu Ser Asp Glu
                85                  90                  95

Ile Ala Asp Leu His Tyr Asn Gly Phe Ser Asn Ser Ile Leu Trp Pro
            100                 105                 110

Leu Phe His Tyr His Pro Gly Glu Ile Asn Phe Asp Glu Asn Ala Trp
        115                 120                 125

Leu Ala Tyr Asn Glu Ala Asn Gln Thr Phe Thr Asn Glu Ile Ala Lys
    130                 135                 140

Thr Met Asn His Asn Asp Leu Ile Trp Val His Asp Tyr His Leu Met
145                 150                 155                 160
```

Leu Val Pro Glu Met Leu Arg Val Lys Ile His Glu Lys Gln Leu Gln
                165                 170                 175

Asn Val Lys Val Gly Trp Phe Leu His Thr Pro Phe Pro Ser Ser Glu
            180                 185                 190

Ile Tyr Arg Ile Leu Pro Val Arg Gln Glu Ile Leu Lys Gly Val Leu
        195                 200                 205

Ser Cys Asp Leu Val Gly Phe His Thr Tyr Asp Tyr Ala Arg His Phe
    210                 215                 220

Leu Ser Ser Val Gln Arg Val Leu Asn Val Asn Thr Leu Pro Asn Gly
225                 230                 235                 240

Val Glu Tyr Gln Gly Arg Phe Val Asn Val Gly Ala Phe Pro Ile Gly
                245                 250                 255

Ile Asp Val Asp Lys Phe Thr Asp Gly Leu Lys Lys Glu Ser Val Gln
            260                 265                 270

Lys Arg Ile Gln Gln Leu Lys Glu Thr Phe Lys Gly Cys Lys Ile Ile
        275                 280                 285

Val Gly Val Asp Arg Leu Asp Tyr Ile Lys Gly Val Pro Gln Lys Leu
    290                 295                 300

His Ala Met Glu Val Phe Leu Asn Glu His Pro Glu Trp Arg Gly Lys
305                 310                 315                 320

Val Val Leu Val Gln Val Ala Val Pro Ser Arg Gly Asp Val Glu Glu
                325                 330                 335

Tyr Gln Tyr Leu Arg Ser Val Val Asn Glu Leu Val Gly Arg Ile Asn
            340                 345                 350

Gly Gln Phe Gly Thr Val Glu Phe Val Pro Ile His Phe Met His Lys
        355                 360                 365

Ser Ile Pro Phe Glu Glu Leu Ile Ser Leu Tyr Ala Val Ser Asp Val
    370                 375                 380

Cys Leu Val Ser Ser Thr Arg Asp Gly Met Asn Leu Val Ser Tyr Glu
385                 390                 395                 400

Tyr Ile Ala Cys Gln Glu Glu Lys Lys Gly Ser Leu Ile Leu Ser Glu
                405                 410                 415

Phe Thr Gly Ala Ala Gln Ser Leu Asn Gly Ala Ile Ile Val Asn Pro
            420                 425                 430

Trp Asn Thr Asp Asp Leu Ser Asp Ala Ile Asn Glu Ala Leu Thr Leu
        435                 440                 445

Pro Asp Val Lys Lys Glu Val Asn Trp Glu Lys Leu Tyr Lys Tyr Ile
    450                 455                 460

Ser Lys Tyr Thr Ser Ala Phe Trp Gly Glu Asn Phe Val His Glu Leu
465                 470                 475                 480

Tyr Ser Thr Ser Ser Ser Thr Ser Ser Ala Thr Lys Asn
                485                 490                 495

<210> SEQ ID NO 134
<211> LENGTH: 896
<212> TYPE: PRT
<213> ORGANISM: Saccharomyces cerevisiae

<400> SEQUENCE: 134

Met Thr Thr Thr Ala Gln Asp Asn Ser Pro Lys Lys Arg Gln Arg Ile
1               5                   10                  15

Ile Asn Cys Val Thr Gln Leu Pro Tyr Lys Ile Gln Leu Gly Glu Ser
            20                  25                  30

Asn Asp Asp Trp Lys Ile Ser Ala Thr Thr Gly Asn Ser Ala Leu Phe

-continued

```
                35                  40                  45
Ser Ser Leu Glu Tyr Leu Gln Phe Asp Ser Thr Glu Tyr Glu Gln His
 50                  55                  60

Val Val Gly Trp Thr Gly Glu Ile Thr Arg Thr Glu Arg Asn Leu Phe
 65                  70                  75                  80

Thr Arg Glu Ala Lys Glu Lys Pro Gln Asp Leu Asp Asp Pro Leu
                 85                  90                  95

Tyr Leu Thr Lys Glu Gln Ile Asn Gly Leu Thr Thr Thr Leu Gln Asp
                100                 105                 110

His Met Lys Ser Asp Lys Glu Ala Lys Thr Asp Thr Gln Thr Ala
                115                 120                 125

Pro Val Thr Asn Asn Val His Pro Val Trp Leu Leu Arg Lys Asn Gln
130                 135                 140

Ser Arg Trp Arg Asn Tyr Ala Glu Lys Val Ile Trp Pro Thr Phe His
145                 150                 155                 160

Tyr Ile Leu Asn Pro Ser Asn Glu Gly Glu Gln Glu Lys Asn Trp Trp
                165                 170                 175

Tyr Asp Tyr Val Lys Phe Asn Glu Ala Tyr Ala Gln Lys Ile Gly Glu
                180                 185                 190

Val Tyr Arg Lys Gly Asp Ile Ile Trp Ile His Asp Tyr Leu Leu
                195                 200                 205

Leu Leu Pro Gln Leu Leu Arg Met Lys Phe Asn Asp Glu Ser Ile Ile
210                 215                 220

Ile Gly Tyr Phe His His Ala Pro Trp Pro Ser Asn Glu Tyr Phe Arg
225                 230                 235                 240

Cys Leu Pro Arg Arg Lys Gln Ile Leu Asp Gly Leu Val Gly Ala Asn
                245                 250                 255

Arg Ile Cys Phe Gln Asn Glu Ser Phe Ser Arg His Phe Val Ser Ser
                260                 265                 270

Cys Lys Arg Leu Leu Asp Ala Thr Ala Lys Lys Ser Lys Asn Ser Ser
                275                 280                 285

Asn Ser Asp Gln Tyr Gln Val Ser Val Tyr Gly Gly Asp Val Leu Val
290                 295                 300

Asp Ser Leu Pro Ile Gly Val Asn Thr Thr Gln Ile Leu Lys Asp Ala
305                 310                 315                 320

Phe Thr Lys Asp Ile Asp Ser Lys Leu Ser Ile Lys Gln Ala Tyr
                325                 330                 335

Gln Asn Lys Lys Ile Ile Ile Gly Arg Asp Arg Leu Asp Ser Val Arg
                340                 345                 350

Gly Val Val Gln Lys Leu Arg Ala Phe Glu Thr Phe Leu Ala Met Tyr
                355                 360                 365

Pro Glu Trp Arg Asp Gln Val Leu Ile Gln Val Ser Ser Pro Thr
                370                 375                 380

Ala Asn Arg Asn Ser Pro Gln Thr Ile Arg Leu Glu Gln Gln Val Asn
385                 390                 395                 400

Glu Leu Val Asn Ser Ile Asn Ser Glu Tyr Gly Asn Leu Asn Phe Ser
                405                 410                 415

Pro Val Gln His Tyr Tyr Met Arg Ile Pro Lys Asp Val Tyr Leu Ser
                420                 425                 430

Leu Leu Arg Val Ala Asp Leu Cys Leu Ile Thr Ser Val Arg Asp Gly
                435                 440                 445

Met Asn Thr Thr Ala Leu Glu Tyr Val Thr Val Lys Ser His Met Ser
450                 455                 460
```

```
Asn Phe Leu Cys Tyr Gly Asn Pro Leu Ile Leu Ser Glu Phe Ser Gly
465                 470                 475                 480

Ser Ser Asn Val Leu Lys Asp Ala Ile Val Asn Pro Trp Asp Ser
            485                 490                 495

Val Ala Val Ala Lys Ser Ile Asn Met Ala Leu Lys Leu Asp Lys Glu
                500                 505                 510

Glu Lys Ser Asn Leu Glu Ser Lys Leu Trp Lys Glu Val Pro Thr Ile
            515                 520                 525

Gln Asp Trp Thr Asn Lys Phe Leu Ser Ser Leu Lys Glu Gln Ala Ser
530                 535                 540

Ser Asn Asp Asp Met Glu Arg Lys Met Thr Pro Ala Leu Asn Arg Pro
545                 550                 555                 560

Val Leu Leu Glu Asn Tyr Lys Gln Ala Lys Arg Leu Phe Leu Phe
                565                 570                 575

Asp Tyr Asp Gly Thr Leu Thr Pro Ile Val Lys Asp Pro Ala Ala Ala
                580                 585                 590

Ile Pro Ser Ala Arg Leu Tyr Thr Ile Leu Gln Lys Leu Cys Ala Asp
            595                 600                 605

Pro His Asn Gln Ile Trp Ile Ile Ser Gly Arg Asp Gln Lys Phe Leu
610                 615                 620

Asn Lys Trp Leu Gly Gly Lys Leu Pro Gln Leu Gly Leu Ser Ala Glu
625                 630                 635                 640

His Gly Cys Phe Met Lys Asp Val Ser Cys Gln Asp Trp Val Asn Leu
                645                 650                 655

Thr Glu Lys Val Asp Met Ser Trp Gln Val Arg Val Asn Glu Val Met
                660                 665                 670

Glu Glu Phe Thr Thr Arg Thr Pro Gly Ser Phe Ile Glu Arg Lys Lys
            675                 680                 685

Val Ala Leu Thr Trp His Tyr Arg Arg Thr Val Pro Glu Leu Gly Glu
690                 695                 700

Phe His Ala Lys Glu Leu Lys Glu Lys Leu Leu Ser Phe Thr Asp Asp
705                 710                 715                 720

Phe Asp Leu Glu Val Met Asp Gly Lys Ala Asn Ile Glu Val Arg Pro
                725                 730                 735

Arg Phe Val Asn Lys Gly Glu Ile Val Lys Arg Leu Val Trp His Gln
                740                 745                 750

His Gly Lys Pro Gln Asp Met Leu Lys Gly Ile Ser Glu Lys Leu Pro
            755                 760                 765

Lys Asp Glu Met Pro Asp Phe Val Leu Cys Leu Gly Asp Asp Phe Thr
770                 775                 780

Asp Glu Asp Met Phe Arg Gln Leu Asn Thr Ile Glu Thr Cys Trp Lys
785                 790                 795                 800

Glu Lys Tyr Pro Asp Gln Lys Asn Gln Trp Gly Asn Tyr Gly Phe Tyr
            805                 810                 815

Pro Val Thr Val Gly Ser Ala Ser Lys Lys Thr Val Ala Lys Ala His
                820                 825                 830

Leu Thr Asp Pro Gln Gln Val Leu Glu Thr Leu Gly Leu Leu Val Gly
                835                 840                 845

Asp Val Ser Leu Phe Gln Ser Ala Gly Thr Val Asp Leu Asp Ser Arg
            850                 855                 860

Gly His Val Lys Asn Ser Glu Ser Ser Leu Lys Ser Lys Leu Ala Ser
865                 870                 875                 880
```

```
Lys Ala Tyr Val Met Lys Arg Ser Ala Ser Tyr Thr Gly Ala Lys Val
            885                 890                 895
```

<210> SEQ ID NO 135
<211> LENGTH: 704
<212> TYPE: PRT
<213> ORGANISM: Saccharomyces cerevisiae

<400> SEQUENCE: 135

```
Met Thr Val Asp His Asp Phe Asn Ser Glu Asp Ile Leu Phe Pro Ile
1               5                   10                  15

Glu Ser Met Ser Ser Ile Gln Tyr Val Glu Asn Asn Pro Asn Asn
            20                  25                  30

Ile Asn Asn Asp Val Ile Pro Tyr Ser Leu Asp Ile Lys Asn Thr Val
            35                  40                  45

Leu Asp Ser Ala Asp Leu Asn Asp Ile Gln Asn Gln Glu Thr Ser Leu
        50                  55                  60

Asn Leu Gly Leu Pro Pro Leu Ser Phe Asp Ser Pro Leu Pro Val Thr
65                  70                  75                  80

Glu Thr Ile Pro Ser Thr Thr Asp Asn Ser Leu His Leu Lys Ala Asp
                85                  90                  95

Ser Asn Lys Asn Arg Asp Ala Arg Thr Ile Glu Asn Asp Ser Glu Ile
            100                 105                 110

Lys Ser Thr Asn Asn Ala Ser Gly Ser Gly Ala Asn Gln Tyr Thr Thr
        115                 120                 125

Leu Thr Ser Pro Tyr Pro Met Asn Asp Ile Leu Tyr Asn Met Asn Asn
    130                 135                 140

Pro Leu Gln Ser Pro Ser Pro Ser Ser Val Pro Gln Asn Pro Thr Ile
145                 150                 155                 160

Asn Pro Pro Ile Asn Thr Ala Ser Asn Glu Thr Asn Leu Ser Pro Gln
                165                 170                 175

Thr Ser Asn Gly Asn Glu Thr Leu Ile Ser Pro Arg Ala Gln Gln His
            180                 185                 190

Thr Ser Ile Lys Asp Asn Arg Leu Ser Leu Pro Asn Gly Ala Asn Ser
        195                 200                 205

Asn Leu Phe Ile Asp Thr Asn Pro Asn Asn Leu Asn Glu Lys Leu Arg
    210                 215                 220

Asn Gln Leu Asn Ser Asp Thr Asn Ser Tyr Ser Asn Ser Ile Ser Asn
225                 230                 235                 240

Ser Asn Ser Asn Ser Thr Gly Asn Leu Asn Ser Ser Tyr Phe Asn Ser
                245                 250                 255

Leu Asn Ile Asp Ser Met Leu Asp Asp Tyr Val Ser Ser Asp Leu Leu
            260                 265                 270

Leu Asn Asp Asp Asp Asp Thr Asn Leu Ser Arg Arg Arg Phe Ser
        275                 280                 285

Asp Val Ile Thr Asn Gln Phe Pro Ser Met Thr Asn Ser Arg Asn Ser
    290                 295                 300

Ile Ser His Ser Leu Asp Leu Trp Asn His Pro Lys Ile Asn Pro Ser
305                 310                 315                 320

Asn Arg Asn Thr Asn Leu Asn Ile Thr Thr Asn Ser Thr Ser Ser Ser
                325                 330                 335

Asn Ala Ser Pro Asn Thr Thr Thr Met Asn Ala Asn Ala Asp Ser Asn
            340                 345                 350

Ile Ala Gly Asn Pro Lys Asn Asn Asp Ala Thr Ile Asp Asn Glu Leu
        355                 360                 365
```

Thr Gln Ile Leu Asn Glu Tyr Asn Met Asn Phe Asn Asp Asn Leu Gly
    370             375             380

Thr Ser Thr Ser Gly Lys Asn Lys Ser Ala Cys Pro Ser Ser Phe Asp
385             390             395             400

Ala Asn Ala Met Thr Lys Ile Asn Pro Ser Gln Gln Leu Gln Gln Gln
            405             410             415

Leu Asn Arg Val Gln His Lys Gln Leu Thr Ser Ser His Asn Asn Ser
        420             425             430

Ser Thr Asn Met Lys Ser Phe Asn Ser Asp Leu Tyr Ser Arg Arg Gln
    435             440             445

Arg Ala Ser Leu Pro Ile Ile Asp Asp Ser Leu Ser Tyr Asp Leu Val
450             455             460

Asn Lys Gln Asp Glu Asp Pro Lys Asn Asp Met Leu Pro Asn Ser Asn
465             470             475             480

Leu Ser Ser Ser Gln Gln Phe Ile Lys Pro Ser Met Ile Leu Ser Asp
            485             490             495

Asn Ala Ser Val Ile Ala Lys Val Ala Thr Thr Gly Leu Ser Asn Asp
        500             505             510

Met Pro Phe Leu Thr Glu Glu Gly Gln Asn Ala Asn Ser Thr Pro
    515             520             525

Asn Phe Asp Leu Ser Ile Thr Gln Met Asn Met Ala Pro Leu Ser Pro
530             535             540

Ala Ser Ser Ser Ser Thr Ser Leu Ala Thr Asn His Phe Tyr His His
545             550             555             560

Phe Pro Gln Gln Gly His His Thr Met Asn Ser Lys Ile Gly Ser Ser
            565             570             575

Leu Arg Arg Arg Lys Ser Ala Val Pro Leu Met Gly Thr Val Pro Leu
        580             585             590

Thr Asn Gln Gln Asn Asn Ile Ser Ser Ser Ser Val Asn Ser Thr Gly
    595             600             605

Asn Gly Ala Gly Val Thr Lys Glu Arg Arg Pro Ser Tyr Arg Arg Lys
610             615             620

Ser Met Thr Pro Ser Arg Arg Ser Ser Val Val Ile Glu Ser Thr Lys
625             630             635             640

Glu Leu Glu Glu Lys Pro Phe His Cys His Ile Cys Pro Lys Ser Phe
            645             650             655

Lys Arg Ser Glu His Leu Lys Arg His Val Arg Ser Val His Ser Asn
        660             665             670

Glu Arg Pro Phe Ala Cys His Ile Cys Asp Lys Lys Phe Ser Arg Ser
    675             680             685

Asp Asn Leu Ser Gln His Ile Lys Thr His Lys Lys His Gly Asp Ile
690             695             700

<210> SEQ ID NO 136
<211> LENGTH: 172
<212> TYPE: PRT
<213> ORGANISM: Saccharomyces cerevisiae

<400> SEQUENCE: 136

Met Ser Ala Asn Ser Lys Asp Arg Asn Gln Ser Asn Gln Asp Ala Lys
1               5               10              15

Arg Gln Gln Gln Asn Phe Pro Lys Lys Ile Ser Glu Gly Glu Ala Asp
            20              25              30

Leu Tyr Leu Asp Gln Tyr Asn Phe Thr Thr Thr Ala Ala Ile Val Ser

```
                35                  40                  45
Ser Val Asp Arg Lys Ile Phe Val Leu Leu Arg Asp Gly Arg Met Leu
 50                  55                  60

Phe Gly Val Leu Arg Thr Phe Asp Gln Tyr Ala Asn Leu Ile Leu Gln
 65                  70                  75                  80

Asp Cys Val Glu Arg Ile Tyr Phe Ser Glu Asn Lys Tyr Ala Glu
                 85                  90                  95

Glu Asp Arg Gly Ile Phe Met Ile Arg Gly Glu Asn Val Val Met Leu
                100                 105                 110

Gly Glu Val Asp Ile Asp Lys Glu Asp Gln Pro Leu Glu Ala Met Glu
                115                 120                 125

Arg Ile Pro Phe Lys Glu Ala Trp Leu Thr Lys Gln Lys Ile Asp Glu
            130                 135                 140

Lys Arg Phe Lys Glu Glu Thr His Lys Gly Lys Lys Met Ala Arg His
145                 150                 155                 160

Gly Ile Val Tyr Asp Phe His Lys Ser Asp Met Tyr
                165                 170
```

<210> SEQ ID NO 137
<211> LENGTH: 751
<212> TYPE: PRT
<213> ORGANISM: Saccharomyces cerevisiae

<400> SEQUENCE: 137

```
Met Ser Gln Val Asn Thr Ser Gln Gly Pro Val Ala Gln Gly Arg Gln
  1               5                  10                  15

Arg Arg Leu Ser Ser Leu Ser Glu Phe Asn Asp Pro Phe Ser Asn Ala
                 20                  25                  30

Glu Val Tyr Tyr Gly Pro Pro Thr Asp Pro Arg Lys Gln Lys Gln Ala
                 35                  40                  45

Lys Pro Ala Lys Ile Asn Arg Thr Arg Thr Met Ser Val Phe Asp Asn
 50                  55                  60

Val Ser Pro Phe Lys Lys Thr Gly Phe Gly Lys Leu Gln Gln Thr Arg
 65                  70                  75                  80

Arg Gly Ser Glu Asp Asp Thr Tyr Ser Ser Gln Gly Asn Arg Arg
                 85                  90                  95

Phe Phe Ile Glu Asp Val Asp Lys Thr Leu Asn Glu Leu Leu Ala Ala
                100                 105                 110

Glu Asp Thr Asp Lys Asn Tyr Gln Ile Thr Ile Glu Asp Thr Gly Pro
            115                 120                 125

Lys Val Leu Lys Val Gly Thr Ala Asn Ser Tyr Gly Tyr Lys His Ile
            130                 135                 140

Asn Ile Arg Gly Thr Tyr Met Leu Ser Asn Leu Leu Gln Glu Leu Thr
145                 150                 155                 160

Ile Ala Lys Ser Phe Gly Arg His Gln Ile Phe Leu Asp Glu Ala Arg
                165                 170                 175

Ile Asn Glu Asn Pro Val Asn Arg Leu Ser Arg Leu Ile Asn Thr Gln
                180                 185                 190

Phe Trp Asn Ser Leu Thr Arg Arg Val Asp Leu Asn Asn Val Gly Glu
            195                 200                 205

Ile Ala Lys Asp Thr Lys Ile Asp Thr Pro Gly Ala Lys Asn Pro Arg
            210                 215                 220

Ile Tyr Val Pro Tyr Asp Cys Pro Glu Gln Tyr Glu Phe Tyr Val Gln
225                 230                 235                 240
```

-continued

```
Ala Ser Gln Met His Pro Ser Leu Lys Leu Glu Val Glu Tyr Leu Pro
            245                 250                 255
Lys Lys Ile Thr Ala Glu Tyr Val Lys Ser Val Asn Asp Thr Pro Gly
260                 265                 270
Leu Leu Ala Leu Ala Met Glu Glu His Phe Asn Pro Ser Thr Gly Glu
            275                 280                 285
Lys Thr Leu Ile Gly Tyr Pro Tyr Ala Val Pro Gly Gly Arg Phe Asn
290                 295                 300
Glu Leu Tyr Gly Trp Asp Ser Tyr Met Met Ala Leu Gly Leu Leu Glu
305                 310                 315                 320
Ala Asn Lys Thr Asp Val Ala Arg Gly Met Val Glu His Phe Ile Phe
            325                 330                 335
Glu Ile Asn His Tyr Gly Lys Ile Leu Asn Ala Asn Arg Ser Tyr Tyr
            340                 345                 350
Leu Cys Arg Ser Gln Pro Pro Phe Leu Thr Glu Met Ala Leu Val Val
            355                 360                 365
Phe Lys Lys Leu Gly Gly Arg Ser Asn Pro Asp Ala Val Asp Leu Leu
            370                 375                 380
Lys Arg Ala Phe Gln Ala Ser Ile Lys Glu Tyr Lys Thr Val Trp Thr
385                 390                 395                 400
Ala Ser Pro Arg Leu Asp Pro Glu Thr Gly Leu Ser Arg Tyr His Pro
            405                 410                 415
Asn Gly Leu Gly Ile Pro Pro Glu Thr Glu Ser Asp His Phe Asp Thr
            420                 425                 430
Val Leu Leu Pro Tyr Ala Ser Lys His Gly Val Thr Leu Asp Glu Phe
            435                 440                 445
Lys Gln Leu Tyr Asn Asp Gly Lys Ile Lys Glu Pro Lys Leu Asp Glu
            450                 455                 460
Phe Phe Leu His Asp Arg Gly Val Arg Glu Ser Gly His Asp Thr Thr
465                 470                 475                 480
Tyr Arg Phe Glu Gly Val Cys Ala Tyr Leu Ala Thr Ile Asp Leu Asn
            485                 490                 495
Ser Leu Leu Tyr Lys Tyr Glu Ile Asp Ile Ala Asp Phe Ile Lys Glu
            500                 505                 510
Phe Cys Asp Asp Lys Tyr Glu Asp Pro Leu Asp His Ser Ile Thr Thr
            515                 520                 525
Ser Ala Met Trp Lys Glu Met Ala Lys Ile Arg Gln Glu Lys Ile Thr
            530                 535                 540
Lys Tyr Met Trp Asp Asp Glu Ser Gly Phe Phe Phe Asp Tyr Asn Thr
545                 550                 555                 560
Lys Ile Lys His Arg Thr Ser Tyr Glu Ser Ala Thr Thr Phe Trp Ala
            565                 570                 575
Leu Trp Ala Gly Leu Ala Thr Lys Glu Gln Ala Gln Lys Met Val Glu
            580                 585                 590
Lys Ala Leu Pro Lys Leu Glu Met Leu Gly Gly Leu Ala Ala Cys Thr
            595                 600                 605
Glu Arg Ser Arg Gly Pro Ile Ser Ile Ser Arg Pro Ile Arg Gln Trp
610                 615                 620
Asp Tyr Pro Phe Gly Trp Ala Pro His Gln Ile Leu Ala Trp Glu Gly
625                 630                 635                 640
Leu Arg Ser Tyr Gly Tyr Leu Thr Val Thr Asn Arg Leu Ala Tyr Arg
            645                 650                 655
Trp Leu Phe Met Met Thr Lys Ala Phe Val Asp Tyr Asn Gly Ile Val
```

-continued

```
            660                 665                 670
Val Glu Lys Tyr Asp Val Thr Arg Gly Thr Asp Pro His Arg Val Glu
        675                 680                 685

Ala Glu Tyr Gly Asn Gln Gly Ala Asp Phe Lys Gly Ala Ala Thr Glu
        690                 695                 700

Gly Phe Gly Trp Val Asn Ala Ser Tyr Ile Leu Gly Leu Lys Tyr Met
705                 710                 715                 720

Asn Ser His Ala Arg Arg Ala Leu Gly Ala Cys Ile Pro Pro Ile Ser
                725                 730                 735

Phe Phe Ser Ser Leu Arg Pro Gln Glu Arg Asn Leu Tyr Gly Leu
                740                 745                 750
```